(12) United States Patent
Nishizawa et al.

(10) Patent No.: US 7,910,741 B2
(45) Date of Patent: *Mar. 22, 2011

(54) NITROGEN-CONTAINING HETEROCYCLIC DERIVATIVES AND DRUGS CONTAINING THE SAME AS THE ACTIVE INGREDIENT

(75) Inventors: Rena Nishizawa, Mishima-gun (JP); Yoshikazu Takaoka, Mishima-gun (JP); Shiro Shibayama, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 898 days.

This patent is subject to a terminal disclaimer.

(21) Appl. No.: 10/549,120

(22) PCT Filed: Mar. 12, 2004

(86) PCT No.: PCT/JP2004/003333
§ 371 (c)(1),
(2), (4) Date: Sep. 14, 2005

(87) PCT Pub. No.: WO2004/080966
PCT Pub. Date: Sep. 23, 2004

(65) Prior Publication Data
US 2006/0178399 A1    Aug. 10, 2006

(30) Foreign Application Priority Data
Mar. 14, 2003  (JP) ............... P. 2003-070347
Nov. 14, 2003  (JP) ............... P. 2003-385683

(51) Int. Cl.
    C07D 211/68    (2006.01)
    A61K 31/445    (2006.01)
(52) U.S. Cl. .................. 546/194; 514/318
(58) Field of Classification Search .......... 546/194, 546/223, 208, 210; 514/317, 318, 326
    See application file for complete search history.

(56) References Cited

U.S. PATENT DOCUMENTS

| | | | |
|---|---|---|---|
| 3,375,256 A | 3/1968 | Bach et al. | |
| 5,169,855 A * | 12/1992 | Cain et al. | 514/319 |
| 5,486,534 A | 1/1996 | Lee et al. | |
| 6,096,780 A | 8/2000 | Shiraishi et al. | |
| 6,268,354 B1 | 7/2001 | Nishimura et al. | |
| 6,376,536 B1 | 4/2002 | Shiraishi et al. | |
| 6,515,027 B1 | 2/2003 | Bondinell et al. | |
| 6,720,321 B2 | 4/2004 | Cirillo et al. | |
| 6,765,009 B2 | 7/2004 | Francesco et al. | |
| 6,894,063 B2 | 5/2005 | Greenlee et al. | |
| 6,903,085 B1 | 6/2005 | Thom et al. | |
| 7,053,090 B2 | 5/2006 | Habashita et al. | |
| 7,071,213 B2 | 7/2006 | Friary et al. | |
| 7,247,725 B2 | 7/2007 | Butora et al. | |
| 2002/0165223 A1 | 11/2002 | Greenlee et al. | |
| 2003/0069276 A1 | 4/2003 | Edlin et al. | |
| 2003/0083333 A1 | 5/2003 | Cirillo et al. | |
| 2003/0100608 A1 | 5/2003 | Cirillo et al. | |
| 2003/0114517 A1 | 6/2003 | Greenlee et al. | |
| 2003/0195192 A1 | 10/2003 | Haviv et al. | |
| 2004/0006081 A1 | 1/2004 | Burrows et al. | |
| 2004/0010013 A1 | 1/2004 | Friary et al. | |
| 2004/0082584 A1 | 4/2004 | Habashita et al. | |
| 2004/0158067 A1 | 8/2004 | Hutchison et al. | |
| 2005/0038100 A1 | 2/2005 | Greenlee et al. | |
| 2005/0215557 A1 | 9/2005 | Habashita et al. | |
| 2005/0250792 A1 | 11/2005 | Thom et al. | |
| 2005/0261325 A1 | 11/2005 | Butora et al. | |
| 2005/0267114 A1 | 12/2005 | Takaoka et al. | |
| 2005/0282861 A1 | 12/2005 | Friary et al. | |
| 2006/0178397 A1 | 8/2006 | MacDonald et al. | |
| 2006/0178399 A1 | 8/2006 | Nishizawa et al. | |
| 2007/0066624 A1 | 3/2007 | Zhou et al. | |
| 2008/0057074 A1 | 3/2008 | Takaoka et al. | |
| 2009/0131403 A1 | 5/2009 | Kusuda et al. | |

FOREIGN PATENT DOCUMENTS

| | | |
|---|---|---|
| EP | 0449187 A2 | 10/1991 |
| EP | 0748805 A1 | 12/1996 |
| EP | 1020445 A1 | 7/2000 |
| EP | 1 236 726 A1 | 9/2002 |
| EP | 1378510 A1 | 1/2004 |
| EP | 1422219 A1 | 5/2004 |

(Continued)

OTHER PUBLICATIONS http://wordnetweb.princeton.edu/perl/webwn?s=medicament.—Definition of the term "medicament", 2010.*

(Continued)

*Primary Examiner* — Rita J Desai
*Assistant Examiner* — John Mabry
(74) *Attorney, Agent, or Firm* — Sughrue Mion, PLLC

(57) ABSTRACT

A compound represented by the following general formula (I), its salt, solvates thereof or prodrugs thereof:

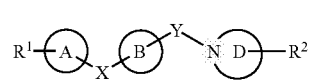

(I)

(wherein each symbol is as defined in the description.) The compounds represented by the general formula (I) are useful in preventing and/or treating various inflammatory diseases (asthma, nephritis, nephropathy, hepatitis, arthritis, rheumatoid arthritis, rhinitis, conjunctivitis, ulcerative colitis, etc.), immunological diseases (autoimmune diseases, rejection in organ transplantation, immunosuppression, psoriasis, multiple sclerosis, etc.), infection with human immunodeficiency virus (acquired immunodeficiency syndrome, etc.), allergic diseases (atopic dermatitis, urticaria, allergic bronchopulmonary aspergillosis, allergic eosinophilic gastroenteritis, etc.), ischemic reperfusion injury, acute respiratory distress syndrome, shock accompanying bacterial infection, diabetes, cancer metastasis and so on.

11 Claims, No Drawings

FOREIGN PATENT DOCUMENTS

| | | | |
|---|---|---|---|
| EP | 1541574 | A1 | 6/2005 |
| EP | 1604981 | A1 | 12/2005 |
| EP | 1790637 | A1 | 5/2007 |
| JP | 4-356462 | A | 12/1992 |
| JP | 2000-128782 | A2 | 5/2000 |
| JP | 2001-518505 | A | 10/2001 |
| JP | 2004-528318 | A | 9/2004 |
| JP | 2004-534787 | A | 11/2004 |
| JP | 2007-63268 | A | 3/2007 |
| RU | 2199535 | C2 | 2/2003 |
| WO | 96/10012 | A1 | 4/1996 |
| WO | 97/36903 | A1 | 10/1997 |
| WO | 99-01127 | A1 | 1/1999 |
| WO | 9917773 | A1 | 4/1999 |
| WO | WO 99/31062 | * | 6/1999 |
| WO | 99-32100 | A2 | 7/1999 |
| WO | 0224636 | A2 | 3/2002 |
| WO | 02053560 | A1 | 7/2002 |
| WO | 02/074758 | A2 | 9/2002 |
| WO | 02/074770 | A1 | 9/2002 |
| WO | 02/079186 | A2 | 10/2002 |
| WO | 02/083628 | A1 | 10/2002 |
| WO | 02/098869 | A2 | 12/2002 |
| WO | 03/020703 | A1 | 3/2003 |
| WO | 03037271 | A2 | 5/2003 |
| WO | 03/066592 | A1 | 8/2003 |
| WO | 03/104230 | A1 | 12/2003 |
| WO | WO 2004/026873 | A1 | 4/2004 |
| WO | WO 2004/043925 | * | 5/2004 |
| WO | 2004/046110 | A1 | 6/2004 |
| WO | 2004/080966 | A1 | 9/2004 |
| WO | 2004-096131 | A2 | 11/2004 |
| WO | 2006/030925 | A1 | 3/2006 |
| WO | 2007/022371 | A2 | 2/2007 |
| WO | 2007/105637 | A1 | 9/2007 |

OTHER PUBLICATIONS

Office Action, App. No. 2004800130029, Chinese Patent Office, May 11, 2007.
Subhash P. Khanapure et al., "Synthesis and Structure-Activity Relationship of Novel, Highly Potent Metharyl and Methcycloalkyl Cyclooxgenase-2 (COX-2) Selective Inhibitors", Journal of Medicinal Chemistry, 2003, pp. 5484-5504, vol. 46, No. 25, American Chemical Society.
Daniel Ledniger et al., "Mammalian Antifertility Agents. IV. Basic 3,4-Dihydronaphthalenes and 1,2,3,4-Tetrahydro-1-Naphthols",1967, pp. 79-84, vol. 10, Journal Medicinal Chemistry.
European Patent Office Communication re: Observations by a Third Party for EP057858086 dated May 13, 2008.
Millet et al.,"Potent and Selective Farnesy/Transferase Inhibitors", J.Med. Chem., 2004, vol. 47, pp. 6812-6820.
International Search Report dated Jun. 1, 2004.
Mashkovskiy, M.D., "Medicinal Drugs", 2001, p. 11, vol. 1, 14th Ed., S.B. Divov, Moscow.
Russian Office Action dated Jul. 9, 2009 in Russian Application No. 2007113814.
Office Action issued in counterpart European Patent Application No. 04720257.7 dated Dec. 15, 2009.
Singaporean Office Action dated Jan. 19, 2010 in Singapore Application No. 200806533-6.
Extended European Search Report dated Feb. 18, 2010 in European Application No. 05785808.6-1521.
Chinese Office Action dated Mar. 10, 2010 in Chinese application No. 200810133648.0.
Japanese Office Action issued May 18, 2010 in corresponding Japanese Application No. 2005-503613.
New Zealand Office Action dated Apr. 8, 2010 in New Zealand application No. 571019.
McClellan William, et al., "Preparation of N-arylcarbonyl- and heteroarylcarbonyl benzenesulfonamide inhibitors of Bcl-XI and Bcl-2 as promoters of apoptosis" XP002503148, Database (Online) Chemical Abstract Service, pp. 1-3, 2002.
Supplementary European Search Report dated Nov. 26, 2008.
Office Action issued on Apr. 14, 2010 in counterpart Russian Application No. 2007113814.
Vietnamese Office Action issued Jun. 10, 2010 in Vietnamese application No. 1-2005-01233.
Office Action issued May 11, 2010 in counterpart Chinese Application No. 200810133649.5.
European Search Report issued on Oct. 19, 2010 in counterpart European application No. 07 738 169.7 of the co-pending U.S. Appl. No. 12/282,464.
Office Action issued on Sep. 10, 2010 in counterpart European application No. 04 720 257.7.
Office Action issued on Sep. 23, 2010 in counterpart Norwegian application No. 2005 4244.
Office Action issued on Sep. 28, 2010 in counterpart European application No. 05 785 808.6 of co-pending U.S. Appl. No. 11/662,639.
Shomir Ghosh et. al.: "Design, Synthesis, and Progress toward Optimization of Potent Small Molecule Antagonists of CC Chemokine Receptor 8 (CCR8)", Journal of Medicinal Chemistry, vol. 49. No. 9, May 4, 2006; pp. 2669-2672.
The Second Office Action dated Oct. 12, 2010 from The Patent Office of the People's Republic of China issued in co-pending U.S. Appl. No. 11/662,639 of counterpart Chinese application No. 200580038925.4.
Office Action dated Oct. 19, 2010 from the Canadian Intellectual Property Office issued in counterpart Canadian application No. 2,517,888.
Australian Office Action issued in Application No. 2005-283326; dated Nov. 9, 2010.

* cited by examiner

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Forward primer hCCR5XbaI

<400> SEQUENCE: 1
agctagtcta gatccgttcc cctacaagaa actctcc                            37

<210> SEQ ID NO 2
<211> LENGTH: 37
<212> TYPE: DNA
<213> ORGANISM: Artificial Sequence
<220> FEATURE:
<223> OTHER INFORMATION: Revese primer hCCR5XbaI

<400> SEQUENCE: 2
agctagtcta gagtgcacaa ctctgactgg gtcacca                            37
```

NITROGEN-CONTAINING HETEROCYCLIC DERIVATIVES AND DRUGS CONTAINING THE SAME AS THE ACTIVE INGREDIENT

TECHNICAL FIELD

The present invention relates to (1) compounds represented by formula (I)

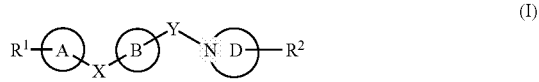

(wherein all symbols have the same meanings as described hereinafter), salts thereof or solvates thereof, or prodrugs thereof, and (2) treatment and/or prevention for diseases through the intervention of CCR5 comprising compounds represented by formula (I), salts thereof or solvates thereof, or prodrugs thereof, as an active ingredient.

BACKGROUND ART

Chemokine is known as a basic protein having endogeneous leukocyte chemotactic and activating abilities and strong heparin-binding abilities. At present, it is considered that chemokine is related to not only the control of infiltration of specific leukocyte at the time of inflammations and immune responses but also the development and homing of lymphocyte under physiological conditions and migration of hemocyte precursor cells and somatic cells.

Differentiation, proliferation and cell death of hemocytes are controlled by various types of cytokine. In the living body, inflammations are found topically and differentiation, maturation and the like of lymphocytes are carried out at certain specified sites. That is, various necessary cells migrate into certain specified sites and accumulate therein to cause a series of inflammations and immune responses. Accordingly, migration of cells is also an indispensable phenomenon in addition to differentiation, proliferation and death of cells.

Migration of hemocytes in the living body starts firstly in the development stage by the shift of hematopoiesis started in the AGM region into permanent hematopoiesis in bone marrow via fetal liver. Furthermore, precursor cells of T cells and thymus dendritic cells migrate from the fetal liver into the bone marrow and then into the thymus gland and cytodifferentiate under thymus environment. The T cell which received clone selection migrates into secondary lymphoid tissues and takes part in an immune response in the periphery. The Langerhans' cell of the skin activated and differentiated by capturing an antigen migrates into the T cell region of a topical lymph node and activates naive T cell therein as a dendritic cell. The memory T cell performs its homing again into the lymph node via lymphatic and blood vessels. Also, B cell, T cell in the intestinal epithelium, γδ T cell, NKT cell and dendritic cell migrate from bone marrow without passing through the thymus gland and differentiate to take part in an immune response.

Chemokine deeply takes part in the migration of such various cells. Chemokine receptors are greatly related to the control of inflammation and immune responses through a mechanism in which they are expressed at certain specified periods in variously specific cells and the effector cells are accumulated in a region where chemokine is produced.

Acquired immunodeficiency syndrome (called AIDS) which is induced by human immunodeficiency virus (hereinafter referred to as "HIV") is one of the diseases of which their therapeutic methods are most earnestly desired in recent years. Once infection with HIV is completed in a CD4-positive cell which is a principal target cell, HIV repeats its proliferation in the body of the patient and, sooner or later, completely destroys T cell which takes charge of the immunological function. During this process, the immunological function is gradually reduced to cause fever, diarrhea, lymph node enlargement and the like various immunodeficiency conditions which are apt to cause complications with *pneumocystis carinii* pneumonia and the like various opportunistic infections. Such conditions are the onset of AIDS, and it is well known that they induce and worsen Kaposi sarcoma and the like malignant tumors.

As the recent preventive and therapeutic methods for AIDS, attempts have been made to, e.g., (1) inhibit growth of HIV by the administration of a reverse transcriptase inhibitor or a protease inhibitor and (2) prevent or alleviate opportunistic infections by the administration of a drug having immunopotentiation activity.

Helper T cells which take charge of the central of immune system are mainly infected with HIV. It is known since 1985 that HIV uses the membrane protein CD4 expressing on the membrane of T cells in the infection (*Cell*, 52, 631 (1985)). The CD4 molecule is composed of 433 amino acid residues, and its expression can be found in macrophages, some B cells, vascular endothelial cells, Langerhans' cells in skin tissues, dendritic cells in lymphoid tissues, glia cells of the central nervous system and the like, in addition to the mature helper T cells. However, since it has been revealed that the infection with HIV is not completed by the CD4 molecule alone, a possibility has been suggested on the presence of factors other than the CD4 molecule, which are related to the infection of cells with HIV.

CCR5, which is a receptor of RANTES, MIP-1α and MIP-1β, is also used at the time of the infection with a macrophage tropic (R5) HIV (*Science*, 272, 1955 (1996)).

Accordingly, substances which can compete with CCR5 for HIV, or which can bind to HIV virus thus causing the virus unable to bind to CCR5, could become HIV infection inhibitors.

Based on the above, it is considered that CCR5 receptors are deeply related to the inflammation, immune disease or HIV infection. For example, it is considered that they are related to various inflammatory diseases (asthma, nephritis, nephropathy, hepatitis, arthritis, rheumatoid arthritis, rhinitis, conjunctivitis, ulcerative colitis and the like), immunologic diseases (autoimmune diseases, rejection in organ transplantation, immunosuppression, psoriasis, multiple sclerosis and the like), infection with human immunodeficiency virus (acquired immunodeficiency syndrome and the like), allergic diseases (atopic dermatitis, urticaria, allergic bronchopulmonary aspergillosis, allergic eosinophilic gastroenteritis and the like), ischemic reperfusion injury, acute respiratory distress syndrome, shock accompanying bacterial infection, diabetes mellitus, or cancer metastasis and the like.

It is reported that the aminopiperidine derivatives represented by formula (a)

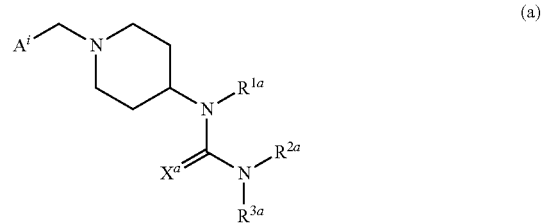

(wherein $R^{1a}$ is hydrogen atom or C1-12 alkyl, $R^{2a}$ and $R^{1a}$ are each independently hydrogen atom or C1-12 alkyl, $X^a$ is nitrogen atom or oxygen atom, $A^a$ is

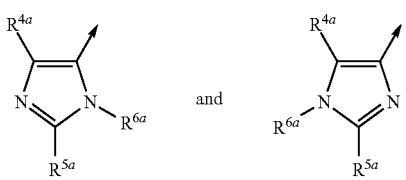

(wherein $R^{4a}$ is hydrogen atom, C1-12 alkyl, C3-8 cycloalkyl, aryl, substituted aryl, aryl-C(=O)— or aryl-CH(OH)—, $R^{5a}$ is hydrogen, C1-12 alkyl, C1-4 alkoxy, halogen or COR, $R^{6a}$ is hydrogen, C1-12 alkyl or substituted C1-4 alkyl. With the proviso that the definition of each symbol is a excerpt partially.) are useful as inhibitors of the chemokine receptors (ref. specification of WO02/79186).

It is described that the sulfonic acid derivatives represented by formula (b)

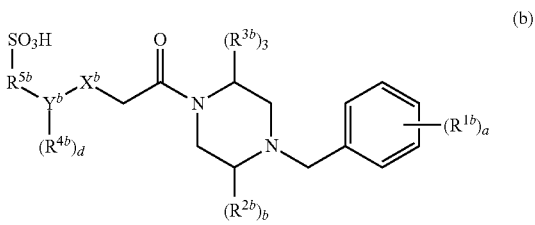

are selective antagonists of CCR1 receptors (ref specification of WO02/102787).

Moreover, 1-(4-pyridyl)-piperazine derivatives are described as CCR5 antagonists (ref. specification of U.S. Pat. No. 6,391,865).

On the other hand, it is reported that triazaspiro[5.5]undecane derivatives, quaternary ammonium salts thereof or N-oxides thereof, or pharmacologically acceptable salts thereof regulate the effect of chemokine/chemokine receptor, so they are used for prevention and/or treatment of various inflammatory diseases, asthma, atopic dermatitis, urticaria, allergic diseases (allergic bronchopulmonary aspergillosis or allergic eosinophilic gastroenteritis etc.), nephritis, nephropathy, hepatitis, arthritis, rheumatoid arthritis, psoriasis, rhinitis, conjunctivitis, ischemic reperfusion disorder, multiple sclerosis, ulcerative colitis, acute respiratory distress syndrome, cytotoxic shock, diabetes, autoimmune disease, in transplanted organ rejection reactions, immunosuppression, cancer metastasis and acquired immune deficiency syndrome (ref specification of WO01/40227).

It is described that the compounds represented by formula (c)

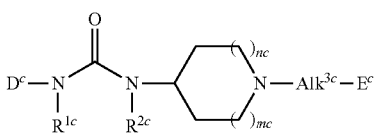

(wherein mc and nc, which are the same or different, is each zero or the integer 1 or 2, $Alk^{3c}$ is a covalent bond or a straight or branched C1-6 alkylene chain, $R^{1c}$ and $R^{2c}$, which are the same or different, is each a hydrogen atom or a straight or branched C1-6 alkyl group, $D^c$ is an optionally substituted aromatic or heteroaromatic group, $E^c$ is an optionally substituted C7-10 cycloalkyl, C7-10 cycloalkenyl or C7-10 polycycloaliphatic group.) are modulators of CXCR3 (ref. specification of WO03/070242).

DISCLOSURE OF THE INVENTION

The compound which regulates CCR5 receptor is used as prevention and treatment for diseases through the intervention of CCR5 receptor. Therefore it is desired that safety CCR5 regulators, especially CCR5 antagonists, are developed.

In order to find a compound binding and regulating CCR5 receptor specifically, the present inventors have conducted intensive studies and found, as a result, that the objects can be accomplished by the compound represented by formula (I), and thus the present invention has been accomplished.

The present invention relates to 1. a compound represented by formula (I):

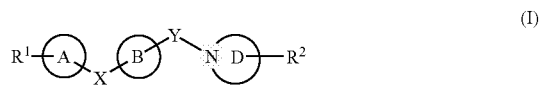

wherein $R^1$ represents a hydrogen atom or an acidic group which may be protected;

X and Y each independently represents a bond or a spacer containing 1 to 3 atoms as a main chain;

ring A and ring B, which are the same or different, each represents a 3- to 15-membered homocyclic group or heterocyclic group which may have a substituent(s);

ring D represents a 3- to 15-membered nitrogen-containing heterocyclic group which may have a substituent(s);

$R^2$ represents (1) a hydrogen atom, (2) a hydrocarbon group which may have a substituent(s), (3) a cyano group, (4) a hydroxy group which may be protected, (5) an amino group which may have a substituent(s), (6) an oxo group, (7) a 3- to 15-membered heterocyclic group which may have a substituent(s) or (8) =N—OR$^6$, wherein R$^6$ represents a hydrogen atom or C1-4 alkyl, a salt thereof or a solvate thereof, or a prodrug thereof, 2. the compound according to the above-described 1, wherein $R^1$ is an acidic group which may be protected, 3. the compound according to the above-described 2, wherein the acidic group is carboxy or sulfonamide, 4. the compound according to the above-described 1, wherein X and Y are each independently a bond or a divalent group selected from (1) —CR$^7$R$^8$—, (2) —NR$^9$—, (3) —CO—, (4) —O—, (5) —S—, (6) —SO—, (7) —SO$_2$— and (8) —C(=N—OR$^{16}$)—, wherein R$^7$ and R$^8$ each independently represents a hydrogen atom, C1-4 alkyl, —OR$^{11}$ or phenyl; R$^9$ represents a hydrogen atom C1-4 alkyl, or phenyl; R$^{10}$ and R$^{11}$ each independently represents a hydrogen atom or C1-4 alkyl, 5. the compound according to the above-described 4, wherein X is a bond, —O— or —CH$_2$—, 6. the compound according to the above-described 1, wherein Y is C1-3 alkylene, 7. the compound according to the above-described 1, wherein ring D is a 5- to 10-membered nitrogen-containing heterocyclic group which may have a substituent(s), 8. the compound according to the above-described 1, wherein ring A and ring B, which are the same or different, are each a 5- to 10-membered homocyclic group or heterocyclic group which may have a substituent(s), 9. the compound according to the above-described 1, wherein ring A and ring B, which are the same or different, are each a 5- or 6-membered aromatic ring which may have a substituent (s), 10. the compound according to the above-described 1, wherein $R^2$ is

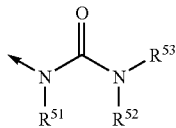

wherein the arrow represents a binding position to ring D; $R^{51}$, $R^{52}$ and $R^{53}$ each independently represents (1) a hydrogen atom, (2) a hydrocarbon group which may have a substituent(s), (3) a 3- to 15-membered heterocyclic group which may have a substituent(s), (4) a C1-4 alkoxy group which may have a substituent(s), (5) a phenoxy group which may have a substituent(s) or (6) a benzyloxy group which may have a substituent(s), 11. the compound according to the above-described 1, which is represented by formula (Ia):

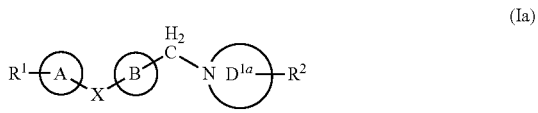

wherein ring $D^{1a}$ is piperidine or piperazine which may have a substituent(s) and other symbols have the same meanings as those described in the above-described 1, 12. the compound according to the above-described 1, which is selected from the group consisting of
(1) N-[4-(4-{[4-(butyl{[(2,4-difluorophenyl)amino]carbonyl}amino)-1-piperidinyl]methyl}phenoxy)phenyl]methanesulfonamide,
(2) N-[4-(4-{[4-(butyl{[(6-methyl-3-pyridinyl)amino]carbonyl}amino)-1-piperidinyl]methyl}phenoxy)phenyl]methanesulfonamide,
(3) N-[4-(4-{[4-(butyl{[(2,4-difluorophenyl)amino]carbonyl}amino)piperidin-1-yl]methyl}-3,5-dimethyl-1H-pyrazol-1-yl)phenyl]methanesulfonamide,
(4) N-[4-(4-{[4-(butyl{[(1-methyl-1H-pyrazol-4-yl)amino]carbonyl}amino)piperidin-1-yl]methyl}phenoxy)phenyl]methanesulfonamide,
(5) 3-[({butyl[1-(4-{4-[(methylsulfonyl)amino]phenoxy}benzyl)piperidin-4-yl]amino}carbonyl)amino]benzamide,
(6) N-{4-[4-({4-[{[(4-fluorophenyl)amino]carbonyl}(phenyl)amino]piperidin-1-yl}methyl)phenoxy]phenyl}methanesulfonamide,
(7) 5-[({butyl[1-(4-{4-[(methylsulfonyl)amino]phenoxy}benzyl)piperidin-4-yl]amino}carbonyl)amino]-2-fluorobenzamide,
(8) 5-[({butyl[1-(4-{4-[(methylsulfonyl)amino]phenoxy}benzyl)piperidin-4-yl]amino}carbonyl)amino]-2,4-difluorobenzamide,
(9) N-[4-(4-{[4-(butyl{[(3-cyano-4-fluorophenyl)amino]carbonyl}amino)piperidin-1-yl]methyl}phenoxy)phenyl]methanesulfonamide, and
(10) N-[4-(4-{[4-(butyl{[(3-hydroxycyclohexyl)amino]carbonyl}amino)piperidin-1-yl]methyl}phenoxy)phenyl]methanesulfonamide, and N-{4-[4-({4-[{[(4-fluorophenyl)amino]carbonyl}(1,3-thiazol-4-ylmethyl)amino]piperidin-1-yl}methyl)phenoxy]phenyl}methanesulfonamide, 13. a CCR5 regulator comprising the compound according to the above-described 1, a salt thereof or a solvate thereof, or a prodrug thereof, 14. the CCR5 regulator according to the above-described 13, which is a CCR5 antagonist, 15. the CCR5 regulator according to the above-described 13, which is an agent for treatment and/or prevention for a disease through the intervention of CCR5, 16. the CCR5 regulator according to the above-described 15, wherein the disease through the intervention of CCR5 is infection with human immunodeficiency virus, 17. the CCR5 regulator according to the above-described 16, wherein the infection with human immunodeficiency virus is acquired immune deficiency syndrome, 18. the CCR5 regulator according to the above-described 15, wherein the disease through the intervention of CCR5 is immunological diseases, 19. the CCR5 regulator according to the above-described 18, wherein the immunological disease is rejection in organ transplantation, 20. the CCR5 regulator according to the above-described 15, wherein the disease through the intervention of CCR5 is inflammatory diseases, 21. the CCR5 regulator according to the above-described 20, wherein the inflammatory disease is asthma, 22. an agent for prevention and/or treatment for infection with human immunodeficiency virus, immunological diseases or inflammatory diseases, which comprises the compound represented by formula (I) according to the above-described 1, a salt thereof or a solvate thereof, or a prodrug thereof, 23. a pharmaceutical composition, which comprises the compound represented by formula (I) according to the above-described 1, a salt thereof or a solvate thereof, or a prodrug thereof, 24. a medicament which comprises the compound represented by formula (I) according to the above-described 1, a salt thereof or a solvate thereof, or a prodrug thereof, in combination with one or at least two of a reverse transferase inhibitor, a protease inhibitor, a CCR2 antagonist, a CCR3 antagonist, a CCR4 antagonist, a CCR5 antagonist, a CXCR4 antagonist, a fusion inhibitor, an antibody against a surface antigen of HIV-1, and a vaccine of HIV-1, 25. a method for treating or preventing a disease through the intervention of CCR5 in a mammal, which comprises administering to a mammal an effective amount of a compound represented by formula (I):

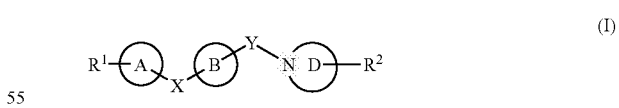

wherein $R^1$ represents a hydrogen atom or an acidic group which may be protected;
X and Y each independently represents a bond or a spacer containing 1 to 3 atoms as a main chain;
ring A and ring B, which are the same or different, each represents a 3- to 15-membered homocyclic group or heterocyclic group which may have a substituent(s);
ring D represents a 3- to 15-membered nitrogen-containing heterocyclic group which may have a substituent(s);
$R^2$ represents (1) a hydrogen atom, (2) a hydrocarbon group which may have a substituent(s), (3) a cyano group, (4)

a hydroxy group which may be protected, (5) an amino group which may have a substituent(s), (6) an oxo group, (7) a 3- to 15-membered heterocyclic group which may have a substituent(s) or (8) =N—OR$^6$, wherein R$^6$ represents a hydrogen atom or C1-4 alkyl, a salt thereof or a solvate thereof, or a prodrug thereof, 26. use of a compound represented by formula (I):

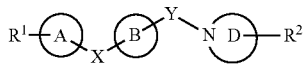

wherein R$^1$ represents a hydrogen atom or an acidic group which may be protected;

X and Y each independently represents a bond or a spacer containing 1 to 3 atoms as a main chain;

ring A and ring B, which are the same or different, each independently represents a 3- to 15-membered homocyclic group or heterocyclic group which may have a substituent(s);

ring D represents a 3- to 15-membered nitrogen-containing heterocyclic group which may have a substituent(s);

R$^2$ represents (1) a hydrogen atom, (2) a hydrocarbon group which may have a substituent(s), (3) a cyano group, (4) a hydroxy group which may be protected, (5) an amino group which may have a substituent(s), (6) an oxo group, (7) a 3- to 15-membered heterocyclic group which may have a substituent(s) or (8) =N—OR$^6$, wherein R$^6$ represents a hydrogen atom or C1-4 alkyl, a salt thereof or a solvate thereof, or a prodrug thereof for the manufacture of an agent for prevention and/or treatment for a disease through the intervention of CCR5.

The "acidic group which may be protected" represented by R$^1$ represents the "acidic group" which may be protected by a "protecting group". Examples of the "acidic group" include hydroxy, alkoxy, carboxy (—COOH), sulfo (—SO$_3$H), sulfino (—SO$_2$H), sulfonamide (—SO$_2$NH$_2$ or —NR$^{101}$SO$_3$H (R$^{101}$ is hydrogen atom or hydrocarbon group which may have a substituent(s).)), phosphono (—PO(OH)$_2$), phenol (—C$_6$H$_4$OH) or various types of Brønsted acid such as a nitrogen-containing ring residue having hydrogen from which can be removed as proton. The "Brønsted acid" means a substance which gives hydrogen ion to other substance. Examples of the "nitrogen-containing ring residue having hydrogen from which can be removed as proton" include:

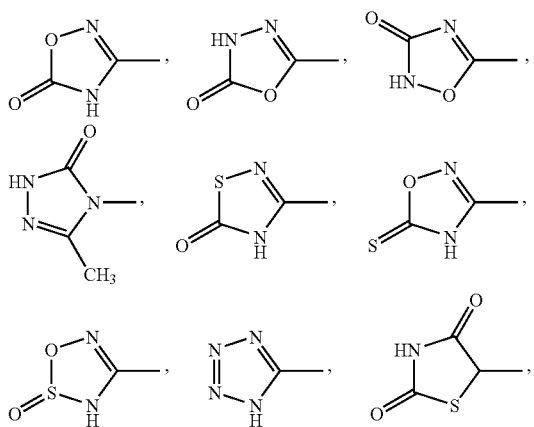

Preferred as "acidic group" is carboxy or sulfonamide. More preferred is sulfonamide.

Examples of the "protecting group" include hydrocarbon group which may have a substituent(s), C1-6 alkoxy, amino group which may have a substituent(s),

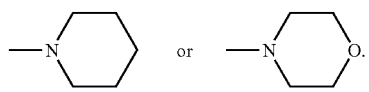

The "hydrocarbon group" in the "hydrocarbon group which may have a substituent(s)" includes, for example, C1-15 alkyl such as methyl, ethyl, propyl, isopropyl, butyl, isobutyl, s-butyl, t-butyl, pentyl, hexyl, heptyl, octyl, nonyl, decyl, undecyl, dodecyl, tridecyl, tetradecyl, pentadecyl etc.; C3-8 cycloalkyl such as cyclopropyl, cyclobutyl, cyclopentyl, cyclohexyl etc.; C2-10 alkenyl such as vinyl, allyl, 2-methylallyl, 2-butenyl, 3-butenyl, 3-octenyl etc.; C2-10 alkynyl such as ethynyl, 2-propynyl, 3-hexynyl etc.; C3-10 cycloalkenyl such as cyclopropenyl, cyclopentenyl, cyclohexenyl etc.; C6-14 aryl such as phenyl, naphthyl etc., C7-16 aralkyl such as benzyl, phenylethyl etc.; (C3-8 cycloalkyl)-(C1-4 alkyl) such as cyclohexylmethyl, cyclohexylethyl, cyclohexylpropyl, 1-methyl-1-cyclohexylmethyl, cyclopropylethyl etc.

The "substituents" in the "hydrocarbon group which may have a substituent(s)" include, for example, (1) nitro, (2) hydroxy group, (3) oxo, (4) thioxo, (5) cyano, (6) carbamoyl, (7) aminocarbonyl substituted by C1-8 hydrocarbon etc. (e.g., N-butylaminocarbonyl, N-cyclohexylmethylaminocarbonyl, N-butyl-N-cyclohexylmethylaminocarbonyl, N-cyclohexylaminocarbonyl, phenylaminocarbonyl etc.), (8) carboxy, (9) C1-4 alkoxy-carbonyl such as methoxycarbonyl, ethoxycarbonyl etc., (10) sulfo, (11) halogen such as fluorine, chlorine, bromine or iodine, (12) C1-4 lower alkoxy which may be substituted by halogen (e.g., methoxy, ethoxy, propoxy, isopropoxy, butoxy, isobutoxy, s-butoxy, t-butoxy, difluoromethoxy or trifluoro, ethoxy), (13) phenoxy, (14) halogenophenoxy such as o-, m- or p-chlorophenoxy, or o-, m- or p-bromophenoxy etc., (15) C1-4 lower alkylthio such as methylthio, ethylthio, n-propylthio, isopropylthio, n-butylthio, t-butylthio etc., (16) phenylthio, (17) C1-4 lower alkylsulfinyl such as methylsulfinyl or ethylsulfinyl etc., (18) C1-4 lower alkylsulfonyl such as methylsulfonyl or ethylsulfonyl etc., (19) amino, (20) C1-6 lower acylamino such as acetylamino or propionylamino etc., (21) primary or secondary amino substituted by hydrocarbon group (e.g., methylamino, ethylamino, n-propylamino, isopropylamino, n-butylamino, dimethylamino, diethylamino, cyclohexylamino, 1-carbamoyl-2-cyclohexylethylamino, N-butyl-N-cyclohexylmethylamino or phenylamino etc.), (the "hydrocarbon group" has the same meanings as above "hydrocarbon group" and may be substituted by oxo, amino which may be substituted by optional substituents (e.g., hydrocarbon), carbamoyl, halogen or hydroxy group etc.), (22) C1-4 lower acyl such as formyl or acetyl etc., (23) benzoyl, (24) 5 or 6 membered heterocyclic group such as 2- or 3-thienyl, 2- or 3-furyl, 3-, 4- or 5-pyrazolyl, 4-tetrahydropyranyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyromidinyl, 3- or 4-pyridazinyl, quinolyl, isoquinolyl or indolyl etc. which includes 1 to 4 hetero atoms selected from oxygen, sulfur and nitrogen besides carbon atom, and optionally has 1 to 4 substituents selected from (a) halogen such as bromine, chlorine, or fluorine, (b) hydrocarbon such as methyl, ethyl, propyl, isopropyl, benzyl, cyclohexyl, cyclohexylmethyl or cyclohexylethyl etc. optionally substituted by oxo or hydroxy group etc., (the "hydrocarbon group" has the same meanings as above "hydrocarbon group"), (c) halogenophenoxy such as o-, m- or p-chlorophenoxy, or o-, m- or p-bromophenoxy etc., and (d) oxo etc., (25) C1-10 haloalkyl such as difluoromethyl, trifluoromethyl, trifluoroethyl or trichloroethyl etc., (26) hydroxyimino, (27) alkyloxyimino such as methyloxyimino or ethyloxyimino etc., (28) alkylsulfonylamino such as methylsulfonylamino, ethylsulfonylamino or benzylsulfonylamino etc., or (29) arylsulfonylamino such as phenylsulfonylamino or p-toluenesulfonylamino etc. The "hydrocarbon group which may have a substituent(s)" can have 1 to 10 of substituents selected from above (1) to (29). If the "hydrocarbon group" is cycloalkyl, cycloalkenyl, aryl or aralkyl, it may have 1 to 4 of C1-4 lower alkyl such as methyl, ethyl, propyl, isopropyl or butyl etc. as substituent. When the number of substituents is two or more, each substituent may be same or different.

The substituents of amino group in the "amino group which may have a substituent(s)" in the "protecting group" includes the above-described "hydrocarbon group".

The "C1-6 alkoxy" in the "protecting group" includes, for example, methoxy, ethoxy, propoxy, butoxy, pentyloxy or hexyloxy etc.

Preferred as the "protecting group" in $R^1$ is hydrocarbon group which may have a substituent(s), and more preferred is C1-4 alkyl etc.

The "acidic group which may be protected" represented by $R^1$ includes, for example, ester such as methoxycarbonyl or ethoxycarbonyl or amide such as carbamoyl.

Preferred as $R^1$ is $—SO_2NR^{102}R^{103}$ or $—NR^{101}SO_2R^{104}$, $—COOR^{105}$, $—CONR^{106}R^{107}$ (wherein $R^{102}$-$R^{107}$ is hydrogen atom or the above described protecting group and other symbols have the same meanings as described above.) and more preferred is $—SO_2NR^{102}R^{103}$ or $—NR^{101}SO_2R^{104}$.

The "spacer containing 1 to 3 atoms as a main chain" represented by X and Y means a space formed by 1 to 3 continued atoms of a main chain. In this case, the "number of atoms as a main chain" should be counted such that atoms as a main chain become minimum. The "spacer having from 1 to 3 atoms as a main chain" include, for example, a bivalent group comprising 1 to 3 selected from $—CR^7R^8—$, $—NR^9—$, $—CO—$, $—O—$, $—S—$, $—SO—$, $—SO_2—$ and $—C(=N—OR^{10})—$ (wherein $R^7$ and $R^8$ are each independently hydrogen atom, C1-4 alkyl, $—OR^{11}$ or phenyl, $R^9$ is hydrogen atom, C1-4 alkyl or phenyl, $R^{10}$ and $R^{11}$ are each independently hydrogen atom or C1-4 alkyl.). In the case, the "C1-4 alkyl" includes methyl, ethyl, propyl or butyl etc. Concretely, the "spacer having from 1 to 3 atoms as a main chain" include, for example, $—CR^7R^8—$, $—NR^9—$, $—CO—$, $—O—$, $—S—$, $—C(=N—OR^{10})—$, $—NR^9CO—$, $—CONR^9—$, $—NR^9COCR^7R^8—$ or $—CONR^9CR^7R^8—$ (wherein $R^7$-$R^{10}$ have the same meanings as described above.). Preferably spacer in "spacer having from 1 to 3 atoms as a main chain" represented by X is $—CR^7R^8—$, $—NR^9—$, $—CO—$, $—O—$, $—S—$, $—SO—$, $—SO_2—$ or $—C(=N—OR^{10})—$ (wherein $R^7$ and $R^8$ are each independently hydrogen atom, C1-4 alkyl, $—OR^{11}$ or phenyl, $R^9$ is hydrogen atom, C1-4 alkyl or phenyl, $R^{10}$ and $R^{11}$ are each independently hydrogen atom or C1-4 alkyl.) etc.

Preferred as X is a bond, $—O—$ or $—CH_2—$ etc.

Preferred as the "spacer having from 1 to 3 atoms as a main chain" represented by Y is "C1-3 alkylene". "C1-3 alkylene" includes methylene, ethylene or propylene etc. More preferably, Y is methylene.

The "3- to 15-membered homocycle" in the "3- to 15-membered homocyclic group or heterocyclic group which may have a substituent(s)" represented by ring A and ring B includes, for example, a "cyclic hydrocarbon" etc. The "cyclic hydrocarbon" includes, for example, a "unsaturated cyclic hydrocarbon" or a "saturated cyclic hydrocarbon". The "saturated cyclic hydrocarbon" includes, for example, cycloalkane such as cyclopropane, cyclobutane, cyclopentane, cyclohexane, cycloheptane, cyclooctane, cyclononane, cyclodecane, cycloundecane, cyclododecane, cyclotridecane, cyclotetradecane or cyclopentadecane etc; perhydropentalene; perhydroazulene; perhydroindene; perhydronaphthalene; perhydroheptalene; spiro[4.4]nonane; spiro[4.5]decane; spiro[5.5]undecane; bicyclo[2.2.1]heptane; bicyclo[3.1.1]heptane; bicyclo[2.2.2]octane; adamantane; noradamantane etc. The "unsaturated cyclic hydrocarbon" includes, for example, cycloalkene such as cyclopentene, cyclohexene, cycloheptene, cyclooctene, cyclopentadiene, cyclohexadiene, cycloheptadiene or cyclooctadiene etc; benzene; pentalene; azulene; indene; indan; naphthalene; dihydronaphthalene; tetrahydronaphthalene; heptalene; biphenylene; as-indacene; s-indacene; acenaphthene; acenaphthylene; fluorene; phenalene; phenanthrene; anthracene; bicyclo[2.2.1]hept-2-ene; bicyclo[3.1.1]hept-2-ene; bicyclo[2.2.2]oct-2-ene etc.

The "3- to 15-membered heterocycle" in the "3- to 15-membered homocyclic group or heterocyclic group which may have a substituent(s)" represented by ring A and ring B includes a "3- to 15-membered unsaturated heterocycle" or a "3- to 15-membered saturated heterocycle".

The "3- to 15-membered unsaturated heterocycle" includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, beta-carboline, acridine, phenazine, dibenzofuran, xanthene, dibenzothiophene, phenothiazine, phenoxazine, phenoxathiin, thianthrene, phenanthridine, phenanthroline, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, dihydroacridine, tetrahydroacridine, dihydrodibenzofuran, dihydrodibenzothiophene, tetrahydrodibenzofuran, tetrahydrodibenzothiophene, dioxaindan, benzodioxane, chroman, benzodithiolane, benzodithiane etc. The "3- to 15-membered saturated heterocycle" includes, for example, aziridine, azetidine, azocane, pyrrolidine, imidazolidine, triazolidine, tetrazolidine, pyrazolidine, piperidine, piperazine, perhydropyrimidine, perhydropyridazine, perhydroazepine, perhydrodiazepine, oxirane, oxetane, tetrahydrofuran, tetrahydropyran, perhydrooxepine, thiirane, thietane, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine, perhydrodibenzofuran, perhydrodibenzothiophene, dioxolane, dioxane, dithiolane, dithiane

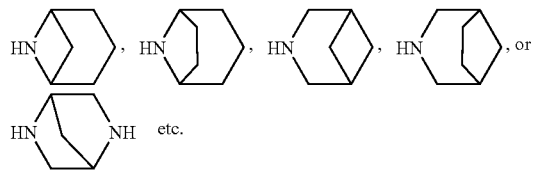

etc.

Preferred as the "3- to 15-membered homocyclic group or heterocyclic group" represented by ring A and ring B is a "5- to 10-membered homocyclic group or heterocyclic group". Concretely, the "5- to 10-membered homocyclic group" includes, for example, C5-10 saturated cyclic hydrocarbon such as C5-10 cycloalkane (e.g., cyclopentane, cyclohexane or cycloheptane) or C5-10 unsaturated cyclic hydrocarbon such as C5-10 cycloalkene (e.g., cyclopentene, cyclohexene, cycloheptene, cyclooctene, cyclopentadiene, cyclohexadiene, cycloheptadiene or cyclooctadiene); benzene; naphthalene; indene etc. The "5- to 10-membered heterocyclic group" includes 5- to 10-membered unsaturated heterocyclic group such as pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrofuran, dihydropyran, dihydrooxepine, tetrahydrooxepine, dihydrothiophene, dihydrothiopyran, dihydrothiepine, tetrahydrothiepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydrobenzofuran, dihydroisobenzofuran, dihydrobenzothiophene, dihydroisobenzothiophene, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, benzoxathiane, dihydrobenzoxazine, dihydrobenzothiazine, pyrazinomorpholine, dihydrobenzoxazole, dihydrobenzothiazole, dihydrobenzimidazole, dioxaindan, benzodioxane, chroman, benzodithiolane or benzodithiane; or 5- to 10-membered saturated heterocyclic group such as pyrrolidine, imidazolidine, triazolidine, tetrazolidine, pyrazolidine, piperidine, piperazine, perhydropyrimidine, perhydropyridazine, perhydroazepine, perhydrodiazepine, tetrahydrofuran, tetrahydropyran, perhydrooxepine, tetrahydrothiophene, tetrahydrothiopyran, perhydrothiepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, oxathiane, perhydrobenzofuran, perhydroisobenzofuran, perhydrobenzothiophene, perhydroisobenzothiophene, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, dioxolane, dioxane, dithiolane, dithiane etc.

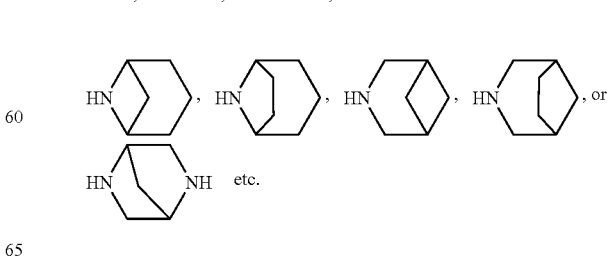

etc.

More preferably, ring A or ring B is a "5- to 10-membered unsaturated homocyclic group or heterocyclic group". The "5- to 10-membered unsaturated homocyclic group or heterocyclic group" is a "5- to 10-membered unsaturated cyclic hydrocarbon" or "5- to 10-membered unsaturated heterocyclic group". More preferred is 5- or 6-aromatic ring such as benzene, pyrrole, imidazole, triazole, tetrazole, pyrazole, pyridine, pyrazine, pyrimidine, pyridazine, triazine, furan, thiophene, oxazole, isoxazole, thiazole, isothiazole, furazan, oxadiazole or thiadiazole etc.

The "substituents" in the "3- to 15-membered homocyclic group or heterocyclic group which may have a substituent(s)" represented by ring A or ring B includes, for example, (1) hydrocarbon group which may have a substituent(s) (the "hydrocarbon group which may have a substituent(s)" has the same meanings as the above-described "hydrocarbon group which may have a substituent(s)".), (2) C1-6 alkoxy group which may be substituted by halogen atom (e.g., methoxy, ethoxy, propoxy, isopropoxy, n-butoxy, isobutoxy, sec-butoxy, tert-butoxy or trifluoromethoxy), (3) (C1-4 alkoxy)-(C1-4 alkyl) group such as methoxyethyl etc., (4) phenoxy group, (5) C1-8 alkanoyl group such as formyl, acetyl, propynoyl, n-butyryl, iso-butyryl or cyclohexyl carbonyl etc., (6) benzoyl group, (7) C1-8 alkanoyloxy group such as formyloxy, acetyloxy, propynyloxy, n-butyryloxy, iso-butyryloxy or cyclohexyl carbonyloxy etc., or benzoyloxy group, (8) carboxy group, (9) C2-7 alkoxycarbonyl group such as methoxycarbonyl, ethoxycarbonyl, n-propoxycarbonyl, iso-propoxycarbonyl, n-butoxycarbonyl, isobutoxycarbonyl, tert-butoxycarbonyl group etc.) (10) carbamoyl group, (11) N-mono-C1-4 alkylcarbamoyl group such as N-methylcarbamoyl, N-ethylcarbamyl, N-propylcarbamoyl, N-isopropylcarbamoyl or N-butylcarbamoyl etc., (12) N,N-di-C1-4 alkylcarbamoyl group such as N,N-dimethylcarbamoyl, N,N-diethylcarbamoyl, N,N-dipropylcarbamoyl or N,N-dibutylcarbamoyl etc. (13) cyclic aminocarbonyl such as 1-aziridinylcarbonyl, 1-azetidinylcarbonyl, 1-pyrrolidinylcarbonyl, 1-piperidinylcarbonyl, N-methylpiperazinylcarbonyl, morpholinocarbonyl etc., (14) halogen atom such as fluorine, chlorine, bromine or iodine, (15) mono-, di- or tri-halogeno-C1-4alkyl group such as chloromethyl, dichloromethyl, trifluoromethyl or trifluoroethyl etc. (16) oxo group, (17) amidino group, (18) imino group, (19) amino group, (20) mono-C1-4alkylamino group such as methylamino, ethylamino, propylamino, isopropylamino or butylamino etc., (21) di-C1-4alkylamino group such as dimethylamino, diethylamino, dipropylamino, diisopropylamino or dibutylamino etc., (22) 3- to 6-membered cyclic amino group which includes carbon atom and 1 to 3 hetero atoms selected from oxygen, sulfur and nitrogen besides one nitrogen atom (e.g., aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl or N-ethylpiperadinyl etc), (23) C1-8 alkanoylamide group such as formamide, acetamide, trifluoroacetamide, propionylamide, butyrylamide, isobutyrylamide, cyclohexylcarbonylamino etc., (24) benzamide group, (25) carbamoylamino group, (26) N—C1-4 alkylcarbamoylamino group such as N-methylcarbamoylamino, N-ethylcarbamoylamino, N-propylcarbamoylamino, N-isopropylcarbamoylamino, N-butylcarbamoylamino etc., (27) N,N-di-C1-4 alkylcarbamoylamino group such as N,N-dimethylcarbamoylamino, N,N-diethylcarbamoylamino, N,N-dipropylcarbamoylamino, N,N-dibutylcarbamoylamino etc. (28) C1-3 alkylenedioxy group such as methylenedioxy or ethylenedioxy etc. (29) —B(OH)$_2$, (30) hydroxy group, (31) epoxy group, (32) nitro group, (33) cyano group, (34) mercapto group, (35) sulfo group, (36) sulfino group, (37) phosphono group, (38) sulfamoyl group, (39) C1-6 monoalkylsulfamoyl such as N-methylsulfamoyl, N-ethylsulfamoyl, N-propylsulfamoyl, N-isopropylsulfamoyl or N-butylsulfamoyl etc., (40) di-C1-4 alkylsulfamoyl group such as N,N-dimethylsulfamoyl, N,N-diethylsulfamoyl, N,N-dipropylsulfamoyl or N,N-dibutylsulfamoyl etc., (41) C1-6 alkylthio group such as methylthio, ethylthio, propylthio, isopropylthio, n-butylthio, sec-butylthio or tert-butylthio etc., (42) phenylthio group, (43) C1-6 alkylsulfinyl group such as methylsulfinyl, ethylsulfinyl, propylsulfinyl or butylsulfinyl etc., (44) phenylsulfinyl, (45) C1-6 alkylsulfonyl such as methylsulfonyl, ethylsulfonyl, propylsulfonyl or butylsulfonyl etc., (46) phenylsulfonyl group, or (47) azide group etc. 1 to 10 of the above-described substituents may be substituted at replaceable positions in ring A and ring B. When the number of substituents is two or more, each substituent are the same or different. Preferred as substituents in ring A and ring B is hydrocarbon group which may have a substituent(s), alkoxy group, carboxy group or alkanoylamide group etc., and more preferred is hydrocarbon group or alkoxy group.

The "nitrogen-containing heterocycle" in the "3- to 15-membered nitrogen-containing heterocyclic group which may have a substituent(s)" represented by ring D refers to a heterocycle which may contain, in addition to at least one nitrogen atom besides carbon atom, 1 to 3 hetero atoms selected from nitrogen, oxygen and sulfur atoms. The "3- to 15-membered nitrogen-containing heterocycle" includes a "3- to 15-membered nitrogen-containing unsaturated heterocycle" and "3- to 15-membered nitrogen-containing saturated heterocycle".

The "3- to 15-membered nitrogen-containing unsaturated heterocycle" includes, for example, pyrrole, imidazole, triazole, tetrazole, pyrazole, indole, isoindole, indazole, purine, benzimidazole, benzazepine, benzodiazepine, benzotriazole, carbazole, beta-carboline, phenothiazine, phenoxazine, perimidine, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, dihydroacridine, tetrahydroacridine etc. The "3- to 15-membered nitrogen-containing saturated heterocycle" includes, for example, aziridine, azetidine, azocane, pyrrolidine, imidazolidine, triazolidine, tetrazolidine, pyrazolidine, piperidine, piperazine, perhydropyrimidine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, tetrahydrothiazepine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole, perhydrocarbazole, perhydroacridine,

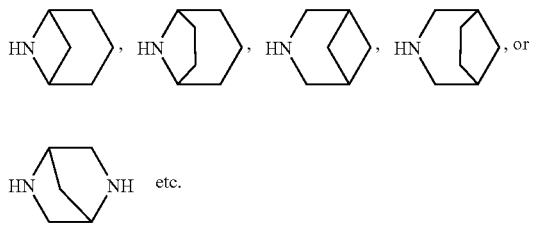

Preferred as the "3- to 15-membered nitrogen-containing heterocycle" is a "5- to 10-membered nitrogen-containing heterocycle". A "5- to 10-membered nitrogen-containing unsaturated heterocycle" includes, for example, pyrrole, imidazole, triazole, tetrazole, pyrazole, indole, isoindole, indazole, purine, benzimidazole, benzotriazole, pyrroline, imidazoline, triazoline, tetrazoline, pyrazoline, dihydropyridine, tetrahydropyridine, dihydropyrazine, tetrahydropyrazine, dihydropyrimidine, tetrahydropyrimidine, dihydropyridazine, tetrahydropyridazine, dihydroazepine, tetrahydroazepine, dihydrodiazepine, tetrahydrodiazepine, dihydrooxazole, dihydroisoxazole, dihydrothiazole, dihydroisothiazole, dihydrofurazan, dihydrooxadiazole, dihydrooxazine, dihydrooxadiazine, dihydrooxazepine, tetrahydrooxazepine, dihydrooxadiazepine, tetrahydrooxadiazepine, dihydrothiadiazole, dihydrothiazine, dihydrothiadiazine, dihydrothiazepine, tetrahydrothiazepine, dihydrothiadiazepine, tetrahydrothiadiazepine, indoline, isoindoline, dihydroindazole, dihydroquinoline, tetrahydroquinoline, dihydroisoquinoline, tetrahydroisoquinoline, dihydrophthalazine, tetrahydrophthalazine, dihydronaphthyridine, tetrahydronaphthyridine, dihydroquinoxaline, tetrahydroquinoxaline, dihydroquinazoline, tetrahydroquinazoline, dihydrocinnoline, tetrahydrocinnoline, dihydrobenzoxazine, dihydrobenzothiazine, pyrazinomorpholine, dihydrobenzoxazole, dihydrobenzothiazole, dihydrobenzimidazole etc. A "5- to 10-membered nitrogen-containing saturated heterocycle" includes, for example, azocane, pyrrolidine, imidazolidine, triazolidine, tetrazolidine, pyrazolidine, piperidine, piperazine, perhydropyrimidine, perhydropyridazine, perhydroazepine, perhydrodiazepine, tetrahydrooxazole (oxazolidine), tetrahydroisoxazole (isoxazolidine), tetrahydrothiazole (thiazolidine), tetrahydroisothiazole (isothiazolidine), tetrahydrofurazan, tetrahydrooxadiazole (oxadiazolidine), tetrahydrooxazine, tetrahydrooxadiazine, perhydrooxazepine, perhydrooxadiazepine, tetrahydrothiadiazole (thiadiazolidine), tetrahydrothiazine, tetrahydrothiadiazine, perhydrothiazepine, perhydrothiadiazepine, morpholine, thiomorpholine, perhydroindazole, perhydroquinoline, perhydroisoquinoline, perhydrophthalazine, perhydronaphthyridine, perhydroquinoxaline, perhydroquinazoline, perhydrocinnoline, perhydrobenzoxazole, perhydrobenzothiazole, perhydrobenzimidazole,

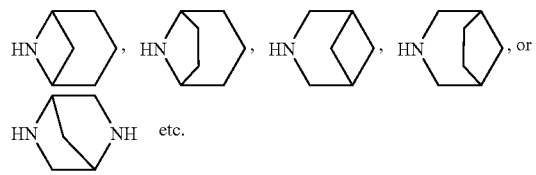

Moreover, preferred as "nitrogen-containing heterocycle" is piperidine or piperazine. More preferred is piperidine.

The "substituents" in "3- to 15-membered nitrogen-containing heterocyclic group which may have a substituent(s)" represented by ring D have the same meanings as the above-described "substituents" in "3- to 15-membered homocyclic group or heterocyclic group which may have "substituents" represented by ring A and ring B.

Preferably, ring D has no substituent or is substituted by hydrocarbon group have a substituent(s), mono-C1-4 alkylamino group or di-C1-4 alkylamino group etc. More preferably, ring D has no substituent.

The "hydrocarbon group" in the "hydrocarbon group which may have a substituent(s)" represented by $R^2$ has the same meaning as the "hydrocarbon group which may have a substituent(s)" defined in the "protecting group" of the "acidic group which may be protected" represented by $R^1$. Preferred as the "hydrocarbon group which may have a substituent(s)" represented by $R^2$ is alkyl group substituted by oxo group or (C3-8 cycloalkyl)-(C1-4 alkyl) group substituted by oxo group.

Among $R^2$, the "hydroxy group which may be protected" is the "hydroxy group" which may be protected by a "protecting group". The "protecting group" of hydroxy group includes, for example, (1) C1-6 alkyl group (e.g., methyl, ethyl or n-propyl etc.) which may have 1 to 4 of substituents selected from halogen atom such as chlorine, bromine or fluorine etc.; C6-10 aryl such as phenyl or naphthyl etc.; C7-12 aralkyl group such as benzyl or phenylethyl etc.; and nitro group etc., (2) C6-10 aryl (e.g., phenyl or naphthyl etc.) which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., (3) C7-12 aralkyl group (e.g., benzyl, phenylethyl or naphthylmethyl etc.) which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., (4) formyl, (5) C1-6 alkylcarbonyl group (e.g., acetyl or propionyl etc.) which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., (6) C6-10 aryl-oxycarbonyl group (e.g., phenyloxycarbonyl or naphthyloxycarbonyl etc.) which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., (7) C6-10 arylcarbonyl group (e.g., benzoyl or naphthylcarbonyl etc.) which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., (8) C7-12 aralkylcarbonyl group (e.g., benzylcarbonyl or phenethylcarbonyl etc.) which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., (9) pyranyl or furanyl which may have 1 to 4 of substituents selected from halogen atom such as chlorine, bromine or fluorine etc.; C1-6 alkyl group such as methyl, ethyl or n-propyl etc.; C6-10 aryl such as phenyl or naphthyl etc.; C7-12 aralkyl group such as benzyl or phenylethyl etc.; and nitro group etc., or (10) tri-C1-4 alkylsilyl such as trimethylsilyl or triethylsilyl etc.

The "substituents" in the "amino group which may have a substituent(s)" represented by $R^2$ includes hydrocarbon group which may have a substituent(s), $-SO_2R^{201}$, $=NR^{202}$, $-OR^{203}$ (wherein $R^{201}$-$R^{203}$ is hydrocarbon group which may have a substituent(s)) etc. The "hydrocarbon group which may have a substituent(s)" has the same meaning as the "hydrocarbon group which may have a substituent(s)" defined in the "protecting group" of the "acidic group which may be protected" represented by $R^1$. Preferred as the "substituents" in the "amino group which may have a substituent(s)" represented by $R^2$ is the "hydrocarbon group which may have a substituent(s)".

The "3- to 15-membered heterocyclic group which may have a substituent(s)" represented by $R^2$ has the same meanings as the "3- to 15-membered heterocyclic group which may have a substituent(s)" represented by ring A or ring B. Preferred as the "3- to 15-membered heterocyclic group which may have a substituent(s)" represented by $R^2$ is piperidine or piperazine which may have a substituent(s) and more preferred is

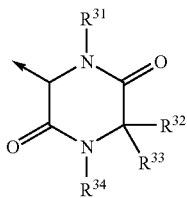

(wherein the arrow represents a binding position to ring D, and $R^{31}$, $R^{32}$, $R^{33}$ and $R^{34}$ each independently have the same meanings as the "substituents" of the "3- to 15-membered heterocyclic group which may have a substituent(s)" represented by ring A or ring B.) etc.

Preferred as $R^2$ is, for example, hydrocarbon group which may have a substituent(s) or amino group which may have a substituent(s) etc., and more preferred is

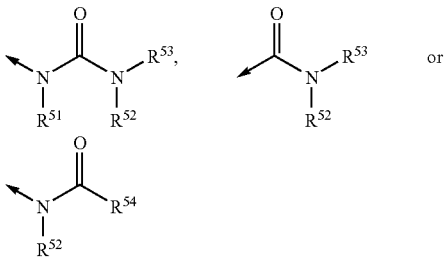

(wherein the arrow represents a binding position to ring D, and $R^{51}$, $R^{52}$, $R^{53}$ and $R^{54}$ are each independently hydrogen atom, hydrocarbon group which may have a substituent(s), 3- to 15-membered heterocyclic group which may have a substituent(s), C1-4 alkoxy group which may have a substituent(s), phenoxy which may have a substituent(s) or benzyloxy which may have a substituent(s).) etc. The "hydrocarbon group which may have a substituent(s)" and "3- to 15-membered heterocyclic group which may have a substituent(s)" have the same meanings as described above respectively. C1-4 alkoxy group includes, for example, methoxy, ethoxy, propoxy, isopropoxy, butoxy, isobutoxy, s-butoxy or t-butoxy etc. C1-4 alkoxy group, phenoxy group or benzyloxy group may have optional substituents. The substituents of C1-4 alkoxy group, phenoxy group or benzyloxy group include, for example, the above-described "substituents" of the "hydrocarbon group which may have a substituent(s)".

Preferably, $R^{51}$, $R^{52}$, $R^{53}$ or $R^{54}$ is hydrogen atom, hydrocarbon group which may have a substituent(s) or 3- to 15-membered heterocyclic group which may have a substituent(s) etc. Moreover, the compound wherein either among $R^{52}$ and $R^{53}$ is hydrogen atom is preferred.

In the present invention, the compound represented by formula (I) including the combination of the above-described preferable group and ring is preferred. For example, a compound wherein ring D is piperidine or piperazine and Y is methylene group, i.e., a compound represented by formula (Ia)

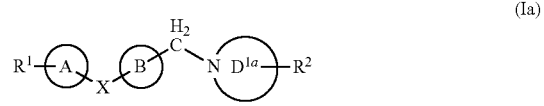

(wherein ring $D^{1a}$ is piperidine or piperazine which may have a substituent(s) and other symbols have the same meanings as described above.); a compound wherein ring D is piperidine or piperazine, $R^2$ is

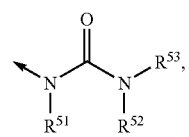

i.e., a compound represented by formula (Ib)

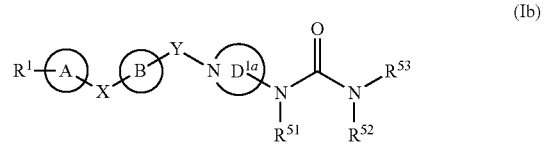

(wherein all symbols have the same meanings as described above.); a compound wherein $R^1$ is $-SO_2NR^{102}R^{103}$ or $-NR^{101}SO_2R^{104}$, X is a bond, $-CR^7R^8-$, $-NR^9-$, $-CO-$, $-O-$, $-S-$, $-SO-$, $-SO_2-$, $-C(=N-OR^{10})-$ (wherein $R^7$ and $R^8$ are each independently hydrogen atom, C1-4 alkyl, $-OR^{11}$ or phenyl, $R^9$ is hydrogen atom, C1-4 alkyl or phenyl, $R^{10}$ and $R^{11}$ are each independently hydrogen atom or C1-4 alkyl.), Y is methylene, ring A and ring B are each independently benzene which may have a substituent(s), ring D is piperidine and $R^2$ is

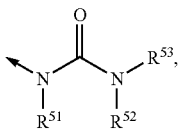

i.e., a compound represented by formula (Ic)

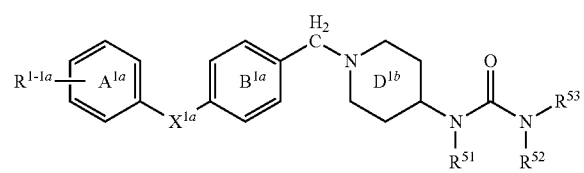

(wherein $R^{1-1a}$ is $—SO_2NR^{102}R^{103}$ or $—NR^{101}SO_2R^{104}$, $X^{1a}$ is a bond, $—CR^7R^8—$, $—NR^9—$, $—CO—$, $—O—$, $—S—$, $—SO—$, $—SO_2—$, $—C(=N—OR^{10})—$ (wherein $R^7$ and $R^8$ are each independently hydrogen atom, C1-4 alkyl, $—OR^{11}$ or phenyl, $R^9$ is hydrogen atom, C1-4 alkyl or phenyl, $R^{10}$ and $R^{11}$ are each independently hydrogen atom or C1-4 alkyl.), ring $A^{1a}$ and ring $B^{1a}$ are each independently benzene which may have a substituent(s), ring $D^{1b}$ is piperidine which may have a substituent(s) and other symbols have the same meanings as described above.); or a compound wherein $R^1$ is $—SO_2NR^{102}R^{103}$ or $—NR^{101}SO_2R^{104}$, X is a bond, $—CR^7R^8—$, $—NR^9—$, $—CO—$, $—O—$, $—S—$, $—SO—$, $—SO_2—$, $—C(=N—OR^{10})—$ (wherein $R^7$ and $R^8$ are each independently hydrogen atom, C1-4 alkyl, $—OR^{11}$ or phenyl, $R^9$ is hydrogen atom, C1-4 alkyl or phenyl, $R^{10}$ and $R^{11}$ are each independently hydrogen atom or C1-4 alkyl.), Y is methylene, ring A and ring B are each independently benzene or unsaturated mono-heterocyclic group which may have a substituent(s), ring D is piperidine or piperazine, $R^2$ is

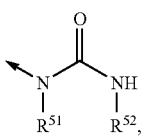

i.e., a compound represented by formula (Id)

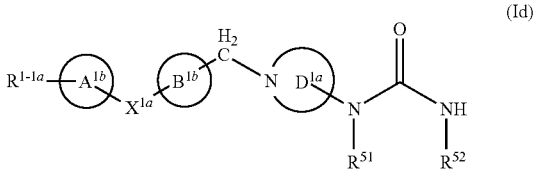

(wherein ring $A^{1b}$ and ring $B^{1b}$ are each independently benzene or 5- or 6-membered aromatic ring which may have a substituent(s) and other symbols have the same meanings as described above.) etc. is preferred.

Concretely, the compound of the present invention includes the compound described in Example, or 2-[3-methyl-4-(4-{4-[(methylsulfonyl)amino] phenoxy}benzyl)piperazin-1-yl]-N-phenylhexanamide, N-{4-[4-({4-[(anilinocarbonyl)(butyl)amino]-4'-methyl-1, 4'-bipiperidin-1'-yl}methyl)phenoxy] phenyl}methanesulfonamide, N-[4-(4-{[3-[(anilinocarbonyl)(butyl)amino]-4-(3-fluorophenyl)pyrrolidin-1-yl]methyl}phenoxy)phenyl]methanesulfonamide, N-[4-(4-{[3-(butylamino)-4-(3-fluorophenyl)pyrrolidin-1-yl]methyl}phenoxy)phenyl]methanesulfonamide, N-butyl-N-(1-{3-ethyl-1-[4-(methylsulfonyl)benzyl]-1H-pyrazol-4-yl}piperidin-4-yl)-N'-phenylurea, N-butyl-N-[1-({4-methyl-2-[4-(trifluoromethyl)phenyl]-1H-imidazol-5-yl}methyl)piperidin-4-yl]-N'-phenylurea, N-{4-[4-({3-[(anilinocarbonyl)(butyl)amino]-8-azabicyclo [3.2.1]oct-8-yl}methyl)phenoxy] phenyl}methanesulfonamide, N-[4-(4-{[4-(3-isopropyl-5-methyl-4H-1,2,4-triazol-4-yl) piperidin-1-yl]methyl}phenoxy)phenyl]methanesulfonamide, N-[4-(4-{[4-(2-methyl-1H-benzimidazol1-yl)piperidin-1-yl]methyl}phenoxy)phenyl]methanesulfonamide, N-[4-(4-{[4-[(anilinocarbonyl)(butyl)amino]-3,4-dihydroquinolin-1(2H)-yl]methyl}phenoxy)phenyl]methanesulfonamide, N-[4-(4-{[4-(2-oxo-3-phenyl-6-propyltetrahydropyrimidin-1(2H)-yl)piperidin-1-yl]methyl}phenoxy)phenyl]methanesulfonamide, N-(4-{4-[(3-butyl-2-oxo-1,2,3,3a,4,5-hexahydro-6H-pyrido [4,3,2-de]quinazolin-6-yl)methyl]phenoxy}phenyl)methanesulfonamide, N-(4-{4-[(1-butyl-2-oxo-4-phenyloctahydropyrido[4,3-d] pyrimidin-6(2H)-yl)methyl]phenoxy}phenyl)methanesulfonamide, N-{4-[4-({8-[(anilinocarbonyl)(butyl)amino]-3-azabicyclo [3.2.1]oct-3-yl}methyl)phenoxy] phenyl}methanesulfonamide, N-[4-(4-{[(2Z)-1-butyl-2-(phenylimino)hexahydro-2H-pyrido[4,3-d][1,3]oxazin-6(4H)-yl]methyl}phenoxy)phenyl]methanesulfonamide or N-[7-({4-[(anilinocarbonyl)(butyl)amino]piperidin-1-yl}methyl)-9H-xanthen-2-yl]methanesulfonamide etc.

Particularly preferred are compounds described in Example, salts thereof and solvates thereof, and prodrugs thereof.

More preferred are

N-[4-(4-{[4-(butyl{[(2,4-difluorophenyl)amino] carbonyl}amino)-1-piperidinyl]methyl}phenoxy)phenyl] methanesulfonamide, N-[4-(4-{[4-(butyl{[(6-methyl-3-pyridinyl)amino] carbonyl}amino)-1-piperidinyl]methyl}phenoxy)phenyl] methanesulfonamide, N-[4-(4-{[4-(butyl{[(2,4-difluorophenyl)amino] carbonyl}amino)piperidin-1-yl]methyl}-3,5-dimethyl-1H-pyrazol-1-yl)phenyl]methanesulfonamide, N-[4-(4-{[4-(butyl{[(1-methyl-1H-pyrazol-4-yl)amino] carbonyl}amino)piperidin-1-yl]methyl}phenoxy)phenyl] methanesulfonamide, 3-[({butyl[1-(4-{4-[(methylsulfonyl)amino] phenoxy}benzyl)piperidin-4-yl]amino}carbonyl)amino] benzamide, N-{4-[4-({4-[{[(4-fluorophenyl)amino]carbonyl}(phenyl) amino]piperidin-1-yl}methyl)phenoxy] phenyl}methanesulfonamide, 5-[({butyl[1-(4-{4-[(methylsulfonyl)amino] phenoxy}benzyl)piperidin-4-yl]amino}carbonyl)amino]-2-fluorobenzamide, 5-[({butyl[1-(4-{4-[(methylsulfonyl)amino]
phenoxy}benzyl)piperidin-4-yl]amino}carbonyl)amino]-
2,4-difluorobenzamide, N-[4-(4-{[4-(butyl{[(3-cyano-4-fluorophenyl)amino]
carbonyl}amino)piperidin-1-yl]methyl}phenoxy)phenyl]
methanesulfonamide, N-[4-(4-{[4-(butyl{[(3-hydroxycyclohexyl)amino]
carbonyl}amino)piperidin-1-yl]methyl}phenoxy)phenyl]
methanesulfonamide or N-{4-[4-({4-[{[(4-fluorophenyl)amino]carbonyl}(1,3-thia-
zol-4-ylmethyl)amino]piperidin-1-yl}methyl)phenoxy]
phenyl}methanesulfonamide, salts thereof and solvates thereof, and prodrugs thereof.

Unless otherwise specifically mentioned, all isomers are included in the present invention. For example, alkyl, alkenyl, alkynyl, alkoxy, alkylthio, alkylene, alkenylene and alkynylene include straight chain and branched ones. Moreover, all of isomers due to double bond, ring and fused ring (E-, Z-, cis- and trans-forms), isomers due to presence of asymmetric carbon(s) etc. (R-, S-, α- and β-configuration, enantiomer and diastereomer), optically active substances having optical rotation (D-, L-, d- and l-forms), polar compound by chromatographic separation (more polar compound and less polar compound), equilibrium compounds, rotational isomers, a mixture thereof in any proportion and a racemic mixture are included in the present invention.

According to the present invention, unless otherwise indicated and as is apparent for those skilled in the art, symbol  indicates that it is bound to the opposite side of the sheet (namely α-configuration), symbol  indicates that it is bound to the front side of the sheet (namely β-configuration), and symbol  indicates that it is a mixture of α-configuration and β-configuration.

The compound of the present invention can be converted into a salt by known methods. The salt is preferably a pharmacological acceptable salt.

The salt includes salt with alkaline metal, salt with alkaline earth metal, ammonium salt, amine salt or acid addition salt etc.

The salt is preferably water-soluble. The suitable salt is, for example, salt with alkaline metal (such as potassium and sodium), salt with alkaline earth metal (such as calcium and magnesium), ammonium salt and salt with pharmacological acceptable organic amine (such as tetramethylammonium, triethylamine, methylamine, dimethylamine, cyclopentylamine, benzylamine, phenethyl amine, piperidine, monoethanolamine, diethanolamine, tris(hydroxymethyl)methylaminomethane, lysine, arginine and N-methyl-D-glucamine).

The acid addition salt is preferably water-soluble. The suitable acid addition salt is, for example, inorganic acid salt such as hydrochloride, hydrobromide, hydroiodide, sulfate, phosphate and nitrate; or organic acid salt such as acetate, lactate, tartrate, benzoate, citrate, methanesulfonate, ethanesulfonate, benzenesulfonate, toluenesulfonate, isothionate, glucuronate and gluconate; etc.

The compound represented by formula (I) and the salt thereof can be converted into the solvates.

The solvate is preferably non toxic and water-soluble. The suitable solvate is, for example, solvate of water or alcohol (e.g., ethanol).

All of the compound represented by formula (I) or the pharmacological acceptable salt thereof are preferred; concretely, compounds described in Example or pharmacological acceptable salts thereof are preferred.

Moreover, the salt includes a quaternary ammonium salt. The quaternary ammonium salt of the compound represented by formula (I) is the compound where nitrogen of the compounds represented by formula (I) is quarternalized by $R^0$.

The $R^0$ is C1-8 alkyl or C1-8 alkyl substituted by phenyl.

The compound of the present invention can be converted into an N-oxide by known methods. The N-oxide is the compound where nitrogen of the compound represented by formula (I) is oxidized.

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and that the carboxyl group of the compound of formula (I) is, for example, esterified or amidated (e.g., compounds in which the carboxyl group of the compound of formula (I) is made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiologic condition as described in "*Iyakuhin no kaihatsu*, Vol. 7 (Bunshi-sekkei), pp. 163-198 (Hirokawa-Shoten), 1990". And the compound of formula (I) may also be labeled by a radio isotope (such as $^3H$, $^{14}C$, $^{35}S$, $^{125}I$ etc,).

Processes for the Preparation of the Compound of the Present Invention:

The compound of the present invention represented by formula (I) can be prepared by methods which properly improved and combined known methods, such as methods described below, methods described in Examples or methods described in *Comprehensive Organic Transformations: A Guide to Functional Group Preparations,* 2nd Edition (Richard C. Larock, John Wiley & Sons Inc, 1999). In each method described below, a starting material can be used as a salt thereof. An example of the salt includes a salt of compound of formula (I) described above.

Among the compounds represented by formula (I), a compound wherein a spacer which is adjacent with ring D is —$CH_2$—, —CO— or —$SO_2$— can be prepared by alkylation, amidation or sulfonamidation by a compound represented by formula (II)

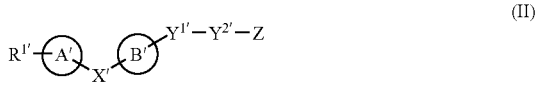 (II)

(wherein Z is hydroxy group or a leaving group (e.g., halogen atom, p-toluenesulfonyloxy group, methanesulfonyloxy group, trifluoro methanesulfonyloxy group etc.), $Y^{1'}$ is a bond or a spacer containing 1 or 2 atoms as a main chain, $Y^{2'}$ is —$CH_2$—, —CO— or —$SO_2$—, and $R^{1'}$, X', ring A' and ring B' have the same meanings as $R^1$, X, ring A and ring B respectively. With proviso that, carboxy group, hydroxy group, amino group or thiol group in $R^{1'}$, X', ring A' or ring B' may be protected, if necessary. Other symbols have the same meaning as described above.) and a compound represented by formula (III)

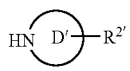 (III)

(wherein $R^{2'}$ and ring D' have the same meanings as $R^2$ and D respectively. With proviso that, carboxy group, hydroxy group, amino group or thiol group in $R^{2'}$ or ring D' may be protected, if necessary.), if necessary, followed by removal of the protecting group.

The alkylation is well known. For example, it may be carried out in an organic solvent (e.g., dimethylsulfoxide), in the presence of alkaline (e.g., potassium carbonate or sodium carbonate), and sodium iodide or potassium iodide at 0 to 150° C.

The amidation is known. For example, it includes the method
(1) via an acyl halide,
(2) via a mixed acid anhydride,
(3) using a condensing agent.

These methods are explained as follows.

(1) The method via an acyl halide may be carried out, for example, by reacting carboxylic acid with an acyl halide (e.g., oxalyl chloride or thionyl chloride) in an organic solvent (e.g., chloroform, dichloromethane, diethyl ether or tetrahydrofuran) or without a solvent at −20° C. to reflux temperature. And then the obtained acyl halide derivative may be reacted with amine in an organic solvent (e.g., chloroform, dichloromethane, diethyl ether or tetrahydrofuran) in the presence of a base (e.g., pyridine, triethylamine, dimethylaniline, dimethylaminopyridine or diisopropylethylamine etc.) at 0 to 40° C. As an alternative, the obtained acyl halide derivative may be reacted with amine in an organic solvent (e.g., dioxane, tetrahydrofuran) using an alkaline aqueous solution (e.g., sodium bicarbonate, sodium hydroxide) at 0 to 40° C.

(2) The method via a mixed acid anhydride may be carried out, for example, by reacting carboxylic acid with an acyl halide (e.g., pivaloyl chloride, tosyl chloride or mesyl chloride) or an acid derivative (e.g., ethyl chloroformate or isobutyl chloroformate) in an organic solvent (e.g., chloroform, dichloromethane, diethyl ether, tetrahydrofuran) or without a solvent, in the presence of a base (e.g., pyridine, triethylamine, dimethylaniline, dimethylaminopyridine or diisopropylethylamine) at 0 to 40° C. And then the obtained mixed acid anhydride derivative may be reacted with amine in an organic solvent (e.g., chloroform, methylene chloride, diethyl ether or tetrahydrofuran), at 0 to 40° C.

(3) The method using a condensing agent may be carried out, for example, by reacting carboxylic acid with amine in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzothiazole (HOBt), at 0 to 40° C.

The reaction described in (1), (2) and (3) may be carried out under an inert gas (e.g., argon, nitrogen) to avoid water in order to obtain a preferable result.

The sulfoneamidation is well known. For example, it may be carried out by reacting sulfonic acid with acyl halide (e.g., oxalyl chloride or thionyl chloride, phosphorus pentachloride or phosphorus trichloride) in an organic solvent (e.g., chloroform, dichloromethane, dichloroethane, diethyl ether, tetrahydrofuran or methyl t-butyl ether) or without a solvent at −20° C. to reflux temperature. And then the obtained sulfonyl halide derivative may be reacted with amine in an organic solvent (e.g., chloroform, dichloromethane, diethyl ether or tetrahydrofuran) in the presence of a base (e.g., diisopropylethylamine, pyridine, triethylamine, dimethylaniline or dimethylaminopyridine etc.) at 0 to 40° C.

The removal of the protecting group is known and may be carried out by following method.

The carboxyl-protective group includes, for example, methyl, ethyl, allyl, t-butyl, trichloroethyl, benzyl (Bn) or phenacyl etc.

The protecting group of hydroxy includes, for example, methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc), and 2,2,2-trichloroethoxycarbonyl (Troc) etc.

The protecting group of amino includes such as benzyloxycarbonyl, t-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) or 2-(trimethylsilyl)ethoxymethyl (SEM) etc.

The protective group of thiol includes, for example, benzyl, methoxybenzyl, methoxymethyl (MOM), 2-tetrahydropyranyl (THP), diphenylmethyl and acetyl (Ac) etc.

With regard to the protective group for carboxyl, hydroxyl, amino and thiol, there is no particular limitation to the above ones so far as it is a group which is able to be easily and selectively detached. For example, a deprotection reaction may be carried out by a method mentioned in "T. W. Greene, *Protective Groups in Organic Synthesis*, John Wiley & Sons Inc, 1999".

The reaction for removing the protective group for carboxyl, hydroxyl, amino or thiol is known and its examples are as follows.

(1) a hydrolyzing reaction with an alkali;
(2) a deprotection reaction under an acidic condition;
(3) a deprotection reaction by hydrogenolysis;
(4) a deprotection reaction of silyl;
(5) a deprotection reaction using a metal; and
(6) a deprotection reaction using metal complex.

Those methods will be specifically illustrated as follows.

(1) A deprotection reaction using an alkali is carried out, for example, at 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and dioxane etc.).

(2) A deprotection reaction under an acidic condition is carried out, for example, at 0 to 100° C. in an organic acid (e.g., acetic acid, trifluoroacetic acid, methanesulfonic acid or p-tosylate), an inorganic acid (e.g., hydrochloric acid and sulfuric acid) or a mixture thereof (such as hydrogen bromide/acetic acid) in an organic solvent (such as dichloromethane, chloroform, dioxane, ethyl acetate and anisole etc.).

(3) A deprotection reaction by hydrogenolysis is carried out, for example, at 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as dimethylformamide), water, ethyl acetate, acetic acid or a mixed solvent comprising two or more thereof].

(4) A deprotection reaction of silyl is carried out, for example, at 0 to 40° C. using tetrabutylammonium fluoride in an organic solvent miscible with water (such as tetrahydrofuran and acetonitrile etc.).

(5) A deprotection reaction using metal is carried out, for example, at 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction using a metal complex is carried out, for example, at 0 to 40° C. using a metal complex [such as tetrakistriphenylphosphine palladium (0), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, dimethylformamide, tetrahydrofuran, ethyl acetate, acetonitrile, dioxane and ethanol), water or a mixed solvent thereof.

Apart from the above, the deprotection may also be effected, for example, according to the methods described in T. W. Greene, *Protective Groups in Organic Synthesis*, Wiley, New York, 1999.

As persons skilled in the art can easily understand that the aimed compound of the present invention is able to be easily produced by using appropriate ones among those deprotection reactions.

Among the compounds represented by formula (I), a compound wherein $R^2$ is amino group which may have a substituent(s), i.e., a compound represented by formula (I-a)

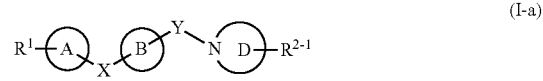

(wherein $R^{2-1}$ is amino group which may have a substituent(s) and other symbols have the same meanings as described above.) can be prepared by reductive amination of a compound represented by formula (IV)

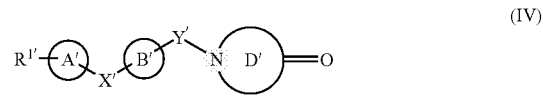

(wherein all symbols have the same meanings as described above.) and a compound represented by formula (V)

(wherein $R^{301}$ and $R^{302}$, which are the same or different, are hydrogen atom or have the same meanings as the "substituents" of the above-described "amino group which may have a substituent(s)", and other symbols have the same meanings as described above. With proviso that, carboxy group, hydroxy group, amino group or thiol group in $R^{301}$ or $R^{302}$ may be protected, if necessary.), if necessary, followed by removal of the protecting group. The reductive amination is well known. For example, it may be carried out in an organic solvent (e.g., dichloroethane, dichloromethane or dimethylformamide) in the presence of tertiary amine (e.g., triethylamine or diisopropylethylamine) and reducing agent (e.g., sodium triacetoxyborohydride or sodium cyanoborohydride) at 0 to 40° C.

The removal of the protecting group may be carried out by the above described method.

Among the compounds represented by formula (I), a compound wherein $R^2$ is

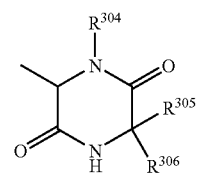

(wherein $R^{304}$, $R^{305}$ and $R^{306}$, which are the same or different, have the same meanings as the "substituents" of the above-described "3- to 15-membered homocyclic group or heterocyclic group which may have a substituent(s)" represented by ring A and ring B, and other symbols have the same meanings as described above.), i.e., a compound represented by formula (I-b)

(I-b)

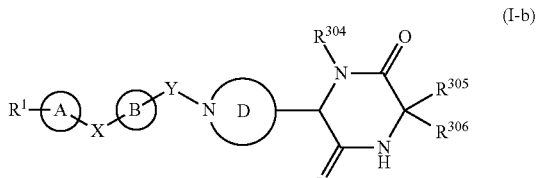

(wherein all symbols have the same meanings as described above) can be prepared by cyclization of a compound represented by formula (VI)

(VI)

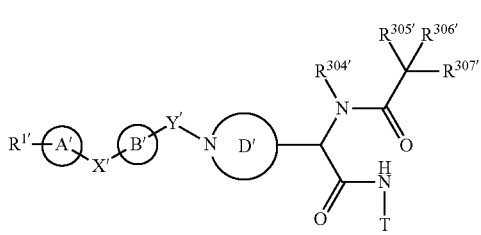

(wherein T is C1-4 alkyl group, C5-6 mono-carbocycle, or C1-4 alkyl substituted by C5-6 mono-carbocycle or 5- or 6-membered mono-heterocycle containing 1 or 2 nitrogen atoms and/or one oxygen atom, $R^{304'}$, $R^{305'}$ and $R^{306'}$ are the same meanings as $R^{304}$, $R^{305}$ and $R^{306}$ respectively and other symbols are the same meanings as described above. With proviso that, carboxy group, hydroxy group, amino group or thiol group in $R^{304'}$, $R^{305'}$ and $R^{306'}$ may be protected, if necessary.), if necessary, followed by removal of the protecting group.

The cyclization is well known. For example, it may be carried out in an organic solvent (e.g., dichloroethane or toluene), with tertiary amine (e.g., triethylamine or diisopropylethylamine) or acid (e.g., acetic acid or trifluoroacetic acid), or without tertiary amine or acid at 60 to 120° C. This cyclization reaction is carried out with the cleavage of T group.

The removal of the protecting group may be carried out by the above described method.

Among the compounds represented by formula (I), a compound wherein $R^2$ is

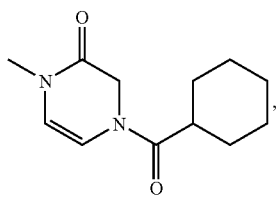

i.e., a compound represented by formula (I-c)

(I-c)

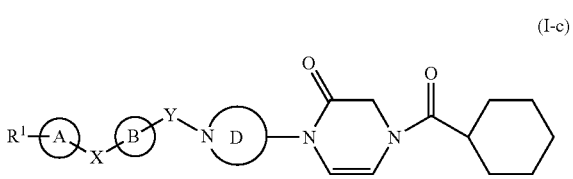

(wherein all symbols have the same meanings as described above.) can be prepared by cyclization of a compound represented by formula (VII)

(VII)

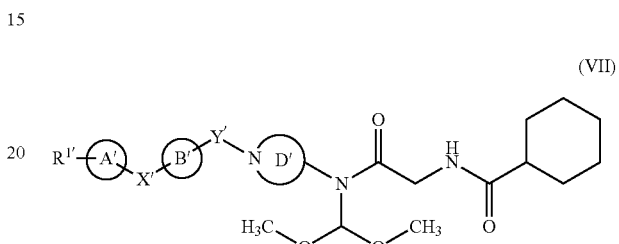

(wherein all symbols have the same meanings as described above.), if necessary, followed by removal of the protecting group.

The cyclization is well known. For example, it may be carried out in an organic solvent (e.g., dichloroethane or toluene) with acid (e.g., hydrochloric acid, sulfuric acid or p-toluenesulfonic acid) at 60 to 120° C.

The removal of the protecting group may be carried out by the above described method.

Among the compound represented by formula (I), a compound wherein $R^2$ is

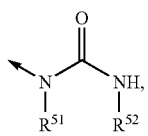

i.e., a compound represented by formula (I-d)

(I-d)

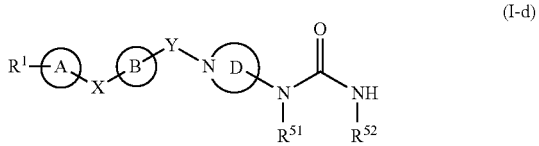

(wherein all symbols have the same meanings as described above.) can be prepared by a below reaction using a compound represented by formula (IX)

(IX)

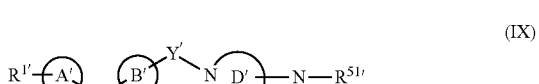

(wherein $R^{51'}$ has the same meaning as $R^{51}$ and other symbols have the same meanings as described above. With proviso that, carboxy group, hydroxy group, amino group or thiol group in R$^{51'}$ may be protected, if necessary.) and a compound represented by (X)

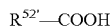 (X)

(wherein R$^{52'}$ has the same meaning as R$^{52}$ and other symbols have the same meanings as described above. With proviso that, carboxy group, hydroxy group, amino group or thiol group in R$^{52'}$ may be protected, if necessary.), if necessary, followed by removal of the protecting group.

The reaction is well known. For example, it may be carried out in an organic solvent (e.g., N,N-dimethylformamide, toluene or tetrahydrofuran) with base (e.g., pyridine, triethylamine, dimethylaniline, dimethylaminopyridine or diisopropylethylamine) at 20 to 120° C.

The removal of the protecting group may be carried out by the above described method.

Moreover, the compound represented by formula (I-d) can be prepared by a below reaction using the compound represented by formula (IX) and a compound represented by formula (XI)

 (XI)

(wherein the symbol has the same meaning as described above.), if necessary, followed by removal of the protecting group.

The reaction is well known. For example, it may be carried out in an organic solvent (e.g., tetrahydrofuran or N,N-dimethylformamiden) in the presence of triphosgene with base (e.g., triethylamine) at 0 to 40° C. Moreover, it may be carried out in an organic solvent (e.g., methylene chloride or N,N-dimethylformamiden) in the presence of 1,1'-carbonylbis-1H-imidazole (CDI) with base (e.g., triethylamine or N-methylmorpholine) or without base at 0 to 80° C.

The removal of the protecting group may be carried out by the above described method.

Among a compound represented by formula (I), a compound wherein Y is methylene, i.e., a compound represented by formula (I-e)

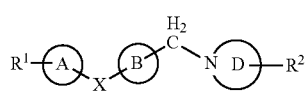 (I-e)

(wherein all symbols have the same meanings as described above) can be prepared by reductive amination of a compound represented by formula (XII)

 (XII)

(wherein all symbols have the same meanings as described above.) and the compound represented by formula (III), if necessary, followed by removal of the protecting group.

The reductive amination is well known. For example, it may be carried out in an organic solvent (e.g., dichloroethane, dichloromethane, dimethylformamide, acetic acid or a mixture of them) in the presence of reducing agent (e.g., sodium triacetoxyborohydride, sodium cyanoborohydride or sodium borohydride) at 0 to 40° C.

The removal of the protecting group may be carried out by the above described method.

Among the compounds represented by formula (I), a compound wherein at least one nitrogen atom is quaternary ammonium salt, i.e., a compounds of formula (I-2)

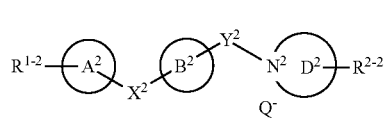 (I-2)

(wherein R$^{1-2}$, R$^{2-2}$, X$^2$, Y$^2$, ring A$^2$, ring B$^2$ and ring D$^2$ have the same meanings as R$^1$, R$^2$, X, Y, ring A, ring B and ring D respectively, and N$^2$ is nitrogen atom. With the proviso that, at least one nitrogen atom is quaternary ammonium salt, and Q is halogen.) can be prepared by reacting the compound of formula (I) with the compounds of formula (VIII)

 (VIII)

(wherein R$^0$ is C1-4 alkyl or C1-4 alkyl substituted by phenyl, and Q is halogen.).

The reaction is well known, and it may be carried out, for example, in an organic solvent (acetone, dimethylformamide or methyl ethyl ketone etc.) at 0 to 40° C.

Among the compounds of formula (I), a compound where at least one nitrogen is N-oxide, i.e., a compound of formula (I-3)

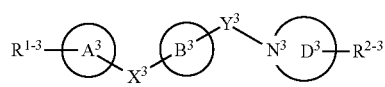 (I-3)

(wherein R$^{1-3}$, R$^{2-3}$, X$^3$, Y$^3$, ring A$^3$, ring B$^3$ and ring D$^3$ have the same meanings as R$^1$, R$^2$, X, Y, ring A, ring B and ring D respectively and N$^3$ is nitrogen atom. With the proviso that, at least one nitrogen represents N-oxide.) can be prepared by an oxidation of a compound of formula (I).

The oxidation is well known and it may be carried out, for example, in a suitable organic solvent (e.g., dichloromethane, chloroform, benzene, hexane or t-butylalcohol) in the presence of an excessive oxidizing reagent (hydrogen peroxide, sodium periodate, acyl nitrite, sodium perborate, peroxidized acid (for example, 3-chloroperbenzoic acid or peracetic acid etc.), OXONE (brand name, OXONE is an abbreviation for potassium peroxymonosulfate.), potassium permanganate or chromic acid etc.) at 20 to 60° C.

The compound of the present invention can be prepared by these reactions or reactions modified a part of them.

Among the compound represented by formula (I), other compounds than the above-described can be prepared easily by combination of known methods, for example the methods described in *Comprehensive Organic Transformations: A Guide to Functional Group Preparations,* 2nd Edition (Richard C. Larock, John Wiley & Sons Inc, 1999).

Other starting compounds or compounds used as reagent are known compounds can be prepared easily by combination of known methods, for example the methods described in *Comprehensive Organic Transformations: A Guide to Functional Group Preparations,* 2nd Edition (Richard C. Larock, John Wiley & Sons Inc, 1999) or Elmer J. Rauckman et al., *J. Org. Chem.,* vol. 41, No. 3, 1976, p 564-565 etc In each reaction of the specification, the reactions with heating, as will be apparent to those skilled in the art, it may be carried with water bath, oil bath, sand bath and microwave.

In each reaction of the specification, it may be used a solid phase reagent which is supported by polymer (for example, polystyrene, polyacrylamide, polypropylene or polyethyleneglycol etc.).

In each reaction of the specification, the obtained products may be purified by conventional techniques. For example, the purification may be carried out by distillation at atmospheric or reduced pressure, by high performance liquid chromatography with silica gel or magnesium silicate, by thin layer chromatography, by ion-exchange resin, by scavenger resin, by column chromatography, by washing or by recrystallization. The purification may be done each reaction or after several reactions.

Toxicity:

The toxicity of the compounds of the present invention is very low and therefore the compounds may be considered safe for pharmaceutical use.

Application to Pharmaceuticals:

The compounds of the present invention represented by formula (I) regulate the effect of CCR5 receptor in animal included human, especially human, so they are used for prevention and/or treatment of various inflammatory diseases (asthma, nephritis, nephropathy, hepatitis, arthritis, rheumatoid arthritis, rhinitis, conjunctivitis, ulcerative colitis, etc.), immunological diseases (autoimmune diseases, rejection in organ transplantation, immunosuppression, psoriasis, multiple sclerosis, etc.), infection with human immunodeficiency virus (acquired immunodeficiency syndrome, etc.), allergic diseases (atopic dermatitis, urticaria, allergic bronchopulmonary aspergillosis, allergic eosinophilic gastroenteritis, etc.), ischemic reperfusion injury, acute respiratory distress syndrome, shock accompanying bacterial infection, diabetes, cancer metastasis and so on.

For the purpose above described, the compounds of the present invention by formula (I), salts thereof or solvates salts, or prodrugs thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered for example, in the form of solid for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound(s) may be admixed with vehicles (such as lactose, mannitol, glucose, microcrystalline cellulose or starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions, emulsions, syrups and elixirs. In such forms, one or more of the active compound(s) may be dissolved, suspended or emulsified into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulsified into solvent(s). The solvents may include distilled water for injection, saline, vegetable oil, propylene glycol, polyethylene glycol, alcohol such as ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared according to sterile methods. They may also be manufactured in the form of sterile solid forms such as freeze-dried products, which may be dissolved in sterile water or some other sterile diluent(s) for injection immediately before use.

Other forms for parenteral administration include liquids for external use, ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents, such as sodium sulfate, isotonic buffers, such as sodium chloride, sodium citrate or citric acid. For preparation of such sprays, for example, the method described in the U.S. Pat. No. 2,868,691 or 3,095,355 may be used.

The compounds of the present invention represented by formula (I), salts thereof or solvates thereof, or prodrugs thereof may be used together with other drugs, for example, preventive and/or treating agent(s) for HIV infection (particularly agents for prevention and/or treatment for AIDS). In that case, the drug as such may be mixed with pharmacologically acceptable excipient, binder, disintegrating agent, lubricant, stabilizer, solubilizer, diluent, etc. either separately or simultaneously to make into a pharmaceutical preparation and that can be administered either orally or parenterally as a pharmaceutical composition for prevention and/or treatment of HIV infection.

The compounds of the present invention represented by formula (I), salts thereof or solvates thereof, or prodrugs thereof have an infection inhibiting activity to HIV-I which acquired resistance to other agents for preventive and/or treating HIV infection (particularly agents for prevention and/or treatment for AIDS). Therefore, it is also able to be used for HIV-infected patients to whom other agents for preventive and/or treating HIV infection are no longer effective. In that case, although the compound of the present invention may be used solely, it may be also used together with agents for preventive and/or treating HIV infection where infected HIV-1 strain acquired resistance or with other drugs.

The present invention covers the case where the compounds represented by formula (I), salts thereof or solvates thereof, or prodrugs thereof is combined with drugs which do not inhibit the HIV infection whereby preventive and/or treating effect for HIV infection is enhanced as compared with a single preparation.

Examples of other agent for preventive and/or treating HIV infection used for a combination with the compounds of the present invention represented by formula (I), salts thereof or solvates thereof, or prodrugs thereof are reverse transcriptase inhibitor, protease inhibitor, chemokine antagonist (such as CCR2 antagonist, CCR3 antagonist, CCR4 antagonist, CCR5 antagonist and CXCR4 antagonist), fusion inhibitor, antibody to surface antigen of HIV-1 and vaccine of HIV-1.

Reverse transcriptase inhibitors are concretely (1) nucleoside/nucleotide reverse transcriptase inhibitors: zidovudine (brand name: Retrovir), didanosine (brand name: Videx), zalcitabine (brand name: HIVID), stavudine (brand name: Zerit), lamivudine (brand name: Epivir), abacavir (brand name: Ziagen), adefovir, adefovir dipivoxil, emtricitabine (brand name: Coviracil) or PMPA (brand name: Tenofovir) etc. and (2) nonnucleoside reverse transcriptase inhibitors: nevirapine (brand name: Viramune), delavirdine (brand name: Rescriptor), efavirenz (brand name: Sustiva, Stocklin) or capravirine (AG1549) etc.

Protease inhibitors are concretely indinavir (brand name: Crixivan), ritonavir (brand name: Norvir), nelfinavir (brand name: Viracept), saquinavir (brand name: Invirase, Fortovase), amprenavir (brand name: Agenerase), lopinavir (brand name: Kaletra) or tipranavir etc.

As chemokine antagonists, internal ligand of chemokine receptor, its derivatives, its non-peptide low molecular compound or antibody of chemokine receptor are included.

The examples of internal ligand of chemokine receptor are concretely, MIP-1α, MIP-1β, RANTES, SDF-1α, SDF-1β, MCP-1, MCP-2, MCP-4, Eotaxin and MDC etc.

The derivatives of internal ligand are concretely, AOP-RANTES, Met-SDF-1α, Met-SDF-1β etc.

Antibodies of chemokine receptor are concretely, Pro-140 etc.

CCR2 antagonists are concretely written in specification of WO99/07351, WO99/40913, WO00/46195, WO00/46196, WO00/46197, WO00/46198, WO00/46199, WO00/69432 or WO00/69815 or in *Bioorg. Med. Chem. Lett.*, 10, 1803 (2000) etc.

CCR3 antagonists are concretely written in specification of DE19837386, WO99/55324, WO99/55330, WO00/04003, WO00/27800, WO00/27835, WO00/27843, WO00/29377, WO00/31032, WO00/31033, WO00/34278, WO00/35449, WO00/35451, WO00/35452, WO00/35453, WO00/35454, WO00/35876, WO00/35877, WO00/41685, WO00/51607, WO00/51608, WO00/51609, WO00/51610, WO00/53172, WO00/53600, WO00/58305, WO00/59497, WO00/59498, WO00/59502, WO00/59503, WO00/62814, WO00/73327 or WO01/09088 etc.

CCR5 antagonists are concretely TAK-779, SCH-351125 (SCH-C), SCH-417690(SCH-D), UK-427857, GW873140A (ONO-4128), TAK-220 etc. Moreover, it includes compounds written in specification of WO99/17773, WO99/32100, WO00/06085, WO00/06146, WO00/10965, WO00/06153, WO00/21916, WO00/37455, EP1013276, WO00/38680, WO00/39125, WO00/40239, WO00/42045, WO00/53175, WO00/42852, WO00/66551, WO00/66558, WO00/66559, WO00/66141, WO00/68203, JP2000309598, WO00/51607, WO00/51608, WO00/51609, WO00/51610, WO00/56729, WO00/59497, WO00/59498, WO00/59502, WO00/59503, WO00/76933, WO98/25605 or WO99/04794, WO99/38514 or in *Bioorg. Med. Chem. Lett.*, 10, 1803 (2000) etc.

CXCR4 antagonists are concretely AMD-3100, AMD-070, T-22, KRH-1120, KRH-1636 or the compounds written in specification of WO00/66112 etc.

Fusion Inhibitors are concretely, T-20 (Pentafuside) and T-1249 etc.

The examples of combination agents written above are intended to illustrate the present invention, but do not limit them.

The typical examples of the usual the dosage level in clinical trials of reverse transcriptase inhibitors or protease inhibitors written below are intended to illustrate the present invention, but do not limit them.

Zidovudine: 100 mg capsule, 200 mg per dose, 3 times per day; 300 mg tablet, 300 mg per dose, twice per day;

didanosine: 25-200 mg tablet, 125-200 mg per dose, twice per day;

zalcitabine: 0.375-0.75 mg tablet, 0.75 mg per dose, 3 times per day;

stavudine: 15-40 mg capsule, 30-40 mg per dose, twice per day;

lamivudine: 150 mg tablet, 150 mg per dose, twice per day;

abacavir: 300 mg tablet, 300 mg per dose, twice per day;

nevirapine: 200 mg tablet, 200 mg per dose, once per day for 14 days and then twice per day;

delavirdine: 100 mg tablet, 400 mg per dose, 3 times per day;

efavirenz: 50-200 mg capsule, 600 mg per dose, once per day;

indinavir: 200-400 mg capsule, 800 mg per dose, 3 times per day;

ritonavir: 100 mg capsule, 600 mg per dose, twice per day;

nelfinavir: 250 mg tablet, 750 mg per dose, 3 times per day;

saquinavir: 200 mg capsule, 1,200 mg per dose, 3 times per day;

amprenavir: 50-150 mg tablet, 1,200 mg per dose, twice per day.

EFFECT OF THE INVENTION

The compounds of the present invention represented by formula (I) has CCR5 antagonistic action, so they are useful as prevention and/or treatment for diseases through the intervention of CCR5 receptor.

BEST MODE FOR CARRYING OUT THE INVENTION

The present invention is explained below in detail based on Reference Examples, Examples, Biological Examples or Formulation Examples, but the present invention is not limited thereto.

In chromatographic separations and TLC, the solvents in parenthesis show the eluting and developing solvents and the ratios of the solvents used are by volume.

Unless otherwise specified, NMR data is $^1$H-NMR data.

The solvents in parenthesis in NMR show the solvents used for measurement.

All the compounds described in the present specification were named using ACD/Name (registered trademark, ver. 6.0, Advanced Chemistry Development Inc.) or ACD/Name Batch (registered trademark, ver. 4.5, Advanced Chemistry Development Inc.), or named according to IUPAC nomenclature system. For example, a compound represented by

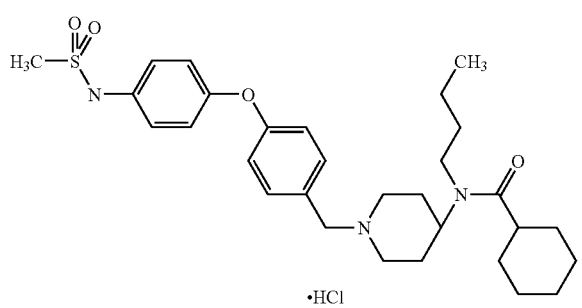

·HCl was named N-butyl-N-[1-(4-{4-[(methylsulfonyl)amino]phenoxy}benzyl)piperidin-4-yl]cyclohexanecarboxamide hydrochloride.

Example 1

1-(4-(4-methylsulfonylaminophenoxy)benzyl)piperidin-4-ol

To a solution of 4-(4-methylsulfonylaminophenoxy)benzaldehyde (2.50 g) in dimethyl formamide (25 mL) were added 4-hydroxypiperidine (1.74 g) and acetic acid (2.5 mL), and the solution was stirred. To the reaction solution was added sodium triacetoxyborohydride (2.18 g) and the solution was stirred for 2 days. After finishing the reaction, the reaction solution was neutralized with 2N aqueous solution of sodium hydroxide and extracted with ethyl acetate. The organic layer was washed with brine, dried over magnesium sulfate and concentrated. The obtained residue was purified by column chromatography on silica gel (methylene chloride:methanol=10:1) to give the title compound (1.90 g) having the following physical data.

TLC:Rf 0.48(chloroform:methanol=5:1);
NMR (DMSO-$d_6$): δ 1.29-1.42 (m, 2H), 1.63-1.73 (m, 2H), 1.95-2.05 (m, 2H), 2.59-2.68 (m, 2H), 2.95 (s, 3H), 3.38 (s, 2H), 3.43 (m, 1H), 4.51 (d, J=4.5 Hz, 1H), 6.91 (d, J=8.5 Hz, 2H), 6.99 (d, J=9.0 Hz, 2H), 7.21 (d, J=9.0 Hz, 2H), 7.25 (d, J=8.5 Hz, 2H), 9.59 (br s, 1H).

Example 2

1-(4-(4-methylsulfonylaminophenoxy)benzyl)piperidin-4-one

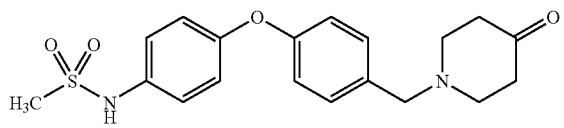

To a solution of the compound prepared in Example 1 (1.79 g) in dimethylsulfoxide (5 mL) was added triethylamine (3 mL). To the reaction solution was added sulfur trioxide pyridine complex (1.52 g) under cooling with ice and the solution was stirred for one hour. After finishing the reaction, water was added to the reaction solution, which was extracted with ethyl acetate. The organic layer was washed with brine, dried over magnesium sulfate and concentrated. The obtained residue was purified by column chromatography on silica gel (methylene chloride:methanol=20:1) to give the title compound (1.76 g) having the following physical data.

TLC:Rf 0.51(chloroform:methanol=10:1);
NMR (DMSO-$d_6$): δ 2.33 (t, J=6.0 Hz, 4H), 2.66 (t, J=6.0 Hz, 4H), 2.95 (s, 3H), 3.57 (s, 2H), 6.94 (d, J=8.5 Hz, 2H), 7.00 (d, J=9.0 Hz, 2H), 7.22 (d, J=9.0 Hz, 2H), 7.33 (d, J=8.5 Hz, 2H), 9.59 (s, 1H).

Example 3

N-[4-(4-{[4-(butylamino)piperidin-1-yl]methyl}phenoxy)phenyl]methanesulfonamide dihydrochloride

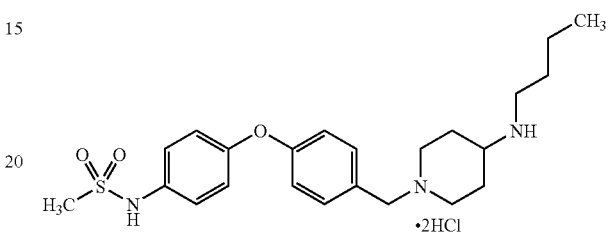

·2HCl

To a solution of the compound prepared in Example 2 (400 mg) in dimethylformamide (5 mL) were added n-butylamine (0.2 mL) and triethylamine (0.2 mL) and the solution was stirred. To the reaction solution was added sodium triacetoxyborohydride (440 mg) and the solution was stirred for 20 hours. After finishing the reaction, water was added to the reaction solution, which was extracted with ethyl acetate. The organic layer was washed with brine, dried over magnesium sulfate and concentrated. The obtained residue was purified by column chromatography on silica gel (methylene chloride:methanol=5:1). 4N hydrogen chloride/ethyl acetate solution was added to the reaction mixture, which was concentrated to give the compound of the present invention (267 mg) having the following physical data.

TLC:Rf 0.22(chloroform:methanol=5:1);
NMR (CD$_3$OD): δ 0.99 (t, J=7.5 Hz, 3H), 1.38-1.51 (m, 2H), 1.63-1.74 (m, 2H), 1.97-2.10 (m, 2H), 2.31-2.41 (m, 2H), 2.95 (s, 3H), 3.02-3.08 (m, 2H), 3.10-3.18 (m, 2H), 3.45 (m, 1H), 3.55-3.65 (m, 2H), 4.31 (s, 2H), 7.03 (d, J=9.0 Hz, 2H), 7.06 (d, J=9.0 Hz, 2H), 7.29 (d, J=9.0 Hz, 2H), 7.53 (d, J=9.0 Hz, 2H).

Example 4

N-butyl-N-[1-(4-{4-[(methylsulfonyl)amino]phenoxy}benzyl)piperidin-4-yl]-2-(tetrahydro-2H-pyran-4-yl)acetamide hydrochloride

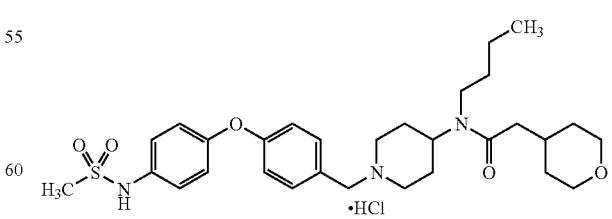

·HCl

To a solution of the compound prepared in Example 3 (183 mg) in dimethylformamide (3 mL) were added 4-tetrahydropyranylacetic acid (70 mg), 1-ethyl-3-(3-dimethylaminopropyl)carbodiimide hydrochloride (105 mg) and dimethylaminopyridine (155 mg) and the solution was stirred over night. After finishing the reaction, water was added to the reaction solution, which was extracted with ethyl acetate. The organic layer was washed with brine, dried over magnesium sulfate and concentrated. The obtained residue was purified by column chromatography on silica gel (methylene chloride: methanol=25:1). 4N hydrogen chloride/ethyl acetate solution was added to the reaction mixture, which was concentrated to give the compound of the present invention (79 mg) having the following physical data.

TLC:Rf 0.49(chloroform:methanol=10:1);

NMR (CD$_3$OD): δ 0.98 (t, J=7.0 Hz, 3H), 1.24-1.69 (m, 8H), 1.87-2.40 (m, 7H), 2.95 (s, 3H), 3.02-3.48 (m, 6H), 3.49-3.61 (m, 2H), 3.87-3.95 (m, 2H), 4.12 (m, 1H), 4.27-4.30 (m, 2H), 7.03 (d, J=9.0 Hz, 2H), 7.06 (d, J=8.5 Hz, 2H), 7.29 (d, J=9.0 Hz, 2H), 7.49 (d, J=8.5 Hz, 2H).

Example 4(1)

2-cyclohexyl-N-[1-(4-{4-[(methylsulfonyl)amino] phenoxy}benzyl)piperidin-4-yl]-N-propylacetamide hydrochloride By the same procedure as described in Example 3→Example 4, using n-propylamine and a corresponding cyclohexylacetic acid instead of n-butylamine and 4-tetrahydropyranylacetic acid respectively, the compound of the present invention having the following physical data was obtained.

TLC:Rf 0.40(chloroform:methanol=10:1);

NMR (CD$_3$OD): δ 0.86-1.39 (m, 9H), 1.48-2.14 (m, 9H), 2.22 (d, J=7.0 Hz, 2H), 2.27-2.39 (m, 2H), 2.95 (s, 3H), 3.02-3.25 (m, 4H), 3.49-3.61 (m, 2H), 4.13 (m, 1H), 4.27-4.29 (m, 2H), 7.03 (d, J=9.0 Hz, 2H), 7.06 (d, J=8.5 Hz, 2H), 7.29 (d, J=9.0 Hz, 2H), 7.49 (d, J=8.5 Hz, 2H).

Reference Example 1

1-t-butoxycarbonyl-4-butylaminopiperidine

To a solution of 1-t-butoxycarbonylpyperidin-4-one (10.0 g) in dimethylformamide (200 mL) were added n-butylamine (6.0 mL) and triethylamine (7.0 mL) and the solution was stirred. To the reaction solution was added sodium triacetoxyborohydride (16.0 g) and the solution was stirred for 1.5 hours. After finishing the reaction, water was added to the reaction solution, which was extracted with ethyl acetate. The organic layer was washed with brine, dried over magnesium sulfate and concentrated to give the title compound having the following physical data.

TLC:Rf 0.28(chloroform:methanol=10:1);

NMR (CDCl$_3$): δ 0.92 (t, J=7.0 Hz, 3H), 1.19-1.53 (m, 6H), 1.45 (s, 9H), 1.82-1.87 (m, 2H), 2.55-2.66 (m, 3H), 2.74-2.82 (m, 2H), 4.00-4.10 (m, 2H).

Reference Example 2

1-t-butoxycarbonyl-4-(N-cyclohexylcarbonyl-N-butylamino)piperidine

To a solution of the compound prepared in Reference Example 1 in methylene chloride (100 mL) were added cyclohexylacetic acid (7.5 g), 1-ethyl-3-[3-(dimethylamino)propyl]carbodiimide hydrochloride (14.5 g) and 4-N,N-dimethylaminopyridine (9.2 g) and the solution was stirred overnight. After finishing the reaction, water was added to the reaction solution, which was extracted with ethyl acetate. The organic layer was washed with brine, dried over magnesium sulfate and concentrated. The obtained residue was purified by column chromatography on silica gel (hexane:ethyl acetate=1:1) to give the title compound (8.97 g) having the following physical data.

TLC:Rf 0.50(hexane:ethyl acetate=2:1);

NMR (CDCl$_3$): δ 0.87-1.01 (m, 2H), 0.95 (t, J=7.5 Hz, 3H), 1.05-1.81 (m, 16H), 1.46 (s, 9H), 1.89 (m, 1H), 2.16 (d, J=7.0 Hz, 2H), 2.68-2.85 (m, 2H), 3.08-3.18 (m, 2H), 4.09-4.35 (m, 2H), 4.52 (m, 1H).

Reference Example 3

4-[(N-cyclohexylcarbonyl-N-butyl)amino]piperidine hydrochloride

To a solution of the compound prepared in Reference Example 2 (8.92 g) in methylene chloride (20 mL) was added trifluoroacetic acid (20 mL) and the solution was stirred for 30 minutes. After finishing the reaction, the reaction solution was alkalinized with 1N aqueous solution of sodium hydroxide and was extracted with methylene chloride. The organic layer was washed with brine, dried over magnesium sulfate and concentrated. 4N hydrogen chloride/ethyl acetate solution was added to the obtained residue, which was concentrated to give the title compound (7.98 g) having the following physical data.

TLC:Rf 0.35(chloroform:methanol=5:1);

NMR (CD$_3$OD): δ 0.92-1.08 (m, 2H), 0.98 (t, J=7.5 Hz, 3H), 1.15-2.36 (m, 17H), 2.23 (d, J=7.0 Hz, 2H), 3.01-3.30 (m, 4H), 3.41-3.53 (m, 2H), 4.15 (m, 1H).

Example 5(1)-Example 5(54)

By the same procedure as described in Example 1 and the conversion to hydrochloride salt by a conventional method, using the compound prepared in Reference Example 3 or a corresponding amine derivative instead of 4-hydroxypiperidine, and using 4-(4-methylsulfonylaminophenoxy)benzaldehyde or a corresponding aldehyde derivative, the following compounds of the present invention were obtained.

Example 5(1)

N-butyl-2-cyclohexyl-N-[1-(4-{2-methoxy-4-[(methylsulfonyl)amino]phenoxy}benzyl)piperidin-4-yl] acetamide hydrochloride

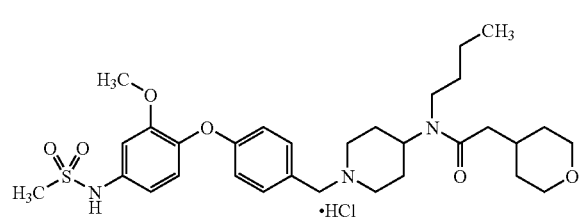

TLC:Rf 0.49(chloroform:methanol=10:1);

NMR (CDCl$_3$): δ 0.87-1.01 (m, 2H), 0.93 (t, J=7.0 Hz, 3H), 1.07-2.06 (m, 15H), 2.19 (d, J=7.0 Hz, 2H), 2.49-2.84 (m, 4H), 3.02 (s, 3H), 3.17-3.27 (m, 2H), 3.49-3.59 (m, 2H), 3.81 (s, 3H), 4.10 (br s, 2H), 4.72 (m, 1H), 6.88-6.93 (m, 3H), 6.99 (d, J=8.5 Hz, 1H), 7.13 (d, J=2.5 Hz, 1H), 7.53 (d, J=8.5 Hz, 2H), 7.94 (br s, 1H), 12.14 (s, 1H).

Example 5(2)

N-butyl-N-[1-(4-{4-[(methylsulfonyl)amino]phenoxy}benzyl)piperidin-4-yl]cyclohexanecarboxamide hydrochloride TLC:Rf 0.62(methylene chloride:methanol=10:1);
NMR (CD$_3$OD): δ 7.55-7.46 (m, 2H), 7.29 (d, J=8.7 Hz, 2H), 7.10-7.00 (m, 4H), 4.33-4.25 (m, 2H), 4.19 (m, 1H), 3.62-3.48 (m, 2H), 3.30-3.02 (m, 4H), 2.95 (s, 3H), 2.48 (m, 1H), 2.35-2.08 (m, 2H), 1.98-1.63 (m, 7H), 1.63-1.18 (m, 9H), 1.03-0.88 (m, 3H).

Example 5(3)

N-butyl-2-cyclohexyl-N-[1-(4-{4-[(methylsulfonyl)amino]phenoxy}benzyl)piperidin-4-yl]acetamide hydrochloride TLC:Rf 0.62(methylene chloride:methanol=10:1);
NMR (CD$_3$OD): δ 7.55-7.46 (m, 2H), 7.29 (d, J=9.0 Hz, 2H), 7.10-7.00 (m, 4H), 4.32-4.24 (m, 2H), 4.16 (m, 1H), 3.63-3.48 (m, 2H), 3.30-3.01 (m, 4H), 2.95 (s, 3H), 2.40-2.08 (m, 4H), 2.00-1.60 (m, 8H), 1.60-1.10 (m, 7H), 1.10-0.90 (m, 5H).

Example 5(4)

N-butyl-3-cyclohexyl-N-[1-(4-{4-[(methylsulfonyl)amino]phenoxy}benzyl)piperidin-4-yl]propanamide hydrochloride TLC:Rf 0.64(methylene chloride:methanol=10:1);
NMR (CD$_3$OD): δ 7.56-7.46 (m, 2H), 7.29 (d, J=9.0 Hz, 2H), 7.10-7.00 (m, 4H), 4.32-4.23 (m, 2H), 4.16 (m, 1H), 3.62-3.47 (m, 2H), 3.30-3.00 (m, 4H), 2.95 (s, 3H), 2.50-2.03 (m, 4H), 2.02-1.84 (m, 2H), 1.82-1.60 (m, 5H), 1.60-1.10 (m, 10H), 1.05-0.83 (m, 5H).

Example 5(5)

N-butyl-2-cyclohexyl-N-{1-[(3,5-dimethyl-1-{4-[(methylsulfonyl)amino]phenyl}-1H-pyrazol-4-yl)methyl]piperidin-4-yl}acetamide hydrochloride TLC:Rf 0.41(chloroform:methanol=10:1);
NMR (CD$_3$OD): δ 0.91-1.06 (m, 2H), 0.98 (t, J=7.5 Hz, 3H), 1.14-1.83 (m, 13H), 1.89-1.97 (m, 2H), 2.23 (d, J=6.5 Hz, 2H), 2.32-2.40 (m, 2H), 2.36 (s, 3H), 2.39 (s, 3H), 3.04 (s, 3H), 3.12-3.29 (m, 4H), 3.61-3.71 (m, 2H), 4.25 (s, 2H), 4.27 (m, 1H), 7.41 (d, J=9.0 Hz, 2H), 7.46 (d, J=9.0 Hz, 2H).

Example 5(6)

N-(1-{4-[4-(aminosulfonyl)phenoxy]benzyl}piperidin-4-yl)-N-butyl-2-cyclohexylacetamide hydrochloride TLC:Rf 0.37(chloroform:methanol=10:1);
NMR (CD$_3$OD): δ 0.91-1.04 (m, 2H), 0.98 (t, J=7.0 Hz, 3H), 1.12-1.99 (m, 15H), 2.22 (d, J=6.5 Hz, 2H), 2.25-2.36 (m, 2H), 2.97-3.30 (m, 4H), 3.46-3.60 (m, 2H), 4.10 (m, 1H), 4.29 (s, 2H), 7.13 (d, J=9.0 Hz, 2H), 7.17 (d, J=8.5 Hz, 2H), 7.55 (d, J=8.5 Hz, 2H), 7.90 (d, J=9.0 Hz, 2H).

Example 5(7)

N-butyl-2-cyclohexyl-N-[1-({4'-[(methylsulfonyl)amino]biphenyl-3-yl}methyl)piperidin-4-yl]acetamide hydrochloride TLC:Rf 0.50(chloroform:methanol=10:1);
NMR (CD$_3$OD): δ 0.87-1.05 (m, 2H), 0.96 (t, J=7.0 Hz, 3H), 1.13-2.14 (m, 15H), 2.21 (d, J=7.0 Hz, 2H), 2.25-2.38 (m, 2H), 2.99 (s, 3H), 3.08-3.28 (m, 4H), 3.54-3.65 (m, 2H), 4.15 (m, 1H), 4.37-4.39 (m, 2H), 7.36 (d, J=9.0 Hz, 2H), 7.47 (d, J=7.5 Hz, 1H), 7.57 (t, J=7.5 Hz, 1H), 7.67 (d, J=9.0 Hz, 2H), 7.74-7.82 (m, 2H).

Example 5(8)

N-{4-[4-({4-[butyl(2-cyclohexylethyl)amino]piperidin-1-yl}methyl)phenoxy]phenyl}methanesulfonamide dihydrochloride TLC:Rf 0.32(chloroform:methanol=10:1);
NMR (CD$_3$OD): δ 0.94 (t, J=7.0 Hz, 3H), 0.98-1.08 (m, 2H), 1.18-1.41 (m, 7H), 1.53-1.80 (m, 8H), 2.24-2.49 (m, 4H), 2.96 (s, 3H), 3.05-3.21 (m, 6H), 3.70-3.81 (m, 3H), 4.32 (d, J=13.0 Hz, 1H), 4.53 (d, J=13.0 Hz, 1H), 7.04 (d, J=9.0 Hz, 2H), 7.08 (d, J=8.5 Hz, 2H), 7.30 (d, J=9.0 Hz, 2H), 7.56 (d, J=8.5 Hz, 2H).

Example 5(9)

N-[(1S)-2-amino-1-(cyclohexylmethyl)-2-oxoethyl]-1-(4-{4-[(methylsulfonyl)amino]phenoxy}benzyl)piperidine-4-carboxamide hydrochloride TLC:Rf 0.34(chloroform:methanol=4:1);
NMR (CD$_3$OD): δ 0.84-1.06 (m, 2H), 1.13-1.41 (m, 4H), 1.55-2.14 (m, 11H), 2.59 (m, 1H), 2.95 (s, 3H), 2.97-3.09 (m, 2H), 3.50-3.59 (m, 2H), 4.29 (s, 2H), 4.39 (dd, J=9.5, 5.5 Hz, 1H), 7.03 (d, J=9.0 Hz, 2H), 7.06 (d, J=9.0 Hz, 2H), 7.29 (d, J=9.0 Hz, 2H), 7.49 (d, J=9.0 Hz, 2H).

Example 5(10)

N-{4-[4-({4-[(3S)-3-(cyclohexylmethyl)-2,5-dioxopiperazin-1-yl]piperidin-1-yl}methyl)phenoxy]phenyl}methanesulfonamide hydrochloride TLC:Rf 0.73(chloroform:methanol=5:1);
NMR (CD$_3$OD): δ 7.49 (brd, J=8.7 Hz, 2H), 7.29 (brd, J=9.0 Hz, 2H), 7.07 (brd, J=8.7 Hz, 2H), 7.03 (brd, J=9.0 Hz, 2H), 4.44 (m, 1H), 4.29 (s, 2H), 4.04 (d, J=16.8 Hz, 1H), 3.96 (t, J=6.6 Hz, 1H), 3.83 (d, J=16.8 Hz, 1H), 3.64-3.52 (m, 2H), 3.15 (m, 2H), 2.95 (s, 3H), 2.20-1.60 (m, 10H), 1.49 (m, 1H), 1.39-1.10 (m, 4H), 1.09-0.80 (m, 2H).

Example 5(11)

N-{4-[4-({4-[4-(cyclohexylcarbonyl)-2-oxopiperazin-1-yl]piperidin-1-yl}methyl)phenoxy]phenyl}methanesulfonamide hydrochloride TLC:0.45(methylene chloride:methanol=10:1);
NMR (CD$_3$OD): δ 7.50 (d, J=8.7 Hz, 2H), 7.29 (d, J=8.7 Hz, 2H), 7.05 (d, J=8.7 Hz, 2H), 7.03 (d, J=8.7 Hz, 2H), 4.50

(m, 1H), 4.26 (m, 1H), 4.23 (s, 2H), 4.14 (m, 1H), 3.82-3.76 (m, 2H), 3.53-3.33 (m, 4H), 3.09-3.01 (m, 2H), 2.95 (s, 3H), 2.65 (m, 1H), 2.19-1.88 (m, 4H), 1.79-1.70 (m, 5H), 1.49-1.21 (m, 5H).

Example 5(12)

N-butyl-2-cyclohexyl-N-[1-(4-{2-methoxy-4-[(methylsulfonyl)amino]phenoxy}benzyl)piperidin-3-yl]acetamide hydrochloride TLC:Rf 0.49(chloroform:methanol=10:1);
NMR (CDCl$_3$): δ 0.87-1.00 (m, 2H), 0.94 (t, J=7.5 Hz, 3H), 1.08-1.93 (m, 16H), 2.11 (d, J=7.0 Hz, 2H), 2.25 (m, 1H), 2.45-2.64 (m, 2H), 3.02 (s, 3H), 3.18-3.37 (m, 4H), 3.80 (s, 3H), 3.86-4.00 (m, 2H), 4.20 (dd, J=13.0, 4.0 Hz, 1H), 6.87-6.92 (m, 3H), 6.99 (d, J=8.5 Hz, 1H), 7.13 (d, J=2.5 Hz, 1H), 7.55 (d, J=8.5 Hz, 2H), 7.83 (br s, 1H), 11.87 (s, 1H).

Example 5(13)

N-butyl-2-cyclohexyl-N-[1-(4-{[(4-methylphenyl)sulfonyl]amino}benzyl)piperidin-4-yl]acetamide hydrochloride TLC:Rf 0.45 (chloroform:methanol=10:1);
NMR (CD$_3$OD): δ 0.89-1.06 (m, 2H), 0.96 (t, J=7.0 Hz, 3H), 1.12-2.09 (m, 15H), 2.21 (d, J=7.0 Hz, 2H), 2.22-2.32 (m, 2H), 2.36 (s, 3H), 2.97-3.27 (m, 4H), 3.41-3.54 (m, 2H), 4.11 (m, 1H), 4.18-4.20 (m, 2H), 7.21 (d, J=8.5 Hz, 2H), 7.29 (d, J=8.5 Hz, 2H), 7.36 (d, J=8.5 Hz, 2H), 7.69 (d, J=8.5 Hz, 2H).

Example 5(14)

1-(4-(4-(N-cyclohexylmethylcarbonyl-N-methylsulfonylamino)phenoxy)benzyl)-4-(N-propyl-N-cyclohexylmethylcarbonylamino)piperidine hydrochloride TLC:Rf 0.82(chloroform:methanol=10:1);
NMR (CD$_3$OD): δ 0.77-1.39 (m, 13H), 1.47-1.96 (m, 16H), 2.05 (d, J=7.0 Hz, 2H), 2.22 (d, J=7.0 Hz, 2H), 2.24-2.41 (m, 2H), 3.04-3.26 (m, 4H), 3.48 (s, 3H), 3.51-3.65 (m, 2H), 4.13 (m, 1H), 4.31-4.33 (m, 2H), 7.13 (d, J=9.0 Hz, 2H), 7.18 (d, J=8.5 Hz, 2H), 7.38 (d, J=9.0 Hz, 2H), 7.56 (d, J=8.5 Hz, 2H).

Example 5(15)

4-(4-{[4-(4-bromobenzoyl)piperidin-1-yl]methyl}phenoxy)benzoic acid hydrochloride TLC:Rf 0.35(chloroform:methanol=10:1);
NMR (DMSO-d$_6$): δ 1.83-2.15 (m, 4H), 2.94-3.09 (m, 2H), 3.39-3.50 (m, 2H), 3.65 (s, 1H), 4.31 (br s, 2H), 7.09 (d, J=9.0 Hz, 2H), 7.19 (d, J=8.5 Hz, 2H), 7.65 (d, J=8.5 Hz, 2H), 7.76 (d, J=8.5 Hz, 2H), 7.93 (d, J=8.5 Hz, 2H), 7.97 (d, J=9.0 Hz, 2H), 10.52 (br s, 1H), 12.86 (br s, 1H).

Example 5(16)

4-[4-({4-[(3S)-3-(cyclohexylmethyl)-2,5-dioxopiperazin-1-yl]piperidin-1-yl}methyl)phenoxy]benzoic acid hydrochloride TLC:Rf 0.65(chloroform:methanol=5:1);
NMR (CD$_3$OD): δ 8.04 (brd, J=8.7 Hz, 2H), 7.59 (brd, J=8.1 Hz, 2H), 7.17 (brd, J=8.1 Hz, 2H), 7.07 (brd, J=8.7 Hz, 2H), 4.46 (m, 1H), 4.34 (s, 2H), 4.05 (d, J=17.1 Hz, 1H), 3.97 (dd, J=6.6, 5.4 Hz, 1H), 3.85 (d, J=17.1 Hz, 1H), 3.68-3.53 (m, 2H), 3.17 (m, 2H), 2.24-2.04 (m, 2H), 1.94 (m, 1H), 1.84-1.56 (m, 7H), 1.48 (m, 1H), 1.38-1.08 (m, 4H), 1.08-0.80 (m, 2H).

Example 5(17)

5-chloro-2-{4-[1-(3,4-dimethoxybenzyl)piperidin-4-yl]benzyl}-1H-isoindole-1,3(2H)-dione hydrochloride TLC:Rf 0.48(methylene chloride:methanol=10:1);
NMR (CD$_3$OD): δ 7.86-7.81 (m, 2H), 7.33 (d, J=8.0 Hz, 2H), 7.23 (d, J=8.0 Hz, 2H), 7.14 (s, 1H), 7.06-7.01 (m, 3H), 4.78 (s, 2H), 4.26 (s, 2H), 3.88 (s, 3H), 3.85 (s, 3H), 3.58-3.54 (m, 2H), 3.10-3.00 (m, 2H), 2.90 (m, 1H), 2.10-1.90 (m, 4H).

Example 5(18)

N-butyl-2-cyclohexyl-N-[1-(4-phenoxybenzyl)piperidin-4-yl]acetamide hydrochloride TLC:Rf 0.82(methylene chloride:methanol=10:1);
NMR (CD$_3$OD): δ 7.50-7.37 (m, 4H), 7.18 (t, J=7.2 Hz, 1H), 7.07-7.02 (m, 4H), 4.27 (s, 2H), 4.15 (m, 1H), 3.60-3.50 (m, 2H), 3.30-3.00 (m, 4H), 2.20-2.00 (m, 4H), 2.00-1.80 (m, 2H), 1.80-1.40 (m, 8H), 1.40-1.10 (m, 5H), 1.00-0.90 (m, 2H), 0.97 (t, J=7.4 Hz, 3H).

Example 5(19)

4-[4-({4-[butyl(cyclohexylacetyl)amino]piperidin-1-yl}methyl)phenoxy]benzoic acid hydrochloride TLC:Rf 0.43(methylene chloride:methanol=10:1);
NMR (CD$_3$OD): δ 8.04(d, J=8.3 Hz, 2H), 7.56 (d, J=8.3 Hz, 2H), 7.17 (d, J=8.3 Hz, 2H), 7.07 (d, J=8.3 Hz, 2H), 4.31 (s, 2H), 4.16 (m, 1H), 3.60-3.50 (m, 2H), 3.30-3.00 (m, 4H), 2.20-2.00 (m, 4H), 2.00-1.80 (m, 2H), 1.80-1.40 (m, 8H), 1.40-1.10 (m, 5H), 1.00-0.90 (m, 2H), 0.97 (t, J=7.0 Hz, 3H).

Example 5(20)

N-butyl-2-cyclohexyl-N-{1-[(3,5-dimethyl-1-phenyl-1H-pyrazol-4-yl)methyl]piperidin-4-yl}acetamide dihydrochloride TLC:Rf 0.47(methylene chloride:methanol=10:1);
NMR (CD$_3$OD): δ 7.58-7.45 (m, 5H), 4.24 (s, 2H), 4.15 (m, 1H), 3.60-3.50 (m, 2H), 3.30-3.00 (m, 4H), 2.37 (s, 3H), 2.36 (s, 3H), 2.40-2.10 (m, 4H), 2.00-1.80 (m, 2H), 1.80-1.40 (m, 8H), 1.40-1.10 (m, 5H), 1.00-0.90 (m, 2H), 0.98 (t, J=7.4 Hz, 3H).

Example 5(21)

N-butyl-2-cyclohexyl-N-(1-{[1-(4-hydroxyphenyl)-3,5-dimethyl-1H-pyrazol-4-yl]methyl}piperidin-4-yl)acetamide dihydrochloride TLC:Rf 0.37(methylene chloride:methanol=10:1);
NMR (CD$_3$OD): δ 7.26(d, J=9.0 Hz, 2H), 6.92 (d, J=9.0 Hz, 2H), 4.24 (s, 2H), 4.15 (m, 1H), 3.70-3.60 (m, 2H), 3.30-3.00 (m, 4H), 2.37 (s, 3H), 2.32 (s, 3H), 2.40-2.20 (m, 4H), 2.00-1.80 (m, 2H), 1.80-1.40 (m, 8H), 1.40-1.10 (m, 5H), 1.00-0.90 (m, 2H), 0.98 (t, J=7.4 Hz, 3H).

Example 5(22)

N-{4-[4-({4-[4-(cyclohexylcarbonyl)piperazin-1-yl]piperidin-1-yl}methyl)phenoxy]phenyl}methanesulfonamide dihydrochloride TLC:Rf 0.59(methylene chloride:methanol=5:1);
NMR (CD$_3$OD): δ 1.21-1.49 (m, 6H), 1.70-1.98 (m, 10H), 2.20-2.35 (m, 2H), 2.60-2.70 (m, 2H), 2.95 (s, 3H), 2.95-3.23 (m, 4H), 3.55-3.80 (m, 4H), 4.28 (s, 2H), 7.03 (d, J=8.5 Hz, 2H), 7.06 (d, J=8.5 Hz, 2H), 7.29 (d, J=8.5 Hz, 2H), 7.49 (d, J=8.5 Hz, 2H).

Example 5(23)

N-{4-[4-({4-[5-(cyclohexylcarbonyl)-2,5-diazabicyclo[2.2.1]hept-2-yl]piperidin-1-yl}methyl)phenoxy]phenyl}methanesulfonamide dihydrochloride TLC:Rf 0.46(methylene chloride:methanol=5:1);
NMR (CD$_3$OD): δ 1.15-1.49 (m, 6H), 1.60-1.98 (m, 10H), 2.35-2.88 (m, 6H), 2.95 (s, 3H), 3.08-3.72 (m, 4H), 3.89 (d, J=9.5 Hz, 1H), 4.04 (s, 2H), 4.62 (d, J=22.5 Hz, 1H), 7.01 (d, J=8.7 Hz, 2H), 7.02 (d, J=8.7 Hz, 2H), 7.28 (d, J=8.7 Hz, 2H), 7.42 (d, J=8.7 Hz, 2H).

Example 5(24)

2-cyclohexyl-N-[1-(4-{4-[(methylsulfonyl)amino]phenoxy}benzyl)piperidin-4-yl]acetamide hydrochloride TLC:Rf 0.46(methylene chloride:methanol=10:1);
NMR (CD$_3$OD): δ 0.89-1.00 (m, 2H), 1.21-1.29 (m, 3H), 1.68-1.71 (m, 8H), 2.03 (d, J=6.9 Hz, 2H), 2.11-2.16 (m, 2H), 2.95 (s, 3H), 3.06-3.14 (m, 2H), 3.49-3.53 (m, 2H), 3.90 (m, 1H), 4.27 (s, 2H), 7.03 (d, J=8.7 Hz, 2H), 7.06 (d, J=8.7 Hz, 2H), 7.29 (d, J=8.7 Hz, 2H), 7.47 (d, J=8.7 Hz, 2H).

Example 5(25)

2-cyclohexyl-N-[1-(4-phenoxybenzyl)piperidin-4-yl]acetamide hydrochloride

TLC:Rf 0.62(methylene chloride:methanol=10:1);
NMR (CD$_3$OD): δ 0.90-1.00 (m, 2H), 1.13-1.29 (m, 3H), 1.67-1.78 (m, 8H), 2.03 (d, J=6.9 Hz, 2H), 2.12-2.15 (m, 2H), 3.05-3.13 (m, 2H), 3.49-3.53 (m, 2H), 3.90 (m, 1H), 4.27 (s, 2H), 7.02-7.08 (m, 4H), 7.18 (m, 1H), 7.37-7.42 (m, 2H), 7.46-7.50 (m, 2H).

Example 5(26)

2-cyclohexyl-N-{1-[(3,5-dimethyl-1-phenyl-1H-pyrazol-4-yl)methyl]piperidin-4-yl}acetamide dihydrochloride TLC:Rf 0.40(methylene chloride:methanol=10:1);
NMR (CD$_3$OD): δ 0.91-1.02 (m, 2H), 1.14-1.34 (m, 3H), 1.69-1.85 (m, 8H), 2.05 (d, J=6.9 Hz, 2H), 2.13-2.19 (m, 2H), 2.36 (s, 3H), 2.38 (s, 3H), 3.14-3.24 (m, 2H), 3.61-3.66 (m, 2H), 3.93 (m, 1H), 4.25 (s, 2H), 7.45-7.60 (m, 5H).

Example 5(27)

N-{4-[4-({4-[(5S)-5-(cyclohexylmethyl)-1-isopropyl-3,6-dioxopiperazin-2-yl]piperidin-1-yl}methyl)phenoxy]phenyl}methanesulfonamide hydrochloride TLC:Rf 0.69(chloroform:methanol=5:1);
NMR (CD$_3$OD): δ 0.80-2.36 (m, 24H), 2.95 (s, 3H), 3.04 (m, 1H), 3.46-3.69 (m, 3H), 3.78-4.12 (m, 3H), 4.26 (brs, 2H), 7.00-7.18 (m, 4H), 7.26-7.34 (m, 2H), 7.40-7.48 (m, 2H).

Example 5(28)

N-{4-[4-({4-[(5S)-5-(cyclohexylmethyl)-1-(2-methoxyethyl)-3,6-dioxopiperazin-2-yl]piperidin-1-yl}methyl)phenoxy]phenyl}methanesulfonamide hydrochloride TLC:Rf 0.67(chloroform:methanol=5:1);
NMR (CD$_3$OD): δ 0.80-2.32 (m, 21H), 2.95 (s, 3H), 2.84-3.02 (m, 3H), 3.40-3.60 (m, 4H), 3.80-4.14 (m, 3H), 4.26 (brs, 2H), 7.00-7.14 (m, 4H), 7.21-7.32 (m, 2H), 7.41-7.52 (m, 2H).

Example 5(29)

N-{4-[4-({4-[(5S)-5-(cyclohexylmethyl)-1-methyl-3,6-dioxopiperazin-2-yl]piperidin-1-yl}methyl)phenoxy]phenyl}methanesulfonamide hydrochloride TLC:Rf 0.64(chloroform:methanol=5:1);
NMR (CD$_3$OD): δ 0.96 (m, 1H), 1.12-1.36 (m, 3H), 1.44-2.38 (m, 14H), 2.95 (s, 3H), 2.98 (m, 2H), 3.36 (brs, 3H), 3.42-3.60 (m, 2H), 3.86-4.34 (m, 2H), 4.25 (brs, 2H), 6.98-7.08 (m, 4H), 7.24-7.30 (m, 2H), 7.40-7.52 (m, 2H).

Example 5(30)

N-{4-[4-({4-[(5S)-1-benzyl-5-(cyclohexylmethyl)-3,6-dioxopiperazin-2-yl]piperidin-1-yl}methyl)phenoxy]phenyl}methanesulfonamide hydrochloride TLC:Rf 0.78(chloroform:methanol=5:1);
NMR (CD$_3$OD): δ 0.80-2.40 (m, 18H), 2.95 (s, 3H), 3.44-3.56 (m, 3H), 3.79 (m, 1H), 4.02-4.30 (m, 4H), 5.22 (m, 2H), 7.00-7.08 (m, 4H), 7.24-7.40 (m, 6H), 7.40-7.50 (m, 3H).

Example 5(31)

(3S)-3-(cyclohexylmethyl)-1-isopropyl-6-[1-(4-phenoxybenzyl)piperidin-4-yl]piperazine-2,5-dione hydrochloride TLC:Rf 0.84(chloroform:methanol=5:1);
NMR (CD$_3$OD): δ 0.80-2.38 (m, 24H), 3.03 (m, 2H), 3.46-3.70 (m, 3H), 3.76-4.10 (m, 2H), 4.26 (brs, 2H), 7.00-7.06 (m, 4H), 7.19 (m, 1H), 7.36-7.58 (m, 4H).

Example 5(32)

(3S)-3-(cyclohexylmethyl)-1-(2-methoxyethyl)-6-[1-(4-phenoxybenzyl)piperidin-4-yl]piperazine-2,5-dione hydrochloride TLC:Rf 0.77(chloroform:methanol=5:1);
NMR (CD$_3$OD): δ 0.80-1.10 (m, 2H), 1.12-2.10 (m, 16H), 2.16-2.62 (m, 2H), 2.98-4.14 (m, 11H), 4.26 (brs, 2H), 7.00-7.10 (m, 4H), 7.18 (m, 1H), 7.30-7.54 (m, 4H).

Example 5(33)

(3S)-1-benzyl-3-(cyclohexylmethyl)-6-[1-(4-phenoxybenzyl)piperidin-4-yl]piperazine-2,5-dione hydrochloride TLC:Rf 0.86(chloroform:methanol=5:1);
NMR (CD$_3$OD): δ 0.84-2.40 (m, 18H), 2.76-3.04 (m, 2H), 3.42-3.60 (m, 2H), 3.78 (m, 1H), 4.10 (m, 1H), 4.16-4.34 (m, 3H), 5.20 (m, 1H), 6.98-7.14 (m, 4H), 7.19 (m, 1H), 7.20-7.52 (m, 9H).

Example 5(34)

(3S)-3-(cyclohexylmethyl)-6-{1-[(3,5-dimethyl-1-phenyl-1H-pyrazol-4-yl)methyl]piperidin-4-yl}-1-isopropylpiperazine-2,5-dione hydrochloride TLC:Rf 0.74(chloroform:methanol=5:1);
NMR (CD$_3$OD): δ 0.84-2.36 (m, 24H), 2.36 (brs, 3H), 2.38 (brs, 3H), 3.04-3.24 (m, 2H), 3.60-4.10 (m, 5H), 4.25 (brs, 2H), 7.40-7.60 (m, 5H).

Example 5(35)

(3S)-3-(cyclohexylmethyl)-6-{1-[(3,5-dimethyl-1-phenyl-1H-pyrazol-4-yl)methyl]piperidin-4-yl}-1-methylpiperazine-2,5-dione hydrochloride TLC:Rf 0.74(chloroform:methanol=5:1);
NMR (CD$_3$OD): δ 0.84-2.40 (m, 18H), 2.35 (m, 6H), 3.00 (brs, 3H), 3.09 (m, 2H), 3.56-3.70 (m, 2H), 3.82-4.12 (m, 2H), 4.24 (brs, 2H), 7.40-7.60 (m, 5H).

Example 5(36)

(3S)-3-(cyclohexylmethyl)-6-{1-[(3,5-dimethyl-1-phenyl-1H-pyrazol-4-yl)methyl]piperidin-4-yl}-1-(2-methoxyethyl)piperazine-2,5-dione hydrochloride TLC:Rf 0.74(chloroform:methanol=5:1);
NMR (CD$_3$OD): δ 0.80-2.40 (m, 18H), 2.35 (brs, 3H), 2.38 (brs, 3H), 3.00-3.20 (m, 3H), 3.33 (s, 3H), 3.49-3.72 (m, 4H), 3.88-4.16 (m, 3H), 4.25 (brs, 2H), 7.40-7.62 (m, 5H).

Example 5(37)

N-butyl-1-(4-phenoxybenzyl)piperidine-4-carboxamide hydrochloride

TLC:Rf 0.58(chloroform:methanol=10:1);
NMR (CD$_3$OD): δ 0.92 (t, J=7.2 Hz, 3H), 1.28-1.52 (m, 4H), 1.82-2.05 (m, 4H), 2.49 (m, 1H), 2.98-3.07 (m, 2H), 3.16 (t, J=7.0 Hz, 2H), 3.52-3.56 (m, 2H), 4.28 (s, 2H), 7.02-7.06 (m, 4H), 7.18 (t, J=7.5 Hz, 1H), 7.37-7.42 (m, 2H), 7.48 (d, J=8.7 Hz, 2H).

Example 5(38)

N-(cyclohexylmethyl)-1-(4-phenoxybenzyl)piperidine-4-carboxamide hydrochloride

TLC:Rf 0.64(chloroform:methanol=10:1);
NMR (CD$_3$OD): δ 0.86-0.97 (m, 2H), 1.15-1.28 (m, 4H), 1.46 (m, 1H), 1.60-1.78 (m, 4H), 1.89-2.05 (m, 4H), 2.52 (m, 1H), 3.00 (d, J=7.2 Hz, 2H), 3.00-3.07 (m, 2H), 3.51-3.56 (m, 2H), 4.29 (s, 2H), 7.01-7.06 (m, 4H), 7.18 (m, 1H), 7.37-7.42 (m, 2H), 7.49 (d, J=8.7 Hz, 2H).

Example 5(39)

N-butyl-N-(cyclohexylmethyl)-1-(4-phenoxybenzyl)piperidine-4-carboxamide hydrochloride TLC:Rf 0.71(chloroform:methanol=10:1);
NMR (CD$_3$OD): δ 0.89-1.00 (m, 5H), 1.18-1.71 (m, 13H), 1.92-2.00 (m, 5H), 2.92-3.55 (m, 6H), 3.51-3.55 (m, 2H), 4.28 (s, 2H), 7.02-7.07 (m, 4H), 7.18 (t, J=7.2 Hz, 1H), 7.37-7.42 (m, 2H), 7.47 (d, J=8.4 Hz, 2H).

Example 5(40)

1-benzyl-4-{[1-(4-phenoxybenzyl)piperidin-4-yl]carbonyl}piperazine dihydrochloride TLC:Rf 0.59(chloroform:methanol=10:1);
NMR (CD$_3$OD): δ 1.90-2.10 (m, 4H), 3.00-3.60 (m, 12H), 4.30 (s, 2H), 4.39 (s, 2H), 4.63 (m, 1H), 7.02-7.06 (m, 4H), 7.18 (t, J=7.0 Hz, 1H), 7.37-7.42 (m, 2H), 7.48-7.58 (m, 7H).

Example 5(41)

1-(cyclohexylmethyl)-4-{[1-(4-phenoxybenzyl)piperidin-4-yl]carbonyl}piperazine dihydrochloride TLC:Rf 0.62(chloroform:methanol=10:1);
NMR (CD$_3$OD): δ 1.02-1.43 (m, 5H), 1.70-2.01 (m, 10H), 3.03 (d, J=6.6 Hz, 2H), 3.03-3.69 (m, 12H), 4.31 (s, 2H), 4.59 (m, 1H), 7.02-7.07 (m, 4H), 7.18 (t, J=7.5 Hz, 1H), 7.37-7.42 (m, 2H), 7.50 (d, J=8.7 Hz, 2H).

Example 5(42)

N-butyl-1-(4-{4-[(methylsulfonyl)amino]phenoxy}benzyl)piperidine-4-carboxamide hydrochloride TLC:Rf 0.26(chloroform:methanol=10:1);
NMR (CD$_3$OD): δ 0.92 (t, J=7.2 Hz, 3H), 1.30-1.52 (m, 4H), 1.84-2.04 (m, 4H), 2.48 (m, 1H), 2.95 (s, 3H), 2.95-3.07 (m, 2H), 3.16 (t, J=7.2 Hz, 2H), 3.51-3.56 (m, 2H), 4.28 (s, 2H), 7.02-7.08 (m, 4H), 7.29 (d, J=9.0 Hz, 2H), 7.47 (d, J=8.7 Hz, 2H).

Example 5(43)

N-(cyclohexylmethyl)-1-(4-{4-[(methylsulfonyl)amino]phenoxy}benzyl)piperidine-4-carboxamide hydrochloride TLC:Rf 0.28(chloroform:methanol=10:1);
NMR (CD$_3$OD): δ 0.85-1.00 (m, 2H), 1.15-1.46 (m, 5H), 1.65-2.13 (m, 8H), 2.49 (m, 1H), 2.95 (s, 3H), 3.00 (d, J=7.0 Hz, 2H), 3.00-3.06 (m, 2H), 3.52-3.56 (m, 2H), 4.28 (s, 2H), 7.02-7.08 (m, 4H), 7.29 (d, J=8.7 Hz, 2H), 7.47 (d, J=8.4 Hz, 2H).

Example 5(44)

N-butyl-N-(cyclohexylmethyl)-1-(4-{4-[(methylsulfonyl)amino]phenoxy}benzyl)piperidine-4-carboxamide hydrochloride TLC:Rf 0.45 (chloroform:methanol=10:1);
NMR (CD$_3$OD): δ 0.89-1.00 (m, 5H), 1.21-2.00 (m, 18H), 2.95 (s, 3H), 3.00-3.36 (m, 6H), 3.51-3.54 (m, 2H), 4.27 (s, 2H), 7.02-7.08 (m, 4H), 7.29 (d, J=9.0 Hz, 2H), 7.47 (d, J=8.1 Hz, 2H).

Example 5(45)

N-{4-[4-({4-[(4-benzylpiperazin-1-yl)carbonyl]piperidin-1-yl}methyl)phenoxy]phenyl}methanesulfonamide dihydrochloride TLC:Rf 0.28(chloroform:methanol=10:1);
NMR (CD$_3$OD): δ 1.90-2.10 (m, 4H), 2.95 (s, 3H), 3.05-3.56 (m, 12H), 4.30 (s, 2H), 4.39 (s, 2H), 4.63 (m, 1H), 7.02-7.08 (m, 4H), 7.29 (d, J=9.0 Hz, 2H), 7.47-7.55 (m, 7H).

Example 5(46)

N-(4-{4-[(4-{[4-(cyclohexylmethyl)piperazin-1-yl]carbonyl}piperidin-1-yl)methyl]phenoxy}phenyl)methanesulfonamide dihydrochloride TLC:Rf 0.30(chloroform:methanol=10:1);
NMR (CD$_3$OD): δ 1.05-1.43 (m, 5H), 1.70-2.01 (m, 10H), 2.95 (s, 3H), 3.03 (d, J=6.9 Hz, 2H), 3.03-3.63 (m, 12H), 4.31 (s, 2H), 4.59 (m, 1H), 7.02-7.08 (m, 4H), 7.29 (d, J=9.0 Hz, 2H), 7.49 (d, J=8.7 Hz, 2H).

Example 5(47)

1-(cyclohexylmethyl)-4-[1-(4-phenoxybenzyl)piperidin-4-yl]piperazine-2-carboxylic acid trihydrochloride TLC:Rf 0.07(chloroform:methanol:acetic acid=10:1:1);
NMR (CD$_3$OD): δ 1.01-1.11 (m, 2H), 1.19-1.41 (m, 4H), 1.66-2.02 (m, 8H), 2.19-2.31 (m, 2H), 2.97-3.37 (m, 8H), 3.45-3.64 (m, 3H), 3.80 (m, 1H), 4.29 (s, 2H), 4.35 (s, 1H), 7.01-7.06 (m, 4H), 7.18 (t, J=8.0 Hz, 1H), 7.39 (t, J=8.0 Hz, 2H), 7.52 (d, J=9.0 Hz, 2H).

Example 5(48)

1-benzyl-4-[1-(4-phenoxybenzyl)piperidin-4-yl]piperazine-2-carboxylic acid trihydrochloride TLC:Rf 0.05(chloroform:methanol:acetic acid=10:1:1);
NMR (CD$_3$OD): δ 1.86-2.03 (m, 2H), 2.15-2.27 (m, 2H), 2.86-3.62 (m, 11H), 4.13-4.35 (m, 4H), 4.57 (d, J=12.5 Hz, 1H), 7.01-7.06 (m, 4H), 7.18 (t, J=7.5 Hz, 1H), 7.39 (t, J=8.0 Hz, 2H), 7.45-7.56 (m, 7H).

Example 5(49)

1-(cyclohexylcarbonyl)-4-[1-(4-phenoxybenzyl)piperidin-4-yl]piperazine-2-carboxylic acid dihydrochloride TLC:Rf 0.14(chloroform:methanol:acetic acid=10:1:1);
NMR (CD$_3$OD): δ 1.22-1.57 (m, 5H), 1.67-1.85 (m, 5H), 2.06-2.78 (m, 5H), 2.96-3.23 (m, 4H), 3.46-3.70 (m, 5H), 4.08 (m, 1H), 4.31 (m, 1H), 4.33 (s, 2H), 5.53 (s, 1H), 7.02-7.07 (m, 4H), 7.18 (t, J=7.5 Hz, 1H), 7.36-7.42 (m, 2H), 7.54 (d, J=8.5 Hz, 2H).

Example 5(50)

1-benzoyl-4-[1-(4-phenoxybenzyl)piperidin-4-yl]piperazine-2-carboxylic acid dihydrochloride TLC:Rf 0.09(chloroform:methanol:acetic acid=10:1:1);
NMR (CD$_3$OD): δ 1.92-2.41 (m, 4H), 2.87-3.95 (m, 11H), 4.31 (s, 2H), 5.53 (s, 1H), 7.02-7.07 (m, 4H), 7.18 (t, J=7.5 Hz, 1H), 7.36-7.42 (m, 2H), 7.45-7.54 (m, 7H).

Example 5(51)

4-(cyclohexylmethyl)-2-methyl-1-[1-(4-phenoxybenzyl)piperidin-4-yl]piperazine trihydrochloride TLC:Rf 0.18(chloroform:methanol=10:1);
NMR (CD$_3$OD): δ 0.97-1.13 (m, 2H), 1.20-1.44 (m, 3H), 1.55 (d, J=6.5 Hz, 3H), 1.65-1.95 (m, 6H), 2.08-2.47 (m, 4H), 3.10-3.28 (m, 4H), 3.40-4.21 (m, 10H), 4.33 (s, 2H), 7.02-7.07 (m, 4H), 7.18 (t, J=7.5 Hz, 1H), 7.37-7.42 (m, 2H), 7.53 (d, J=8.5 Hz, 2H).

Example 5(52)

4-benzyl-2-methyl-1-[1-(4-phenoxybenzyl)piperidin-4-yl]piperazine trihydrochloride TLC:Rf 0.20(chloroform:methanol=10:1);
NMR (CD$_3$OD): δ 1.48 (d, J=6.5 Hz, 3H), 2.01-2.38 (m, 4H), 3.12-3.25 (m, 2H), 3.38-3.72 (m, 8H), 3.92 (br s, 2H), 4.31 (s, 2H), 4.41 (d, J=13.0 Hz, 1H), 4.47 (d, J=13.0 Hz, 1H), 7.01-7.06 (m, 4H), 7.18 (t, J=7.5 Hz, 1H), 7.36-7.42 (m, 2H), 7.49-7.53 (m, 5H), 7.58-7.62 (m, 2H).

Example 5(53)

4-(cyclohexylcarbonyl)-2-methyl-1-[1-(4-phenoxybenzyl)piperidin-4-yl]piperazine dihydrochloride TLC:Rf 0.38(chloroform:methanol=10:1);
NMR (CD$_3$OD): δ 1.16-1.57 (m, 8H), 1.66-1.84 (m, 5H), 2.05-2.75 (m, 5H), 3.00-4.73 (m, 12H), 4.33 (s, 2H), 7.01-7.07 (m, 4H), 7.18 (t, J=7.5 Hz, 1H), 7.36-7.42 (m, 2H), 7.53 (d, J=8.5 Hz, 2H).

Example 5(54)

4-benzoyl-2-methyl-1-[1-(4-phenoxybenzyl)piperidin-4-yl]piperazine dihydrochloride TLC:Rf 0.40(chloroform:methanol=10:1);
NMR (CD$_3$OD): δ 1.29-1.55 (br, 3H, -Me), 2.07-2.54 (m, 4H), 3.09-4.17 (m, 12H), 4.33 (s, 2H), 7.01-7.07 (m, 4H), 7.18 (t, J=7.5 Hz, 1H), 7.36-7.42 (m, 2H), 7.46-7.55 (m, 7H).

Reference Example 4

N-(4-(4-bis(2-chloroethyl)aminomethylphenoxy)phenyl)methanesulfonamide

To a solution of 4-(4-methylsulfonylaminophenoxy)benzaldehyde (1.27 g) in dimethylformamide (5 mL)/acetic acid (0.5 mL) was added N,N-bis(2-chloroethyl)amine (856 mg) and the solution was stirred at room temperature for 10 minutes. Sodium triacetoxyborohydride (31.39 g) was added to the solution, which was stirred at room temperature overnight. Water was added to the reaction mixture, which was extracted with ethyl acetate three times. The extract was washed with brine (30 mL), dried over anhydrous sodium sulfate and concentrated. The obtained residue purified by column chromatography on silica gel (hexane:ethyl acetate=5:1) to give the title compound (790 mg) having the following physical data.

TLC:Rf 0.60(chloroform:methanol=9:1);

NMR (CDCl$_3$): δ 7.32 (brd, J=8.4 Hz, 2H), 7.22 (brd, J=8.7 Hz, 2H), 7.01 (brd, J=8.7 Hz, 2H), 6.96 (brd, J=8.4 Hz, 2H), 3.72 (s, 2H), 3.51 (t, J=7.2 Hz, 4H), 3.00 (s, 3H), 2.93 (t, J=7.2 Hz, 4H).

Example 6

1-(4-(4-methylsulfonylaminophenoxy)benzyl)-4-(1-methoxycarbonylpentyl)piperazine To a solution of the compound prepared in Reference Example 2 (266 mg) in dimethylformamide (3 mL) was added DL-norleucine methyl ester hydrochloride (117 mg). To the obtained solution was triethylamine (0.267 mL) and catalytic amount of sodium iodide and the solution was stirred at 60° C. overnight. Water was added to the reaction mixture, which was extracted with ethyl acetate three times. The extract was washed with brine (30 mL), dried over anhydrous sodium sulfate and concentrated to give the compound of the present invention (210 mg) having the following physical data.

TLC:Rf 0.67(chloroform:methanol=9:1);

NMR (CDCl$_3$): δ 7.32-7.24 (m, 2H), 7.20 (brd, J=9.0 Hz, 2H), 6.98 (brd, J=9.0 Hz, 2H), 6.94 (brd, J=9.0 Hz, 2H), 3.72 (s, 2H), 3.69 (s, 3H), 3.15 (dd, J=4.8, 3.6 Hz, 1H), 3.00 (s, 3H), 2.70-2.36 (m, 8H), 1.80-1.18 (m, 6H), 0.89 (t, J=5.4 Hz, 3H).

Example 7

2-[4-(4-{4-[(methylsulfonyl)amino]phenoxy}benzyl)piperazin-1-yl]hexanoic acid dihydrochloride

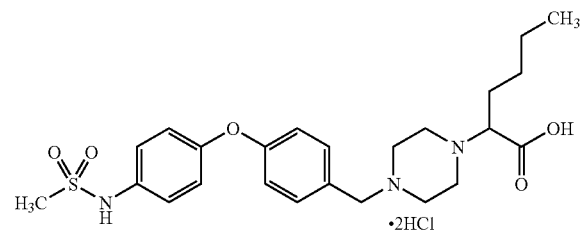

To a solution of the compound obtained in Example 6 (210 mg) in ethanol (5 mL) was added 2N aqueous solution of sodium hydroxide (0.215 mL) and the solution was stirred at 40° C. overnight. The reaction mixture was concentrated. The obtained residue was purified by column chromatography on silica gel (ethyl acetate:methanol=8:1) and converted to hydrochloride salt by a conventional method to give the compound of the present invention (141.6 mg) having the following physical data.

TLC:Rf 0.55 (chloroform:methanol=5:1);

NMR (CD$_3$OD): δ 7.53 (brd, J=8.7 Hz, 2H), 7.29 (brd, J=9.0 Hz, 2H), 7.06 (brd, J=8.7 Hz, 2H), 7.03 (brd, J=9.0 Hz, 2H), 4.37 (s, 2H), 3.75 (brt, J=6.3 Hz, 1H), 3.56-3.34 (m, 8H), 2.95 (s, 3H), 1.92-1.80 (m, 2H), 1.48-1.32 (m, 4H), 1.00-0.86 (m, 3H).

Example 8

N-cyclohexyl-2-[4-(4-{4-[(methylsulfonyl)amino]phenoxy}benzyl)piperazin-1-yl]hexanamide dihydrochloride To a solution of the compound prepared in Example 7 (46.7 mg) in dimethylformamide (2 mL) were added cyclohexylamine (16.8 μL), 1-ethyl-3-[3-(dimethylamino)propyl]carbodiimide hydrochloride (28.2 mg) and 1-hydroxybenztriazol (19.87 mg) and the solution was stirred at room temperature overnight. The reaction mixture was concentrated. The obtained residue was purified by column chromatography on silica gel (chloroform:methanol=9:1) and converted to hydrochloride salt by a conventional method to give the compound of the present invention (22.7 mg) having the following physical data.

TLC:Rf 0.75(chloroform:methanol=5:1);

NMR (CD$_3$OD): δ 7.49 (brd, J=8.7 Hz, 2H), 7.29 (brd, J=9.0 Hz, 2H), 7.05 (brd, J=9.0 Hz, 2H), 7.02 (brd, J=8.7 Hz, 2H), 4.30 (s, 2H), 3.68 (m, 1H), 3.50-3.00 (m, 8H), 2.95 (s, 3H), 1.90-1.58 (m, 8H), 1.44-1.12 (m, 9H), 0.92 (brt, J=7.5 Hz, 3H).

Example 9(1)-Example 9(3)

By the same procedure as described in Reference Example 4→Example 6→Example 7→Example 8, using 4-(4-methylsulfonylaminophenoxy)benzamide, DL-norleucine methyl ester and cyclohexylamine, or using a corresponding aldehyde derivative, amino acid derivative and amine derivative instead of them respectively, the following compounds of the present invention were obtained.

Example 9(1)

N-(cyclohexylmethyl)-2-[4-(4-{4-[(methylsulfonyl)amino]phenoxy}benzyl)piperazin-1-yl]hexanamide dihydrochloride TLC:Rf 0.82(chloroform:methanol=5:1);

NMR (CD$_3$OD): δ 7.53 (brd, J=8.7 Hz, 2H), 7.29 (brd, J=9.0 Hz, 2H), 7.06 (brd, J=9.0 Hz, 2H), 7.03 (brd, J=8.7 Hz, 2H), 4.37 (s, 2H), 3.61 (m, 1H), 3.60-3.28 (m, 8H), 3.15 (dd, J=7.5, 15.0 Hz, 1H), 2.99 (dd, J=7.5, 15.0 Hz, 1H), 2.95 (s, 3H), 1.90-1.62 (m, 6H), 1.58-1.16 (m, 9H), 1.04-0.88 (m, 2H), 0.93 (t, J=7.2 Hz, 3H).

Example 9(2)

N-cyclohexyl-2-[4-(4-{4-[(methylsulfonyl)amino]phenoxy}benzyl)piperazin-1-yl]pentanamide dihydrochloride TLC:Rf 0.78(chloroform:methanol=5:1);

NMR (CD$_3$OD): δ 7.52 (brd, J=6.6 Hz, 2H), 7.29 (brd, J=8.4 Hz, 2H), 7.10-7.01 (m, 4H), 4.36 (brs, J=2H), 3.69 (m, 1H), 3.60-3.20 (m, 9H), 2.95 (s, 3H), 1.92-1.70 (m, 6H), 1.65 (m, 1H), 1.46-1.14 (m, 7H), 0.97 (t, J=7.5 Hz, 3H).

Example 9(3)

2-(4-{4-[4-(aminosulfonyl)phenoxy]benzyl}piperazin-1-yl)-N-cyclohexylhexanamide dihydrochloride TLC:Rf 0.84(chloroform:methanol=5:1);

NMR (CD$_3$OD): δ 7.90 (brd, J=9.3 Hz, 2H), 7.63 (brd, J=11.4 Hz, 2H), 7.18 (brd, J=11.4 Hz, 2H), 7.13 (brd, J=9.3

Hz, 2H), 4.45 (s, 2H), 3.80-3.42 (m, 9H), 1.96-1.56 (m, 7H), 1.46-1.18 (m, 10H), 0.93 (t, J=7.2 Hz, 3H).

Reference Example 5 t-butyl 1-benzyloxycarbonyl-4-cyclohexylmethylaminocarbonylpiperidin-4-ylcarbamate To a solution of 1-benzyloxycarbonyl-4-(t-butoxycarbonylamino)piperidin-4-carboxylic acid (297 mg) in dimethylformamide (2.5 mL) were added 1-ethyl-3-[3-(dimethylamino)propyl]carbodiimide hydrochloride (226 mg), 4-N,N-dimethylaminopiperidine (144 mg) and cyclohexylmethylamine (0.15 mL) and the solution was stirred at room temperature overnight. Water was added to the reaction mixture, which was extracted with ethyl acetate. The extract was washed with brine, dried over anhydrous sodium sulfate and concentrated. The obtained residue was purified by column chromatography on silica gel (ethyl acetate:methanol=40:1-10:1) to give the title compound having the following physical data.
TLC:Rf 0.18(dichloromethane:methanol=5:1).

Reference Example 6 t-butyl 4-cyclohexylmethylaminocarbonylpiperidin-4-ylcarbamate

To a solution of the compound prepared in Reference Example 5 in methanol (3 mL) was added 5% palladium-carbon (15 mg). The reaction mixture was stirred at room temperature for 2 hours under an atmosphere of hydrogen. Under an atmosphere of argon, the reaction mixture was filtrated through CELITE (brand name). The filtrate was concentrated and the obtained residue was used in the next reaction without purification.

Example 10

1-(4-(4-methylsulfonylaminophenoxy)benzyl)-4-cyclohexylmethylaminocarbonyl-4-(t-butoxycarbonylamino)piperidine dihydrochloride To a solution of the compound prepared in Reference Example 6 in dimethylformamide (5 mL) and acetic acid (0.2 mL) were added 4-(4-methylsulfonylaminophenoxy)benzaldehyde (274 mg) and sodium triacetoxyborohydride (249 mg), and the solution was stirred at room temperature overnight. The reaction mixture was concentrated, purified by column chromatography on silica gel (ethyl acetate:methanol=50:1-40:1) and converted to hydrochloride salt by a conventional method to give the title compound (190 mg) having the following physical data.
TLC:Rf 0.49(dichloromethane:methanol=10:1);
NMR (CD$_3$OD): δ 7.35 (d, J=9.0 Hz, 2H), 7.25 (d, J=9.0 Hz, 2H), 6.98 (d, J=9.0 Hz, 2H), 6.96 (d, J=9.0 Hz, 2H), 3.69 (s, 2H), 3.01-2.99 (m, 2H), 2.93 (s, 3H), 2.88-2.85 (m, 2H), 2.53-2.44 (m, 2H), 2.16-2.02 (m, 4H), 1.75-1.64 (m, 6H), 1.43 (s, 9H), 1.28-1.18 (m, 3H), 0.96-0.89 (m, 2H).

Example 11

1-(4-(4-methylsulfonylaminophenoxy)benzyl)-4-cyclohexylmethylaminocarbonyl-4-aminopiperidine dihydrochloride To a solution of the compound prepared in Example 10 (190 mg) in tetrahydrofuran (3 mL) and dioxane (3 mL) was added 4N hydrogen chloride/ethyl acetate solution (9 mL) and the solution was stirred at room temperature overnight. The reaction mixture was concentrated to give the compound of the present invention having the following physical data. The compound was used in the next reaction without purification.
TLC:Rf 0.35 (methylene chloride:methanol=10:1).

Example 12(1) and Example 12(2)

To a solution of the compound prepared in Example 11 in dimethylformamide (3 mL) and acetic acid (0.1 mL) were added butanal (0.03 mL) and sodium triacetoxyborohydride (103 mg), and the solution was stirred at room temperature overnight. Water was added to the reaction mixture, which was extracted with ethyl acetate. The extract was washed with brine, dried over anhydrous sodium sulfate and concentrated. The obtained residue was purified by column chromatography on silica gel (ethyl acetate:methanol=50:1) and high performance thin layer chromatography (dichloromethane:methanol=10:1), and converted to hydrochloride salt by a conventional method to give the compound of the present invention having the following physical data.

Example 12(1)

4-(butylamino)-N-(cyclohexylmethyl)-1-(4-{4-[(methylsulfonyl)amino]phenoxy}benzyl)piperidine-4-carboxamide dihydrochloride

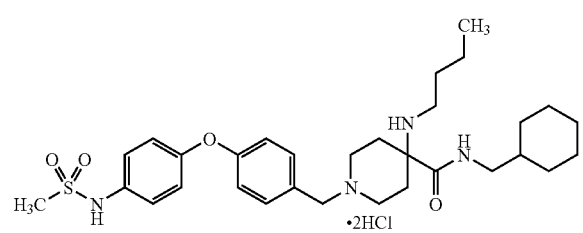

TLC:Rf 0.48(methylene chloride:methanol=10:1);
NMR (CD$_3$OD): δ 7.52 (d, J=9.0 Hz, 2H), 7.29 (d, J=9.0 Hz, 2H), 7.06 (d, J=9.0 Hz, 2H), 7.03 (d, J=9.0 Hz, 2H), 4.34 (s, 2H), 3.70-3.56 (m, 3H), 3.20-2.79 (m, 7H), 2.95 (s, 3H), 2.46-2.30 (m, 2H), 1.73-1.58 (m, 8H), 1.46-1.38 (m, 2H), 1.28-1.15 (m, 3H), 1.05-0.95 (m, 2H), 0.97 (t, J=7.2 Hz, 3H).

Example 12(2)

N-(cyclohexylmethyl)-4-(dibutylamino)-1-(4-{4-[(methylsulfonyl)amino]phenoxy}benzyl)piperidine-4-carboxamide dihydrochloride TLC:Rf 0.46(methylene chloride:methanol=10:1);
NMR (CD$_3$OD): δ 7.54 (d, J=8.7 Hz, 2H), 7.29 (d, J=8.7 Hz, 2H), 7.05 (d, J=8.7 Hz, 2H), 7.03 (d, J=8.7 Hz, 2H), 4.33 (s, 2H), 3.67-3.63 (m, 2H), 3.37-3.00 (m, 8H), 2.95 (s, 3H), 2.84-2.80 (m, 2H), 2.64-2.51 (m, 2H), 1.84-1.57 (m, 10H), 1.46-1.17 (m, 7H), 1.05-0.92 (m, 2H), 0.98 (t, J=7.2 Hz, 6H).

Example 13 methyl (2S)-2-{[4-[(butylamino)carbonyl]-1-(4-{4-[(methylsulfonyl)amino]phenoxy}benzyl)piperidin-4-yl]amino}-3-cyclohexylpropanoate hydrochloride

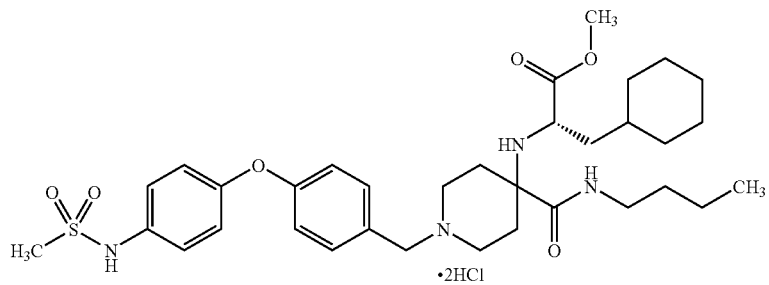

To a solution of the compound prepared in Example 2 (200 mg) in methanol (5.3 mL) were added L-cyclohexylalanin (91.4 mg), n-butylisocyanide (50.8 μL) and triethylamine (74.5 μL), and the solution was stirred at 65° C. for 12 hours. After cooling at 0° C., 4N hydrogen chloride/ethyl acetate solution (0.3 mL) was added thereto. The solution was stirred and concentrated. The obtained residue was purified by column chromatography on silica gel (ethyl acetate:methanol=8:1) and converted to hydrochloride salt by a conventional method to give the compound of the present invention (102.2 mg) having the following physical data.

TLC:Rf 0.55 (chloroform:methanol=9:1);
NMR (CD$_3$OD): δ 7.60-7.44 (m, 2H), 7.29 (brd, J=9.0 Hz, 2H), 7.09-6.96 (m, 4H), 4.31 (brs, 2H), 3.80-3.62 (m, 5H), 3.52-3.02 (m, 5H), 2.95 (s, 3H), 2.30-1.82 (m, 2H), 1.80-1.40 (m, 11H), 1.40-1.10 (m, 6H), 1.04-0.80 (m, 5H).

Example 14

1-(4-(4-methylsulfonylaminophenoxy)benzyl)piperidin-4-ylmethanol

To a solution of 4-piperidylmethanol (1.0 g) and 4-(4-methylsulfonylaminophenoxy)benzaldehyde (2.53 g) in dimethylformamide (10 mL) was added acetic acid (1.0 mL) and the solution was stirred at room temperature for 5 min. Sodium triacetoxyborohydride (2.75 g) was added to the reaction solution, which was stirred for 12 hours. Water (20 mL) and ethyl acetate (30 mL) were added to the reaction mixture, which was stirred and extracted with ethyl acetate three times. The organic layer was washed with brine (15 mL), dried over anhydrous sodium sulfate and concentrated. The obtained residue was purified by column chromatography on silica gel (hexane:ethyl acetate=1:1) to give the compound of the present invention (2.40 g) having the following physical data.

TLC:Rf 0.16(chloroform:methanol=5:1);
NMR (CDCl$_3$): δ 7.31-7.26 (m, 2H), 7.23-7.00 (m, 2H), 7.02-6.92 (m, 4H), 3.50 (d, J=6.3 Hz, 2H), 3.47 (s, 2H), 3.00 (s, 3H), 2.98-2.86 (m, 2H), 1.97 (td, J=11.7, 2.7 Hz, 2H), 1.79-1.64 (m, 2H), 1.50 (m, 1H), 1.36-1.20 (m, 2H).

Example 15

1-(4-(4-methylsulfonylaminophenoxy)benzyl)-4-piperidinylcarboxaldehyde

To a solution of the compound prepared in Example 14 (2.40 g) in methylene chloride (20 mL) were added triethylamine (3.43 mL) and dimethylsulfoxide (1.99 mL). Sulfur trioxide pyridine complex (1.96 g) was added to the reaction mixture, which was stirred at room temperature for 5 hours. Water was added to the reaction mixture, which was extracted with methylene chloride three times. The organic layer was wash with brine (20 mL), dried over anhydrous sodium sulfate and concentrated. The obtained residue was purified by column chromatography on silica gel (hexane:ethyl acetate=1:1) to give the compound of the present invention (3.04 g) having the following physical data.

TLC:Rf 0.32(chloroform:methanol=5:1);
NMR (CDCl$_3$): δ 9.65 (d, J=1.2 Hz, 1H), 7.32-7.24 (m, 2H), 7.24-7.18 (m, 2H), 7.02-6.90 (m, 4H), 3.47 (s, 2H), 3.00 (s, 3H), 2.82 (m, 2H), 2.26 (m, 2H), 2.11 (m, 2H), 1.90 (m, 2H), 1.71 (m, 2H).

Example 16

N-{4-[4-({4-[(5S)-1-butyl-5-(cyclohexylmethyl)-3,6-dioxopiperazin-2-yl]piperidin-1-yl}methyl)phenoxy]phenyl}methane sulfonamide hydrochloride

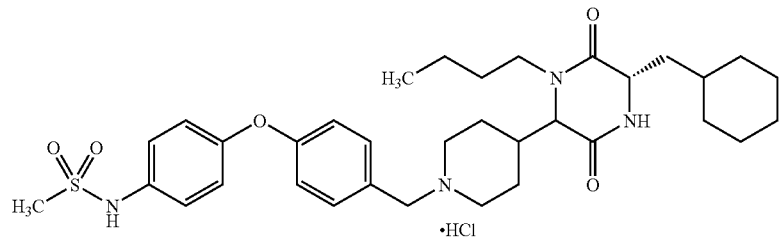

A solution of the compound prepared in Example 15 (500 mg), N-(t-butoxycarbonyl)-L-cyclohexylalanin (396 mg), n-butylamine (0.140 mL) and 2-morpholinoethylisocyanide (0.179 mL) in methanol (13 mL) was stirred at 65° C. for 12 hours. Concentrated hydrochloric acid (0.5 mL) was added to the reaction solution, which was stirred for 2 hours and concentrated. Methylene chloride (15 mL) and sodium hydrogen carbonate solution (15 mL) were thereto. The solution was stirred and extracted with methylene chloride twice. The organic layer was washed with brine (15 mL), dried over anhydrous sodium sulfate and concentrated. To the obtained residue was added 1.25M acetic acid/ethyl acetate solution (20 mL) and the solution was stirred at 70° C. for 12 hours. Ethyl acetate was added to the reaction solution, which was washed with water. Sodium hydrogen carbonate (15 mL) was added thereto, and the solution was stirred and extracted with ethyl acetate twice. The organic layer was washed with brine (15 mL), dried over anhydrous sodium sulfate and concentrated. The obtained residue was purified by column chromatography on silica gel (ethyl acetate:methanol=8:1) and converted to hydrochloride salt by a conventional method to give the compound of the present invention (470.4 mg) having the following physical data.

TLC:Rf 0.58(chloroform:methanol=5:1);
NMR (CD$_3$OD): δ 7.48 (brd, J=8.7 Hz, 2H), 7.29 (brd, J=8.7 Hz, 2H), 7.08-7.00 (m, 4H), 4.26 (s, 2H), 4.12 (m, 1:2 H), 4.04-3.92 (m, 1H), 3.88 (d, J=5.2 Hz, 1:2 H), 3.82 (d, J=6.0 Hz, 1:2 Hz), 3.80 (m, 1:2 H), 3.60-3.48 (m, 2H), 3.08-2.78 (m, 3H), 2.95 (s, 3H), 2.34-2.10 (m, 1H), 2.10-1.44 (m, 13H), 1.40-1.12 (m, 6H), 1.10-0.84 (m, 2H), 0.94 (t, J=7.2 Hz, 3:2 H), 0.93 (t, J=7.2 Hz, 3:2 H).

Example 16(1)-(3)

By the same procedure as described in Example 14→Example 15→Example 16 using a corresponding carboxylic acid and aldehyde instead of N-(t-butoxycarbonyl)-L-cyclohexylalanine and 4-(4-methylsulfonylaminophenoxy)benzaldehyde respectively, the compounds of the present invention having the following physical data were obtained.

Example 16(1)

N-(4-{4-[(4-{(5R)-1-butyl-5-[(R)-cyclohexyl(hydroxy)methyl]-3,6-dioxopiperazin-2-yl}piperidin-1-yl)methyl]phenoxy}phenyl)methanesulfonamide hydrochloride TLC:Rf 0.51(chloroform:methanol=5:1);
NMR (CD$_3$OD): δ 7.47 (brd, J=9.0 Hz, 2H), 7.29 (brd, J=9.0 Hz, 2H), 7.07-7.00 (m, 4H), 4.25 (s, 2H), 4.18 (m, 1H), 3.98-3.72 (m, 2H), 3.57-3.45 (m, 2H), 3.26 (m, 1H), 3.06-2.78 (m, 3H), 2.95 (s, 3H), 2.46-2.18 (m, 1H), 2.14-1.86 (m, 4H), 1.86-1.48 (m, 7H), 1.44-0.82 (m, 8H), 0.94 (t, J=7.2 Hz, 3H).

Example 16(2)

4-[4-({4-[(5S)-1-butyl-5-(cyclohexylmethyl)-3,6-dioxopiperazin-2-yl]piperidin-1-yl}methyl)phenoxy]benzoic acid hydrochloride TLC:Rf 0.53(chloroform:methanol=5:1);
NMR (CD$_3$OD): δ 8.04 (brd, J=8.7 Hz, 2H), 7.54 (brd, J=8.7 Hz, 2H), 7.16 (brd, J=8.7 Hz, 2H), 7.06 (brd, J=8.7 Hz, 2H), 4.30 (s, 2H), 4.12 (m, ½H), 4.05-3.92 (m, 1H), 3.92-3.76 (m, 3/2H), 3.61-3.46 (m, 2H), 3.10-2.78 (m, 3H), 2.36-1.92 (m, 5H), 1.90-1.44 (m, 10H), 1.40-1.14 (m, 5H), 1.04-0.82 (m, 5H).

Example 16(3)

4-{4-[(4-{(5R)-1-butyl-5-[(R)-cyclohexyl(hydroxy)methyl]-3,6-dioxopiperazin-2-yl}piperidin-1-yl)methyl]phenoxy}benzoic acid hydrochloride TLC:Rf 0.39(chloroform:methanol=5:1);
NMR (CD$_3$OD): δ 8.07-8.00 (m, 2H), 7.60-7.46 (m, 2H), 7.17 (brd, J=8.7 Hz, 2H), 7.10-7.00 (m, 2H), 4.30 (s, 2H), 4.21-4.14 (m, 1H), 4.00-3.74 (m, 2H), 3.72-3.46 (m, 2H), 3.26 (m, 1H), 3.09-2.84 (m, 3H), 2.50-2.20 (m, 2H), 2.16-1.88 (m, 5H), 1.88-1.48 (m, 6H), 1.44-0.84 (m, 10H).

Reference Example 7

1-benzyl-4-[N-(2-dimethoxyethyl)amino]piperidine

To a solution of 4-amino-1-benzylpiperidine (5 g) in dimethylformamide (100 mL) were added to dimethoxyacetoaldehyde (5.5 mL), sodium triacetoxyborohydride (8.36 g) and acetic acid (1.5 mL), and the solution was stirred overnight. Water was added to the reaction solution, which was extracted with ethyl acetate. The organic layer was washed with brine, dried over anhydrous sodium sulfate and concentrated. The obtained residue was purified by column chromatography on silica gel (ethyl acetate:methanol=40:1-1:1) to give the title compound (2.74 g) having the following physical data.

TLC:Rf 0.27 (dichloromethane:methanol=5:1)
NMR (CDCl$_3$): δ 7.31-7.20 (m, 5H), 4.46 (t, J=5.5 Hz, 1H), 3.50 (s, 2H), 3.38 (s, 6H), 2.87-2.83 (m, 2H), 2.74 (d, J=5.5 Hz, 2H), 2.45 (m, 1H), 2.07-1.98 (m, 2H), 1.86-1.82 (m, 2H), 1.46-1.34 (m, 2H).

Reference Example 8

1-benzyl-4-(N-(2-dimethoxyethyl)-N-(2-cyclohexylcarbonylaminoacetyl)amino)piperidine To a solution of the compound prepared in Reference Example 7 (2.74 g) in dimethylformamide (30 mL) were added 1-ethyl-3-[3-(dimethylamino)propyl]carbodiimide hydrochloride (2.82 g), 4-N,N-dimethylaminopyridine (2.4 g) and N-cyclohexylcarbonylglycin (2.0 g), and the solution was stirred at room temperature overnight. Water was added to the reaction solution, which was extracted with ethyl acetate. The organic layer was washed with brine, dried over anhydrous sodium sulfate and concentrated. The obtained residue was purified by column chromatography on silica gel (ethyl acetate:methanol=10:1) to give the title compound (1.45 g) having the following physical data.

TLC:Rf 0.36(ethyl acetate:methanol=10:1).

Reference Example 9

4-(N-(2-dimethoxyethyl)-N-(2-cyclohexylcarbonylaminoacetyl)amino)piperidine

To a solution of the compound prepared in Reference Example 7 (900 mg) in methanol (8 mL) was added palladium hydroxide on carbon (200 mg) and the solution was stirred at 50° C. for 3 hours under an atmosphere of hydrogen. After cooling, the reaction mixture was filtrated through CELITE (brand name) and the filtrate was concentrated to give the title compound. The compound was used in the next reaction without purification.

Example 17

1-(4-(4-methylsulfonylaminophenoxy)benzyl)-4-(N-(2-dimethoxyethyl)-N-(2-cyclohexylcarbonylaminoacetyl)amino)piperidine To a solution of the compound prepared in Reference Example 9 (300 mL) in dimethylformamide (5 mL)/acetic acid (0.2 mL) were added 4-(4-methylsulfonylaminophenoxy)benzaldehyde (270 mg) and sodium triacetoxyborohydride (268 mg) and the solution was stirred at room temperature overnight. The reaction mixture was concentrated and purified by column chromatography on silica gel (ethyl acetate:methanol=30:1-10:1) to give the title compound (223 mg) having the following physical data.

TLC:Rf 0.41 (ethyl acetate:methanol=10:1);
NMR (CDCl$_3$): δ 7.29-7.21 (m, 4H), 6.99 (d, J=9.0 Hz, 2H), 6.94 (d, J=9.0 Hz, 2H), 4.60 (t, J=5.5 Hz, 1H), 4.20 (m, 1H), 4.13 (dd, J=16.5, 4.0 Hz, 2H), 3.56-3.33 (m, 6H), 3.40 (s, 6H), 3.05-2.96 (m, 2H), 2.19-1.22 (m, 15H).

Example 18

N-{4-[4-({4-[4-(cyclohexylcarbonyl)-2-oxo-3,4-dihydropyrazin-1(2H)-yl]piperidin-1-yl}methyl)phenoxy]phenyl}methanesulfonamide hydrochloride

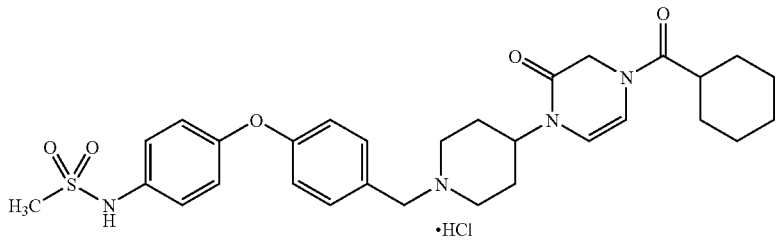

To a suspension of the compound prepared in Example 17 in toluene (9 mL) was added p-toluenesulfonic acid (20 mg) and the suspension was stirred and heated at 100° C. for 3 hours. After cooling, a saturated aqueous solution of sodium hydrogen carbonate was added to the reaction mixture, which was extracted with ethyl acetate. The organic layer was washed with brine, dried over anhydrous sodium sulfate and concentrated. The obtained residue was purified by column chromatography on silica gel (ethyl acetate:methanol=30:1) and high performance thin layer chromatography (dichloromethane:methanol=15:1), and converted to hydrochloride salt by a conventional method to give the compound of the present invention (20 mg) having the following physical data.

TLC:Rf 0.78(methylene chloride:methanol=10:1);
NMR (CD$_3$OD): δ 7.50 (d, J=9.0 Hz, 2H), 7.29 (d, J=9.0 Hz, 2H), 7.06 (d, J=9.0 Hz, 2H), 7.03 (d, J=9.0 Hz, 2H), 6.60 (d, J=6.0 Hz, 1H), 5.86 (d, J=6.0 Hz, 1H), 4.58 (m, 1H), 4.30 (s, 2H), 4.27 (s, 2H), 3.61-3.57 (m, 2H), 3.20-3.12 (m, 2H), 2.95 (s, 3H), 2.26-1.21 (m, 15H).

Example 18(1)

1-(1-benzylpiperidin-4-yl)-4-(cyclohexylcarbonyl)-3,4-dihydropyrazin-2(1H)-one hydrochloride By the same procedure as described in Example 18 using the compound prepared in Reference Example 8 instead of the compound prepared in Reference Example 17, the compound of the present invention having the following physical data was obtained.

TLC:Rf 0.53 (methylene chloride:methanol=10:1);
NMR (CD$_3$OD): δ 7.52 (s, 5H), 6.60 (d, J=6.0 Hz, 1H), 5.84 (d, J=6.0 Hz, 1H), 4.58 (m, 1H), 4.33 (s, 2H), 4.27 (s, 2H), 3.6-3.56 (m, 2H), 3.22-3.14 (m, 2H), 2.69 (m, 1H), 2.19-1.29 (m, 14H).

Example 19

E-form: 4-[4-({4-[(E)-(4-bromophenyl)(ethoxyimino)methyl]piperidin-1-yl}methyl)phenoxy]benzoic acid hydrochloride Z-form: 4-[4-({4-[(Z)-(4-bromophenyl)(ethoxyimino)methyl]piperidin-1-yl}methyl)phenoxy]benzoic acid hydrochloride To a solution of the compound prepared in Example 5(15) (912 mg) in ethanol (10 mL) were added pyridine (5 mL) and O-ethylhydroxyamine hydrochloride (340 mg) and the solution was refluxed for 3 hours. After finishing the reaction, the reaction solution was concentrated. Water and 2N hydrochloric acid were added thereto and the solution was extracted with ethyl acetate. The organic layer was washed with brine and concentrated. The obtained residue was purified by column chromatography on silica gel (ethyl acetate:methanol=25:1) and 4N hydrogen chloride/ethyl acetate solution was added to the obtained residue, which was concentrated to give the compound of the present invention (E-form: 409 mg, Z-form: 500 mg) having the following physical data.

E-Form:
TLC:Rf 0.37(chloroform:methanol=10:1);
NMR (CD$_3$OD): δ 1.29 (t, J=7.0 Hz, 3H), 1.90-2.00 (m, 2H), 2.14-2.28 (m, 2H), 2.86-2.96 (m, 2H), 3.38-3.48 (m, 3H), 4.16 (s, 2H), 4.18 (q, J=7.0 Hz, 2H), 7.02 (d, J=9.0 Hz, 2H), 7.11 (d, J=9.0 Hz, 2H), 7.36 (d, J=9.0 Hz, 2H), 7.50 (d, J=9.0 Hz, 2H), 7.52 (d, J=9.0 Hz, 2H), 8.00 (d, J=9.0 Hz, 2H).

Z-Form:
TLC:Rf 0.35(chloroform:methanol=10:1);
NMR (CD$_3$OD): δ 1.16 (t, J=7.0 Hz, 3H), 1.76-1.91 (m, 2H), 2.03-2.14 (m, 2H), 2.89 (m, 1H), 3.02-3.11 (m, 2H), 3.50-3.58 (m, 2H), 4.03 (q, J=7.0 Hz, 2H), 4.31 (s, 2H), 7.06 (d, J=9.0 Hz, 2H), 7.16 (d, J=9.0 Hz, 2H), 7.25 (d, J=9.0 Hz, 2H), 7.55 (d, J=9.0 Hz, 2H), 7.57 (d, J=9.0 Hz, 2H), 8.03 (d, J=9.0 Hz, 2H).

Example 20(1)-Example 20(79)

By the same procedure as described in Example 1 and the conversion to hydrochloride salt by a conventional method, using a corresponding amine derivative instead of 4-hydroxypiperidine, and using 4-(4-methylsulfonylaminophenoxy)

Example 20(1)

N-benzyl-1-(4-{4-[(methylsulfonyl)amino]phenoxy}benzyl)-4-piperidinecarboxamide hydrochloride

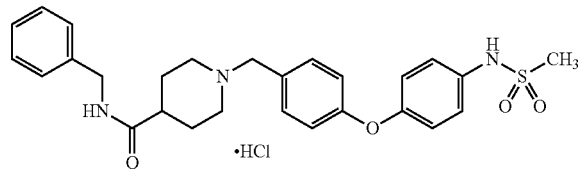

TLC:Rf 0.67(methylene chloride:methanol=5:1);
NMR (CD₃OD): δ 1.92-2.03 (m, 4H), 2.51 (m, 1H), 2.82-2.92 (m, 2H), 2.95 (s, 3H), 3.40-3.44 (m, 2H), 4.15 (s, 2H), 4.35 (s, 2H), 7.02 (d, J=8.7 Hz, 2H), 7.04 (d, J=8.7 Hz, 2H), 7.23-7.33 (m, 7H), 7.45 (d, J=8.7 Hz, 2H).

Example 20(2)

4-[4-({4-[(cyclohexylacetyl)amino]-1-piperidinyl}methyl)phenoxy]benzoic acid hydrochloride TLC:Rf 0.37(methylene chloride:methanol=5:1);
NMR (CD₃OD): δ 0.94-1.00 (m, 2H), 1.14-1.30 (m, 4H), 1.60-1.80 (m, 6H), 1.99-2.17 (m, 5H), 3.08-3.16 (m, 2H), 3.52-3.56 (m, 2H), 3.92 (m, 1H), 4.31 (s, 2H), 7.07 (d, J=8.7 Hz, 2H), 7.18 (d, J=8.7 Hz, 2H), 7.56 (d, J=8.7 Hz, 2H), 8.04 (d, J=8.7 Hz, 2H).

Example 20(3)

4-[4-({4-[(benzylamino)carbonyl]-1-piperidinyl}methyl)phenoxy]benzoic acid hydrochloride TLC:Rf 0.26(methylene chloride:methanol=5:1);
NMR (CD₃OD): δ 1.90-2.08 (m, 4H), 2.56 (m, 1H), 2.99-3.07 (m, 2H), 3.48-3.53 (m, 2H), 4.28 (s, 2H), 4.36 (s, 2H), 7.06 (d, J=8.7 Hz, 2H), 7.16 (d, J=8.4 Hz, 2H), 7.21-7.34 (m, 5H), 7.54 (d, J=8.4 Hz, 2H), 8.03 (d, J=8.7 Hz, 2H).

Example 20(4)

4-[4-({4-[(butylamino)carbonyl]-1-piperidinyl}methyl)phenoxy]benzoic acid hydrochloride TLC:Rf 0.20(methylene chloride:methanol=5:1);
NMR (CD₃OD): δ 0.93 (t, J=7.2 Hz, 3H), 1.28-1.53 (m, 4H), 1.95-2.00 (m, 4H), 2.51 (m, 1H), 3.06-3.20 (m, 4H), 3.51-3.53 (m, 2H), 4.32 (s, 2H), 7.07 (d, J=9.0 Hz, 2H), 7.17 (d, J=8.5 Hz, 2H), 7.55 (d, J=8.5 Hz, 2H), 8.04 (d, J=9.0 Hz, 2H).

Example 20(5)

4-{4-[(4-{[(cyclohexylmethyl)amino]carbonyl}-1-piperidinyl)methyl]phenoxy}benzoic acid hydrochloride TLC:Rf 0.21(methylene chloride:methanol=5:1);
NMR (CD₃OD): δ 0.87 (m, 2H), 1.19-1.31 (m, 3H), 1.46 (m, 1H), 1.64-1.73 (m, 5H), 1.90-2.06 (m, 4H), 2.52 (m, 1H), 3.00-3.09 (m, 4H), 3.53-3.58 (m, 2H), 4.33 (s, 2H), 7.07 (d, J=9.0 Hz, 2H), 7.18 (d, J=8.7 Hz, 2H), 7.56 (d, J=8.7 Hz, 2H), 8.04 (d, J=9.0 Hz, 2H).

Example 20(6)

N-(cyclohexylmethyl)-4-hydroxy-1-(4-{4-[(methylsulfonyl)amino]phenoxy}benzyl)-4-piperidinecarboxamide hydrochloride TLC:Rf 0.36(chloroform:methanol=5:1);
NMR (CD₃OD): δ 0.82-1.02 (m, 2H), 1.12-1.36 (m, 4H), 1.49 (m, 1H), 1.60-1.88 (m, 6H), 2.31 (m, 2H), 2.95 (s, 3H), 3.04 (brt, J=6.6 Hz, 2H), 3.22-3.45 (m, 4H), 4.32 (s, 2H), 6.98-7.01 (m, 4H), 7.29 (brd, J=9.0 Hz, 2H), 7.50 (brd, J=9.0 Hz, 2H), 8.09 (m, 1H).

Example 20(7)

N-(cyclohexylmethyl)-4-methoxy-1-(4-{4-[(methylsulfonyl)amino]phenoxy}benzyl)-4-piperidinecarboxamide hydrochloride TLC:Rf 0.50(chloroform:methanol=5:1);
NMR (CD₃OD): δ 0.80-1.04 (m, 2H), 1.18-1.40 (m, 4H), 1.50 (m, 1H), 1.60-1.90 (m, 6H), 2.30 (m, 2H), 2.91 (s, 3H), 3.04 (m, 2H), 3.20-3.52 (m, 7H), 4.33 (s, 2H), 7.02-7.18 (m, 4H), 7.45 (brt, J=9.0 Hz, 2H), 7.53 (brt, J=8.7 Hz, 2H), 8.08 (m, 1H).

Example 20(8)

N-[4-(4-{[4-(cyclohexylcarbonyl)-1-piperazinyl]methyl}phenoxy)phenyl]methanesulfonamide hydrochloride TLC:Rf 0.89(chloroform:methanol=5:1);
NMR (CD₃OD): δ 1.18-1.56 (m, 5H), 1.64-1.85 (m, 5H), 2.65 (m, 1H), 2.95 (m, 3H), 2.90-3.20 (m, 3H), 3.32-3.58 (m, 3H), 4.28 (m, 1H), 4.35 (s, 2H), 4.67 (m, 1H), 7.00-7.12 (m, 4H), 7.29 (brd, J=9.0 Hz, 2H), 7.52 (brd, J=8.7 Hz 2H).

Example 20(9)

N-[4-(4-{[4-(cyclohexylacetyl)-1-piperazinyl]methyl}phenoxy)phenyl]methanesulfonamide hydrochloride TLC:Rf 0.85(chloroform:methanol=5:1);
NMR (CD₃OD): δ 0.90-1.06 (m, 2H), 1.08-1.40 (m, 3H), 1.60-1.80 (m, 6H), 2.31 (brd, J=6.0 Hz, 2H), 2.95 (s, 3H), 2.86-3.18 (m, 3H), 3.36-3.60 (m, 3H), 4.21 (m, 1H), 4.35 (s, 2H), 4.69 (m, 1H), 7.00-7.12 (m, 4H), 7.29 (brd, J=9.0 Hz, 2H), 7.51 (brd, J=8.7 Hz, 2H).

Example 20(10)

N-(cyclohexylmethyl)-4-methyl-1-(4-{4-[(methyl-sulfonyl)amino]phenoxy}benzyl)-4-piperidinecarboxamide hydrochloride TLC:Rf 0.67(chloroform:methanol=5:1);
NMR (CD$_3$OD): δ 0.80-1.00 (m, 2H), 1.12-1.32 (m, 4H), 1.49 (m, 1H), 1.62-1.80 (m, 6H), 2.22-2.34 (m, 2H), 2.95 (s, 6H), 2.96-3.08 (m, 2H), 3.24-3.38 (m, 4H), 4.22 (s, 2H), 6.98-7.10 (m, 4H), 7.29 (brd, J=9.3 Hz, 2H), 7.46 (brd, J=8.7 Hz, 2H), 7.81 (m, 1H).

Example 20(11)

4-butoxy-N-(cyclohexylmethyl)-1-(4-{4-[(methyl-sulfonyl)amino]phenoxy}benzyl)-4-piperidinecarboxamide hydrochloride TLC:Rf 0.87(chloroform:methanol=5:1);
NMR (CD$_3$OD): δ 0.95 (t, J=7.2 Hz, 3H), 0.82-1.04 (m, 2H), 1.10-1.58 (m, 7H), 1.58-1.78 (m, 6H), 2.06-2.24 (m, 4H), 2.95 (s, 3H), 3.05 (t, J=3.0 Hz, 2H), 3.08-3.44 (m, 6H), 4.32 (s, 2H), 7.00-7.12 (m, 4H), 7.29 (brd, J=8.7 Hz, 2H), 7.50 (brd, J=8.7 Hz, 2H), 8.00 (m, 1H).

Example 20(12)

N-cyclohexyl-4-(4-{4-[(methylsulfonyl)amino]phenoxy}benzyl)-1-piperazinecarboxamide hydrochloride TLC:Rf 0.77(chloroform:methanol=5:1);
NMR (CD$_3$OD): δ 1.08-1.44 (m, 5H), 1.58-1.92 (m, 5H), 2.95 (s, 3H), 2.95-3.60 (m, 9H), 4.31 (s, 2H), 7.00-7.12 (m, 4H), 7.29 (brd, J=9.3 Hz, 2H), 7.49 (brd, J=8.4 Hz, 2H).

Example 20(13)

N-benzyl-4-(4-{4-[(methylsulfonyl)amino]phenoxy}benzyl)-1-piperazinecarboxamide hydrochloride TLC:Rf 0.73(chloroform:methanol=5:1);
NMR (CD$_3$OD): δ 2.95 (s, 3H), 3.22 (m, 4H), 3.70 (m, 4H), 4.28 (s, 2H), 4.35 (s, 2H), 7.00-7.08 (m, 4H), 7.18-7.36 (m, 7H), 7.44-7.56 (m, 2H).

Example 20(14)

4-(4-{4-[(methylsulfonyl)amino]phenoxy}benzyl)-N-phenyl-1-piperazinecarboxamide hydrochloride TLC:Rf 0.73(chloroform:methanol=5:1);
NMR (CD$_3$OD): δ 2.95 (s, 3H), 3.10-3.42 (m, 8H), 4.29 (s, 2H), 7.00-7.10 (m, 5H), 7.21-7.40 (m, 6H), 7.49 (brd, J=8.4 Hz, 2H).

Example 20(15)

N-[4-(4-{[4-(cyclohexylacetyl)-1-piperidinyl]methyl}phenoxy)phenyl]methanesulfonamide hydrochloride TLC:Rf 0.59(chloroform:methanol=5:1);
NMR (CD$_3$OD): δ 0.80-1.02 (m, 2H), 1.08-1.40 (m, 3H), 1.60-1.90 (m, 8H), 2.04-2.20 (m, 2H), 2.41 (d, J=6.9 Hz, 2H), 2.72 (m, 1H), 2.95 (s, 3H), 3.05 (m, 2H), 3.48 (m, 2H), 4.27 (s, 2H), 7.00-7.10 (m, 4H), 7.29 (brd, J=9.0 Hz, 2H), 7.48 (brd, J=9.0 Hz, 2H).

Example 20(16)

N-(4-{4-[(4-hydroxy-1-piperidinyl)methyl]phenoxy}phenyl)methanesulfonamide hydrochloride TLC:Rf 0.38(methylene chloride:methanol=5:1);
NMR (CD$_3$OD): δ 1.71-2.16 (m, 4H), 2.95 (s, 3H), 3.06-3.53 (m, 4H), 4.08 (m, 1H), 4.27 (s, 2H), 7.03 (d, J=9.0 Hz, 2H), 7.06 (d, J=9.0 Hz, 2H), 7.29 (d, J=9.0 Hz, 2H), 7.48 (d, J=9.0 Hz, 2H).

Example 20(17)

1-(4-{4-[(methylsulfonyl)amino]phenoxy}benzyl)-4-piperidinecarboxamide hydrochloride TLC:Rf 0.36(methylene chloride:methanol=5:1);
NMR (CD$_3$OD): δ 1.83-2.21 (m, 4H), 2.54 (m, 1H), 2.95 (s, 3H), 2.98-3.06 (m, 2H), 3.52-3.56 (m, 2H), 4.28 (s, 2H), 7.03 (d, J=8.7 Hz, 2H), 7.06 (d, J=8.7 Hz, 2H), 7.29 (d, J=8.7 Hz, 2H), 7.48 (d, J=8.7 Hz, 2H).

Example 20(18)

benzyl 1-(4-{4-[(methylsulfonyl)amino]phenoxy}benzyl)-4-piperidinecarboxylate hydrochloride TLC:Rf 0.36(methylene chloride:methanol=10:1);
NMR (CD$_3$OD): δ 1.85-1.94 (m, 2H), 2.06-2.12 (m, 2H), 2.60-2.78 (m, 3H), 2.94 (s, 3H), 3.20-3.25 (m, 2H), 3.99 (s, 2H), 5.14 (s, 2H), 6.99-7.02 (m, 4H), 7.27 (d, J=8.7 Hz, 2H), 7.32-7.36 (m, 5H), 7.40 (d, J=8.7 Hz, 2H).

Example 20(19)

t-butyl 1-(4-{4-[(methylsulfonyl)amino]phenoxy}benzyl)-4-piperidinylcarbamate

TLC:Rf 0.35(methylene chloride:methanol=10:1);
NMR (CD$_3$OD): δ 1.42 (s, 9H), 1.42-1.53 (m, 2H), 1.81-1.85 (m, 2H), 2.07-2.14 (m, 2H), 2.83-2.87 (m, 2H), 2.93 (s, 3H), 3.30-3.36 (m, 1H), 3.49 (s, 2H), 6.93 (d, J=8.7 Hz, 2H), 6.97 (d, J=8.7 Hz, 2H), 7.24 (d, J=8.7 Hz, 2H), 7.30 (d, J=8.7 Hz, 2H).

Example 20(20)

N-{4-[4-(1-piperidinylmethyl)phenoxy]phenyl}methanesulfonamide hydrochloride

TLC:Rf 0.34(methylene chloride:methanol=10:1);
NMR (CD$_3$OD): δ 1.48-1.97 (m, 6H), 2.90-2.99 (m, 2H), 2.95 (s, 3H), 3.42-3.46 (m, 2H), 4.25 (s, 2H), 7.03 (d, J=8.7 Hz, 2H), 7.06 (d, J=8.7 Hz, 2H), 7.29 (d, J=8.7 Hz, 2H), 7.47 (d, J=8.7 Hz, 2H).

Example 20(21)

N-[1-(4-{4-[(methylsulfonyl)amino]phenoxy}benzyl)-4-piperidinyl]-2-tetrahydro-2H-pyran-4-ylacetamide hydrochloride TLC:Rf 0.17(ethyl acetate:methanol=5:1);
NMR (CD$_3$OD): δ 1.20-1.40 (m, 2H), 1.54-1.64 (m, 2H), 1.67-1.84 (m, 2H), 1.88-2.21 (m, 5H), 2.95 (s, 3H), 3.06-3.18

(m, 2H), 3.30-3.46 (m, 2H), 3.46-3.56 (m, 2H), 3.85-3.97 (m, 3H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 20(22)

1-(4-{4-[(methylsulfonyl)amino]phenoxy}benzyl)-N-(tetrahydro-2H-pyran-4-ylmethyl)-4-piperidinecarboxamide hydrochloride TLC:Rf 0.18(ethyl acetate:methanol=5:1);
NMR (CD$_3$OD): δ 1.18-1.32 (m, 2H), 1.56-1.64 (m, 2H), 1.73 (m, 1H), 1.84-2.10 (m, 4H), 2.53 (m, 1H), 2.95 (s, 3H), 2.96-3.11 (m, 4H), 3.28-3.42 (m, 2H), 3.49-3.58 (m, 2H), 3.87-3.96 (m, 2H), 4.29 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 20(23)

4-methyl-N-[1-(4-{4-[(methylsulfonyl)amino]phenoxy}benzyl)-4-piperidinyl]benzenesulfonamide hydrochloride TLC:Rf 0.65(chloroform:methanol=5:1);
NMR (CD$_3$OD): δ 1.56-1.76 (m, 2H), 1.84-2.04 (m, 2H), 2.41 (s, 3H), 2.95 (s, 3H), 3.00 (m, 1H), 3.14-3.45 (m, 4H), 4.20 (s, 2H), 6.98-7.10 (m, 4H), 7.22-7.34 (m, 2H), 7.38-7.52 (m, 4H), 7.72-7.80 (m, 2H).

Example 20(24)

N-{[1-(4-{4-[(methylsulfonyl)amino]phenoxy}benzyl)-4-piperidinyl]carbonyl}benzenesulfonamide hydrochloride TLC:Rf 0.44(chloroform:methanol=5:1);
NMR (CD$_3$OD): δ 1.68-1.86 (m, 2H), 1.92-2.10 (m, 2H), 2.53 (m, 1H), 2.95 (s, 3H), 2.90-3.04 (m, 2H), 3.42-3.54 (m, 2H), 4.26 (s, 2H), 6.98-7.06 (m, 4H), 7.22-7.36 (m, 2H), 7.40-7.50 (m, 2H), 7.52-7.62 (m, 2H), 7.68 (m, 1H), 8.00 (brd, J=7.5 Hz, 2H).

Example 20(25)

N-[1-(4-{4-[(methylsulfonyl)amino]phenoxy}benzyl)-4-piperidinyl]methanesulfonamide hydrochloride TLC:Rf 0.78(chloroform:methanol=5:1);
NMR (CD$_3$OD): δ 1.70-1.92 (m, 2H), 2.08-2.26 (m, 2H), 2.95 (s, 3H), 2.98 (s, 3H), 3.00-3.18 (m, 2H), 3.28-3.46 (m, 2H), 3.54 (m, 1H), 4.22 (s, 2H), 6.98-7.10 (m, 4H), 7.26-7.34 (m, 2H), 7.42-7.56 (m, 2H).

Example 20(26)

4-[(cyclohexylcarbonyl)amino]-1-(4-{4-[(methylsulfonyl)amino]phenoxy}benzyl)-4-piperidinecarboxylic acid hydrochloride TLC:Rf 0.20(chloroform:methanol:acetic acid=20:4:1);
NMR (CD$_3$OD): δ 1.18-1.48 (m, 6H), 1.63-1.86 (m, 4H), 2.16-2.42 (m, 5H), 2.95 (s, 3H), 3.00-3.14 (m, 2H), 3.26-3.41 (m, 2H), 4.23 (s, 2H), 7.00-7.10 (m, 4H), 7.28 (brd, J=9.0 Hz, 2H), 7.47 (brd, J=8.7 Hz, 2H).

Example 20(27)

4-cyclohexyl-N-[1-(4-{4-[(methylsulfonyl)amino]phenoxy}benzyl)-4-piperidinyl]butanamide hydrochloride TLC:Rf 0.58(methanol:methylene chloride=1:8);
NMR (CD$_3$OD): δ 0.80-0.96 (m, 2H), 1.12-1.30 (m, 6H), 1.54-1.84 (m, 9H), 2.00-2.18 (m, 4H), 2.95 (s, 3H), 3.03-3.14 (m, 2H), 3.46-3.56 (m, 2H), 3.89 (m, 1H), 4.28 (s, 2H), 7.03 (d, J=8.7 Hz, 2H), 7.05 (d, J=8.7 Hz, 2H), 7.29 (d, J=8.7 Hz, 2H), 7.50 (d, J=8.7 Hz, 2H).

Example 20(28)

3-cyclohexyl-N-[1-(4-{4-[(methylsulfonyl)amino]phenoxy}benzyl)-4-piperidinyl]propanamide hydrochloride TLC:Rf 0.52(methanol:methylene chloride=1:8);
NMR (CD$_3$OD): δ 0.83-0.98 (m, 2H), 1.12-1.53 (m, 4H), 1.48 (dd, J=6.6, 15.0 Hz, 2H), 1.60-1.78 (m, 7H), 2.04-2.24 (m, 4H), 2.95 (s, 3H), 3.02-3.24 (m, 2H), 3.35-3.58 (m, 2H), 3.90 (m, 1H), 4.27 (s, 2H), 7.03 (d, J=8.7 Hz, 2H), 7.06 (d, J=8.7 Hz, 2H), 7.29 (d, J=8.7 Hz, 2H), 7.48 (d, J=8.7 Hz, 2H).

Example 20(29)

N-[1-({1-[4-(aminosulfonyl)phenyl]-3,5-dimethyl-1H-pyrazol-4-yl}methyl)-4-piperidinyl]-2-cyclohexylacetamide dihydrochloride TLC:Rf 0.30(methylene chloride:methanol=10:1);
NMR (CD$_3$OD): δ 0.90-1.10 (m, 2H), 1.10-1.40 (m, 3H), 1.60-1.90 (m, 8H), 2.05 (d, J=6.6 Hz, 2H) 2.10-2.20 (m, 2H), 2.39 (s, 3H), 2.44 (s, 3H), 3.10-3.30 (m, 2H), 3.60-3.70 (m, 2H), 3.90 (m, 1H), 4.26 (s, 2H), 7.70 (d, J=7.7 Hz, 2H), 8.07 (d, J=7.7 Hz, 2H).

Example 20(30)

2-cyclohexyl-N-{1-[(1-{4-[(cyclohexylamino)sulfonyl]phenyl}-3,5-dimethyl-1H-pyrazol-4-yl)methyl]-4-piperidinyl}acetamide dihydrochloride TLC:Rf 0.46(methylene chloride:methanol=10:1);
NMR (CD$_3$OD): δ 0.90-1.10 (m, 2H), 1.10-1.40 (m, 8H), 1.60-1.90 (m, 13H), 2.05 (d, J=7.2 Hz, 2H) 2.10-2.30 (m, 2H), 2.39 (s, 3H), 2.44 (s, 3H), 3.00-3.20 (m, 3H), 3.60-3.70 (m, 2H), 3.93 (m, 1H), 4.26 (s, 2H), 7.71 (d, J=8.7 Hz, 2H), 8.03 (d, J=8.7 Hz, 2H).

Example 20(31)

2-cyclohexyl-N-[1-({1-[4-({[2-(dimethylamino)ethyl]amino}sulfonyl)phenyl]-3,5-dimethyl-1H-pyrazol-4-yl}methyl)-4-piperidinyl]acetamide trihydrochloride TLC:Rf 0.08(methylene chloride:methanol=10:1);
NMR (CD$_3$OD): δ 0.90-1.10 (m, 2H), 1.10-1.40 (m, 3H), 1.60-1.90 (m, 8H), 2.05 (d, J=6.9 Hz, 2H) 2.10-2.30 (m, 2H), 2.39 (s, 3H), 2.47 (s, 3H), 2.95 (s, 6H), 3.10-3.20 (m, 6H), 3.60-3.70 (m, 2H), 3.90 (m, 1H), 4.26 (s, 2H), 7.78 (d, J=8.9 Hz, 2H), 8.07 (d, J=8.9 Hz, 2H).

Example 20(32)

2-cyclohexyl-N-[1-({3,5-dimethyl-1-[4-({[2-(4-morpholinyl)ethyl]amino}sulfonyl)phenyl]-1H-pyrazol-4-yl}methyl)-4-piperidinyl]acetamide trihydrochloride TLC:Rf 0.39(methylene chloride:methanol=10:1);
NMR (CD$_3$OD): δ 0.90-1.10 (m, 2H), 1.10-1.40 (m, 3H), 1.60-1.90 (m, 8H), 2.05 (d, J=7.2 Hz, 2H) 2.10-2.30 (m, 2H), 2.39 (s, 3H), 2.46 (s, 3H), 3.10-3.40 (m, 8H), 3.50-3.70 (m, 4H), 3.80-3.90 (m, 3H), 4.10-4.20 (m, 2H), 4.26 (s, 2H), 7.77 (d, J=8.7 Hz, 2H), 8.07 (d, J=8.7 Hz, 2H).

Example 20(33)

2-cyclohexyl-N-{1-[(1-{4-[(dimethylamino)sulfonyl]phenyl}-3,5-dimethyl-1H-pyrazol-4-yl)methyl]-4-piperidinyl}acetamide dihydrochloride TLC:Rf 0.53(methylene chloride:methanol=10:1);
NMR (CD$_3$OD): δ 0.90-1.10 (m, 2H), 1.10-1.40 (m, 3H), 1.60-1.90 (m, 8H), 2.05 (d, J=6.9 Hz, 2H) 2.10-2.30 (m, 2H), 2.39 (s, 3H), 2.46 (s, 3H), 2.74 (s, 6H), 3.10-3.20 (m, 2H), 3.60-3.70 (m, 2H), 3.90 (m, 1H), 4.26 (s, 2H), 7.76-7.80 (m, 2H), 7.94-7.97 (m, 2H).

Example 20(34)

2-cyclohexyl-N-(1-{[1-(4-{[(2-hydroxyethyl)(methyl)amino]sulfonyl}phenyl)-3,5-dimethyl-1H-pyrazol-4-yl]methyl}-4-piperidinyl)acetamide dihydrochloride TLC:Rf 0.43(methylene chloride:methanol=10:1);
NMR (CD$_3$OD): δ 0.90-1.10 (m, 2H), 1.10-1.40 (m, 3H), 1.60-1.90 (m, 8H), 2.05 (d, J=6.9 Hz, 2H) 2.10-2.30 (m, 2H), 2.39 (s, 3H), 2.45 (s, 3H), 2.87 (s, 3H), 3.10-3.20 (m, 2H), 3.19 (t, J=5.9 Hz, 2H), 3.60-3.80 (m, 2H), 3.69 (t, J=5.9 Hz, 2H), 3.93 (m, 1H), 4.26 (s, 2H), 7.75 (d, J=8.7 Hz, 2H), 7.99 (d, J=8.7 Hz, 2H).

Example 20(35)

2-cyclohexyl-N-{1-[(1-{4-[(diethylamino)sulfonyl]phenyl}-3,5-dimethyl-1H-pyrazol-4-yl)methyl]-4-piperidinyl}acetamide dihydrochloride TLC:Rf 0.53(methylene chloride:methanol=10:1);
NMR (CD$_3$OD): δ 0.90-1.10 (m, 2H), 1.15 (t, J=7.1 Hz, 6H), 1.10-1.40 (m, 3H), 1.60-1.75 (m, 6H), 1.75-1.90 (m, 2H), 2.05 (d, J=7.2 Hz, 2H), 2.10-2.30 (m, 2H), 2.40 (s, 3H), 2.45 (s, 3H), 3.10-3.20 (m, 2H), 3.20-3.40 (m, 4H), 3.60-3.80 (m, 2H), 3.94 (m, 1H), 4.26 (s, 2H), 7.73 (d, J=8.6 Hz, 2H), 7.99 (d, J=8.6 Hz, 2H).

Example 20(36)

2-cyclohexyl-N-[1-({3,5-dimethyl-1-[4-(4-morpholinylsulfonyl)phenyl]-1H-pyrazol-4-yl}methyl)-4-piperidinyl]acetamide dihydrochloride TLC:Rf 0.50(methylene chloride:methanol=10:1);
NMR (CD$_3$OD): δ 0.90-1.10 (m, 2H), 1.10-1.40 (m, 3H), 1.60-1.75 (m, 6H), 1.75-1.90 (m, 2H), 2.06 (d, J=7.2 Hz, 2H), 2.10-2.30 (m, 2H), 2.40 (s, 3H), 2.48 (s, 3H), 3.02 (t, J=4.7 Hz, 4H), 3.10-3.20 (m, 2H), 3.60-3.80 (m, 2H), 3.71 (t, J=4.7 Hz, 4H), 3.94 (m, 1H), 4.27 (s, 2H), 7.80 (d, J=8.6 Hz, 2H), 7.95 (d, J=8.6 Hz, 2H).

Example 20(37)

2-cyclohexyl-N-{1-[(3,5-dimethyl-1-{4-[(4-methyl-1-piperazinyl)sulfonyl]phenyl}-1H-pyrazol-4-yl)methyl]-4-piperidinyl}acetamide dihydrochloride TLC:Rf 0.48(methylene chloride:methanol=10:1);
NMR (CD$_3$OD): δ 0.90-1.10 (m, 2H), 1.10-1.40 (m, 3H), 1.60-1.80 (m, 6H), 1.80-2.00 (m, 2H), 2.06 (d, J=6.9 Hz, 2H), 2.10-2.30 (m, 2H), 2.40 (s, 3H), 2.48 (s, 3H), 2.80-3.00 (m, 2H), 2.90 (s, 3H), 3.10-3.40 (m, 4H), 3.50-3.80 (m, 4H), 3.90-4.10 (m, 3H), 4.27 (s, 2H), 7.84 (d, J=8.6 Hz, 2H), 8.01 (d, J=8.6 Hz, 2H).

Example 20(38)

ethyl[4-({4-[4-({4-[(cyclohexylacetyl)amino]-1-piperidinyl}methyl)-3,5-dimethyl-1H-pyrazol-1-yl]phenyl}sulfonyl)-1-piperazinyl]acetate trihydrochloride TLC:Rf 0.43(methylene chloride:methanol=10:1);
NMR (CD$_3$OD): δ 0.90-1.10 (m, 2H), 1.10-1.40 (m, 3H), 1.30 (t, J=7.1 Hz, 3H), 1.60-1.90 (m, 8H), 2.05 (d, J=6.9 Hz, 2H), 2.10-2.30 (m, 2H), 2.40 (s, 3H), 2.49 (s, 3H), 3.10-3.20 (m, 2H), 3.40-4.00 (m, 11H), 4.22 (s, 2H), 4.27 (s, 2H), 4.29 (q, J=7.2 Hz, 2H), 7.84 (d, J=8.6 Hz, 2H), 8.02 (d, J=8.6 Hz, 2H).

Example 20(39)

2-cyclohexyl-N-{1-[(3,5-dimethyl-1-{4-[(methylsulfonyl)amino]phenyl}-1H-pyrazol-4-yl)methyl]-4-piperidinyl}acetamide dihydrochloride TLC:Rf 0.45(methylene chloride:methanol=10:1);
NMR (CD$_3$OD): δ 0.90-1.10 (m, 2H), 1.10-1.40 (m, 3H), 1.60-1.90 (m, 8H), 2.05 (d, J=7.2 Hz, 2H), 2.10-2.30 (m, 2H), 2.36 (s, 3H), 2.37 (s, 3H), 3.03 (s, 3H), 3.10-3.20 (m, 2H), 3.60-3.70 (m, 2H), 3.90 (m, 1H), 4.24 (s, 2H), 7.39-7.46 (m, 4H).

Example 20(40)

2-cyclohexyl-N-[1-(4-{2,6-dimethyl-4-[(methylsulfonyl)amino]phenoxy}benzyl)-4-piperidinyl]acetamide hydrochloride TLC:Rf 0.46(methylene chloride:methanol=10:1);
NMR (CD$_3$OD): δ 0.90-1.10 (m, 2H), 1.10-1.40 (m, 3H), 1.60-1.80 (m, 8H), 2.03 (d, J=6.9 Hz, 2H), 2.07 (s, 6H), 2.10-2.20 (m, 2H), 2.97 (s, 3H), 3.00-3.10 (m, 2H), 3.40-3.60 (m, 2H), 3.90 (m, 1H), 4.24 (s, 2H), 6.84 (d, J=3.9 Hz, 2H), 7.04 (s, 2H), 7.45 (d, J=8.7 Hz, 2H).

Example 20(41)

N-(1-{4-[4-(aminosulfonyl)phenoxy]benzyl}-4-piperidinyl)-2-cyclohexylacetamide hydrochloride TLC:Rf 0.33(methylene chloride:methanol=10:1);
NMR (CD$_3$OD): δ 0.90-1.10 (m, 2H), 1.10-1.40 (m, 3H), 1.60-1.80 (m, 8H), 2.04 (d, J=7.2 Hz, 2H), 2.10-2.20 (m, 2H), 3.00-3.10 (m, 2H), 3.50-3.60 (m, 2H), 3.92 (m, 1H), 4.32 (s, 2H), 7.11-7.19 (m, 4H), 7.58-7.62 (m, 2H), 7.88-7.93 (m, 2H).

Example 20(42)

2-cyclohexyl-N-(1-{4-[4-(methylsulfonyl)phenoxy]benzyl}-4-piperidinyl)acetamide hydrochloride TLC:Rf 0.43(methylene chloride:methanol=10:1);
NMR (CD$_3$OD): δ 0.90-1.10 (m, 2H), 1.10-1.40 (m, 3H), 1.60-1.80 (m, 8H), 2.05 (d, J=6.9 Hz, 2H), 2.10-2.20 (m, 2H), 3.00-3.10 (m, 2H), 3.12 (s, 3H), 3.50-3.60 (m, 2H), 3.91 (m, 1H), 4.33 (s, 2H), 7.19-7.23 (m, 4H), 7.59 (d, J=8.6 Hz, 2H), 7.95 (d, J=8.6 Hz, 2H).

Example 20(43)

2-cyclohexyl-N-[1-({4'-[(methylsulfonyl)amino]-1,1'-biphenyl-3-yl}methyl)-4-piperidinyl]acetamide hydrochloride TLC:Rf 0.38(methylene chloride:methanol=10:1);
NMR (CD$_3$OD): δ 0.90-1.10 (m, 2H), 1.10-1.40 (m, 3H), 1.60-1.80 (m, 8H), 2.02 (d, J=6.9 Hz, 2H), 2.10-2.20 (m, 2H), 2.99 (s, 3H), 3.00-3.10 (m, 2H), 3.50-3.60 (m, 2H), 3.90 (m, 1H), 4.37 (s, 2H), 7.35 (d, J=8.7 Hz, 2H), 7.45-7.60 (m, 2H), 7.67 (d, J=8.7 Hz, 2H), 7.70-7.80 (m, 2H).

Example 20(44)

2-cyclohexyl-N-(1-{4-[4-(methylsulfanyl)phenoxy]benzyl}-4-piperidinyl)acetamide hydrochloride TLC:Rf 0.60(methylene chloride:methanol=10:1);
NMR (CD$_3$OD): δ 0.90-1.10 (m, 2H), 1.10-1.40 (m, 3H), 1.60-1.80 (m, 8H), 2.03 (d, J=7.2 Hz, 2H), 2.10-2.20 (m, 2H), 2.47 (s, 3H), 3.00-3.10 (m, 2H), 3.50-3.60 (m, 2H), 3.90 (m, 1H), 4.27 (s, 2H), 6.99 (d, J=8.5 Hz, 2H), 7.04 (d, J=8.5 Hz, 2H) 7.32 (d, J=8.5 Hz, 2H), 7.48 (d, J=8.5 Hz, 2H).

Example 20(45)

N-butyl-N-[1-(4-{4-[(methylsulfonyl)amino]phenoxy}benzyl)-4-piperidinyl]propanamide hydrochloride TLC:Rf 0.34(methylene chloride:methanol=10:1);
NMR (CD$_3$OD): δ 0.97 (t, J=7.2 Hz, 3H), 1.10 (t, J=7.4 Hz, 3H), 1.20-1.70 (m, 4H), 1.80-2.10 (m, 2H), 2.20-2.50 (m, 2H), 2.35 (q, J=7.6 Hz, 2H), 2.95 (s, 3H), 3.00-3.40 (m, 4H), 3.40-3.60 (m, 2H), 4.11 (m, 1H), 4.26 (s, 2H), 7.03 (d, J=8.9 Hz, 2H), 7.06 (d, J=8.9 Hz, 2H) 7.29 (d, J=8.9 Hz, 2H), 7.48 (d, J=8.9 Hz, 2H).

Example 20(46)

N-benzyl-N-[1-(4-{4-[(methylsulfonyl)amino]phenoxy}benzyl)-4-piperidinyl]propanamide hydrochloride TLC:Rf 0.44(methylene chloride:methanol=10:1);
NMR (CD$_3$OD): δ 1.08 (t, J=7.5 Hz, 3H), 1.80-2.00 (m, 2H), 2.00-2.20 (m, 2H), 2.37 (q, J=7.5 Hz, 2H), 2.95 (s, 3H), 3.00-3.20 (m, 2H), 3.40-3.60 (m, 2H), 4.22 (s, 2H), 4.40 (m, 1H), 4.61 (s, 2H), 7.00-7.05 (m, 4H), 7.22-7.46 (m, 7H), 7.45 (d, J=8.4 Hz, 2H).

Example 20(47)

N-(2-methoxyethyl)-N-[1-(4-{4-[(methylsulfonyl)amino]phenoxy}benzyl)-4-piperidinyl]propanamide hydrochloride TLC:Rf 0.43(methylene chloride:methanol=10:1);
NMR (CD$_3$OD): δ 1.07 (t, J=7.4 Hz, 3H), 1.90-2.00 (m, 2H), 2.42 (q, J=7.4 Hz, 2H), 2.40-2.60 (m, 2H), 2.96 (s, 3H), 3.00-3.20 (m, 2H), 3.34 (s, 3H), 3.40-3.60 (m, 4H), 4.05 (m, 1H), 4.28 (s, 2H), 7.01-7.06 (m, 4H), 7.28-7.31 (m, 2H), 7.51-7.56 (m, 2H).

Example 20(48)

N-(3-hydroxybutyl)-N-[1-(4-{4-[(methylsulfonyl)amino]phenoxy}benzyl)-4-piperidinyl]propanamide hydrochloride TLC:Rf 0.43(methylene chloride:methanol=10:1);
NMR (CD$_3$OD): δ 1.10 (t, J=7.2 Hz, 3H), 1.19 (t, J=6.0 Hz, 2H), 1.60-1.80 (m, 2H), 1.80-2.40 (m, 6H), 2.41 (q, J=7.4 Hz, 2H), 2.95 (s, 3H), 3.00-3.20 (m, 2H), 3.40-3.60 (m, 4H), 3.80 (m, 1H), 4.05 (m, 1H), 4.28 (s, 2H), 7.03 (t, J=8.7 Hz, 2H), 7.05 (t, J=7.4 Hz, 2H), 7.29 (t, J=7.4 Hz, 2H), 7.50 (t, J=8.7 Hz, 2H).

Example 20(49)

N-(cyclohexylmethyl)-N-[1-(4-{-4-[(methylsulfonyl)amino]phenoxy}benzyl)-4-piperidinyl]propanamide hydrochloride TLC:Rf 0.54(methylene chloride:methanol=10:1);
NMR (CD$_3$OD): δ 0.87-0.91 (m, 2H), 1.07 (t, J=7.2 Hz, 3H), 1.10-1.40 (m, 5H), 1.60-1.80 (m, 4H), 1.80-2.00 (m, 2H), 2.36 (q, J=7.2 Hz, 2H), 2.40-2.60 (m, 2H), 2.95 (s, 3H), 3.00-3.20 (m, 2H), 3.16 (d, J=7.5 Hz, 2H), 3.40-3.60 (m, 2H), 3.80 (m, 1H), 4.26 (s, 2H), 7.03 (d, J=8.7 Hz, 2H), 7.06 (d, J=8.7 Hz, 2H), 7.29 (d, J=8.7 Hz, 2H), 7.48 (d, J=8.7 Hz, 2H).

Example 20(50)

4-(acetylamino)-N-(cyclohexylmethyl)-1-(4-{-4-[(methylsulfonyl)amino]phenoxy}benzyl)-4-piperidinecarboxamide hydrochloride TLC:Rf 0.39(chloroform:methanol=9:1);
NMR (CD$_3$OD): δ 0.80-1.00 (m, 2H), 1.08-1.32 (m, 4H), 1.48 (m, 1H), 1.60-1.78 (m, 4H), 2.05 (brs, 3H), 2.10-2.50 (m, 4H), 2.95 (s, 3H), 3.00 (t, J=6.3 Hz, 2H), 3.04-3.50 (m, 4H), 4.30 (s, 2H), 6.98-7.08 (m, 4H), 7.28 (brd, J=9.0 Hz, 2H), 7.49 (brd, J=8.7 Hz, 2H).

Example 20(51)

4-[4-({-4-[(cyclohexylacetyl)amino]-1-piperidinyl}methyl)phenoxy]phenyl methanesulfonate hydrochloride TLC:Rf 0.50(methylene chloride:methanol=10:1);
NMR (CD$_3$OD): δ 0.90-1.10 (m, 2H), 1.20-1.40 (m, 3H), 1.60-1.80 (m, 8H), 2.04 (d, J=7.2 Hz, 2H), 2.10-2.20 (m, 2H), 3.10-3.20 (m, 2H), 3.23 (s, 3H), 3.40-3.60 (m, 2H), 3.91 (m, 1H), 4.29 (s, 2H), 7.08-7.14 (m, 4H), 7.34 (d, J=8.6 Hz, 2H), 7.54 (d, J=8.6 Hz, 2H).

Example 20(52)

N-(cyclopropylmethyl)-N-[1-(4-{4-[(methylsulfonyl)amino]phenoxy}benzyl)-4-piperidinyl]propanamide hydrochloride TLC:Rf 0.43(methylene chloride:methanol=10:1);
NMR (CD$_3$OD): δ 0.30-0.40 (m, 2H), 0.60-0.70 (m, 2H), 0.95 (m, 1H), 1.10 (t, J=7.4 Hz, 3H), 1.90-2.10 (m, 2H), 2.40-2.60 (m, 2H), 2.43 (q, J=7.2 Hz, 2H), 2.95 (s, 3H), 3.00-3.20 (m, 2H), 3.22 (d, J=6.3 Hz, 2H), 3.45-3.60 (m, 2H), 4.00 (m, 1H), 4.28 (s, 2H), 7.02-7.08 (m, 4H), 7.27-7.32 (m, 2H), 7.50 (t, J=8.1 Hz, 2H).

Example 20(53)

N-(2-cyclohexylethyl)-1-(4-{4-[(methylsulfonyl)amino]phenoxy}benzyl)-4-piperidinecarboxamide hydrochloride TLC:Rf 0.64(methylene chloride:methanol=10:1);
NMR (CD$_3$OD): δ 0.89-0.97 (m, 2H), 1.18-1.41 (m, 7H), 1.60-1.74 (m, 4H), 1.87-2.04 (m, 4H), 2.47 (m, 1H), 2.95 (s, 3H), 2.95-3.04 (m, 2H), 3.16-3.21 (m, 2H), 3.52-3.56 (m, 2H), 4.27 (s, 2H), 7.03 (d, J=8.7 Hz, 2H), 7.06 (d, J=8.7 Hz, 2H), 7.29 (d, J=8.7 Hz, 2H), 7.47 (d, J=8.7 Hz, 2H).

Example 20(54)

2-cyclohexyl-N-(1-{4-[4-(methylsulfinyl)phenoxy]benzyl}-4-piperidinyl)acetamide hydrochloride TLC:Rf 0.21(chloroform:methanol=10:1);
NMR (CD$_3$OD): δ 0.90-1.10 (m, 2H), 1.10-1.40 (m, 3H), 1.60-1.80 (m, 8H), 2.04 (d, J=6.9 Hz, 2H), 2.10-2.20 (m, 2H), 2.80 (s, 3H), 3.10-3.20 (m, 2H), 3.50-3.60 (m, 2H), 3.90 (m, 1H), 4.31 (s, 2H), 7.16 (d, J=8.7 Hz, 2H), 7.22 (d, J=9.0 Hz, 2H), 7.58 (d, J=9.0 Hz, 2H), 7.74 (d, J=8.7 Hz, 2H).

Example 20(55)

N-[2-(ethylsulfanyl)ethyl]-1-(4-{4-[(methylsulfonyl)amino]phenoxy}benzyl)-4-piperidinecarboxamide hydrochloride TLC:Rf 0.30(methylene chloride:methanol=10:1);
NMR (CD$_3$OD): δ 1.23 (t, J=7.5 Hz, 3H), 1.88-2.08 (m, 4H), 2.46-2.67 (m, 5H), 2.94-3.07 (m, 2H), 2.95 (s, 3H), 3.37 (t, J=7.0 Hz, 2H), 3.52-3.56 (m, 2H), 4.28 (s, 2H), 7.03 (d, J=9.0 Hz, 2H), 7.06 (d, J=9.0 Hz, 2H), 7.29 (d, J=9.0 Hz, 2H), 7.48 (d, J=9.0 Hz, 2H).

Example 20(56)

2-cyclohexyl-N-[1-(4-{2-methoxy-4-[(methylsulfonyl)amino]phenoxy}benzyl)-4-piperidinyl]acetamide hydrochloride TLC:Rf 0.30(chloroform:methanol=10:1);
NMR (CD$_3$OD): δ 0.90-1.10 (m, 2H), 1.10-1.40 (m, 3H), 1.60-1.80 (m, 8H), 2.03 (d, J=6.9 Hz, 2H), 2.10-2.20 (m, 2H), 2.99 (s, 3H), 3.00-3.20 (m, 2H), 3.40-3.60 (m, 2H), 3.72 (s, 3H), 3.89 (m, 1H), 4.31 (s, 2H), 6.83-6.94 (m, 3H), 6.99-7.05 (m, 2H), 7.39-7.45 (m, 2H).

Example 20(57)

2-cyclohexyl-N-[1-(4-{3-[(methylsulfonyl)amino]phenoxy}benzyl)-4-piperidinyl]acetamide hydrochloride TLC:Rf 0.30(chloroform:methanol=10:1);
NMR (CD$_3$OD): δ 0.90-1.10 (m, 2H), 1.10-1.40 (m, 3H), 1.60-1.80 (m, 8H), 2.04 (d, J=6.9 Hz, 2H), 2.10-2.20 (m, 2H), 2.96 (s, 3H), 3.00-3.20 (m, 2H), 3.40-3.60 (m, 2H), 3.90 (m, 1H), 4.29 (s, 2H), 6.79 (dd, J=7.5, 2.4 Hz, 1H), 6.95-7.01 (m, 2H), 7.08-7.11 (m, 2H), 7.31-7.34 (m, 1H), 7.51-7.54 (m, 2H).

Example 20(58)

N-[4-(4-{[4-(cyclohexylacetyl)-3-methyl-1-piperazinyl]methyl}phenoxy)phenyl]methanesulfonamide hydrochloride TLC:Rf 0.72(chloroform:methanol=5:1);
NMR (CD$_3$OD): δ 0.82-1.44 (m, 8H), 1.60-1.85 (m, 6H), 2.30-2.42 (m, 2H), 2.95 (s, 3H), 2.95-3.65 (m, 5H), 4.10-5.15 (m, 4H), 7.00-7.12 (m, 4H), 7.24-7.38 (m, 2H), 7.52 (brd, J=8.7 Hz, 2H).

Example 20(59)

1-(4-{4-[(methylsulfonyl)amino]phenoxy}benzyl)-4-piperidinyl cyclohexylcarbamate hydrochloride TLC:Rf 0.69(ethyl acetate:methanol=10:1);
NMR (CD$_3$OD): δ 1.06-1.42 (m, 6H), 1.54-1.92 (m, 6H), 1.95-2.17 (m, 2H), 2.26 (m, 1H), 2.95 (s, 3H), 3.05-3.58 (m, 5H), 4.29 (s, 2H), 7.03 (d, J=8.7 Hz, 2H), 7.06 (d, J=8.7 Hz, 2H), 7.29 (d, J=8.7 Hz, 2H), 7.49 (dd, J=4.2, 8.7 Hz, 2H).

Example 20(60)

(2R,3R)-3-cyclohexyl-3-hydroxy-2-{[1-(4-{4-[(methylsulfonyl)amino]phenoxy}benzyl)-4-piperidinyl]carbonyl}amino)propanoic acid hydrochloride TLC:Rf 0.23(methylene chloride:methanol=8:2);
NMR (CD$_3$OD): δ 1.00-1.34 (m, 5H), 1.48 (m, 1H), 1.58-1.80 (m, 4H), 1.83-2.11 (m, 5H), 2.58 (m, 1H), 2.95 (s, 3H), 2.87-3.00 (m, 2H), 3.40-3.49 (m, 2H), 3.51 (t, J=6.0 Hz, 1H), 4.18 (s, 2H), 4.39 (d, J=6.0 Hz, 1H), 7.02 (d, J=8.7 Hz, 2H), 7.03 (d, J=8.7 Hz, 2H), 7.28 (d, J=8.7 Hz, 2H), 7.46 (d, J=8.7 Hz, 2H).

Example 20(61)

N-butyl-2-cyclohexyl-N-[1-(4-{3-[(methylsulfonyl)amino]phenoxy}benzyl)-4-piperidinyl]acetamide hydrochloride TLC:Rf 0.32(chloroform:methanol=10:1);
NMR (CD$_3$OD): δ 0.80-1.10 (m, 2H), 0.97 (t, J=7.2 Hz, 3H), 1.20-1.40 (m, 5H), 1.40-1.60 (m, 2H), 1.60-2.00 (m, 8H), 2.30-2.40 (m, 2H), 2.32 (d, J=7.2 Hz, 2H), 2.96 (s, 3H), 3.10-3.30 (m, 4H), 3.50-3.60 (m, 2H), 4.20 (m, 1H), 4.30 (s, 2H), 6.80 (m, 1H), 6.95 (m, 1H), 7.00 (m, 1H), 7.08 (d, J=8.7 Hz, 2H), 7.33 (t, J=8.1 Hz, 1H), 7.55-7.61 (m, 2H).

Example 20(62)

4-[4-({4-[butyl(hexanoyl)amino]-1-piperidinyl}methyl)phenoxy]benzoic acid hydrochloride TLC:Rf 0.34(chloroform:methanol=10:1);
NMR (CD$_3$OD): δ 0.90-1.00 (m, 3H), 0.97 (t, J=7.4 Hz, 3H), 1.20-1.40 (m, 6H), 1.50-1.70 (m, 4H), 1.80-2.00 (m, 2H), 2.20-2.40 (m, 4H), 3.00-3.20 (m, 4H), 3.50-3.70 (m, 2H), 4.10 (m, 1H), 4.31 (s, 2H), 7.07 (d, J=9.0 Hz, 2H), 7.17 (d, J=9.0 Hz, 2H), 7.56 (d, J=9.0 Hz, 2H), 8.04 (d, J=9.0 Hz, 2H).

Example 20(63)

4-[4-({4-[benzyl(hexanoyl)amino]-1-piperidinyl}methyl)phenoxy]benzoic acid hydrochloride TLC:Rf 0.40(chloroform:methanol=10:1);
NMR (CD$_3$OD): δ 0.86 (t, J=7.2 Hz, 3H), 1.20-1.50 (m, 4H), 1.50-1.70 (m, 2H), 1.88-1.95 (m, 2H), 2.00-2.20 (m, 2H), 2.30-2.40 (m, 2H), 3.00-3.20 (m, 2H), 3.50-3.60 (m, 2H), 4.27 (s, 2H), 4.45 (m, 1H), 4.62 (s, 2H), 7.03-7.07 (m, 2H), 7.13-7.37 (m, 7H), 7.52 (d, J=8.4 Hz, 2H), 8.01-8.04 (m, 2H).

Example 20(64)

N-butyl-2-cyclohexyl-N-[1-(4-{2-[(methylsulfonyl)amino]phenoxy}benzyl)-4-piperidinyl]acetamide hydrochloride TLC:Rf 0.50(chloroform:methanol=10:1);
NMR (CD$_3$OD): δ 0.90-1.00 (m, 2H), 0.97 (t, J=7.2 Hz, 3H), 1.20-1.40 (m, 5H), 1.40-1.80 (m, 8H), 1.80-2.00 (m, 2H), 2.21 (d, J=6.9 Hz, 2H), 2.30-2.40 (m, 2H), 2.98 (s, 3H), 3.00-3.30 (m, 4H), 3.50-3.60 (m, 2H), 4.20 (m, 1H), 4.28 (s, 2H), 6.98 (m, 1H), 7.12 (d, J=8.7 Hz, 2H), 7.18-7.21 (m, 2H), 7.52-7.54 (m, 3H).

Example 20(65)

benzyl butyl[1-(4-{4-[(methylsulfonyl)amino]phenoxy}benzyl)-4-piperidinyl]carbamate hydrochloride
TLC:Rf 0.77(ethyl acetate:methanol=10:1);
NMR (CD$_3$OD): δ 0.90 (t, J=7.2 Hz, 3H), 1.21-1.36 (m, 2H), 1.42-1.58 (m, 2H), 1.88-2.00 (m, 2H), 2.09-2.34 (m, 2H), 2.95 (s, 3H), 3.00-3.14 (m, 2H), 3.17-3.28 (m, 2H), 3.43-3.58 (m, 2H), 3.93 (m, 1H), 4.25 (s, 2H), 5.12 (s, 2H), 7.03 (d, J=8.7 Hz, 2H), 7.05 (d, J=8.7 Hz, 2H), 7.24-7.38 (m, 7H), 7.47 (d, J=8.7 Hz, 2H).

Example 20(66)

benzyl allyl[1-(4-{4-[(methylsulfonyl)amino]phenoxy}benzyl)-4-piperidinyl]carbamate hydrochloride TLC:Rf 0.75(ethyl acetate:methanol=10:1);
NMR (CD$_3$OD): δ 1.90-2.01 (m, 2H), 2.09-2.19 (m, 2H), 2.95 (s, 3H), 3.01-3.12 (m, 2H), 3.44-3.55 (m, 2H), 3.89 (d, J=5.5 Hz, 2H), 4.03 (m, 1H), 4.25 (s, 2H), 5.09-5.21 (m, 2H), 5.13 (s, 2H), 5.83 (ddd, J=22.5, 10.2, 5.4 Hz, 1H), 7.03 (d, J=8.7 Hz, 2H), 7.05 (d, J=8.7 Hz, 2H), 7.25-7.38 (m, 7H), 7.47 (d, J=8.7 Hz, 2H).

Example 20(67)

benzyl 2-butynyl[1-(4-{4-[(methylsulfonyl)amino]phenoxy}benzyl)-4-piperidinyl]carbamate hydrochloride TLC:Rf 0.76(ethyl acetate:methanol=10:1);
NMR (CD$_3$OD): δ 1.75 (t, J=2.1 Hz, 3H), 1.95-2.08 (m, 2H), 2.18-2.36 (m, 2H), 2.95 (s, 3H), 3.03-3.18 (m, 2H), 3.47-3.57 (m, 2H), 4.03 (d, J=2.1 Hz, 2H), 4.07 (m, 1H), 4.26 (s, 2H), 5.16 (s, 2H), 7.03 (d, J=8.7 Hz, 2H), 7.06 (d, J=8.7 Hz, 2H), 7.25-7.41 (m, 7H), 7.47 (d, J=8.7 Hz, 2H).

Example 20(68)

N-butyl-2-cyclohexyl-N-(1-{3-[(methylsulfonyl)amino]-4-phenoxybenzyl}-4-piperidinyl)acetamide hydrochloride TLC:Rf 0.48(chloroform:methanol:acetic acid=20:2:1);
NMR (CD$_3$OD): δ 0.90-1.00 (m, 2H), 0.97 (t, J=7.2 Hz, 3H), 1.10-1.40 (m, 5H), 1.50-1.80 (m, 8H), 1.80-2.00 (m, 2H), 2.21 (d, J=6.9 Hz, 2H), 2.30-2.40 (m, 2H), 3.04 (s, 3H), 3.05-3.30 (m, 4H), 3.50-3.70 (m, 2H), 4.14 (m, 1H), 4.28 (s, 2H), 6.89 (d, J=8.4 Hz, 1H), 7.10 (d, J=7.5 Hz, 2H), 7.20-7.29 (m, 2H), 7.40-7.46 (m, 2H), 7.68 (d, J=2.1 Hz, 1H).

Example 20(69)

N-butyl-2-cyclohexyl-N-{1-[4-(4-nitrophenoxy)benzyl]-4-piperidinyl}acetamide hydrochloride TLC:Rf 0.54(chloroform:methanol:acetic acid=20:2:1);
NMR (CD$_3$OD): δ 0.90-1.00 (m, 2H), 0.98 (t, J=7.2 Hz, 3H), 1.10-1.40 (m, 5H), 1.50-1.80 (m, 8H), 1.80-2.00 (m, 2H), 2.22 (d, J=6.6 Hz, 2H), 2.30-2.40 (m, 2H), 3.10-3.30 (m, 4H), 3.50-3.60 (m, 2H), 4.19 (m, 1H), 4.34 (s, 2H), 7.16 (d, J=9.1 Hz, 2H), 7.24 (d, J=8.4 Hz, 2H), 7.63 (d, J=8.4 Hz, 2H), 8.27 (d, J=9.1 Hz, 2H).

Example 20(70)

4-[4-({4-[butyl(cyclohexylacetyl)amino]-1-piperidinyl}methyl)phenoxy]phenyl methanesulfonate hydrochloride TLC:Rf 0.79(chloroform:methanol=10:1);
NMR (CD$_3$OD): δ 0.90-1.00 (m, 2H), 0.97 (t, J=7.2 Hz, 3H), 1.10-1.40 (m, 5H), 1.40-1.80 (m, 8H), 1.80-2.00 (m, 2H), 2.21 (d, J=6.9 Hz, 2H), 2.30-2.40 (m, 2H), 3.00-3.20 (m, 4H), 3.23 (s, 3H), 3.50-3.60 (m, 2H), 4.18 (m, 1H), 4.29 (s, 2H), 7.11 (d, J=9.0 Hz, 4H), 7.35 (d, J=9.0 Hz, 2H), 7.54 (d, J=9.0 Hz, 2H).

Example 20(71)

N-butyl-2-cyclohexyl-N-[1-(4-{2-methyl-4-[(methylsulfonyl)amino]phenoxy}benzyl)-4-piperidinyl]acetamide hydrochloride TLC:Rf 0.44(chloroform:methanol=10:1);
NMR (CD$_3$OD): δ 0.90-1.00 (m, 2H), 0.97 (t, J=7.2 Hz, 3H), 1.10-1.40 (m, 5H), 1.40-1.80 (m, 8H), 1.80-2.00 (m, 2H), 2.16 (s, 3H), 2.21 (d, J=6.9 Hz, 2H), 2.30-2.40 (m, 2H), 2.96 (s, 3H), 3.00-3.20 (m, 4H), 3.50-3.60 (m, 2H), 4.10 (m, 1H), 4.25 (s, 2H), 6.91-6.98 (m, 3H), 7.13 (dd, J=8.6, 2.6 Hz, 1H), 7.20 (m, 1H), 7.44-7.49 (m, 2H).

Example 20(72)

N-butyl-2-cyclohexyl-N-[1-(4-{2,6-dimethyl-4-[(methylsulfonyl)amino]phenoxy}benzyl)-4-piperidinyl]acetamide hydrochloride TLC:Rf 0.33 (chloroform:methanol=10:1);
NMR (CD$_3$OD): δ 0.90-1.00 (m, 2H), 0.97 (t, J=7.2 Hz, 3H), 1.10-1.40 (m, 5H), 1.40-1.80 (m, 8H), 1.80-2.00 (m, 2H), 2.07 (s, 6H), 2.21 (d, J=6.6 Hz, 2H), 2.30-2.40 (m, 2H), 2.97 (s, 3H), 3.00-3.20 (m, 4H), 3.50-3.60 (m, 2H), 4.17 (m, 1H), 4.24 (s, 2H), 6.86 (d, J=8.7 Hz, 2H), 7.04 (s, 2H), 7.45 (d, J=8.7 Hz, 2H).

Example 20(73)

N-butyl-N-[1-(4-{2-chloro-4-[(methylsulfonyl)amino]phenoxy}benzyl)-4-piperidinyl]-2-cyclohexylacetamide hydrochloride TLC:Rf 0.60(chloroform:methanol=10:1);
NMR (CD$_3$OD): δ 0.90-1.00 (m, 2H), 0.97 (t, J=7.4 Hz, 3H), 1.20-1.40 (m, 5H), 1.40-1.60 (m, 2H), 1.60-2.00 (m, 8H), 2.21 (d, J=6.6 Hz, 2H), 2.30-2.40 (m, 2H), 3.01 (s, 3H), 3.10-3.30 (m, 4H), 3.50-3.60 (m, 2H), 4.10 (m, 1H), 4.27 (s, 2H), 6.99 (d, J=8.4 Hz, 2H), 7.13 (d, J=9.0 Hz, 1H), 7.24 (dd, J=9.0, 2.6 Hz, 1H), 7.43 (d, J=2.6 Hz, 1H), 7.48-7.52 (m, 2H).

Example 20(74)

(2R)-2-cyclohexyl-2-hydroxy-N-[1-(4-{4-[(methylsulfonyl)amino]phenoxy}benzyl)-4-piperidinyl]acetamide hydrochloride TLC:Rf 0.48(ethyl acetate:methanol=10:1);
NMR (CD$_3$OD): δ 1.06-1.38 (m, 5H), 1.45-1.94 (m, 8H), 2.05-2.16 (m, 2H), 2.95 (s, 3H), 3.03-3.17 (m, 2H), 3.48-3.57 (m, 2H), 3.79 (d, J=4.0 Hz, 1H), 3.96 (m, 1H), 4.28 (s, 2H), 7.03 (d, J=8.7 Hz, 2H), 7.06 (d, J=8.7 Hz, 2H), 7.29 (d, J=8.7 Hz, 2H), 7.51 (d, J=8.7 Hz, 2H).

Example 20(75)

(2S)-2-cyclohexyl-2-hydroxy-N-[1-(4-{4-[(methylsulfonyl)amino]phenoxy}benzyl)-4-piperidinyl]acetamide hydrochloride TLC:Rf 0.48(ethyl acetate:methanol=10:1);
NMR (CD$_3$OD): δ 1.06-1.38 (m, 5H), 1.45-1.94 (m, 8H), 2.05-2.16 (m, 2H), 2.95 (s, 3H), 3.03-3.17 (m, 2H), 3.48-3.57 (m, 2H), 3.79 (d, J=4.0 Hz, 1H), 3.96 (m, 1H), 4.28 (s, 2H), 7.03 (d, J=8.7 Hz, 2H), 7.06 (d, J=8.7 Hz, 2H), 7.29 (d, J=8.7 Hz, 2H), 7.51 (d, J=8.7 Hz, 2H).

Example 20(76)

methyl 2-[4-({4-[butyl(cyclohexylacetyl)amino]-1-piperidinyl}methyl)phenoxy]-5-[methylsulfonyl)amino]benzoate hydrochloride TLC:Rf 0.50(methylene chloride:methanol=10:1);
NMR (CD$_3$OD): δ 0.90-1.00 (m, 2H), 0.97 (t, J=7.2 Hz, 3H), 1.10-1.40 (m, 5H), 1.50-1.60 (m, 2H), 1.65-1.80 (m, 6H), 1.80-2.00 (m, 2H), 2.21 (d, J=6.9 Hz, 2H), 2.30-2.40 (m, 2H), 3.00 (s, 3H), 3.10-3.30 (m, 4H), 3.50-3.60 (m, 2H), 3.74 (s, 3H), 4.10 (m, 1H), 4.26 (s, 2H), 6.98 (d, J=8.7 Hz, 2H), 7.10 (d, J=8.7 Hz, 1H), 7.45-7.52 (m, 3H), 7.79 (d, J=3.0 Hz, 1H).

Example 20(77)

2-[4-({4-[butyl(cyclohexylacetyl)amino]-1-piperidinyl}methyl)phenoxy]-5-[methylsulfonyl)amino]benzoic acid hydrochloride TLC:Rf 0.40(methylene chloride:methanol=10:1);
NMR (CD$_3$OD): δ 0.95-1.05 (m, 2H), 0.97 (t, J=7.3 Hz, 3H), 1.10-1.40 (m, 5H), 1.50-1.80 (m, 8H), 1.80-2.00 (m, 2H), 2.21 (d, J=6.9 Hz, 2H), 2.30-2.40 (m, 2H), 3.01 (s, 3H), 3.05-3.25 (m, 4H), 3.50-3.60 (m, 2H), 4.10 (m, 1H), 4.26 (s, 2H), 6.95 (d, J=8.7 Hz, 2H), 7.09 (d, J=8.7 Hz, 1H), 7.46-7.51 (m, 3H), 7.83 (d, J=2.7 Hz, 1H).

Example 20(78)

(2R)—N-butyl-2-cyclohexyl-2-hydroxy-N-[1-(4-{4-[(methylsulfonyl)amino]phenoxy}benzyl)-4-piperidinyl]acetamide hydrochloride TLC:Rf 0.55(methylene chloride:methanol=9:1);
NMR (CD$_3$OD): δ 0.90-2.58 (m, 22H), 2.95 (s, 3H), 3.02-3.35 (m, 4H), 3.50-3.60 (m, 2H), 3.94-4.17 (m, 2H), 4.28 (s, 2H), 7.03 (d, J=8.7 Hz, 2H), 7.06 (d, J=8.7 Hz, 2H), 7.29 (d, J=8.7 Hz, 2H), 7.45-7.54 (m, 2H).

Example 20(79)

(2S)—N-butyl-2-cyclohexyl-2-hydroxy-N-[1-(4-{4-[(methylsulfonyl)amino]phenoxy}benzyl)-4-piperidinyl]acetamide hydrochloride TLC:Rf 0.55(methylene chloride:methanol=9:1);
NMR (CD$_3$OD): δ 0.90-2.58 (m, 22H), 2.95 (s, 3H), 3.02-3.35 (m, 4H), 3.50-3.60 (m, 2H), 3.94-4.17 (m, 2H), 4.28 (s, 2H), 7.03 (d, J=8.7 Hz, 2H), 7.06 (d, J=8.7 Hz, 2H), 7.29 (d, J=8.7 Hz, 2H), 7.45-7.54 (m, 2H).

Example 20(80)

(3,4-trans)-N-(cyclohexylmethyl)-3-methyl-1-(4-{4-[(methylsulfonyl)amino]phenoxy}benzyl)-4-piperidinecarboxamide hydrochloride TLC:Rf 0.40(chloroform:methanol=9:1);
NMR (CD$_3$OD): δ 0.84-1.04 (m, 2H), 0.93 (d, J=6.0 Hz, 3H), 1.14-1.34 (m, 4H), 1.48 (m, 1H), 1.60-1.80 (m, 4H), 1.88-2.04 (m, 2H), 2.06-2.18 (m, 2H), 2.72 (m, 1H), 2.88-3.12 (m, 3H), 2.95 (s, 3H), 3.22-3.60 (m, 2H), 4.28 (brs, 2H), 7.00-7.18 (m, 4H), 7.29 (brd, J=9.0 Hz, 2H), 7.48 (brd, J=8.7 Hz, 2H).

Example 20(81)

(3,4-cis)-N-(cyclohexylmethyl)-3-methyl-1-(4-{4-[(methylsulfonyl)amino]phenoxy}benzyl)-4-piperidinecarboxamide hydrochloride TLC:Rf 0.25(chloroform:methanol=9:1);
NMR (CD$_3$OD): δ 0.82-1.06 (m, 2H), 1.00 (d, J=6.9 Hz, 3H), 1.13-1.34 (m, 4H), 1.46 (m, 1H), 1.62-1.80 (m, 4H), 1.92-2.24 (m, 3H), 2.55 (m, 1H), 2.90-3.12 (m, 2H), 2.95 (s, 3H), 3.13-3.62 (m, 4H), 4.29 (brs, 2H), 6.98-7.10 (m, 4H), 7.29 (brd, J=9.0 Hz, 2H), 7.51 (brd, J=8.7 Hz, 2H).

Example 20(82)

N-(cyclohexylmethyl)-1-(4-{4-[(methylsulfonyl)amino]phenoxy}benzyl)-3-azetidinecarboxamide hydrochloride TLC:Rf 0.73(chloroform:methanol=5:1);
NMR (CD$_3$OD): δ 0.80-1.02 (m, 2H), 1.19-1.35 (m, 4H), 1.49 (m, 1H), 1.60-1.80 (m, 4H), 2.95 (s, 3H), 3.06 (m, 2H), 3.61 (m, 1H), 4.12-4.32 (m, 4H), 4.39 (s, 2H), 6.98-7.06 (m, 4H), 7.29 (brd, J=9.0 Hz, 2H), 7.45 (brd, J=8.7 Hz, 2H).

Example 20(83)

(1R,3s,5S)—N-(cyclohexylmethyl)-8-(4-{4-[(methylsulfonyl)amino]phenoxy}benzyl)-8-azabicyclo[3.2.1]octane-3-carboxamide hydrochloride

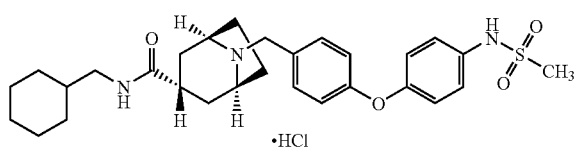

TLC:Rf 0.53(chloroform:methanol=5:1);
NMR (CD$_3$OD): δ 0.85-1.04 (m, 2H), 1.20-1.36 (m, 4H), 1.46 (m, 1H), 1.60-1.78 (m, 4H), 1.85-1.90 (m, 2H), 2.08-2.16 (m, 4H), 2.38-2.50 (m, 2H), 2.88 (m, 1H), 2.95 (s, 3H), 3.00 (d, J=6.9 Hz, 2H), 3.96 (m, 2H), 4.16 (s, 2H), 7.00-7.10 (m, 4H), 7.24-7.32 (m, 2H), 7.53 (brd, J=8.7 Hz, 2H).

Example 20(84)

(3aR,5s,6aS)—N-(cyclohexylmethyl)-2-(4-{4-[(methylsulfonyl)amino]phenoxy}benzyl)octahydrocyclopenta[c]pyrrole-5-carboxamide hydrochloride TLC:Rf 0.55 (chloroform:methanol=5:1);
NMR (CD$_3$OD): δ 0.80-1.02 (m, 2H), 1.04-1.36 (m, 3H), 1.46 (m, 1H), 1.60-2.18 (m, 9H), 2.76-3.04 (m, 7H), 2.95 (s, 3H), 3.60-3.78 (m, 2H), 4.35 (s, 2H), 7.00-7.19 (m, 4H), 7.24-7.32 (m, 2H), 7.42-7.58 (m, 2H).

Example 20(85)

(3aR,5r,6aS)—N-(cyclohexylmethyl)-2-(4-{4-[(methylsulfonyl)amino]phenoxy}benzyl)octahydrocyclopenta[c]pyrrole-5-carboxamide hydrochloride TLC:Rf 0.39(chloroform:methanol=5:1);
NMR (CD$_3$OD): δ 0.80-1.00 (m, 2H), 1.10-1.36 (m, 3H), 1.42 (m, 1H), 1.60-1.82 (m, 6H), 2.18 (m, 1H), 2.24-2.38 (m, 2H), 2.78-3.40 (m, 9H), 2.95 (s, 3H), 4.30 (s, 2H), 7.00-7.10 (m, 4H), 7.22-7.38 (m, 2H), 7.42-7.58 (m, 2H).

Example 21(1)-(11)

By the same procedure as described in Example 14→Example 15→Example 16, using N-(t-butoxycarbonyl)-L-cyclohexylalanine or a corresponding carboxylic acid derivative instead of it; a corresponding aldehyde derivative instead of 4-(4-methylsulfonylaminophenoxy)benzaldehyde; and n-butylamine or a corresponding amine derivative

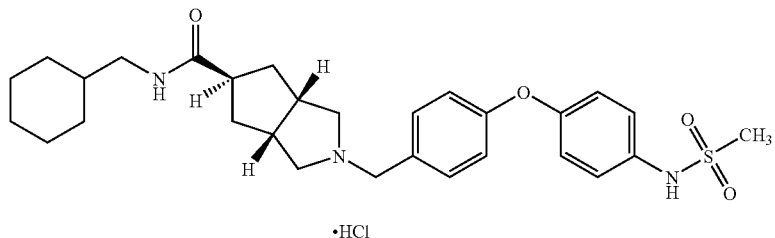

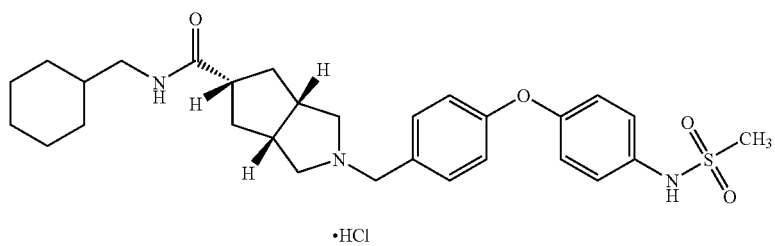

instead of it, the compounds of the present invention having the following physical data were obtained.

Example 21(1)

(3S)-1-benzyl-3-(cyclohexylmethyl)-6-{1-[(3,5-dimethyl-1-phenyl-1H-pyrazol-4-yl)methyl]-4-piperidinyl}-2,5-piperazinedione hydrochloride

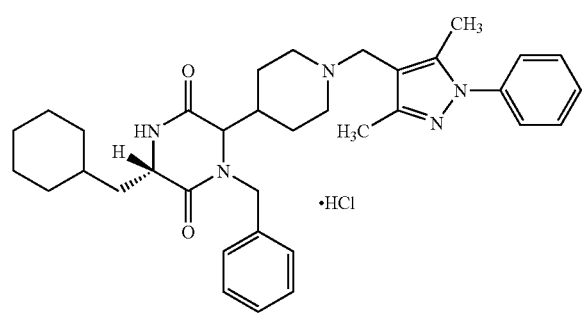

TLC:Rf 0.73(chloroform:methanol=5:1);
NMR (CD$_3$OD): δ 0.82-2.42 (m, 24H), 2.80-3.12 (m, 2H), 3.56-3.70 (m, 2H), 3.79 (m, 1H), 4.02-4.16 (m, 4H), 5.12-5.38 (m, 1H), 7.20-7.62 (m, 10H).

Example 21(2)

(3S)-1-butyl-3-(cyclohexylmethyl)-6-[1-(4-phenoxybenzyl)-4-piperidinyl]-2,5-piperazinedione hydrochloride TLC:Rf 0.73(chloroform:methanol=5:1);
NMR (CD$_3$OD): δ 0.80-1.08 (m, 5H), 1.10-1.42 (m, 6H), 1.42-2.38 (m, 14H), 2.78-3.08 (m, 3H), 3.44-3.60 (m, 2H), 3.62-4.14 (m, 3H), 4.26 (brs, 2H), 7.00-7.06 (m, 4H), 7.18 (m, 1H), 7.38-7.52 (m, 4H).

Example 21(3)

(3R)-1-butyl-3-[(R)-cyclohexyl(hydroxy)methyl]-6-[1-(4-phenoxybenzyl)-4-piperidinyl]-2,5-piperazinedione hydrochloride TLC:Rf 0.62(chloroform:methanol=5:1);
NMR (CD$_3$OD): δ 0.86-2.48 (m, 23H), 2.81-3.08 (m, 3H), 3.27 (m, 1H), 3.45-3.58 (m, 2H), 3.64-4.00 (m, 2H), 4.18 (m, 1H), 4.25 (brs, 2H), 7.00-7.07 (m, 4H), 7.18 (m, 1H), 7.28-7.52 (m, 4H).

Example 21(4)

(3S)-3-benzyl-1-butyl-6-[1-(4-phenoxybenzyl)-4-piperidinyl]-2,5-piperazinedione hydrochloride TLC:Rf 0.65(chloroform:methanol=5:1);
NMR (CD$_3$OD): δ 0.78-2.30 (m, 12H), 2.52-3.96 (m, 9H), 4.14-4.28 (m, 2H), 4.38 (m, 1H), 6.98-7.52 (m, 14H).

Example 21(5)

(3S)-1-butyl-3-cyclohexyl-6-[1-(4-phenoxybenzyl)-4-piperidinyl]-2,5-piperazinedione hydrochloride TLC:Rf 0.65(chloroform:methanol=5:1);
NMR (CD$_3$OD): δ 0.78-1.00 (m, 3H), 1.00-2.38 (m, 20H), 2.78-3.08 (m, 3H), 3.48-4.04 (m, 5H), 4.26 (m, 2H), 6.98-7.10 (m, 4H), 7.18 (m, 1H), 7.39-7.54 (m, 4H).

Example 21(6)

(3S)-1-butyl-3-(hydroxymethyl)-6-[1-(4-phenoxybenzyl)-4-piperidinyl]-2,5-piperazinedione hydrochloride TLC:Rf 0.46(chloroform:methanol=5:1);
NMR (CD$_3$OD): δ 0.76-1.01 (m, 3H), 1.22-1.42 (m, 2H), 1.44-1.72 (m, 3H), 1.86-2.38 (m, 4H), 2.80-3.08 (m, 3H), 3.44-3.60 (m, 2H), 3.64-4.12 (m, 5H), 4.26 (brs, 2H), 6.96-7.10 (m, 4H), 7.18 (m, 1H), 7.36-7.52 (m, 4H).

Example 21(7)

(3S)-1-butyl-3-(cyclohexylmethyl)-6-{1-[(3,5-dimethyl-1-phenyl-1H-pyrazol-4-yl)methyl]-4-piperidinyl}-2,5-piperazinedione hydrochloride TLC:Rf 0.68(chloroform:methanol=5:1);
NMR (CD$_3$OD): δ 0.86-1.08 (m, 5H), 1.16-2.12 (m, 20H), 2.39 (m, 6H), 2.78-3.16 (m, 3H), 3.56-3.70 (m, 2H), 3.76-4.14 (m, 3H), 4.24 (brs, 2H), 7.47-7.56 (m, 5H).

Example 21(8)

(3R)-1-butyl-3-[(R)-cyclohexyl(hydroxy)methyl]-6-{1-[(3,5-dimethyl-1-phenyl-1H-pyrazol-4-yl)methyl]-4-piperidinyl}-2,5-piperazinedione hydrochloride TLC:Rf 0.67(chloroform:methanol=5:1);
NMR (CD$_3$OD): δ 0.90-2.14 (m, 23H), 2.32-2.40 (m, 6H), 2.80-3.14 (m, 3H), 3.28 (m, 1H), 3.56-3.68 (m, 2H), 3.68-4.00 (m, 2H), 4.19 (m, 1H), 4.24 (brs, 2H), 7.42-7.60 (m, 5H).

Example 21(9)

(3S)-3-benzyl-1-butyl-6-{1-[(3,5-dimethyl-1-phenyl-1H-pyrazol-4-yl)methyl]-4-piperidinyl}-2,5-piperazinedione hydrochloride TLC:Rf 0.74(chloroform:methanol=5:1);
NMR (CD$_3$OD): δ 0.78-2.40 (m, 12H), 2.32-2.40 (m, 6H), 2.32-3.95 (m, 8H), 4.12-4.44 (m, 4H), 7.10-7.28 (m, 5H), 7.40-7.61 (m, 5H).

Example 21(10)

(3S)-1-butyl-3-cyclohexyl-6-{1-[(3,5-dimethyl-1-phenyl-1H-pyrazol-4-yl)methyl]-4-piperidinyl}-2,5-piperazinedione hydrochloride TLC:Rf 0.74(chloroform:methanol=5:1);
NMR (CD$_3$OD): δ 0.80-1.00 (m, 3H), 1.02-2.22 (m, 20H), 2.32-2.40 (m, 6H), 2.80-3.18 (m, 3H), 3.58-4.08 (m, 5H), 4.24 (brs, 2H), 7.40-7.60 (m, 5H).

Example 21(11)

(3S)-1-butyl-3-(cyclohexylmethyl)-6-[1-(4-phenoxybenzyl)-4-piperidinyl]-2-piperazinone dihydrochloride TLC:Rf 0.82(chloroform:methanol=5:1);
NMR (CD$_3$OD): δ 0.95 (t, J=7.5 Hz, 3H), 0.85-1.10 (m, 2H), 1.16-1.42 (m, 6H), 1.46-2.10 (m, 13H), 2.21 (m, 1H), 2.81 (m, 1H), 3.00-3.20 (m, 2H), 3.34-3.72 (m, 5H), 3.92-4.08 (m, 2H), 4.30 (s, 2H), 7.00-7.10 (m, 4H), 7.18 (m, 1H), 7.36-7.44 (m, 2H), 7.54 (brd, J=8.4 Hz, 2H).

Example 22

Mixture of N-{4-[4-({4-[(1E)-2-cyclohexyl-N-ethoxyethaneimidyl]-1-piperidinyl}methyl)phenoxy]phenyl}methanesulfonamide hydrochloride and N-{4-[4-({4-[(1Z)-2-cyclohexyl-N-ethoxyethaneimidyl]-1-piperidinyl}methyl)phenoxy]phenyl}methanesulfonamide hydrochloride

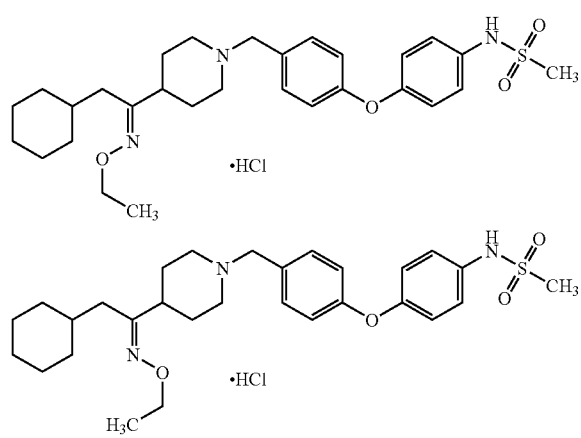

By the same procedure as described in Example 19, using the compound prepared in Example 20(15) instead of the compound prepared in Example 5(15), the compounds of the present invention having the following physical data were obtained.

TLC:Rf 0.67, 0.73(chloroform:methanol=9:1);

NMR (CD$_3$OD): δ 0.84-1.06 (m, 2H), 1.08-1.36 (m, 4H), 1.18 (t, J=7.2 Hz, 3H), 1.58-2.18 (m, 9H), 2.23 (d, J=7.2 Hz, 2H), 2.42 (m, 1H), 2.95 (s, 3H), 3.02 (m, 2H), 3.38-3.56 (m, 2H), 4.00 (q, J=7.2 Hz, 2H), 4.26 (s, 2H), 7.00-7.10 (m, 4H), 7.22-7.36 (m, 2H), 7.47 (brd, J=8.4 Hz, 2H).

Example 23

N-[4-(4-{[4-(butyl{[(1-methylcyclohexyl)amino]carbonyl}amino)-1-piperidinyl]methyl}phenoxy)phenyl]methanesulfonamide hydrochloride

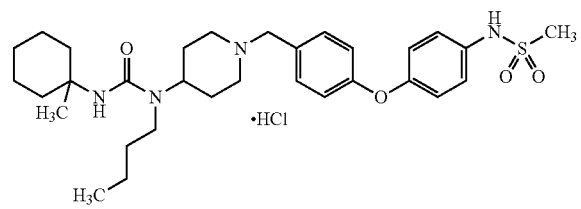

To a solution of the compound prepared in Example 3 (117 mg) in N,N-dimethylformamide (3 mL) and triethylamine (0.1 mL) were added 1-methylcyclohexanecarboxylic acid (50 mg) and diphenylphosphorylazide (0.077 mL) and the solution was stirred at 80° C. for 2 hours. After cooling, a saturated aqueous solution of sodium hydrogen carbonate was added the reaction mixture, which was extracted with ethyl acetate. The organic layer was washed with brine and dried over anhydrous sodium sulfate. The obtained residue was purified by column chromatography on silica gel (ethyl acetate) and high performance thin layer chromatography, and converted to hydrochloride salt by a conventional method to give the compound of the present invention (58 mg) having the following physical data.

TLC:Rf 0.60(ethyl acetate);

NMR (CD$_3$OD): δ 0.96 (t, J=7.2 Hz, 3H), 1.30-1.60 (m, 12H), 1.32 (s, 3H), 1.87-2.07 (m, 6H), 2.95 (s, 3H), 3.05-3.15 (m, 4H), 3.52-3.56 (m, 2H), 4.19 (m, 1H), 4.28 (s, 2H), 7.03 (d, J=9.0 Hz, 2H), 7.06 (d, J=9.0 Hz, 2H), 7.29 (d, J=9.0 Hz, 2H), 7.49 (d, J=9.0 Hz, 2H).

Example 23(1)-(151)

By the same procedure as described in Example 23, using the compound prepared in Example 3 or a corresponding amine derivative, and using 1-methylcyclohexanecarboxylic acid or a corresponding carboxylic acid derivative, the following compounds of the present invention were obtained.

Example 23(1)

3-[({[1-(4-{4-[(methylsulfonyl)amino]phenoxy}benzyl)-4-piperidinyl]amino}carbonyl)amino]benzoic acid hydrochloride TLC:Rf 0.75(n-butanol: acetic acid:water=4:2:1);

NMR (CD$_3$OD): δ 1.70-1.96 (m, 2H), 2.10-2.30 (m, 2H), 2.96 (s, 3H), 3.07-3.20 (m, 2H), 3.46-3.60 (m, 2H), 3.84 (m, 1H), 4.31 (s, 2H), 7.02-7.08 (m, 4H), 7.30 (d, J=8.7 Hz, 2H), 7.35 (t, J=7.8 Hz, 1H), 7.51 (d, J=8.7 Hz, 2H), 7.59-7.66 (m, 2H), 8.04 (s, 1H).

Example 23(2)

N-(4-{4-[(4-{butyl[(butylamino)carbonyl]amino}-1-piperidinyl)methyl]phenoxy}phenyl)methane sulfonamide hydrochloride TLC:Rf 0.51(ethyl acetate:methanol=5:1);

NMR (CD$_3$OD): δ 0.92 (t, J=6.9 Hz, 3H), 0.94 (t, J=6.9 Hz, 3H), 1.40-1.26 (m, 4H), 1.56-1.42 (m, 4H), 1.95-1.83 (m, 2H), 2.20-2.02 (m, 2H), 2.95 (s, 3H), 3.17-3.05 (m, 6H), 3.60-3.50 (m, 2H), 4.13 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(3)

N-(4-{4-[(4-{butyl[(t-butylamino)carbonyl]amino}-1-piperidinyl)methyl]phenoxy}phenyl)methane sulfonamide hydrochloride TLC:Rf 0.65(ethyl acetate:methanol=5:1);

NMR (CD$_3$OD): δ 0.95 (t, J=7.2 Hz, 3H), 1.33 (s, 9H), 1.40-1.25 (m, 2H), 1.58-1.44 (m, 2H), 1.92-1.83 (m, 2H), 2.10-1.97 (m, 2H), 2.95 (s, 3H), 3.15-3.02 (m, 4H), 3.58-3.50

(m, 2H), 4.15 (m, 1H), 4.28 (s, 2H), 7.03 (d, J=8.7 Hz, 2H), 7.06 (d, J=8.7 Hz, 2H), 7.30 (d, J=9.0 Hz, 2H), 7.50 (d, J=8.7 Hz, 2H).

Example 23(4)

N-(4-{4-[(4-{butyl[(cyclohexylamino)carbonyl]amino}-1-piperidinyl)methyl]phenoxy}phenyl)methanesulfonamide hydrochloride TLC:Rf 0.62(ethyl acetate:methanol=5:1);
NMR (CD$_3$OD): δ 0.94 (t, J=7.2 Hz, 3H), 1.95-1.10 (m, 18H), 2.20-2.02 (m, 2H), 2.95 (s, 3H), 3.18-3.02 (m, 4H), 3.60-3.50 (m, 3H), 4.18 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(5)

N-(4-{4-[(4-{benzyl[(butylamino)carbonyl]amino}-1-piperidinyl)methyl]phenoxy}phenyl)methane sulfonamide hydrochloride TLC:Rf 0.71(ethyl acetate:methanol=5:1);
NMR (CD$_3$OD): δ 0.84-0.95 (m, 3H), 1.14-1.50 (m, 4H), 1.86-2.09 (m, 4H), 2.95 (s, 3H), 3.01-3.12 (m, 2H), 3.13 (t, J=6.9 Hz, 2H), 3.44-3.52 (m, 2H), 4.24 (s, 2H), 4.35 (m, 1H), 4.46 (s, 2H), 7.02 (d, J=9.0 Hz, 2H), 7.04 (d, J=9.0 Hz, 2H), 7.20-7.35 (m, 7H), 7.46 (d, J=9.0 Hz, 2H).

Example 23(6)

N-(4-{4-[(4-{benzyl[(cyclohexylamino)carbonyl]amino}-1-piperidinyl)methyl]phenoxy}phenyl)methanesulfonamide hydrochloride TLC:Rf 0.70(ethyl acetate:methanol=5:1);
NMR (CD$_3$OD): δ 1.02-1.40 (m, 6H), 1.52-2.08 (m, 8H), 2.95 (s, 3H), 3.02-3.13 (m, 2H), 3.44-3.60 (m, 3H), 4.22 (s, 2H), 4.39 (m, 1H), 4.43 (s, 2H), 7.02 (d, J=9.0 Hz, 2H), 7.04 (d, J=9.0 Hz, 2H), 7.20-7.36 (m, 7H), 7.46 (d, J=9.0 Hz, 2H).

Example 23(7)

N-(4-{4-[(4-{benzyl[(ethylamino)carbonyl]amino}-1-piperidinyl)methyl]phenoxy}phenyl)methanesulfonamide hydrochloride TLC:Rf 0.42(ethyl acetate:methanol=5:1);
NMR (CD$_3$OD): δ 1.02-1.13 (m, 3H), 1.84-2.08 (m, 4H), 2.95 (s, 3H), 3.00-3.12 (m, 2H), 3.15-3.21 (m, 2H), 3.42-3.52 (m, 2H), 4.23 (s, 2H), 4.32 (m, 1H), 4.46 (s, 2H), 7.01 (d, J=9.0 Hz, 2H), 7.04 (d, J=8.7 Hz, 2H), 7.20-7.34 (m, 7H), 7.46 (d, J=8.7 Hz, 2H).

Example 23(8)

N-{4-[4-({4-[[(cyclohexylamino)carbonyl](2-methoxyethyl)amino]-1-piperidinyl}methyl)phenoxy]phenyl}methanesulfonamide hydrochloride TLC:Rf 0.55(ethyl acetate:methanol=5:1);
NMR (CD$_3$OD): δ 1.12-1.44 (m, 6H), 1.54-2.13 (m, 8H), 2.95 (s, 3H), 3.02-3.14 (m, 2H), 3.28-3.40 (m, 2H), 3.37 (s, 3H), 3.42-3.58 (m, 5H), 4.13 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(9)

4-[({[1-(4-{4-[(methylsulfonyl)amino]phenoxy}benzyl)-4-piperidinyl]amino}carbonyl)amino]benzoic acid hydrochloride TLC:Rf 0.30(methylene chloride:methanol=5:1);
NMR (CD$_3$OD): δ 1.71-1.82 (m, 2H), 2.21-2.26 (m, 2H), 2.96 (s, 3H), 2.99-3.17 (m, 2H), 3.52-3.57 (m, 2H), 3.84 (m, 1H), 4.30 (s, 2H), 7.03-7.08 (m, 4H), 7.30 (d, J=8.6 Hz, 2H), 7.47 (d, J=8.6 Hz, 2H), 7.51 (d, J=8.6 Hz, 2H), 7.91 (d, J=8.6 Hz, 2H).

Example 23(10)

N-[4-(4-{[4-(2,4-dioxo-1,4-dihydro-3(2H)-quinazolinyl)-1-piperidinyl]methyl}phenoxy)phenyl]methanesulfonamide hydrochloride TLC:Rf 0.62(ethyl acetate:methanol=5:1);
NMR (CD$_3$OD): δ 1.93-1.97 (m, 2H), 2.95 (s, 3H), 2.96-3.30 (m, 4H), 3.55-3.59 (m, 2H), 4.31 (s, 2H), 5.19 (m, 1H), 7.04 (d, J=8.7 Hz, 2H), 7.07 (d, J=8.7 Hz, 2H), 7.13 (m, 1H), 7.22 (m, 1H), 7.29 (d, J=8.7 Hz, 2H), 7.50 (d, J=8.7 Hz, 2H), 7.63 (m, 1H), 8.02 (m, 1H).

Example 23(11)

N-{4-[4-({4-[(anilinocarbonyl)(butyl)amino]-1-piperidinyl}methyl)phenoxy]phenyl}methanesulfonamide hydrochloride TLC:Rf 0.71(ethyl acetate:methanol=5:1);
NMR (CD$_3$OD): δ 0.97 (t, J=7.5 Hz, 3H), 1.30-1.45 (m, 2H), 1.54-1.66 (m, 2H), 1.94-2.04 (m, 2H), 2.14-2.32 (m, 2H), 2.95 (s, 3H), 3.05-3.18 (m, 2H), 3.24-3.34 (m, 2H), 3.51-3.63 (m, 2H), 4.19 (m, 1H), 4.29 (s, 2H), 7.03 (d, J=8.7 Hz, 2H), 7.06 (d, J=8.7 Hz, 2H), 7.23-7.34 (m, 7H), 7.51 (d, J=8.7 Hz, 2H).

Example 23(12)

N-[4-(4-{[4-(butyl{[(2-phenylethyl)amino]carbonyl}amino)-1-piperidinyl]methyl}phenoxy)phenyl]methanesulfonamide hydrochloride TLC:Rf 0.75(ethyl acetate:methanol=5:1);
NMR (CD$_3$OD): δ 0.90 (t, J=7.2 Hz, 3H), 1.20-1.46 (m, 4H), 1.84-1.93 (m, 2H), 2.00-2.18 (m, 2H), 2.79 (t, J=7.2 Hz, 2H), 2.95 (s, 3H), 2.99-3.12 (m, 4H), 3.39 (t, J=7.2 Hz, 2H), 3.48-3.57 (m, 2H), 4.06 (m, 1H), 4.27 (s, 2H), 7.03 (d, J=8.7 Hz, 2H), 7.06 (d, J=8.7 Hz, 2H), 7.13-7.27 (m, 5H), 7.29 (d, J=8.7 Hz, 2H), 7.49 (d, J=8.7 Hz, 2H).

Example 23(13)

N-[4-(4-{[4-(butyl{[(4-fluorophenyl)amino]carbonyl}amino)-1-piperidinyl]methyl}phenoxy)phenyl]methanesulfonamide hydrochloride TLC:Rf 0.78(ethyl acetate:methanol=5:1);
NMR (CD$_3$OD): δ 0.97 (t, J=7.5 Hz, 3H), 1.33-1.44 (m, 2H), 1.55-1.66 (m, 2H), 1.94-2.02 (m, 2H), 2.14-2.30 (m, 2H), 2.95 (s, 3H), 3.04-3.14 (m, 2H), 3.22-3.32 (m, 2H), 3.52-3.62 (m, 2H), 4.17 (m, 1H), 4.29 (s, 2H), 6.97-7.08 (m, 6H), 7.27-7.33 (m, 4H), 7.50 (d, J=8.7 Hz, 2H).

Example 23(14)

N-[4-(4-{[4-(butyl{[(2,5-dimethylphenyl)amino]carbonyl}amino)-1-piperidinyl]methyl}phenoxy)phenyl]methanesulfonamide hydrochloride TLC:Rf 0.79(ethyl acetate:methanol=5:1);
NMR (CD$_3$OD): δ 0.99 (t, J=7.2 Hz, 3H), 1.34-1.48 (m, 2H), 1.60-1.71 (m, 2H), 1.95-2.04 (m, 2H), 2.14-2.30 (m, 2H), 2.16 (s, 3H), 2.27 (s, 3H), 2.95 (s, 3H), 3.04-3.16 (m, 2H), 3.24-3.34 (m, 2H), 3.52-3.60 (m, 2H), 4.15 (m, 1H), 4.28 (s, 2H), 6.91-7.10 (m, 7H), 7.29 (d, J=8.7 Hz, 2H), 7.49 (d, J=8.7 Hz, 2H).

Example 23(15)

N-[4-(4-{[4-(benzyl {[(4-fluorophenyl)amino]carbonyl}amino)-1-piperidinyl]methyl}phenoxy)phenyl]methanesulfonamide hydrochloride TLC:Rf 0.82(ethyl acetate:methanol=5:1);
NMR (CD$_3$OD): δ 1.94-2.20 (m, 4H), 2.95 (s, 3H), 3.02-3.14 (m, 2H), 3.44-3.55 (m, 2H), 4.25 (s, 2H), 4.36 (m, 1H), 4.64 (s, 2H), 6.97 (d, J=8.7 Hz, 2H), 7.02 (d, J=8.7 Hz, 2H), 7.05 (d, J=8.7 Hz, 2H), 7.24-7.41 (m, 9H), 7.46 (d, J=8.7 Hz, 2H).

Example 23(16)

N-{4-[4-({4-[{[(4-fluorophenyl)amino]carbonyl}(2-methoxyethyl)amino]-1-piperidinyl}methyl)phenoxy]phenyl}methanesulfonamide hydrochloride TLC:Rf 0.50(ethyl acetate:methanol=5:1);
NMR (CD$_3$OD): δ 1.98-2.08 (m, 2H), 2.10-2.26 (m, 2H), 2.95 (s, 3H), 3.02-3.18 (m, 2H), 3.47 (s, 3H), 3.44-3.64 (m, 6H), 4.14 (m, 1H), 4.29 (s, 2H), 6.98-7.06 (m, 2H), 7.03 (d, J=8.7 Hz, 2H), 7.07 (d, J=8.7 Hz, 2H), 7.22-7.28 (m, 2H), 7.29 (d, J=8.7 Hz, 2H), 7.50 (d, J=8.7 Hz, 2H).

Example 23(17)

N-{4-[4-({4-[butyl({[3-(methylsulfanyl)phenyl]amino}carbonyl)amino]-1-piperidinyl}methyl)phenoxy]phenyl}methanesulfonamide hydrochloride TLC:Rf 0.73(ethyl acetate:methanol=5:1);
NMR (CD$_3$OD): δ 0.98 (t, J=7.2 Hz, 3H), 1.33-1.46 (m, 2H), 1.54-1.66 (m, 2H), 1.93-2.04 (m, 2H), 2.14-2.24 (m, 2H), 2.46 (s, 3H), 2.95 (s, 3H), 3.04-3.18 (m, 2H), 3.24-3.34 (m, 2H), 3.48-3.60 (m, 2H), 4.16 (m, 1H), 4.29 (s, 2H), 6.76 (m, 1H), 7.00-7.22 (m, 7H), 7.30 (d, J=8.7 Hz, 2H), 7.50 (d, J=8.7 Hz, 2H).

Example 23(18)

N-{4-[4-({4-[benzyl({[3-(methylsulfanyl)phenyl]amino}carbonyl)amino]-1-piperidinyl}methyl)phenoxy]phenyl}methanesulfonamide hydrochloride TLC:Rf 0.76(ethyl acetate:methanol=5:1);
NMR (CD$_3$OD): δ 1.90-2.02 (m, 2H), 2.04-2.20 (m, 2H), 2.43 (s, 3H), 2.95 (s, 3H), 3.00-3.15 (m, 2H), 3.42-3.54 (m, 2H), 4.23 (s, 2H), 4.36 (m, 1H), 4.66 (s, 2H), 6.92 (m, 1H), 7.03 (d, J=8.7 Hz, 2H), 7.04 (d, J=8.7 Hz, 2H), 7.15 (d, J=7.8 Hz, 2H), 7.25-7.39 (m, 9H), 7.45 (d, J=8.7 Hz, 2H).

Example 23(19)

N-[4-(4-{[4-(butyl{[(2-chloro-6-methylphenyl)amino]carbonyl}amino)-1-piperidinyl]methyl}phenoxy)phenyl]methanesulfonamide hydrochloride TLC:Rf 0.77(ethyl acetate:methanol=5:1);
NMR (CD$_3$OD): δ 0.98 (t, J=7.2 Hz, 3H), 1.34-1.48 (m, 2H), 1.65-1.75 (m, 2H), 1.96-2.06 (m, 2H), 2.16-2.32 (m, 2H), 2.26 (s, 3H), 2.95 (s, 3H), 3.04-3.16 (m, 2H), 3.26-3.34 (m, 2H), 3.51-3.60 (m, 2H), 4.16 (m, 1H), 4.28 (s, 2H), 7.03 (d, J=8.7 Hz, 2H), 7.06 (d, J=8.7 Hz, 2H), 7.14-7.21 (m, 2H), 7.28-7.31 (m, 3H), 7.50 (d, J=8.7 Hz, 2H).

Example 23(20)

N-(4-{4-[(4-{butyl[(mesitylamino)carbonyl]amino}piperidin-1-yl)methyl]phenoxy}phenyl)methanesulfonamide hydrochloride TLC:Rf 0.77(ethyl acetate:methanol=5:1);
NMR (CD$_3$OD): δ 0.98 (t, J=7.2 Hz, 3H), 1.34-1.46 (m, 2H), 1.61-1.73 (m, 2H), 1.94-2.04 (m, 2H), 2.13-2.30 (m, 2H), 2.15 (s, 6H), 2.23 (s, 3H), 2.95 (s, 3H), 3.04-3.16 (m, 2H), 3.24-3.32 (m, 2H), 3.52-3.60 (m, 2H), 4.15 (m, 1H), 4.28 (s, 2H), 6.87 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(21)

N-{4-[4-({4-[{[(3-acetylphenyl)amino]carbonyl}(butyl)amino]-1-piperidinyl}methyl)phenoxy]phenyl}methanesulfonamide hydrochloride TLC:Rf 0.79(ethyl acetate:methanol=5:1);
NMR (CD$_3$OD): δ 0.97 (t, J=7.2 Hz, 3H), 1.33-1.45 (m, 2H), 1.55-1.68 (m, 2H), 1.96-2.06 (m, 2H), 2.15-2.32 (m, 2H), 2.58 (s, 3H), 2.95 (s, 3H), 3.06-3.19 (m, 2H), 3.25-3.35 (m, 2H), 3.53-3.62 (m, 2H), 4.19 (m, 1H), 4.30 (s, 2H), 7.04 (d, J=8.7 Hz, 2H), 7.07 (d, J=8.7 Hz, 2H), 7.29 (d, J=8.7 Hz, 2H), 7.41 (t, J=8.0 Hz, 1H), 7.50 (d, J=8.7 Hz, 2H), 7.62 (ddd, J=8.0, 2.1, 1.2 Hz, 1H), 7.68 (ddd, J=8.0, 1.5, 1.2 Hz, 1H), 8.00 (m, 1H).

Example 23(22)

N-{4-[4-({4-[[(benzylamino)carbonyl](butyl)amino]-1-piperidinyl}methyl)phenoxy]phenyl}methanesulfonamide hydrochloride TLC:Rf 0.73(ethyl acetate:methanol=5:1);
NMR (CD$_3$OD): δ 0.94 (t, J=7.2 Hz, 3H), 1.26-1.40 (m, 2H), 1.47-1.60 (m, 2H), 1.87-1.98 (m, 2H), 2.06-2.21 (m, 2H), 2.95 (s, 3H), 3.02-3.18 (m, 4H), 3.49-3.59 (m, 2H), 4.15 (m, 1H), 4.27 (s, 2H) 4.36 (s, 2H), 7.03 (d, J=8.7 Hz, 2H), 7.06 (J=8.7 Hz, 2H), 7.23-7.31 (m, 7H), 7.49 (d, J=8.7 Hz, 2H).

Example 23(23)

N-{4-[4-({4-[[(1-adamantylamino)carbonyl](3-hydroxybutyl)amino]-1-piperidinyl}methyl)phenoxy]phenyl}methanesulfonamide hydrochloride TLC:Rf 0.66(ethyl acetate:methanol=5:1);
NMR (CD$_3$OD): δ 1.18 (d, J=6.3 Hz, 3H), 1.38-1.50 (m, 2H), 1.64-1.80 (m, 7H), 1.80-1.94 (m, 2H), 1.95-2.12 (m, 10H), 2.95 (s, 3H), 3.00-3.54 (m, 4H), 3.48-3.57 (m, 2H), 3.74 (m, 1H), 4.12 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(24)

N-[4-(4-{[4-(butyl{[(2-cyclohexylethyl)amino]carbonyl}amino)-1-piperidinyl]methyl}phenoxy)phenyl]methanesulfonamide hydrochloride TLC:Rf 0.52(ethyl acetate:methanol=10:1);
NMR (CD$_3$OD): δ 0.95 (t, J=7.2 Hz, 3H), 0.85-1.02 (m, 2H), 1.13-1.58 (m, 10H), 1.61-1.80 (m, 5H), 1.83-1.95 (m, 2H), 2.03-2.19 (m, 2H), 2.95 (s, 3H), 3.02-3.13 (m, 6H), 3.48-3.58 (m, 2H), 4.14 (m, 1H), 4.27 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(25)

N-[4-(4-{[4-({[(2-cyclohexylethyl)amino]carbonyl}amino)-1-piperidinyl]methyl}phenoxy)phenyl]methanesulfonamide hydrochloride TLC:Rf 0.24(ethyl acetate:methanol=10:1);
NMR (CD$_3$OD): δ 0.85-1.00 (m, 2H), 1.10-1.40 (m, 7H), 1.60-1.78 (m, 6H), 2.08-2.20 (m, 2H), 2.95 (s, 3H), 3.02-3.18 (m, 4H), 3.45-3.55 (m, 2H), 3.72 (m, 1H), 4.27 (s, 2H), 7.03 (d, J=8.7 Hz, 2H), 7.05 (d, J=8.7 Hz, 2H), 7.29 (d, J=8.7 Hz, 2H), 7.50 (d, J=8.7 Hz, 2H).

Example 23(26)

N-{4-[4-({4-[{[(2-cyclohexylethyl)amino]carbonyl}(methyl)amino]-1-piperidinyl}methyl)phenoxy]phenyl}methanesulfonamide hydrochloride TLC:Rf 0.29(ethyl acetate:methanol=10:1);
NMR (CD$_3$OD): δ 0.84-1.00 (m, 2H), 1.15-1.44 (m, 7H), 1.60-1.78 (m, 6H), 1.97-2.13 (m, 2H), 2.74 (s, 3H), 2.95 (s, 3H), 3.03-3.20 (m, 4H), 3.51-3.60 (m, 2H), 4.28 (s, 2H), 4.30 (m, 1H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(27)

N-{4-[4-({4-[{[(2-cyclohexylethyl)amino]carbonyl}(ethyl)amino]-1-piperidinyl}methyl)phenoxy]phenyl}methanesulfonamide hydrochloride TLC:Rf 0.57(ethyl acetate:methanol=10:1);
NMR (CD$_3$OD): δ 0.84-1.01 (m, 2H), 1.12 (t, J=6.9 Hz, 3H), 1.08-1.45 (m, 6H), 1.58-1.80 (m, 5H), 1.85-1.94 (m, 2H), 1.97-2.18 (m, 2H), 2.95 (s, 3H), 3.02-3.14 (m, 6H), 3.48-3.59 (m, 2H), 4.20 (m, 1H), 4.28 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(28)

N-{4-[4-({4-[{[(2-cyclohexylethyl)amino]carbonyl}(propyl)amino]-1-piperidinyl}methyl)phenoxy]phenyl}methanesulfonamide hydrochloride TLC:Rf 0.69(ethyl acetate:methanol=10:1);
NMR (CD$_3$OD): δ 0.91 (t, J=7.5 Hz, 3H), 0.82-1.00 (m, 2H), 1.15-1.40 (m, 6H), 1.42-1.80 (m, 6H), 1.80-2.20 (m, 5H), 2.95 (s, 3H), 2.98-3.22 (m, 6H), 3.42-3.58 (m, 2H), 4.12 (m, 1H), 4.27 (s, 2H), 7.03 (d, J=8.7 Hz, 2H), 7.06 (d, J=8.7 Hz, 2H), 7.30 (d, J=8.7 Hz, 2H), 7.50 (d, J=8.7 Hz, 2H).

Example 23(29)

N-{4-[4-({4-[{[(2-cyclohexylethyl)amino]carbonyl}(2-methoxyethyl)amino]-1-piperidinyl}methyl)phenoxy]phenyl}methanesulfonamide hydrochloride TLC:Rf 0.64(ethyl acetate:methanol=10:1);
NMR (CD$_3$OD): δ 0.85-1.00 (m, 2H), 1.08-1.40 (m, 6H), 1.60-1.80 (m, 5H), 1.87-2.18 (m, 4H), 2.95 (s, 3H), 3.02-3.18 (m, 2H), 3.15 (t, J=6.2 Hz, 2H), 3.29-3.38 (m, 2H), 3.36 (s, 3H), 3.45-3.57 (m, 4H), 4.08 (m, 1H), 4.27 (s, 2H), 7.03 (d, J=8.7 Hz, 2H), 7.06 (d, J=8.7 Hz, 2H), 7.29 (d, J=8.7 Hz, 2H), 7.48 (d, J=8.7 Hz, 2H).

Example 23(30)

N-[4-(4-{[4-(benzyl{[(2-cyclohexylethyl)amino]carbonyl}amino)-1-piperidinyl]methyl}phenoxy)phenyl]methanesulfonamide hydrochloride TLC:Rf 0.73(ethyl acetate:methanol=10:1);
NMR (CD$_3$OD): δ 0.78-0.93 (m, 2H), 1.02-1.33 (m, 6H), 1.56-1.70 (m, 5H), 1.85-2.03 (m, 4H), 2.95 (s, 3H), 2.98-3.20 (m, 4H), 3.42-3.53 (m, 2H), 4.23 (s, 2H), 4.36 (m, 1H), 4.45 (s, 2H), 7.02 (d, J=8.7 Hz, 2H), 7.04 (d, J=8.7 Hz, 2H), 7.15-7.38 (m, 7H), 7.45 (d, J=8.7 Hz, 2H).

Example 23(31)

N-{4-[4-({4-[{[(2-cyclohexylethyl)amino]carbonyl}(cyclohexylmethyl)amino]-1-piperidinyl}methyl)phenoxy]phenyl}methanesulfonamide hydrochloride TLC:Rf 0.71(ethyl acetate:methanol=10:1);
NMR (CD$_3$OD): δ 0.83-1.12 (m, 4H), 1.15-1.41 (m, 10H), 1.52-1.80 (m, 10H), 1.87-1.95 (m, 2H), 2.18-2.30 (m, 2H), 2.95 (s, 3H), 3.02-3.14 (m, 4H), 3.17 (t, J=6.2 Hz, 2H), 3.48-3.57 (m, 2H), 3.91 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(32)

N-[4-(4-{[4-(butyl{[(cyclohexylmethyl)amino]carbonyl}amino)-1-piperidinyl]methyl}phenoxy)phenyl]methanesulfonamide hydrochloride TLC:Rf 0.69(ethyl acetate:methanol=10:1);
NMR (CD$_3$OD): δ 0.95 (t, J=7.2 Hz, 3H), 0.82-1.05 (m, 2H), 1.14-1.42 (m, 5H), 1.43-1.58 (m, 3H), 1.62-1.81 (m, 5H), 1.85-1.98 (m, 2H), 1.99-2.22 (m, 2H), 2.95 (s, 3H), 2.99 (d, J=6.9 Hz, 2H), 3.02-3.17 (m, 4H), 3.48-3.60 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(33)

N-[4-(4-{[4-({[(cyclohexylmethyl)amino]carbonyl}amino)-1-piperidinyl]methyl}phenoxy)phenyl]methanesulfonamide hydrochloride TLC:Rf 0.48(ethyl acetate:methanol=10:1);
NMR (CD$_3$OD): δ 0.83-1.02 (m, 2H), 1.12-1.33 (m, 4H), 1.58-1.80 (m, 6H), 2.03 (m, 1H), 2.09-2.11 (m, 2H), 2.95 (s, 3H), 3.02-3.15 (m, 4H), 3.50-3.58 (m, 2H), 3.72 (m, 1H), 4.27 (s, 2H), 7.03 (d, J=8.7 Hz, 2H), 7.05 (d, J=8.7 Hz, 2H), 7.29 (d, J=8.7 Hz, 2H), 7.49 (d, J=8.7 Hz, 2H).

Example 23(34)

N-{4-[4-({4-[{[(cyclohexylmethyl)amino]carbonyl}(methyl)amino]-1-piperidinyl}methyl)phenoxy]phenyl}methanesulfonamide hydrochloride TLC:Rf 0.52(ethyl acetate:methanol=10:1);
NMR (CD$_3$OD): δ 0.81-1.00 (m, 2H), 1.13-1.32 (m, 4H), 1.48 (m, 1H), 1.60-1.90 (m, 6H), 1.93-2.12 (m, 2H), 2.75 (s, 3H), 2.95 (s, 3H), 2.98 (d, J=6.9 Hz, 2H), 3.04-3.19 (m, 2H), 3.49-3.60 (m, 2H), 4.28 (s, 2H), 4.33 (m, 1H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(35)

N-{4-[4-({4-[{[(cyclohexylmethyl)amino]carbonyl}(ethyl)amino]-1-piperidinyl}methyl)phenoxy]phenyl}methanesulfonamide hydrochloride TLC:Rf 0.55(ethyl acetate:methanol=10:1);
NMR (CD$_3$OD): δ 0.83-0.99 (m, 2H), 1.14 (t, J=6.9 Hz, 3H), 1.08-1.32 (m, 2H), 1.47 (m, 1H), 1.60-1.79 (m, 6H), 1.86-1.95 (m, 2H), 2.00-2.17 (m, 2H), 2.95 (s, 3H), 2.98 (dd, J=7.2, 2.0 Hz, 2H), 3.02-3.25 (m, 4H), 3.49-3.58 (m, 2H), 4.22 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(36)

N-{4-[4-({4-[{[(cyclohexylmethyl)amino]carbonyl}(propyl)amino]-1-piperidinyl}methyl)phenoxy]phenyl}methanesulfonamide hydrochloride TLC:Rf 0.59(ethyl acetate:methanol=10:1);
NMR (CD$_3$OD): δ 0.91 (t, J=7.2 Hz, 3H), 0.83-0.99 (m, 2H), 1.10-1.33 (m, 4H), 1.40-1.80 (m, 7H), 1.85-1.96 (m, 2H), 2.02-2.20 (m, 2H), 2.95 (s, 3H), 2.98 (d, J=7.2 Hz, 2H), 3.00-3.17 (m, 4H), 3.50-3.58 (m, 2H), 4.14 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(37)

N-{4-[4-({4-[{[(cyclohexylmethyl)amino]carbonyl}(2-methoxyethyl)amino]-1-piperidinyl}methyl)phenoxy]phenyl}methanesulfonamide hydrochloride TLC:Rf 0.57(ethyl acetate:methanol=10:1);
NMR (CD$_3$OD): δ 0.85-1.00 (m, 2H), 1.15-1.35 (m, 3H), 1.43 (m, 1H), 1.63-1.80 (m, 5H), 1.88-2.18 (m, 4H), 2.95 (s, 3H), 2.95 (d, J=6.6 Hz, 2H), 3.02-3.15 (m, 2H), 3.25-3.38 (m, 2H), 3.36 (s, 3H), 3.46-3.58 (m, 4H), 4.10 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(38)

N-[4-(4-{[4-(benzyl{[(cyclohexylmethyl)amino]carbonyl}amino)-1-piperidinyl]methyl}phenoxy)phenyl]methanesulfonamide hydrochloride TLC:Rf 070(ethyl acetate:methanol=10:1);
NMR (CD$_3$OD): δ 0.72-0.85 (m, 2H), 1.08-1.40 (m, 4H), 1.50-1.79 (m, 5H), 1.90-2.08 (m, 4H), 2.95 (s, 3H), 2.96 (d, J=6.9 Hz, 2H), 3.02-3.17 (m, 2H), 3.44-3.56 (m, 2H), 4.24 (s, 2H), 4.38 (m, 1H), 4.46 (s, 2H), 7.02 (d, J=8.7 Hz, 2H), 7.04 (d, J=8.7 Hz, 2H), 7.20-7.38 (m, 7H), 7.46 (d, J=8.7 Hz, 2H).

Example 23(39)

N-[4-(4-{[4-((cyclohexylmethyl){[(cyclohexylmethyl)amino]carbonyl}amino)-1-piperidinyl]methyl}phenoxy)phenyl]methanesulfonamide hydrochloride TLC:Rf 0.72(ethyl acetate:methanol=10:1);
NMR (CD$_3$OD): δ 0.82-1.05 (m, 4H), 1.13-1.35 (m, 6H), 1.46 (m, 1H), 1.60-1.85 (m, 11H), 1.87-1.98 (m, 2H), 2.15-2.31 (m, 2H), 2.95 (s, 3H), 2.98 (d, J=6.6 Hz, 2H), 2.94-3.13 (m, 4H), 3.50-3.59 (m, 2H), 3.89 (m, 1H), 4.26 (s, 2H), 7.03 (d, J=8.7 Hz, 2H), 7.06 (d, J=8.7 Hz, 2H), 7.30 (d, J=8.7 Hz, 2H), 7.48 (d, J=8.7 Hz, 2H).

Example 23(40)

N-{4-[4-({4-[[(cyclohexylamino)carbonyl](ethyl)amino]-1-piperidinyl}methyl)phenoxy]phenyl}methanesulfonamide hydrochloride TLC:Rf 0.44(ethyl acetate:methanol=10:1);
NMR (CD$_3$OD): δ 1.12 (t, J=7.0 Hz, 3H), 1.07-1.43 (m, 5H), 1.59-1.96 (m, 7H), 1.97-2.18 (m, 2H), 2.95 (s, 3H), 3.03-3.26 (m, 4H), 3.48-3.61 (m, 3H), 4.21 (m, 1H), 4.28 (s, 2H), 7.03 (d, J=8.7 Hz, 2H), 7.06 (d, J=8.7 Hz, 2H), 7.30 (d, J=8.7 Hz, 2H), 7.50 (d, J=8.7 Hz, 2H).

Example 23(41)

N-{4-[4-({4-[(anilino carbonyl)(ethyl)amino]-1-piperidinyl}methyl)phenoxy]phenyl}methanesulfonamide hydrochloride TLC:Rf 0.56(ethyl acetate:methanol=10:1);
NMR (CD$_3$OD): δ 1.23 (t, J=7.0 Hz, 3H), 1.94-2.04 (m, 2H), 2.10-2.29 (m, 2H), 2.95 (s, 3H), 3.05-3.19 (m, 2H), 3.38 (q, J=7.0 Hz, 2H), 3.52-3.61 (m, 2H), 4.25 (m, 1H), 4.30 (s, 2H), 7.04 (d, J=8.7 Hz, 2H), 7.07 (d, J=8.7 Hz, 2H), 7.24-7.38 (m, 7H), 7.50 (d, J=8.7 Hz, 2H).

Example 23(42)

N-{4-[4-({4-[[(benzylamino)carbonyl](ethyl)amino]-1-piperidinyl}methyl)phenoxy]phenyl}methanesulfonamide hydrochloride TLC:Rf 0.52(ethyl acetate:methanol=10:1);
NMR (CD$_3$OD): δ 1.16 (t, J=7.0 Hz, 3H), 1.89-1.97 (m, 2H), 2.02-2.18 (m, 2H), 2.95 (s, 3H), 3.02-3.15 (m, 2H), 3.25 (q, J=7.0 Hz, 2H), 3.50-3.58 (m, 2H), 4.21 (m, 1H), 4.28 (s, 2H), 4.36 (s, 2H), 7.03 (d, J=8.7 Hz, 2H), 7.06 (d, J=8.7 Hz, 2H), 7.18-7.30 (m, 7H), 7.49 (d, J=8.7 Hz, 2H).

Example 23(43)

N-[4-(4-{[4-(ethyl {[(2-phenylethyl)amino]carbonyl}amino)-1-piperidinyl]methyl}phenoxy)phenyl]methanesulfonamide hydrochloride TLC:Rf 0.67(ethyl acetate:methanol=10:1);
NMR (CD$_3$OD): δ 1.06 (t, J=7.0 Hz, 3H), 1.84-1.93 (m, 2H), 1.98-2.15 (m, 2H), 2.79 (t, J=7.5 Hz, 2H), 2.95 (s, 3H), 3.01-3.20 (m, 4H), 3.38 (t, J=7.5 Hz, 2H), 3.50-3.59 (m, 2H), 4.19 (m, 1H), 4.28 (s, 2H), 7.03 (d, J=8.7 Hz, 2H), 7.06 (d, J=8.7 Hz, 2H), 7.12-7.33 (m, 7H), 7.49 (d, J=8.7 Hz, 2H).

Example 23(44)

N-(4-{4-[(4-{ethyl[(ethylamino)carbonyl]amino}-1-piperidinyl)methyl]phenoxy}phenyl)methane sulfonamide hydrochloride TLC:Rf 0.20(ethyl acetate:methanol=10:1);
NMR (CD$_3$OD): δ 1.09 (t, J=7.2 Hz, 3H), 1.13 (t, J=7.2 Hz, 3H), 1.85-1.95 (m, 2H), 1.98-2.18 (m, 2H), 2.95 (s, 3H), 3.03-3.24 (m, 6H), 3.50-3.59 (m, 2H), 4.21 (m, 1H), 4.29 (s, 2H), 7.03 (d, J=8.7 Hz, 2H), 7.06 (d, J=8.7 Hz, 2H), 7.30 (d, J=8.7 Hz, 2H), 7.50 (d, J=8.7 Hz, 2H).

Example 23(45)

N-{4-[4-({4-[[(t-butylamino)carbonyl](ethyl)amino]-1-piperidinyl}methyl)phenoxy]phenyl}methanesulfonamide hydrochloride TLC:Rf 0.41(ethyl acetate:methanol=10:1);
NMR (CD$_3$OD): δ 1.13 (t, J=7.2 Hz, 3H), 1.33 (s, 9H), 1.82-1.93 (m, 2H), 1.95-2.11 (m, 2H), 2.95 (s, 3H), 3.02-3.15 (m, 2H), 3.18 (t, J=7.2 Hz, 2H), 3.49-3.59 (m, 2H), 4.22 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(46)

N-{4-[4-({4-[[(butylamino)carbonyl](ethyl)amino]-1-piperidinyl}methyl)phenoxy]phenyl}methanesulfonamide hydrochloride TLC:Rf 0.37(ethyl acetate:methanol=10:1);
NMR (CD$_3$OD): δ 0.93 (t, J=7.2 Hz, 3H), 1.13 (t, J=7.0 Hz, 3H), 1.26-1.40 (m, 2H), 1.42-1.54 (m, 2H), 1.85-1.96 (m, 2H), 1.98-2.15 (m, 2H), 2.95 (s, 3H), 3.02-3.24 (m, 6H), 3.49-3.58 (m, 2H), 4.21 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(47)

N-{4-[4-({4-[[(cyclohexylamino)carbonyl](propyl)amino]-1-piperidinyl}methyl)phenoxy]phenyl}methanesulfonamide hydrochloride TLC:Rf 0.67(ethyl acetate:methanol=10:1);
NMR (CD$_3$OD): δ 0.93 (t, J=7.2 Hz, 3H), 1.13-1.41 (m, 5H), 1.48-1.67 (m, 3H), 1.71-1.92 (m, 6H), 2.03-2.20 (m, 2H), 2.95 (s, 3H), 3.03-3.14 (m, 4H), 3.50-3.59 (m, 3H), 4.10 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(48)

N-{4-[4-({4-[(anilino carbonyl)(propyl)amino]-1-piperidinyl}methyl)phenoxy]phenyl}methanesulfonamide hydrochloride TLC:Rf 0.73(ethyl acetate:methanol=10:1);
NMR (CD$_3$OD): δ 0.96 (t, J=7.2 Hz, 3H), 1.59-1.72 (m, 2H), 1.95-2.06 (m, 2H), 2.15-2.31 (m, 2H), 2.95 (s, 3H), 3.05-3.18 (m, 2H), 3.22-3.32 (m, 2H), 3.52-3.61 (m, 2H), 4.18 (m, 1H), 4.29 (s, 2H), 7.03 (d, J=8.7 Hz, 2H), 7.06 (d, J=8.7 Hz, 2H), 7.23-7.37 (m, 7H), 7.50 (d, J=8.7 Hz, 2H).

Example 23(49)

N-{4-[4-({4-[[(benzylamino)carbonyl](propyl)amino]-1-piperidinyl}methyl)phenoxy]phenyl}methanesulfonamide hydrochloride TLC:Rf 0.74(ethyl acetate:methanol=10:1);
NMR (CD$_3$OD): δ 0.91 (t, J=7.0 Hz, 3H), 1.50-1.66 (m, 2H), 1.87-1.98 (m, 2H), 2.04-2.21 (m, 2H), 2.95 (s, 3H), 3.02-3.15 (m, 4H), 3.49-3.58 (m, 2H), 4.14 (m, 1H), 4.27 (s, 2H), 4.36 (s, 2H), 7.03 (d, J=8.7 Hz, 2H), 7.06 (d, J=8.7 Hz, 2H), 7.15-7.32 (m, 7H), 7.49 (d, J=8.7 Hz, 2H).

Example 23(50)

N-{4-[4-({4-[{[(2-phenylethyl)amino]carbonyl}(propyl)amino]-1-piperidinyl}methyl)phenoxy]phenyl}methanesulfonamide hydrochloride TLC:Rf 0.72(ethyl acetate:methanol=10:1);
NMR (CD$_3$OD): δ 0.85 (t, J=7.2 Hz, 3H), 1.38-1.51 (m, 2H), 1.84-1.93 (m, 2H), 2.00-2.19 (m, 2H), 2.75-2.82 (m, 2H), 2.95 (s, 3H), 2.94-3.15 (m, 4H), 3.33-3.41 (m, 2H), 3.48-3.58 (m, 2H), 4.11 (m, 1H), 4.27 (s, 2H), 7.03 (d, J=8.7 Hz, 2H), 7.07 (d, J=8.7 Hz, 2H), 7.13-7.31 (m, 7H), 7.49 (d, J=8.7 Hz, 2H).

Example 23(51)

N-{4-[4-({4-[[(ethylamino)carbonyl](propyl)amino]-1-piperidinyl}methyl)phenoxy]phenyl}methanesulfonamide hydrochloride TLC:Rf 0.56(ethyl acetate:methanol=10:1);
NMR (CD$_3$OD): δ 0.91 (t, J=7.0 Hz, 3H), 1.09 (t, J=7.2 Hz, 3H), 1.46-1.60 (m, 2H), 1.86-1.95 (m, 2H), 2.03-2.19 (m, 2H), 2.95 (s, 3H), 3.00-3.22 (m, 6H), 3.50-3.59 (m, 2H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(52)

N-{4-[4-({4-[[(t-butylamino)carbonyl](propyl)amino]-1-piperidinyl}methyl)phenoxy]phenyl}methanesulfonamide hydrochloride TLC:Rf 0.68(ethyl acetate:methanol=10:1);
NMR (CD$_3$OD): δ 0.91 (t, J=7.2 Hz, 3H), 1.32 (s, 9H), 1.47-1.61 (m, 2H), 1.84-1.94 (m, 2H), 1.95-2.11 (m, 2H), 2.95 (s, 3H), 3.01-3.15 (m, 4H), 3.50-3.57 (m, 2H), 4.16 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(53)

N-{4-[4-({4-[[(butylamino)carbonyl](propyl)amino]-1-piperidinyl}methyl)phenoxy]phenyl}methanesulfonamide hydrochloride TLC:Rf 0.74(ethyl acetate:methanol=10:1);
NMR (CD$_3$OD): δ 0.91 (t, J=7.5 Hz, 3H), 0.92 (t, J=7.5 Hz, 3H), 1.27-1.39 (m, 2H), 1.41-1.59 (m, 4H), 1.85-1.96 (m, 2H), 2.03-2.20 (m, 2H), 2.95 (s, 3H), 3.02-3.22 (m, 6H), 3.50-3.58 (m, 2H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(54)

N-(4-{4-[(4-{butyl[(pentylamino)carbonyl]amino}-1-piperidinyl)methyl]phenoxy}phenyl)methane sulfonamide hydrochloride TLC:Rf 0.69(ethyl acetate:methanol=10:1);
NMR (CD₃OD): δ 0.91 (t, J=7.2 Hz, 3H), 0.95 (t, J=7.2 Hz, 3H), 1.23-1.41 (m, 6H), 1.44-1.58 (m, 4H), 1.86-1.95 (m, 2H), 2.03-2.20 (m, 2H), 2.95 (s, 3H), 3.02-3.17 (m, 6H), 3.48-3.58 (m, 2H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(55)

N-(4-{4-[(4-{benzyl[(pentylamino)carbonyl]amino}-1-piperidinyl)methyl]phenoxy}phenyl)methane sulfonamide hydrochloride TLC:Rf 0.71(ethyl acetate:methanol=10:1);
NMR (CD₃OD): δ 0.86 (t, J=7.2 Hz, 3H), 1.10-1.50 (m, 6H), 1.88-2.09 (m, 4H), 2.95 (s, 3H), 3.01-3.17 (m, 2H), 3.13 (t, J=7.0 Hz, 2H), 3.44-3.52 (m, 2H), 4.24 (s, 2H), 4.35 (m, 1H), 4.46 (s, 2H), 7.02 (d, J=8.7 Hz, 2H), 7.04 (d, J=8.7 Hz, 2H), 7.20-7.36 (m, 7H), 7.45 (d, J=8.7 Hz, 2H).

Example 23(56)

N-(4-{4-[(4-{(2-methoxyethyl)[(pentylamino)carbonyl]amino}-1-piperidinyl)methyl]phenoxy}phenyl)methane sulfonamide hydrochloride TLC:Rf 0.29(ethyl acetate:methanol=10:1);
NMR (CD₃OD): δ 0.91 (t, J=7.0 Hz, 3H), 1.22-1.38 (m, 4H), 1.41-1.54 (m, 2H), 1.87-2.19 (m, 4H), 2.95 (s, 3H), 3.02-3.16 (m, 2H), 3.11 (t, J=7.0 Hz, 2H), 3.28-3.38 (m, 2H), 3.36 (s, 3H), 3.45-3.58 (m, 4H), 4.10 (m, 1H), 4.27 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(57)

N-(4-{4-[(4-{butyl[(isopropylamino)carbonyl]amino}-1-piperidinyl)methyl]phenoxy}phenyl)methanesulfonamide hydrochloride TLC:Rf 0.65(ethyl acetate:methanol=10:1);
NMR (CD₃OD): δ 0.91 (t, J=7.2 Hz, 3H), 1.13 (d, J=6.6 Hz, 6H), 1.28-1.40 (m, 2H), 1.43-1.57 (m, 2H), 1.85-1.96 (m, 2H), 2.02-2.19 (m, 2H), 2.95 (s, 3H), 3.03-3.15 (m, 4H), 3.48-3.58 (m, 2H), 3.91 (m, 1H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(58)

N-(4-{4-[(4-{benzyl[(isopropylamino)carbonyl]amino}-1-piperidinyl)methyl]phenoxy}phenyl)methane sulfonamide hydrochloride TLC:Rf 0.70(ethyl acetate:methanol=10:1);
NMR (CD₃OD): δ 1.05 (d, J=6.6 Hz, 6H), 1.86-2.10 (m, 4H), 2.95 (s, 3H), 3.02-3.15 (m, 2H), 3.44-3.53 (m, 2H), 3.91 (m, 1H), 4.24 (s, 2H), 4.35 (m, 1H), 4.47 (s, 2H), 7.02 (d, J=8.7 Hz, 2H), 7.04 (d, J=8.7 Hz, 2H), 7.21-7.39 (m, 7H), 7.46 (d, J=8.7 Hz, 2H).

Example 23(59)

N-{4-[4-({4-[[(butylamino)carbonyl](2-methoxyethyl)amino]-1-piperidinyl}methyl)phenoxy]phenyl}methanesulfonamide hydrochloride TLC:Rf 0.33(ethyl acetate:methanol=10:1);
NMR (CD₃OD): δ 0.93 (t, J=7.2 Hz, 3H), 1.26-1.51 (m, 4H), 1.87-1.98 (m, 2H), 2.00-2.18 (m, 2H), 2.95 (s, 3H), 3.01-3.16 (m, 2H), 3.12 (t, J=7.0 Hz, 2H), 3.28-3.37 (m, 2H), 3.36 (s, 3H), 3.45-3.58 (m, 4H), 4.10 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(60)

N-[4-(4-{[4-({[(2-methoxyphenyl)amino]carbonyl}amino)-1-piperidinyl]methyl}phenoxy)phenyl]methanesulfonamide hydrochloride TLC:Rf 0.39(methylene chloride:methanol=10:1);
NMR (CD₃OD): δ 1.66-1.73 (m, 2H), 2.22-2.26 (m, 2H), 2.95 (s, 3H), 3.08-3.17 (m, 2H), 3.51-3.55 (m, 2H), 3.80 (m, 1H), 3.86 (s, 3H), 4.29 (s, 2H), 6.86 (m, 1H), 6.94 (m, 2H), 7.04 (d, J=9.0 Hz, 2H), 7.07 (d, J=9.0 Hz, 2H), 7.29 (d, J=9.0 Hz, 2H), 7.49 (d, J=9.0 Hz, 2H), 7.96 (m, 1H).

Example 23(61)

N-[4-(4-{[4-({[(3-methoxyphenyl)amino]carbonyl}amino)-1-piperidinyl]methyl}phenoxy)phenyl]methanesulfonamide hydrochloride TLC:Rf 0.30(methylene chloride:methanol=10:1);
NMR (CD₃OD): δ 1.67-1.79 (m, 2H), 2.20-2.24 (m, 2H), 2.96 (s, 3H), 3.08-3.16 (m, 2H), 3.51-3.55 (m, 2H), 3.75 (s, 3H), 3.81 (m, 1H), 4.29 (s, 2H), 6.56 (m, 1H), 6.82 (m, 1H), 7.02-7.16 (m, 6H), 7.30 (d, J=9.0 Hz, 2H), 7.50 (d, J=9.0 Hz, 2H).

Example 23(62)

N-[4-(4-{[4-({[(4-methoxyphenyl)amino]carbonyl}amino)-1-piperidinyl]methyl}phenoxy)phenyl]methanesulfonamide hydrochloride TLC:Rf 0.25(methylene chloride:methanol=10:1);
NMR (d₆-DMSO): δ 1.66-1.75 (m, 2H), 1.99-2.23 (m, 2H), 2.97 (s, 3H), 2.97-3.05 (m, 2H), 3.31-3.35 (m, 2H), 3.64 (m, 1H), 3.67 (s, 3H), 4.22 (d, J=4.8 Hz, 2H), 6.38 (br-d, J=7.2 Hz, 1H), 6.79 (d, J=9.0 Hz, 2H), 7.03 (d, J=9.0 Hz, 2H), 7.06 (d, J=9.0 Hz, 2H), 7.25 (d, J=9.0 Hz, 2H), 7.26 (d, J=9.0 Hz, 2H), 7.55 (d, J=9.0 Hz, 2H), 8.24 (s, 1H), 9.70 (s, 1H).

Example 23(63)

N-(4-{4-[(4-{[(cyclohexylamino)carbonyl]amino}-1-piperidinyl)methyl]phenoxy}phenyl)methanesulfonamide hydrochloride TLC:Rf 0.25(ethyl acetate:methanol=10:1);
NMR (CD₃OD): δ 1.06-1.41 (m, 5H), 1.53-1.88 (m, 6H), 2.01 (m, 1H), 2.09-2.18 (m, 2H), 2.95 (s, 3H), 3.02-3.12 (m, 2H), 3.40-3.55 (m, 3H), 3.72 (m, 1H), 4.27 (s, 2H), 7.03 (d, J=8.7 Hz, 2H), 7.05 (d, J=8.7 Hz, 2H), 7.29 (d, J=8.7 Hz, 2H), 7.49 (d, J=8.7 Hz, 2H).

Example 23(64)

N-{4-[4-({4-[(anilinocarbonyl)amino]-1-piperidinyl}methyl)phenoxy]phenyl}methanesulfonamide hydrochloride TLC:Rf 0.26(ethyl acetate:methanol=10:1);
NMR (CD$_3$OD): δ 1.64-1.89 (m, 2H), 2.10-2.25 (m, 2H), 2.95 (s, 3H), 3.03-3.25 (m, 2H), 3.36-3.57 (m, 2H), 3.85 (m, 1H), 4.29 (s, 2H), 6.97 (t, J=7.5 Hz, 1H), 7.03 (d, J=8.7 Hz, 2H), 7.06 (d, J=8.7 Hz, 2H), 7.20-7.38 (m, 6H), 7.50 (d, J=8.7 Hz, 2H).

Example 23(65)

N-(4-{4-[(4-{butyl[(cyclopropylamino)carbonyl]amino}-1-piperidinyl)methyl]phenoxy}phenyl)methanesulfonamide hydrochloride TLC:Rf 0.46(ethyl acetate:methanol=10:1);
NMR (CD$_3$OD): δ 0.42-0.50 (m, 2H), 0.62-0.71 (m, 2H), 0.93 (t, J=7.2 Hz, 3H), 1.23-1.37 (m, 2H), 1.41-1.53 (m, 2H), 1.84-1.96 (m, 2H), 2.04-2.23 (m, 2H), 2.51 (m, 1H), 2.95 (s, 3H), 3.02-3.15 (m, 4H), 3.49-3.59 (m, 2H), 4.09 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(66)

N-(4-{4-[(4-{butyl[(cyclobutylamino)carbonyl]amino}-1-piperidinyl)methyl]phenoxy}phenyl)methanesulfonamide hydrochloride TLC:Rf 0.58(ethyl acetate:methanol=10:1);
NMR (CD$_3$OD): δ 0.95 (t, J=7.2 Hz, 3H), 1.26-1.41 (m, 2H), 1.44-1.56 (m, 2H), 1.60-1.73 (m, 2H), 1.84-2.30 (m, 8H), 2.95 (s, 3H), 3.02-3.15 (m, 4H), 3.48-3.59 (m, 2H), 4.10 (m, 1H), 4.20 (m, 1H), 4.27 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(67)

N-(4-{4-[(4-{butyl[(cyclopentylamino)carbonyl]amino}-1-piperidinyl)methyl]phenoxy}phenyl)methanesulfonamide hydrochloride TLC:Rf 0.60(ethyl acetate:methanol=10:1);
NMR (CD$_3$OD): δ 0.94 (t, J=7.2 Hz, 3H), 1.25-1.76 (m, 10H), 1.85-1.98 (m, 4H), 2.02-2.21 (m, 2H), 2.95 (s, 3H), 3.02-3.16 (m, 4H), 3.48-3.59 (m, 2H), 4.03 (m, 1H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(68)

N-(4-{4-[(4-{butyl[(tetrahydro-2H-pyran-4-ylamino)carbonyl]amino}-1-piperidinyl)methyl]phenoxy}phenyl)methane sulfonamide hydrochloride TLC:Rf 0.31(ethyl acetate:methanol=10:1);
NMR (CD$_3$OD): δ 0.95 (t, J=7.2 Hz, 3H), 1.26-1.64 (m, 6H), 1.72-1.95 (m, 4H), 2.03-2.21 (m, 2H), 2.95 (s, 3H), 3.02-3.17 (m, 4H), 3.38-3.59 (m, 4H), 3.78 (m, 1H), 3.86-3.96 (m, 2H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(69)

N-(4-{4-[(4-{butyl[(cycloheptylamino)carbonyl]amino}-1-piperidinyl)methyl]phenoxy}phenyl)methane sulfonamide hydrochloride TLC:Rf 0.67(ethyl acetate:methanol=10:1);
NMR (CD$_3$OD): δ 0.94 (t, J=7.2 Hz, 3H), 1.26-1.72 (m, 14H), 1.78-1.94 (m, 4H), 2.03-2.20 (m, 2H), 2.95 (s, 3H), 3.02-3.16 (m, 4H), 3.49-3.59 (m, 2H), 3.74 (m, 1H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(70)

N-{4-[4-({4-[(anilinocarbonyl)(pentyl)amino]-1-piperidinyl}methyl)phenoxy]phenyl}methanesulfonamide hydrochloride TLC:Rf 0.76(ethyl acetate:methanol=10:1);
NMR (CD$_3$OD): δ 0.92 (t, J=7.2 Hz, 3H), 1.28-1.44 (m, 4H), 1.55-1.69 (m, 2H), 1.93-2.04 (m, 2H), 2.12-2.30 (m, 2H), 2.95 (s, 3H), 3.03-3.18 (m, 2H), 3.23-3.32 (m, 2H), 3.51-3.60 (m, 2H), 4.19 (m, 1H), 4.29 (s, 2H), 7.03 (d, J=8.7 Hz, 2H), 7.06 (d, J=8.7 Hz, 2H), 7.22-7.35 (m, 5H), 7.41 (d, J=7.5 Hz, 2H), 7.50 (d, J=8.7 Hz, 2H).

Example 23(71)

N-{4-[4-({4-[[(cyclohexylamino)carbonyl](pentyl)amino]-1-piperidinyl}methyl)phenoxy]phenyl}methanesulfonamide hydrochloride TLC:Rf 0.78(ethyl acetate:methanol=10:1);
NMR (CD$_3$OD): δ 0.91 (t, J=7.2 Hz, 3H), 1.12-1.41 (m, 9H), 1.46-1.93 (m, 9H), 2.02-2.19 (m, 2H), 2.95 (s, 3H), 3.02-3.15 (m, 4H), 3.48-3.60 (m, 3H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(72)

N-(4-{4-[(4-{allyl[(cyclohexylamino)carbonyl]amino}-1-piperidinyl)methyl]phenoxy}phenyl)methanesulfonamide hydrochloride TLC:Rf 0.74(ethyl acetate:methanol=10:1);
NMR (CD$_3$OD): δ 1.08-1.42 (m, 6H), 1.55-2.12 (m, 8H), 2.95 (s, 3H), 3.03-3.16 (m, 2H), 3.47-3.59 (m, 3H), 3.81 (d, J=5.0 Hz, 2H), 4.27 (s, 2H), 4.32 (m, 1H), 5.18 (dd, J=10.5, 1.5 Hz, 1H), 5.20 (dd J=20.2, 1.5 Hz, 1H), 5.83 (ddd, J=20.2, 10.5, 5.0 Hz, 1H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(73)

N-(4-{4-[(4-{2-butynyl[(cyclohexylamino)carbonyl]amino}-1-piperidinyl)methyl]phenoxy}phenyl)methanesulfonamide hydrochloride TLC:Rf 0.75(ethyl acetate:methanol=10:1);
NMR (CD$_3$OD): δ 1.15-1.43 (m, 5H), 1.77 (t, J=2.4 Hz, 3H), 1.58-2.00 (m, 7H), 2.05-2.20 (m, 2H), 2.95 (s, 3H), 3.03-3.18 (m, 2H), 3.50-3.62 (m, 3H), 3.92 (d, J=2.4 Hz, 2H), 4.23 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(74)

N-(4-{4-[(4-{butyl[(propylamino)carbonyl]amino}-1-piperidinyl)methyl]phenoxy}phenyl)methanesulfonamide hydrochloride TLC:Rf 0.71(ethyl acetate:methanol=10:1);
NMR (CD$_3$OD): δ 0.89 (t, J=7.2 Hz, 3H), 0.94 (t, J=7.2 Hz, 3H), 1.26-1.41 (m, 2H), 1.45-1.58 (m, 4H), 1.85-1.95 (m, 2H), 2.04-2.22 (m, 2H), 2.95 (s, 3H), 3.03-3.16 (m, 6H), 3.48-3.59 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(75)

N-(4-{4-[(4-{pentyl[(propylamino)carbonyl]amino}-1-piperidinyl)methyl]phenoxy}phenyl)methanesulfonamide hydrochloride TLC:Rf 0.73(ethyl acetate:methanol=10:1);
NMR (CD$_3$OD): δ 0.89 (t, J=7.2 Hz, 3H), 0.92 (t, J=7.0 Hz, 3H), 1.23-1.40 (m, 4H), 1.44-1.59 (m, 4H), 1.85-1.95 (m, 2H), 2.03-2.21 (m, 2H), 2.95 (s, 3H), 3.04-3.15 (m, 6H), 3.49-3.58 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(76)

N-{4-[4-({4-[[(butylamino)carbonyl](pentyl)amino]-1-piperidinyl}methyl)phenoxy]phenyl}methanesulfonamide hydrochloride TLC:Rf 0.75(ethyl acetate:methanol=10:1);
NMR (CD$_3$OD): δ 0.91 (d, J=7.2 Hz, 3H), 0.92 (t, J=7.2 Hz, 3H), 1.24-1.41 (m, 6H), 1.43-1.59 (m, 4H), 1.85-1.96 (m, 2H), 2.03-2.21 (m, 2H), 2.95 (s, 3H), 3.03-3.20 (m, 6H), 3.49-3.58 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(77)

N-{4-[4-({4-[[(butylamino)carbonyl](cyclohexylmethyl)amino]-1-piperidinyl}methyl)phenoxy]phenyl}methane sulfonamide hydrochloride TLC:Rf 0.74(ethyl acetate:methanol=10:1);
NMR (CD$_3$OD): δ 0.92 (t, J=7.2 Hz, 3H), 0.83-1.00 (m, 2H), 1.15-1.80 (m, 13H), 1.87-1.98 (m, 2H), 2.13-2.32 (m, 2H), 2.95 (s, 3H), 3.00-3.17 (m, 6H), 3.48-3.57 (m, 2H), 3.89 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(78)

N-(4-{4-[(4-{butyl[(hexylamino)carbonyl]amino}-1-piperidinyl)methyl]phenoxy}phenyl)methanesulfonamide hydrochloride TLC:Rf 0.72(ethyl acetate:methanol=10:1);
NMR (CD$_3$OD): δ 0.89 (t, J=7.2 Hz, 3H), 0.94 (t, J=7.2 Hz, 3H), 1.22-1.39 (m, 8H), 1.41-1.56 (m, 4H), 1.85-1.94 (m, 2H), 2.03-2.21 (m, 2H), 2.95 (s, 3H), 3.02-3.19 (m, 6H), 3.49-3.58 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(79)

N-(4-{4-[(4-{pentyl[(pentylamino)carbonyl]amino}-1-piperidinyl)methyl]phenoxy}phenyl)methane sulfonamide hydrochloride TLC:Rf 0.71(ethyl acetate:methanol=10:1);
NMR (CD$_3$OD): δ 0.90 (t, J=7.2 Hz, 3H), 0.92 (t, J=7.2 Hz, 3H), 1.23-1.40 (m, 8H), 1.44-1.60 (m, 4H), 1.86-1.95 (m, 2H), 2.03-2.20 (m, 2H), 2.95 (s, 3H), 3.02-3.20 (m, 6H), 3.49-3.58 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(80)

N-(4-{4-[(4-{benzyl[(t-butylamino)carbonyl]amino}-1-piperidinyl)methyl]phenoxy}phenyl)methanesulfonamide hydrochloride TLC:Rf 0.69(ethyl acetate:methanol=10:1);
NMR (CD$_3$OD): δ 1.18 (s, 9H), 1.90-2.09 (m, 4H), 2.95 (s, 3H), 3.05-3.17 (m, 2H), 3.47-3.56 (m, 2H), 4.26 (s, 2H), 4.42 (s, 2H), 4.45 (m, 1H), 7.02 (d, J=8.7 Hz, 2H), 7.05 (d, J=8.7 Hz, 2H), 7.23-7.39 (m, 7H), 7.49 (d, J=8.7 Hz, 2H).

Example 23(81)

N-[4-(4-{[4-({[(2-hydroxyphenyl)amino]carbonyl}amino)-1-piperidinyl]methyl}phenoxy)phenyl]methanesulfonamide hydrochloride TLC:Rf 0.53(methylene chloride:methanol=10:1);
NMR (CD$_3$OD): δ 1.65-1.77 (m, 2H), 2.20-2.25 (m, 2H), 2.95 (s, 3H), 3.07-3.15 (m, 2H), 3.50-3.55 (m, 2H), 3.81 (m, 1H), 4.29 (s, 2H), 6.72-6.85 (m, 3H), 7.03 (d, J=8.7 Hz, 2H), 7.06 (d, J=8.7 Hz, 2H), 7.29 (d, J=8.7 Hz, 2H), 7.50 (d, J=8.7 Hz, 2H), 7.69 (m, 1H).

Example 23(82)

N-[4-(4-{[(3aR,6aS)-5-{butyl[(cyclohexylamino)carbonyl]amino}hexahydrocyclopenta[c]pyrrol-2(1H)-yl]methyl}phenoxy)phenyl]methanesulfonamide hydrochloride

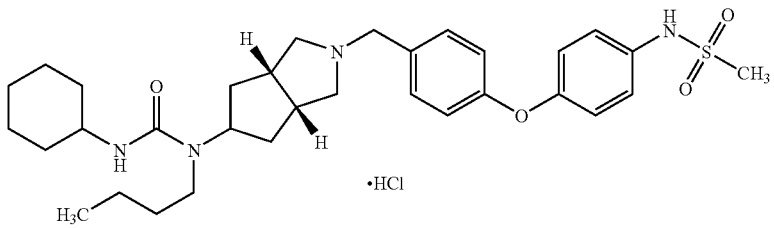

TLC:Rf 0.50(chloroform:methanol=5:1);
NMR (CD$_3$OD): δ 0.88-1.00 (m, 3H), 1.14-1.84 (m, 16H), 2.00-2.22 (m, 2H), 2.70-3.79 (m, 9H), 2.95 (s, 3H), 4.08 (m, 1H), 4.35 (m, 2H), 7.00-7.10 (m, 4H), 7.22-7.34 (m, 2H), 7.45-7.58 (m, 2H).

Example 23(83)

N-[4-(4-{[4-(butyl{[(2-methoxyethyl)amino]carbonyl}amino)-1-piperidinyl]methyl}phenoxy)phenyl]methanesulfonamide hydrochloride TLC:Rf 0.27(ethyl acetate:methanol=10:1);
NMR (CD$_3$OD): δ 0.95 (t, J=7.2 Hz, 3H), 1.27-1.41 (m, 2H), 1.45-1.59 (m, 2H), 1.87-1.97 (m, 2H), 2.03-2.20 (m, 2H), 2.95 (s, 3H), 3.02-3.15 (m, 4H), 3.33 (s, 3H), 3.32-3.36 (m, 2H), 3.40-3.47 (m, 2H), 3.51-3.58 (m, 2H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(84)

N-[4-(4-{[4-(butyl{[(4-hydroxyphenyl)amino]carbonyl}amino)-1-piperidinyl]methyl}phenoxy)phenyl]methanesulfonamide hydrochloride TLC:Rf 0.64(chloroform:methanol=5:1);
NMR (CD$_3$OD): δ 0.97 (t, J=7.5 Hz, 3H), 1.39 (m, 2H), 1.62 (m, 2H), 1.92 (m, 2H), 2.22 (m, 2H), 2.95 (s, 3H), 3.18 (m, 2H), 3.25 (m, 2H), 3.52 (m, 2H), 4.14 (m, 1H), 4.27 (s, 2H), 6.68-6.78 (m, 2H), 7.00-7.10 (m, 6H), 7.24-7.34 (m, 2H), 7.49 (brd, J=8.4 Hz, 2H).

Example 23(85)

N-[4-(4-{[4-(butyl{[(3-hydroxyphenyl)amino]carbonyl}amino)-1-piperidinyl]methyl}phenoxy)phenyl]methanesulfonamide hydrochloride TLC:Rf 0.64(chloroform:methanol=5:1);
NMR (CD$_3$OD): δ 0.96 (t, J=7.5 Hz, 3H), 1.39 (m, 2H), 1.60 (m, 2H), 1.98 (m, 2H), 2.21 (m, 2H), 2.95 (s, 3H), 3.11 (m, 2H), 3.28 (m, 2H), 3.58 (m, 2H), 4.18 (m, 1H), 4.28 (s, 2H), 6.48 (m, 1H), 6.78 (m, 1H), 6.84 (m, 1H), 7.00-7.12 (m, 5H), 7.22-7.40 (m, 2H), 7.50 (brd, J=8.7 Hz, 2H).

Example 23(86)

N-[4-(4-{[4-({[(4-hydroxyphenyl)amino]carbonyl}amino)-1-piperidinyl]methyl}phenoxy)phenyl]methanesulfonamide hydrochloride TLC:Rf 0.44(chloroform:methanol=5:1);
NMR (CD$_3$OD): δ 1.70 (m, 2H), 2.19 (m, 2H), 2.95 (s, 3H), 3.08 (m, 2H), 3.48 (m, 2H), 3.78 (m, 1H), 4.25 (s, 2H), 6.62-6.78 (m, 2H), 7.00-7.36 (m, 8H), 7.47 (brd, J=8.4 Hz, 2H).

Example 23(87)

N-[4-(4-{[4-({[(3-hydroxyphenyl)amino]carbonyl}amino)-1-piperidinyl]methyl}phenoxy)phenyl]methanesulfonamide hydrochloride TLC:Rf 0.51(chloroform:methanol=5:1);
NMR (CD$_3$OD): δ 1.52 (m, 2H), 1.95 (m, 2H), 2.24 (m, 2H), 2.89 (m, 2H), 2.93 (s, 3H), 3.56 (s, 2H), 3.60 (m, 1H), 6.39 (m, 1H), 6.71 (m, 1H), 6.90-7.08 (m, 5H), 7.18-7.38 (m, 5H).

Example 23(88)

N-[4-(4-{[4-(butyl{[(4-methoxyphenyl)amino]carbonyl}amino)-1-piperidinyl]methyl}phenoxy)phenyl]methanesulfonamide hydrochloride TLC:Rf 0.71(chloroform:methanol=5:1);
NMR (CD$_3$OD): δ 0.96 (t, J=7.2 Hz, 3H), 1.26-1.44 (m, 2H), 1.52-1.80 (m, 6H), 2.28 (m, 2H), 2.93 (s, 3H), 3.02 (m, 2H), 3.22 (m, 2H), 3.54 (s, 2H), 3.75 (s, 3H), 4.04 (m, 1H), 6.80-6.88 (m, 2H), 6.90-7.02 (m, 4H), 7.18-7.38 (m, 6H).

Example 23(89)

N-{4-[4-({4-[butyl({[4-(trifluoromethyl)phenyl]amino}carbonyl)amino]-1-piperidinyl}methyl)phenoxy]phenyl}methanesulfonamide hydrochloride TLC:Rf 0.78(chloroform:methanol=5:1);
NMR (CD$_3$OD): δ 0.97 (t, J=7.5 Hz, 3H), 1.32-1.50 (m, 2H), 1.53-1.68 (m, 2H), 1.94-2.06 (m, 2H), 2.08-2.34 (m, 2H), 2.95 (s, 3H), 3.12 (m, 2H), 3.32 (m, 2H), 3.58 (m, 2H), 4.18 (m, 1H), 4.30 (s, 2H), 7.00-7.12 (m, 4H), 7.22-7.38 (m, 2H), 7.42-7.60 (m, 6H).

Example 23(90)

N-{4-[4-({4-[(aminocarbonyl)(butyl)amino]-1-piperidinyl}methyl)phenoxy]phenyl}methanesulfonamide hydrochloride TLC:Rf 0.15 (ethyl acetate:methanol=10:1);
NMR (CD$_3$OD): δ 0.95 (t, J=7.2 Hz, 3H), 1.27-1.42 (m, 2H), 1.50-1.63 (m, 2H), 1.81-2.02 (m, 2H), 2.11-2.30 (m, 2H), 2.95 (s, 3H), 3.05-3.21 (m, 4H), 3.51-3.60 (m, 2H), 4.13 (m, 1H), 4.29 (s, 2H), 7.03 (d, J=8.7 Hz, 2H), 7.05 (d, J=8.7 Hz, 2H), 7.29 (d, J=8.7 Hz, 2H), 7.52 (d, J=8.7 Hz, 2H).

Example 23(91)

N-[4-(4-{[4-(butyl{[(4-hydroxycyclohexyl)amino]carbonyl}amino)-1-piperidinyl]methyl}phenoxy)phenyl]methanesulfonamide hydrochloride TLC:Rf 0.19(ethyl acetate:methanol=10:1);
NMR (CD$_3$OD): δ 0.95 (t, J=7.2 Hz, 3H), 1.27-1.41 (m, 2H), 1.45-1.79 (m, 10H), 1.86-1.95 (m, 2H), 2.03-2.22 (m, 2H), 2.95 (s, 3H), 3.02-3.17 (m, 4H), 3.48-3.65 (m, 3H), 3.87 (m, 1H), 4.15 (m, 1H), 4.29 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(92)

N-[4-(4-{[4-(butyl{[(2-fluorophenyl)amino]carbonyl}amino)-1-piperidinyl]methyl}phenoxy)phenyl]methanesulfonamide hydrochloride TLC:Rf 0.73(ethyl acetate:methanol=10:1);
NMR (CD$_3$OD): δ 0.98 (t, J=7.2 Hz, 3H), 1.32-1.48 (m, 2H), 1.58-1.72 (m, 2H), 1.95-2.06 (m, 2H), 2.14-2.33 (m, 2H), 2.95 (s, 3H), 3.03-3.18 (m, 2H), 3.25-3.35 (m, 2H), 3.52-3.61 (m, 2H), 4.17 (m, 1H), 4.29 (s, 2H), 7.03 (d, J=8.7 Hz, 2H), 7.06 (d, J=8.7 Hz, 2H), 7.10-7.18 (m, 3H), 7.29 (d, J=8.7 Hz, 2H), 7.45 (dt, J=2.4, 7.2 Hz, 1H), 7.51 (d, J=8.7 Hz, 2H).

Example 23(93)

N-[4-(4-{[4-(butyl{[(3-fluorophenyl)amino]carbonyl}amino)-1-piperidinyl]methyl}phenoxy)phenyl]methanesulfonamide hydrochloride TLC:Rf 0.73 (ethyl acetate:methanol=10:1);
NMR (CD$_3$OD): δ 0.97 (t, J=7.2 Hz, 3H), 1.33-1.46 (m, 2H), 1.54-1.67 (m, 2H), 1.93-2.06 (m, 2H), 2.15-2.32 (m, 2H), 2.95 (s, 3H), 3.05-3.18 (m, 2H), 3.26-3.35 (m, 2H), 3.52-3.62 (m, 2H), 4.18 (m, 1H), 4.29 (s, 2H), 6.74 (dt, J=2.4, 8.1 Hz, 1H), 7.04 (d, J=8.7 Hz, 2H), 7.07 (d, J=8.7 Hz, 2H), 7.12 (d, J=4.0 Hz, 1H), 7.20-7.31 (m, 2H), 7.29 (d, J=8.7 Hz, 2H), 7.51 (d, J=8.7 Hz, 2H).

Example 23(94)

N-(4-{4-[(4-{butyl[(4-pyridinylamino)carbonyl]amino}-1-piperidinyl)methyl]phenoxy}phenyl)methanesulfonamide dihydrochloride TLC:Rf 0.53 (chloroform:methanol=10:1);
NMR (CD$_3$OD): δ 0.96 (t, J=7.4 Hz, 3H), 1.30-1.50 (m, 2H), 1.50-1.70 (m, 2H), 2.00-2.10 (m, 2H), 2.30-2.40 (m, 2H), 2.95 (s, 3H), 3.10-3.30 (m, 2H), 3.40-3.50 (m, 2H), 3.50-3.60 (m, 2H), 4.30 (m, 1H), 4.31 (s, 2H), 7.02-7.08 (m, 4H), 7.29 (d, J=8.6 Hz, 2H), 7.54 (d, J=8.6 Hz, 2H), 8.09 (d, J=7.5 Hz, 2H), 8.47 (d, J=7.5 Hz, 2H).

Example 23(95)

N-(4-{4-[(4-{butyl[(3-pyridinylamino)carbonyl]amino}-1-piperidinyl)methyl]phenoxy}phenyl)methanesulfonamide dihydrochloride TLC:Rf 0.50(chloroform:methanol=10:1);
NMR (CD$_3$OD): δ 0.97 (t, J=7.2 Hz, 3H), 1.30-1.50 (m, 2H), 1.50-1.70 (m, 2H), 2.00-2.10 (m, 2H), 2.30-2.40 (m, 2H), 2.95 (s, 3H), 3.10-3.30 (m, 2H), 3.30-3.40 (m, 2H), 3.50-3.70 (m, 2H), 4.30 (m, 1H), 4.31 (s, 2H), 7.02-7.08 (m, 4H), 7.29 (d, J=9.0 Hz, 2H), 7.53 (d, J=9.0 Hz, 2H), 7.95 (dd, J=8.5, 2.4 Hz, 1H), 8.43 (d, J=8.5 Hz, 1H), 8.61 (d, J=8.5 Hz, 1H), 9.20 (d, J=2.4 Hz, 1H).

Example 23(96)

2-[({butyl[1-(4-{4-[(methylsulfonyl)amino]phenoxy}benzyl)-4-piperidinyl]amino}carbonyl)amino]benzoic acid hydrochloride TLC:Rf 0.36(methylene chloride:methanol=9:1);
NMR (CD$_3$OD): δ 0.97 (t, J=7.5 Hz, 3H), 1.35-1.51 (m, 2H), 1.60-1.72 (m, 2H), 1.92-2.04 (m, 2H), 2.16-2.35 (m, 2H), 2.95 (s, 3H), 3.08-3.11 (m, 2H), 3.23-3.35 (m, 2H), 3.52-3.63 (m, 2H), 4.22-4.36 (m, 3H), 7.02 (t, J=7.8 Hz, 1H), 7.03 (d, J=8.7 Hz, 2H), 7.06 (d, J=8.7 Hz, 2H), 7.29 (d, J=8.7 Hz, 2H), 7.49 (dt, J=1.8, 7.8 Hz, 1H), 7.54 (d, J=8.7 Hz, 2H), 8.05 (dd, J=7.8, 1.8 Hz, 1H), 8.42 (d, J=7.8 Hz, 1H).

Example 23(97)

3-[({butyl[1-(4-{4-[(methylsulfonyl)amino]phenoxy}benzyl)-4-piperidinyl]amino}carbonyl)amino]benzoic acid hydrochloride TLC:Rf 0.30(methylene chloride:methanol=9:1);
NMR (CD$_3$OD): δ 0.95 (t, J=7.5 Hz, 3H), 1.30-1.44 (m, 2H), 1.53-1.64 (m, 2H), 1.90-2.03 (m, 2H), 2.20-2.38 (m, 2H), 2.95 (s, 3H), 3.05-3.19 (m, 2H), 3.25-3.36 (m, 2H), 3.49-3.59 (m, 2H), 4.23 (m, 1H), 4.29 (s, 2H), 7.02 (d, J=8.7 Hz, 2H), 7.04 (d, J=8.7 Hz, 2H), 7.29 (d, J=8.7 Hz, 2H), 7.36 (t, J=7.8 Hz, 1H), 7.53 (d, J=8.7 Hz, 2H), 7.60 (ddd, J=7.8, 2.4, 1.8 Hz, 1H), 7.69 (dt, J=7.8, 2.4 Hz, 1H), 8.04 (t, J=1.8 Hz, 1H).

Example 23(98)

4-[({butyl[1-(4-{4-[(methylsulfonyl)amino]phenoxy}benzyl)-4-piperidinyl]amino}carbonyl)amino]benzoic acid hydrochloride TLC:Rf 0.34(methylene chloride:methanol=9:1);
NMR (CD$_3$OD): δ 0.97 (t, J=7.2 Hz, 3H), 1.33-1.46 (m, 2H), 1.54-1.66 (m, 2H), 1.94-2.05 (m, 2H), 2.20-2.38 (m, 2H), 2.95 (s, 3H), 3.06-3.20 (m, 2H), 3.25-3.37 (m, 2H), 3.50-3.60 (m, 2H), 4.20 (m, 1H), 4.29 (s, 2H), 7.03 (d, J=8.7 Hz, 2H), 7.06 (d, J=8.7 Hz, 2H), 7.29 (d, J=8.7 Hz, 2H), 7.49 (d, J=8.5 Hz, 2H), 7.52 (d, J=8.7 Hz, 2H), 7.92 (d, J=8.5 Hz, 2H).

Example 23(99)

[({butyl[1-(4-{4-[(methylsulfonyl)amino]phenoxy}benzyl)-4-piperidinyl]amino}carbonyl)amino]acetic acid hydrochloride TLC:Rf 0.41(methylene chloride:methanol=4:1);
NMR (CD$_3$OD): δ 0.94 (t, J=7.2 Hz, 3H), 1.27-1.41 (m, 2H), 1.48-1.62 (m, 2H), 1.84-1.95 (m, 2H), 2.08-2.26 (m, 2H), 2.95 (s, 3H), 2.98-3.18 (m, 4H), 3.44-3.53 (m, 2H), 3.80 (s, 2H), 4.15 (m, 1H), 4.25 (s, 2H), 7.02 (d, J=8.7 Hz, 2H), 7.03 (d, J=8.7 Hz, 2H), 7.29 (d, J=8.7 Hz, 2H), 7.53 (d, J=8.7 Hz, 2H).

Example 23(100)

N-{4-[4-({4-[[(cyclohexylamino)carbonyl](3-hydroxypropyl)amino]-1-piperidinyl}methyl)phenoxy]phenyl}methanesulfonamide hydrochloride TLC:Rf 0.43(methylene chloride:methanol=10:1);
NMR (CD$_3$OD): δ 1.10-1.50 (m, 6H), 1.60-1.80 (m, 4H), 1.80-2.00 (m, 4H), 2.00-2.20 (m, 2H), 2.95 (s, 3H), 3.00-3.15 (m, 2H), 3.20-3.30 (m, 2H), 3.40-3.70 (m, 5H), 4.10 (m, 1H), 4.27 (s, 2H), 7.03 (d, J=8.7 Hz, 2H), 7.06 (d, J=8.7 Hz, 2H), 7.29 (d, J=9.0 Hz, 2H), 7.48 (d, J=9.0 Hz, 2H).

Example 23(101)

N-{4-[4-({4-[[(cyclohexylamino)carbonyl](4-hydroxybutyl)amino]-1-piperidinyl}methyl)phenoxy]phenyl}methanesulfonamide hydrochloride TLC:Rf 0.42(methylene chloride:methanol=10:1);
NMR (CD$_3$OD): δ 1.10-1.40 (m, 6H), 1.40-1.70 (m, 5H), 1.70-2.00 (m, 6H), 2.00-2.20 (m, 2H), 2.95 (s, 3H), 3.00-3.20 (m, 4H), 3.50-3.60 (m, 2H), 3.59 (t, J=6.0 Hz, 2H), 4.10 (m, 1H), 4.27 (s, 2H), 7.03 (d, J=8.8 Hz, 2H), 7.07 (d, J=8.8 Hz, 2H), 7.29 (d, J=8.8 Hz, 2H), 7.48 (d, J=8.8 Hz, 2H).

Example 23(102)

N-{4-[4-({4-[[(cyclohexylamino)carbonyl](3-hydroxybutyl)amino]-1-piperidinyl}methyl)phenoxy]phenyl}methanesulfonamide hydrochloride TLC:Rf 0.43(methylene chloride:methanol=10:1);
NMR (CD$_3$OD): δ 1.10-1.50 (m, 6H), 1.17 (d, J=6.3 Hz, 3H), 1.70-2.00 (m, 9H), 2.00-2.20 (m, 2H), 2.95 (s, 3H), 3.00-3.20 (m, 4H), 3.50-3.60 (m, 2H), 3.70 (m, 1H), 4.10 (m, 1H), 4.27 (s, 2H), 7.02-7.07 (m, 4H), 7.29 (d, J=8.9 Hz, 2H), 7.50 (d, J=8.9 Hz, 2H).

Example 23(103)

N-{4-[4-({4-[[(cyclohexylamino)carbonyl](2-hydroxybutyl)amino]-1-piperidinyl}methyl)phenoxy]phenyl}methanesulfonamide hydrochloride TLC:Rf 0.44(methylene chloride:methanol=10:1);
NMR (CD$_3$OD): δ 0.97 (t, J=7.4 Hz, 3H), 1.10-2.20 (m, 16H), 2.99 (s, 3H), 3.10-3.20 (m, 4H), 3.40-3.60 (m, 4H), 4.10 (m, 1H), 4.27 (s, 2H), 7.01-7.08 (m, 4H), 7.28-7.31 (m, 2H), 7.48 (d, J=8.7 Hz, 2H).

Example 23(104)

4-[({butyl[1-(4-{4-[(methylsulfonyl)amino]phenoxy}benzyl)-4-piperidinyl]amino}carbonyl)amino]butanoic acid hydrochloride TLC:Rf 0.73(methylene chloride:methanol=4:1);
NMR (CD$_3$OD): δ 0.95 (t, J=7.5 Hz, 3H), 1.28-1.41 (m, 2H), 1.44-1.59 (m, 2H), 1.74-1.85 (m, 2H), 1.87-1.97 (m, 2H), 2.03-2.20 (m, 2H), 2.31 (t, J=6.9 Hz, 2H), 2.95 (s, 3H), 3.02-3.15 (m, 4H), 3.20 (t, J=6.9 Hz, 2H), 3.50-3.58 (m, 2H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(105)

N-[4-(4-{[4-(butyl{[(4-chlorophenyl)amino]carbonyl}amino)-1-piperidinyl]methyl}phenoxy)phenyl]methanesulfonamide hydrochloride TLC:Rf 0.53 (chloroform:methanol=10:1);
NMR (CD$_3$OD): δ 0.96 (t, J=7.2 Hz, 3H), 1.30-1.40 (m, 2H), 1.55-1.60 (m, 2H), 1.95-2.00 (m, 2H), 2.20-2.30 (m, 2H), 2.95 (s, 3H), 3.10-3.20 (m, 2H), 3.30-3.40 (m, 2H), 3.50-3.60 (m, 2H), 4.20 (m, 1H), 4.29 (s, 2H), 7.01-7.08 (m, 4H), 7.23-7.40 (m, 6H), 7.51 (d, J=8.4 Hz, 2H).

Example 23(106)

N-[4-(4-{[4-(butyl{[(3-chlorophenyl)amino]carbonyl}amino)-1-piperidinyl]methyl}phenoxy)phenyl]methanesulfonamide hydrochloride TLC:Rf 0.53 (chloroform:methanol=10:1);
NMR (CD$_3$OD): δ 0.97 (t, J=7.4 Hz, 3H), 1.30-1.40 (m, 2H), 1.55-1.65 (m, 2H), 1.95-2.05 (m, 2H), 2.20-2.30 (m, 2H), 2.96 (s, 3H), 3.10-3.20 (m, 2H), 3.30-3.40 (m, 2H), 3.50-3.60 (m, 2H), 4.15 (m, 1H), 4.29 (s, 2H), 7.00-7.09 (m, 5H), 7.23-7.31 (m, 4H), 7.48-7.51 (m, 3H).

Example 23(107)

N-[4-(4-{[4-(butyl{[(2-chlorophenyl)amino]carbonyl}amino)-1-piperidinyl]methyl}phenoxy)phenyl]methanesulfonamide hydrochloride TLC:Rf 0.53 (chloroform:methanol=10:1);
NMR (CD$_3$OD): δ 0.99 (t, J=7.4 Hz, 3H), 1.30-1.50 (m, 2H), 1.60-1.80 (m, 2H), 2.00-2.10 (m, 2H), 2.20-2.30 (m, 2H), 2.95 (s, 3H), 3.10-3.20 (m, 2H), 3.30-3.40 (m, 2H), 3.50-3.60 (m, 2H), 4.20 (m, 1H), 4.29 (s, 2H), 7.02-7.10 (m, 4H), 7.14 (dd, J=7.5, 1.5 Hz, 1H), 7.27-7.31 (m, 3H), 7.42 (dd, J=7.5, 1.5 Hz, 1H), 7.50 (d, J=8.4 Hz, 2H), 7.63 (dd, J=7.5, 1.5 Hz, 1H).

Example 23(108)

N-[4-(4-{[4-(butyl{[(4-methylphenyl)amino]carbonyl}amino)-1-piperidinyl]methyl}phenoxy)phenyl]methanesulfonamide hydrochloride TLC:Rf 0.53(chloroform:methanol=10:1);
NMR (CD$_3$OD): δ 0.97 (t, J=7.4 Hz, 3H), 1.30-1.40 (m, 2H), 1.55-1.65 (m, 2H), 1.95-2.05 (m, 2H), 2.20-2.30 (m, 2H), 2.28 (s, 3H), 2.95 (s, 3H), 3.10-3.20 (m, 2H), 3.20-3.30 (m, 2H), 3.50-3.60 (m, 2H), 4.20 (m, 1H), 4.29 (s, 2H), 7.02-7.10 (m, 6H), 7.19 (d, J=8.4 Hz, 2H), 7.29 (d, J=9.0 Hz, 2H), 7.50 (d, J=9.0 Hz, 2H).

Example 23(109)

N-[4-(4-{[4-(butyl{[(3-methylphenyl)amino]carbonyl}amino)-1-piperidinyl]methyl}phenoxy)phenyl]methanesulfonamide hydrochloride TLC:Rf 0.59(chloroform:methanol=10:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.20-2.30 (m, 2H), 2.30 (s, 3H), 2.95 (s, 3H), 3.10-3.20 (m, 2H), 3.30-3.40 (m, 2H), 3.50-3.60 (m, 2H), 4.10 (m, 1H), 4.29 (s, 2H), 6.87 (d, J=6.6 Hz, 1H), 7.01-7.15 (m, 7H), 7.29 (d, J=8.9 Hz, 2H), 7.50 (d, J=8.9 Hz, 2H).

Example 23(110)

N-[4-(4-{[4-(butyl{[(2-methylphenyl)amino]carbonyl}amino)-1-piperidinyl]methyl}phenoxy)phenyl]methanesulfonamide hydrochloride TLC:Rf 0.50(chloroform:methanol=10:1);
NMR (CD$_3$OD): δ 0.98 (t, J=7.4 Hz, 3H), 1.30-1.50 (m, 2H), 1.60-1.80 (m, 2H), 1.90-2.10 (m, 2H), 2.20-2.30 (m, 2H), 2.22 (s, 3H), 2.95 (s, 3H), 3.00-3.20 (m, 2H), 3.30-3.40 (m, 2H), 3.50-3.60 (m, 2H), 4.14 (m, 1H), 4.28 (s, 2H), 7.02-7.15 (m, 7H), 7.19 (m, 1H), 7.29 (d, J=8.7 Hz, 2H), 7.49 (d, J=8.7 Hz, 2H).

Example 23(111)

N-[4-(4-{[4-(butyl{[(3-methoxyphenyl)amino]carbonyl}amino)-1-piperidinyl]methyl}phenoxy)phenyl]methanesulfonamide hydrochloride TLC:Rf 0.53(chloroform:methanol=10:1);
NMR (CD$_3$OD): δ 0.97 (t, J=7.2 Hz, 3H), 1.30-1.40 (m, 2H), 1.50-1.70 (m, 2H), 1.90-2.10 (m, 2H), 2.10-2.30 (m, 2H), 2.95 (s, 3H), 3.00-3.20 (m, 2H), 3.30-3.40 (m, 2H), 3.50-3.60 (m, 2H), 3.76 (s, 3H), 4.15 (m, 1H), 4.29 (s, 2H), 6.63 (m, 1H), 6.91 (m, 1H), 7.01-7.08 (m, 5H), 7.16 (m, 1H), 7.29 (d, J=8.9 Hz, 2H), 7.50 (d, J=8.9 Hz, 2H).

Example 23(112)

N-[4-(4-{[4-(butyl{[(2-methoxyphenyl)amino]carbonyl}amino)-1-piperidinyl]methyl}phenoxy)phenyl]methanesulfonamide hydrochloride TLC:Rf 0.55(chloroform:methanol=10:1);
NMR (CD$_3$OD): δ 1.02 (t, J=7.4 Hz, 3H), 1.40-1.50 (m, 2H), 1.60-1.70 (m, 2H), 1.90-2.10 (m, 2H), 2.10-2.30 (m, 2H), 2.95 (s, 3H), 3.00-3.20 (m, 2H), 3.30-3.40 (m, 2H), 3.50-3.60 (m, 2H), 3.87 (s, 3H), 4.26 (m, 1H), 4.29 (s, 2H), 6.89 (m, 1H), 6.99-7.08 (m, 6H), 7.29 (d, J=8.7 Hz, 2H), 7.51 (d, J=8.7 Hz, 2H), 7.76 (dd, J=7.8, 1.5 Hz, 1H).

Example 23(113)

N-{4-[4-({4-[butyl({[3-(trifluoromethyl)phenyl]amino}carbonyl)amino]-1-piperidinyl}methyl)phenoxy]phenyl}methanesulfonamide hydrochloride TLC:Rf 0.55(chloroform:methanol=10:1);
NMR (CD$_3$OD): δ 0.97 (t, J=7.2 Hz, 3H), 1.30-1.50 (m, 2H), 1.60-1.80 (m, 2H), 1.90-2.10 (m, 2H), 2.10-2.30 (m, 2H), 2.95 (s, 3H), 3.00-3.20 (m, 2H), 3.30-3.40 (m, 2H), 3.50-3.60 (m, 2H), 4.20 (m, 1H), 4.29 (s, 2H), 7.02-7.08 (m, 4H), 7.27-7.31 (m, 3H), 7.45 (m, 1H), 7.51 (d, J=8.7 Hz, 2H), 7.60 (d, J=8.4 Hz, 1H), 7.78 (s, 1H).

Example 23(114)

N-[4-(4-{[4-({[(4-hydroxycyclohexyl)amino]carbonyl}amino)-1-piperidinyl]methyl}phenoxy)phenyl]methanesulfonamide hydrochloride TLC:Rf 0.19(ethyl acetate:methanol=5:1);
NMR (CD$_3$OD): δ 1.52-1.72 (m, 9H), 2.01 (m, 1H), 2.10-2.21 (m, 2H), 2.95 (s, 3H), 3.02-3.14 (m, 2H), 3.47-3.62 (m, 3H), 3.72 (m, 1H), 3.78 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(115)

2-[({butyl[1-(4-{4-[(methylsulfonyl)amino]phenoxy}benzyl)-4-piperidinyl]amino}carbonyl)amino]-4-methylpentanoic acid hydrochloride TLC:Rf 0.39(methylene chloride:methanol=4:1);
NMR (CD$_3$OD): δ 0.93 (d, J=6.0 Hz, 6H), 0.95 (t, J=7.5 Hz, 3H), 1.28-1.42 (m, 2H), 1.48-1.79 (m, 5H), 1.82-1.95 (m, 2H), 1.97-2.19 (m, 2H), 2.95 (s, 3H), 2.90-3.05 (m, 2H), 3.08-3.25 (m, 2H), 3.42-3.52 (m, 2H), 4.13 (m, 1H), 4.19 (s, 2H), 4.32 (dd, J=9.0, 6.0 Hz, 1H), 7.02 (d, J=8.7 Hz, 2H), 7.04 (d, J=8.7 Hz, 2H), 7.28 (d, J=8.7 Hz, 2H), 7.47 (d, J=8.7 Hz, 2H).

Example 23(116)

N-{3-[({butyl[1-(4-{4-[(methylsulfonyl)amino]phenoxy}benzyl)-4-piperidinyl]amino}carbonyl)amino]phenyl}methane sulfonamide hydrochloride TLC:Rf 0.32(chloroform:methanol=10:1);
NMR (CD$_3$OD): δ 0.96 (t, J=7.2 Hz, 3H), 1.30-1.50 (m, 2H), 1.50-1.70 (m, 2H), 1.90-2.10 (m, 2H), 2.20-2.40 (m, 2H), 2.95 (s, 3H), 2.96 (s, 3H), 3.05-3.20 (m, 2H), 3.20-3.40 (m, 2H), 3.50-3.60 (m, 2H), 4.23 (m, 1H), 4.29 (s, 2H), 6.90 (m, 1H), 6.99-7.08 (m, 4H), 7.11 (m, 1H), 7.22 (t, J=8.1 Hz, 1H), 7.29 (d, J=9.0 Hz, 2H), 7.38 (t, J=2.1 Hz, 1H), 7.53 (d, J=9.0 Hz, 2H).

Example 23(117)

N-{4-[({butyl[1-(4-{4-[(methylsulfonyl)amino]phenoxy}benzyl)-4-piperidinyl]amino}carbonyl)amino]phenyl}methanesulfonamide hydrochloride TLC:Rf 0.50(methylene chloride:methanol=10:1);
NMR (CD$_3$OD): δ 0.97 (t, J=7.2 Hz, 3H), 1.30-1.50 (m, 2H), 1.50-1.70 (m, 2H), 1.90-2.10 (m, 2H), 2.20-2.40 (m, 2H), 2.90 (s, 3H), 2.95 (s, 3H), 3.00-3.20 (m, 2H), 3.20-3.40 (m, 2H), 3.50-3.60 (m, 2H), 4.20 (m, 1H), 4.29 (s, 2H), 7.02-7.08 (m, 4H), 7.18 (t, J=9.0 Hz, 2H), 7.28-7.33 (m, 4H), 7.55 (d, J=9.0 Hz, 2H).

Example 23(118)

N-[4-(4-{[4-(butyl{[(3-hydroxypropyl)amino]carbonyl}amino)-1-piperidinyl]methyl}phenoxy)phenyl]methanesulfonamide hydrochloride TLC:Rf 0.70(methylene chloride:methanol=4:1);
NMR (CD$_3$OD): δ 0.95 (t, J=7.2 Hz, 3H), 1.26-1.41 (m, 2H), 1.45-1.58 (m, 2H), 1.65-1.77 (m, 2H), 1.86-1.97 (m, 2H), 2.03-2.22 (m, 2H), 2.95 (s, 3H), 3.03-3.15 (m, 4H), 3.27 (t, J=6.3 Hz, 2H), 3.59 (t, J=6.3 Hz, 2H), 3.50-3.65 (m, 2H), 4.14 (m, 1H), 4.25 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(119)

N-[4-(4-{[4-({[(3-hydroxypropyl)amino]carbonyl}amino)-1-piperidinyl]methyl}phenoxy)phenyl]methanesulfonamide hydrochloride TLC:Rf 0.32(methylene chloride:methanol=4:1);
NMR (CD$_3$OD): δ 1.60-1.84 (m, 3H), 2.02 (m, 1H), 2.09-2.20 (m, 2H), 2.95 (s, 3H), 3.02-3.15 (m, 2H), 3.20 (t, J=6.5 Hz, 2H), 3.45-3.61 (m, 2H), 3.57 (t, J=6.5 Hz, 2H), 3.72 (m, 1H), 4.27 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(120)

N-(4-{4-[(4-{butyl[(3-thienylamino)carbonyl]amino}-1-piperidinyl)methyl]phenoxy}phenyl)methanesulfonamide hydrochloride TLC:Rf 0.31(methylene chloride:methanol=10:1);
NMR (CD$_3$OD): δ 0.96 (t, J=7.4 Hz, 3H), 1.30-1.50 (m, 2H), 1.50-1.70 (m, 2H), 1.90-2.10 (m, 2H), 2.10-2.30 (m, 2H), 2.95 (s, 3H), 3.05-3.20 (m, 2H), 3.20-3.40 (m, 2H), 3.50-3.60 (m, 2H), 4.20 (m, 1H), 4.29 (s, 2H), 7.02-7.11 (m, 5H), 7.18 (t, J=3.3, 1.5 Hz, 1H), 7.25-7.31 (m, 3H), 7.51 (d, J=8.7 Hz, 2H).

Example 23(121)

N-(4-{4-[(4-{butyl[(2-thienylamino)carbonyl]amino}-1-piperidinyl)methyl]phenoxy}phenyl)methanesulfonamide TLC:Rf 0.31(methylene chloride:methanol=10:1);
NMR (CD$_3$OD): δ 0.95 (t, J=7.4 Hz, 3H), 1.30-1.40 (m, 2H), 1.50-1.60 (m, 2H), 1.60-1.80 (m, 2H), 1.80-1.90 (m, 2H), 2.10-2.20 (m, 2H), 2.91 (s, 3H), 2.95-3.05 (m, 2H), 3.20-3.30 (m, 2H), 3.51 (s, 2H), 4.00 (m, 1H), 6.65 (m, 1H), 6.77-6.79 (m, 2H), 6.92-6.96 (m, 4H), 7.21-7.24 (m, 2H), 7.31 (d, J=8.7 Hz, 2H).

Example 23(122)

N-(4-{4-[(4-{butyl[(2,3-dihydro-1,4-benzodioxin-6-ylamino)carbonyl]amino}-1-piperidinyl)methyl]phenoxy}phenyl)methane sulfonamide hydrochloride TLC:Rf 0.40(methylene chloride:methanol=10:1);
NMR (CD$_3$OD): δ 0.96 (t, J=7.4 Hz, 3H), 1.30-1.40 (m, 2H), 1.50-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 4.10 (m, 1H), 4.20 (s, 4H), 4.28 (s, 2H), 6.72 (s, 2H), 6.85 (t, J=1.4 Hz, 1H), 7.02-7.11 (m, 4H), 7.29 (d, J=8.9 Hz, 2H), 7.48 (d, J=8.9 Hz, 2H).

Example 23(123)

N-[4-(4-{[4-(butyl{[(3,5-difluorophenyl)amino]carbonyl}amino)-1-piperidinyl]methyl}phenoxy)phenyl]methanesulfonamide hydrochloride TLC:Rf 0.40(methylene chloride:methanol=10:1);
NMR (CD$_3$OD): δ 0.96 (t, J=7.2 Hz, 3H), 1.30-1.40 (m, 2H), 1.50-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.15 (m, 1H), 4.30 (s, 2H), 6.55 (m, 1H), 7.02-7.11 (m, 6H), 7.29 (d, J=8.4 Hz, 2H), 7.51 (d, J=8.4 Hz, 2H).

Example 23(124)

N-[4-(4-{[4-(butyl{[(3,4-difluorophenyl)amino]carbonyl}amino)-1-piperidinyl]methyl}phenoxy)phenyl]methanesulfonamide hydrochloride TLC:Rf 0.44(methylene chloride:methanol=10:1);
NMR (CD$_3$OD): δ 0.97 (t, J=7.5 Hz, 3H), 1.30-1.40 (m, 2H), 1.50-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 7.02-7.16 (m, 6H), 7.29 (d, J=8.6 Hz, 2H), 7.40 (m, 1H), 7.55 (d, J=8.6 Hz, 2H).

Example 23(125)

N-[4-(4-{[4-(butyl{[(1-oxido-3-pyridinyl)amino]carbonyl}amino)-1-piperidinyl]methyl}phenoxy)phenyl]methanesulfonamide hydrochloride TLC:Rf 0.69(methylene chloride:methanol=5:1);
NMR (CD$_3$OD): δ 0.96 (t, J=7.4 Hz, 3H), 1.30-1.50 (m, 2H), 1.50-1.70 (m, 2H), 1.90-2.10 (m, 2H), 2.30-2.40 (m, 2H), 2.95 (s, 3H), 3.10-3.30 (m, 2H), 3.30-3.40 (m, 2H), 3.50-3.60 (m, 2H), 4.31 (s, 2H), 4.35 (m, 1H), 7.02-7.07 (m, 4H), 7.29 (d, J=8.6 Hz, 2H), 7.55 (d, J=8.6 Hz, 2H) 7.88 (dd, J=8.9, 3.5 Hz, 1H), 8.39 (d, J=2.7 Hz, 1H), 8.50 (d, J=2.7 Hz, 1H), 9.39 (s, 1H).

Example 23(126)

N-[4-(4-{[4-(butyl{[(2,4-difluorophenyl)amino]carbonyl}amino)-1-piperidinyl]methyl}phenoxy)phenyl]methanesulfonamide hydrochloride TLC:Rf 0.58(chloroform:methanol=10:1);
NMR (CD$_3$OD): δ 0.98 (t, J=7.4 Hz, 3H), 1.30-1.50 (m, 2H), 1.50-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 4.17 (m, 1H), 4.29 (s, 2H), 6.92-7.00 (m, 2H), 7.02-7.08 (m, 4H), 7.26-7.41 (m, 3H), 7.49-7.52 (m, 2H);
amorphous;
softening point: about 196-198° C.

Example 23(127)

N-{4-[4-({4-[{[(4-bromophenyl)amino]carbonyl}(butyl)amino]-1-piperidinyl}methyl)phenoxy]phenyl}methanesulfonamide hydrochloride TLC:Rf 0.57(chloroform:methanol=10:1);
NMR (CD$_3$OD): δ 0.96 (t, J=7.4 Hz, 3H), 1.30-1.40 (m, 2H), 1.50-1.60 (m, 2H), 1.90-2.10 (m, 2H), 2.10-2.30 (m, 2H), 2.95 (s, 3H), 3.05-3.20 (m, 2H), 3.20-3.30 (m, 2H), 3.50-3.60 (m, 2H), 4.19 (m, 1H), 4.29 (s, 2H), 7.02-7.08 (m, 4H), 7.27-7.31 (m, 4H), 7.39 (d, J=8.7 Hz, 2H), 7.51 (d, J=8.7 Hz, 2H).

Example 23(128)

N-(4-{4-[(4-{butyl[(isobutylamino)carbonyl]amino}-1-piperidinyl)methyl]phenoxy}phenyl)methanesulfonamide hydrochloride TLC:Rf 0.51(chloroform:methanol=10:1);
NMR (CD$_3$OD): δ 0.87 (d, J=6.6 Hz, 6H), 0.95 (t, J=7.4 Hz, 3H), 1.30-1.40 (m, 2H), 1.50-1.60 (m, 2H), 1.76 (m, 1H), 1.80-2.00 (m, 2H), 2.00-2.20 (m, 2H), 2.96 (s, 3H), 2.96 (d, J=7.5 Hz, 2H), 3.00-3.40 (m, 4H), 3.50-3.60 (m, 2H), 4.16 (m, 1H), 4.28 (s, 2H), 7.02-7.08 (m, 4H), 7.29 (d, J=8.9 Hz, 2H), 7.50 (d, J=8.9 Hz, 2H).

Example 23(129)

N-{4-[4-({4-[{[(4-fluorophenyl)amino]carbonyl}(3-methyl-2-butenyl)amino]-1-piperidinyl}methyl)phenoxy]phenyl}methanesulfonamide hydrochloride TLC:Rf 0.62(methylene chloride:methanol=9:1);
NMR (CD$_3$OD): δ 1.75 (s, 6H), 1.92-2.03 (m, 2H), 2.07-2.23 (m, 2H), 2.95 (s, 3H), 3.05-3.19 (m, 2H), 3.50-3.60 (m, 2H), 3.94-4.02 (m, 2H), 4.20-4.35 (m, 3H), 5.18 (m, 1H), 6.98-7.10 (m, 6H), 7.26-7.34 (m, 4H), 7.50 (d, J=8.7 Hz, 2H).

Example 23(130)

N-[4-(4-{4-(3-butynyl {[(4-fluorophenyl)amino]carbonyl}amino)-1-piperidinyl]methyl}phenoxy)phenyl]methanesulfonamide hydrochloride TLC:Rf 0.61(methylene chloride:methanol=9:1);
NMR (CD$_3$OD): δ 1.97-2.10 (m, 2H), 2.19-2.20 (m, 2H), 2.43 (m, 1H), 2.49-2.58 (m, 2H), 2.95 (s, 3H), 3.02-3.19 (m, 2H), 3.46-3.61 (m, 4H), 4.08 (m, 1H), 4.29 (s, 2H), 6.98-7.10 (m, 6H), 7.26-7.34 (m, 4H), 7.50 (d, J=8.7 Hz, 2H).

Example 23(131)

N-[4-(4-{4-(3-butenyl {[(4-fluorophenyl)amino]carbonyl}amino)-1-piperidinyl]methyl}phenoxy)phenyl]methanesulfonamide hydrochloride TLC:Rf 0.61(methylene chloride:methanol=9:1);
NMR (CD$_3$OD): δ 1.95-2.06 (m, 2H), 2.15-2.44 (m, 4H), 2.95 (s, 3H), 3.03-3.18 (m, 2H), 3.28-3.41 (m, 2H), 3.50-3.61 (m, 2H), 4.13 (m, 1H), 4.29 (s, 2H), 5.08 (d, J=10.2 Hz, 1H), 5.14 (d, J=17.1 Hz, 1H), 5.86 (m, 1H), 6.98-7.10 (m, 6H), 7.26-7.35 (m, 4H), 7.50 (d, J=8.7 Hz, 2H).

Example 23(132)

N-{4-[4-({4-[{[(4-fluorophenyl)amino]carbonyl}(2-hydroxybutyl)amino]-1-piperidinyl}methyl)phenoxy]phenyl}methanesulfonamide hydrochloride TLC:Rf 0.59(methylene chloride:methanol=9:1);
NMR (CD$_3$OD): δ 1.02 (t, J=7.5 Hz, 3H), 1.44-1.60 (m, 2H), 1.95-2.28 (m, 4H), 2.95 (s, 3H), 3.01-3.36 (m, 4H), 3.47-3.60 (m, 2H), 3.66 (m, 1H), 4.10 (m, 1H), 4.28 (s, 2H), 6.98-7.10 (m, 6H), 7.22-7.34 (m, 4H), 7.50 (d, J=8.7 Hz, 2H).

Example 23(133)

N-{4-[4-({4-[[(1,3-benzodioxol-5-ylamino)carbonyl](butyl)amino]-1-piperidinyl}methyl)phenoxy]phenyl}methanesulfonamide hydrochloride TLC:Rf 0.29(chloroform:methanol=10:1);
NMR (CD$_3$OD): δ 0.97 (t, J=7.4 Hz, 3H), 1.30-1.40 (m, 2H), 1.50-1.70 (m, 2H), 1.90-2.00 (m, 2H), 2.10-2.20 (m, 2H), 2.95 (s, 3H), 3.05-3.20 (m, 2H), 3.20-3.30 (m, 2H), 3.50-3.60 (m, 2H), 4.15 (m, 1H), 4.29 (s, 2H), 5.90 (s, 2H), 6.70-6.71 (m, 2H), 6.89 (d, J=1.8 Hz, 1H), 7.02-7.08 (m, 4H), 7.29 (d, J=8.7 Hz, 2H), 7.50 (d, J=8.7 Hz, 2H).

Example 23(134)

N-[4-(4-{[4-((4-fluorobenzyl){[(4-fluorophenyl)amino]carbonyl}amino)-1-piperidinyl]methyl}phenoxy)phenyl]methanesulfonamide hydrochloride TLC:Rf 0.59(chloroform:methanol=9:1);
NMR (CD$_3$OD): δ 7.46 (brd, J=8.4 Hz, 2H), 7.40-7.24 (m, 6H), 7.14-6.80 (m, 8H), 4.62 (s, 2H), 4.32 (m, 1H), 4.24 (s, 2H), 3.48 (m, 2H), 3.06 (m, 2H), 2.95 (s, 3H), 2.20-1.88 (m, 4H).

Example 23(135)

N-{4-[4-({4-[{[(4-fluorophenyl)amino]carbonyl}(2-methoxybenzyl)amino]-1-piperidinyl}methyl)phenoxy]phenyl}methanesulfonamide hydrochloride TLC:Rf 0.62(chloroform:methanol=9:1);
NMR (CD$_3$OD): δ 7.45 (brd, J=8.7 Hz, 2H), 7.30-7.19 (m, 6H), 7.16-6.90 (m, 8H), 4.59 (s, 2H), 4.32 (m, 1H), 4.23 (s, 2H), 3.88 (s, 3H), 3.47 (m, 2H), 3.08 (m, 2H), 2.95 (s, 3H), 2.18-1.88 (m, 4H).

Example 23(136)

N-{4-[4-({4-[{[(4-fluorophenyl)amino]carbonyl}(2-methylbenzyl)amino]-1-piperidinyl}methyl)phenoxy]phenyl}methanesulfonamide hydrochloride TLC:Rf 0.68(chloroform:methanol=9:1);
NMR (CD$_3$OD): δ 7.45 (brd, J=8.7 Hz, 2H), 7.30-7.10 (m, 8H), 7.08-6.90 (m, 6H), 4.56 (s, 2H), 4.43 (m, 1H), 4.24 (s, 2H), 3.49 (m, 2H), 3.07 (m, 2H), 2.95 (s, 3H), 2.35 (s, 3H), 2.16-1.86 (m, 4H).

Example 23(137)

N-[4-(4-{[4-(butyl{[(3-hydroxy-4-methylphenyl)amino]carbonyl}amino)-1-piperidinyl]methyl}phenoxy)phenyl]methanesulfonamide hydrochloride TLC:Rf 0.42(chloroform:methanol=10:1);
NMR (CD$_3$OD): δ 0.96 (t, J=7.2 Hz, 3H), 1.20-1.40 (m, 2H), 1.50-1.70 (m, 2H), 1.90-2.00 (m, 2H), 2.10-2.30 (m, 2H), 2.12 (s, 3H), 2.95 (s, 3H), 3.00-3.20 (m, 2H), 3.20-3.40 (m, 2H), 3.50-3.60 (m, 2H), 4.16 (m, 1H), 4.28 (s, 2H), 6.64 (dd, J=8.0, 2.0 Hz, 1H), 6.83 (d, J=2.0 Hz, 1H), 6.94 (d, J=8.0 Hz, 1H), 7.02-7.08 (m, 4H), 7.29 (d, J=8.4 Hz, 2H), 7.49 (d, J=8.4 Hz, 2H).

Example 23(138)

N-[4-(4-{[4-(butyl{[(3,5-dihydroxyphenyl)amino]carbonyl}amino)-1-piperidinyl]methyl}phenoxy)phenyl]methanesulfonamide hydrochloride TLC:Rf 0.75(methylene chloride:methanol=5:1);
NMR (d$_6$-DMSO): δ 0.88 (t, J=7.2 Hz, 3H), 1.20-1.40 (m, 2H), 1.40-1.50 (m, 2H), 1.70-1.80 (m, 2H), 2.10-2.30 (m, 2H), 3.16 (s, 3H), 3.30-3.40 (m, 2H), 3.60-3.90 (m, 4H), 4.14 (m, 1H), 4.22 (d, J=4.8 Hz, 2H), 5.83 (t, J=2.1 Hz, 1H), 6.37 (d, J=2.1 Hz, 2H), 7.02-7.08 (m, 4H), 7.25 (d, J=8.6 Hz, 2H), 7.57 (d, J=8.6 Hz, 2H), 7.88 (s, 1H), 9.71 (s, 1H), 10.51 (s, 1H).

Example 23(139)

N-[4-(4-{[4-(butyl{[(2-hydroxy-2-methylpropyl) amino]carbonyl}amino)-1-piperidinyl] methyl}phenoxy)phenyl]methanesulfonamide hydrochloride TLC:Rf 0.50(methylene chloride:methanol=9:1);
NMR (CD$_3$OD): δ 0.96 (t, J=7.2 Hz, 3H), 1.15 (s, 6H), 1.28-1.44 (m, 2H), 1.50-1.62 (m, 2H), 1.88-1.98 (m, 2H), 2.08-2.25 (m, 2H), 2.95 (s, 3H), 3.02-3.22 (m, 6H), 3.50-3.60 (m, 2H), 4.16 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 23(140)

N-[4-(4-{[4-({[(2-hydroxy-2-methylpropyl)amino] carbonyl}amino)-1-piperidinyl]methyl}phenoxy) phenyl]methanesulfonamide hydrochloride TLC:Rf 0.15(methylene chloride:methanol=9:1);
NMR (CD$_3$OD): δ 1.15 (s, 6H), 1.60-1.78 (m, 2H), 2.00-2.21 (m, 2H), 2.95 (s, 3H), 3.01-3.15 (m, 4H), 3.44-3.55 (m, 2H), 3.73 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(141)

N-[4-(4-{[4-((cyclopropylmethyl) {[(4-fluorophenyl) amino]carbonyl}amino)-1-piperidinyl] methyl}phenoxy)phenyl]methanesulfonamide hydrochloride TLC:Rf 0.43(methylene chloride:methanol=9:1);
NMR (CD$_3$OD): δ 0.32-0.37 (m, 2H), 0.57-0.63 (m, 2H), 1.06 (m, 1H), 1.97-2.10 (m, 2H), 2.25-2.42 (m, 2H), 2.95 (s, 3H), 3.05-3.18 (m, 2H), 3.25 (d, J=6.6 Hz, 2H), 3.51-3.62 (m, 2H), 4.06 (m, 1H), 4.29 (s, 2H), 6.98-7.10 (m, 6H), 7.27-7.35 (m, 4H), 7.50 (d, J=8.7 Hz, 2H).

Example 23(142)

N-[4-(4-{[4-((cyclobutylmethyl) {[(4-fluorophenyl) amino]carbonyl}amino)-1-piperidinyl] methyl}phenoxy)phenyl]methanesulfonamide hydrochloride TLC:Rf 0.43(methylene chloride:methanol=9:1);
NMR (CD$_3$OD): δ 1.75-2.14 (m, 8H), 2.23-2.40 (m, 2H), 2.62 (m, 1H), 2.95 (s, 3H), 3.03-3.15 (m, 2H), 3.36 (d, J=6.9 Hz, 2H), 3.50-3.60 (m, 2H), 3.95 (m, 1H), 4.28 (s, 2H), 6.98-7.08 (m, 6H), 7.27-7.32 (m, 4H), 7.50 (d, J=8.7 Hz, 2H).

Example 23(143)

N-(4-{4-[(4-{{[(4-fluorophenyl)amino]carbonyl}[(1-oxido-3-pyridinyl)methyl]amino}-1-piperidinyl) methyl]phenoxy}phenyl)methanesulfonamide hydrochloride TLC:Rf 0.14(methylene chloride:methanol=9:1);
NMR (CD$_3$OD): δ 1.98-2.32 (m, 4H), 2.95 (s, 3H), 3.09-3.21 (m, 2H), 3.50-3.60 (m, 2H), 4.30 (s, 2H), 4.40 (m, 1H), 4.72 (s, 2H), 6.97-7.10 (m, 6H), 7.29 (d, J=8.7 Hz, 2H), 7.37 (dd, J=9.0, 5.1 Hz, 2H), 7.53 (d, J=8.7 Hz, 2H), 7.84 (t, J=7.0 Hz, 1H), 8.08 (d, J=7.0 Hz, 1H), 8.62 (d, J=7.0 Hz, 1H), 8.69 (s, 1H).

Example 23(144)

N-[4-(4-{[4-((3-fluorobenzyl){[(4-fluorophenyl) amino]carbonyl}amino)-1-piperidinyl] methyl}phenoxy)phenyl]methanesulfonamide hydrochloride TLC:Rf 0.65(chloroform:methanol=5:1);
NMR (CD$_3$OD): δ 7.47 (m, 2H), 7.40-7.22 (m, 5H), 7.16 (m, 1H), 7.10-6.96 (m, 8H), 4.65 (s, 2H), 4.37 (m, 1H), 4.24 (s, 2H), 3.50 (m, 2H), 3.09 (m, 2H), 2.95 (s, 3H), 2.20-1.90 (m, 4H).

Example 23(145)

N-[4-(4-{[4-((2-fluorobenzyl){[(4-fluorophenyl) amino]carbonyl}amino)-1-piperidinyl] methyl}phenoxy)phenyl]methanesulfonamide hydrochloride TLC:Rf 0.65(chloroform:methanol=5:1);
NMR (CD$_3$OD): δ 7.46 (brd, J=8.7 Hz, 2H), 7.40-7.22 (m, 6H), 7.20-6.92 (m, 8H), 4.69 (s, 2H), 4.39 (m, 1H), 4.25 (s, 2H), 3.51 (m, 2H), 3.10 (m, 2H), 2.95 (s, 3H), 2.20-1.89 (m, 4H).

Example 23(146)

N-{4-[4-({4-[{[(4-fluorophenyl)amino]carbonyl}(4-methoxybenzyl)amino]-1-piperidinyl}methyl)phenoxy]phenyl}methanesulfonamide hydrochloride TLC:Rf 0.69(chloroform:methanol=5:1);
NMR (CD$_3$OD): δ 7.45 (brd, J=8.7 Hz, 2H), 7.40-7.20 (m, 6H), 7.10-6.88 (m, 8H), 4.57 (s, 2H), 4.29 (m, 1H), 4.23 (s, 2H), 3.76 (s, 3H), 3.49 (m, 2H), 3.08 (m, 2H), 2.95 (s, 3H), 2.22-1.86 (m, 4H).

Example 23(147)

N-{4-[4-({4-[{[(4-fluorophenyl)amino]carbonyl}(3-methoxybenzyl)amino]-1-piperidinyl}methyl)phenoxy]phenyl}methanesulfonamide hydrochloride TLC:Rf 0.81(chloroform:methanol=5:1);
NMR (CD$_3$OD): δ 7.46 (brd, J=9.0 Hz, 2H), 7.30-7.20 (m, 5H), 7.08-6.94 (m, 6H), 6.92-6.76 (m, 3H), 4.62 (s, 2H), 4.35 (m, 1H), 4.24 (s, 2H), 3.77 (s, 3H), 3.49 (m, 2H), 3.08 (m, 2H), 2.95 (s, 3H), 2.20-1.90 (m, 4H).

Example 23(148)

N-{4-[4-({4-[{[(4-fluorophenyl)amino]carbonyl}(3-methylbenzyl)amino]-1-piperidinyl}methyl)phenoxy]phenyl}methanesulfonamide hydrochloride TLC:Rf 0.85(chloroform:methanol=5:1);
NMR (CD$_3$OD): δ 7.47 (brd, J=9.0 Hz, 2H), 7.34-7.18 (m, 6H), 7.16-6.92 (m, 8H), 4.61 (s, 2H), 4.36 (m, 1H), 4.25 (s, 2H), 3.49 (m, 2H), 3.08 (m, 2H), 2.95 (s, 3H) 2.32 (s, 3H), 2.22-1.90 (m, 4H).

Example 23(149)

4-{{[(4-fluorophenyl)amino]carbonyl}[1-(4-{4-[(methylsulfonyl)amino]phenoxy}benzyl)-4-piperidinyl]amino}butanoic acid hydrochloride TLC:Rf 0.18(methylene chloride:methanol=9:1);
NMR (CD$_3$OD): δ 1.82-2.02 (m, 4H), 2.10-2.30 (m, 2H), 2.43 (t, J=6.3 Hz, 2H), 2.95 (s, 3H), 3.04-3.18 (m, 2H), 3.25-3.35 (m, 2H), 3.50-3.60 (m, 2H), 4.22-4.35 (m, 3H), 7.00 (dd, J=17.1, 9.0 Hz, 2H), 7.03 (d, J=8.7 Hz, 2H), 7.06 (d, J=8.7 Hz, 2H), 7.29 (d, J=8.7 Hz, 2H), 7.42-7.55 (m, 2H), 7.50 (d, J=8.7 Hz, 2H).

Example 23(150)

N-[4-(4-{[4-(butyl{[(3,5-dimethyl-4-isoxazolyl)amino]carbonyl}amino)-1-piperidinyl]methyl}phenoxy)phenyl]methanesulfonamide hydrochloride TLC:Rf 0.53(methylene chloride:methanol=9:1);
NMR (CD$_3$OD): δ 0.98 (t, J=7.2 Hz, 3H), 1.32-1.47 (m, 2H), 1.58-1.70 (m, 2H), 1.95-2.03 (m, 2H), 2.12 (s, 3H), 2.26 (s, 3H), 2.15-2.25 (m, 2H), 2.95 (s, 3H), 3.03-3.17 (m, 2H), 3.21-3.32 (m, 2H), 3.50-3.60 (m, 2H), 4.10 (m, 1H), 4.29 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 23(151)

N-[4-(4-{[4-(butyl{[(6-methyl-3-pyridinyl)amino]carbonyl}amino)-1-piperidinyl]methyl}phenoxy)phenyl]methanesulfonamide dihydro chloride TLC:Rf 0.51(methylene chloride:methanol=9:1);
NMR (CD$_3$OD): δ 0.97 (t, J=7.2 Hz, 3H), 1.31-1.45 (m, 2H), 1.57-1.67 (m, 2H), 1.97-2.08 (m, 2H), 2.22-2.38 (m, 2H), 2.70 (s, 3H), 2.95 (s, 3H), 3.10-3.25 (m, 2H), 3.28-3.36 (m, 2H), 3.52-3.62 (m, 2H), 4.30 (m, 1H), 4.31 (s, 2H), 7.03 (d, J=8.7 Hz, 2H), 7.06 (d, J=8.7 Hz, 2H), 7.29 (d, J=8.7 Hz, 2H), 7.53 (d, J=8.7 Hz, 2H), 7.79 (d, J=8.7 Hz, 1H), 8.49 (dd, J=8.7, 2.7 Hz, 1H), 9.02 (s, 1H).

Example 24

N-[4-(4-{[4-(butyl{[(cyclohexylmethyl)amino]carbonothioyl}amino)-1-piperidinyl]methyl}phenoxy)phenyl]methanesulfonamide hydrochloride To a solution of the compound prepared in Example 3 (70 mg) in dimethylformamide (1 mL) was added triethylamine (38 µL). The solution was added dropwise to a solution of cyclohexylmethyl isothiocyanate (43 mg) in dimethylformamide (0.5 mL) and the mixture was stirred for 1 hour. Water was added to the reaction mixture, which was extracted with ethyl acetate. The organic layer was dried over anhydrous sodium sulfate and concentrated. The obtained residue was purified by column chromatography on silica gel (ethyl acetate:methanol=10:1), and converted to hydrochloride salt by a conventional method to give the compound of the present invention (81.9 mg) having the following physical data.

TLC:Rf 0.69(ethyl acetate:methanol=10:1);
NMR (CD$_3$OD): δ 0.88-1.03 (m, 2H), 0.96 (t, J=7.2 Hz, 3H), 1.14-1.44 (m, 5H), 1.47-1.60 (m, 2H), 1.62-1.82 (m, 6H), 1.93-2.08 (m, 4H), 2.95 (s, 3H), 3.05-3.20 (m, 2H), 3.24-3.36 (m, 2H), 3.47 (d, J=6.6 Hz, 2H), 3.50-3.60 (m, 2H), 4.29 (s, 2H), 5.66 (m, 1H), 7.03 (d, J=8.7 Hz, 2H), 7.06 (d, J=8.7 Hz, 2H), 7.29 (d, J=8.7 Hz, 2H), 7.51 (d, J=8.7 Hz, 2H).

Example 24(1) and Example 24(2)

By the same procedure as described in Example 24, using a corresponding amine derivative instead of the compound prepared in Example 3, the compounds of the present invention having the following physical data were obtained.

Example 24(1)

N-[4-(4-{[4-({[(cyclohexylmethyl)amino]carbonothioyl}amino)-1-piperidinyl]methyl}phenoxy)phenyl]methanesulfonamide hydrochloride TLC:Rf 0.62(ethyl acetate:methanol=10:1);
NMR (CD$_3$OD): δ 0.88-1.05 (m, 2H), 1.13-1.34 (m, 3H), 1.50-1.83 (m, 8H), 2.22-2.35 (m, 2H), 2.95 (s, 3H), 3.05-3.18 (m, 2H), 3.21-3.42 (m, 2H), 3.47-3.58 (m, 2H), 4.28 (s, 2H), 4.42 (m, 1H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 24(2)

N-[4-(4-{[4-(benzyl{[(cyclohexylmethyl)amino]carbonothioyl}amino)-1-piperidinyl]methyl}phenoxy)phenyl]methanesulfonamide hydrochloride TLC:Rf 0.67(ethyl acetate:methanol=10:1);
NMR (CD$_3$OD): δ 0.62-0.78 (m, 2H), 1.00-1.14 (m, 3H), 1.30-1.62 (m, 6H), 1.89-2.13 (m, 4H), 2.95 (s, 3H), 3.09-3.21 (m, 2H), 3.36 (d, J=6.6 Hz, 2H), 3.45-3.56 (m, 2H), 4.27 (s, 2H), 4.71 (s, 2H), 5.87 (m, 1H), 7.02 (d, J=8.7 Hz, 2H), 7.04 (d, J=8.7 Hz, 2H), 7.17-7.38 (m, 7H), 7.48 (d, J=8.7 Hz, 2H).

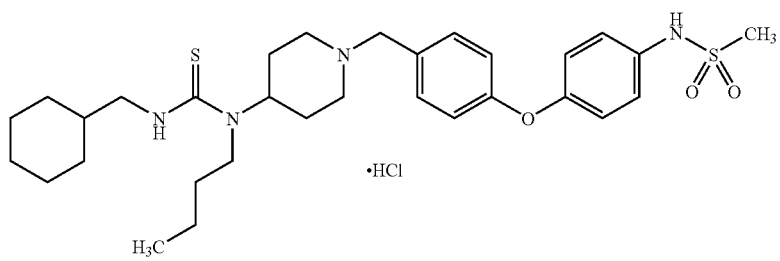

Example 25

N-[4-(4-{[4-(butyl{[(3-hydroxybutyl)amino]carbonyl}amino)-1-piperidinyl]methyl}phenoxy)phenyl]methanesulfonamide hydrochloride

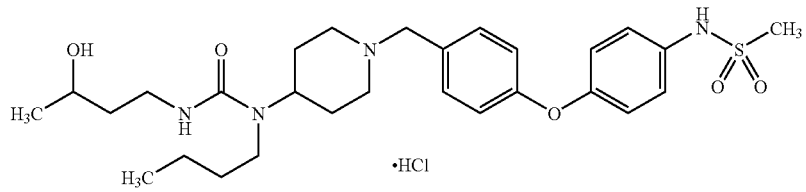

To a solution of (3-{[t-butyl(dimethyl)silyl]oxy}butyl)amine (72.3 mg) in tetrahydrofuran (1 mL) were added triethylamine (97 μL) and triphosgene (44.1 mg) under cooling with ice and stirring, and then the solution was stirred at room temperature for 1 hour. A solution of the compound prepared in Example 3 (100 mg) and triethylamine (55 μL) in N,N-dimethylformamide (1 mL) was added dropwise to the reaction mixture, which was stirred for 15 minutes. A saturated aqueous solution of sodium hydrogen carbonate was added to the reaction mixture, which was extracted with ethyl acetate. The organic layer was dried over anhydrous sodium sulfate and concentrated. A solution of 4N hydrochloric acid in ethyl acetate was added to the obtained residue. The reaction mixture was stirred for 15 minutes and concentrated. The organic layer was dried over anhydrous sodium sulfate and concentrated. The obtained residue was purified by column chromatography on silica gel (ethyl acetate:methanol=10:1), and converted to hydrochloride salt by a conventional method to give the compound of the present invention (99.6 mg) having the following physical data.

TLC:Rf 0.46(methylene chloride:methanol=9:1);
NMR (CD$_3$OD): δ 0.95 (t, J=7.2 Hz, 3H), 1.16 (d, J=6.0 Hz, 3H), 1.26-1.41 (m, 2H), 1.44-1.70 (m, 4H), 1.85-1.97 (m, 2H), 2.05-2.21 (m, 2H), 2.95 (s, 3H), 3.03-3.13 (m, 4H), 3.17-3.38 (m, 2H), 3.50-3.58 (m, 2H), 3.78 (m, 1H), 4.13 (m, 1H), 4.27 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 25(1)-Example 25(10)

By the same procedure as described in Example 25, using (3-{[t-butyl(dimethyl)silyl]oxy}butyl)amine or a corresponding amine derivative, and using the compound prepared in Example 3 or a corresponding amine derivative, the compounds of the present invention having the following physical data were obtained.

Example 25(1)

N-{4-[4-({4-[butyl({[(1R,2R)-2-hydroxycyclohexyl]amino}carbonyl)amino]-1-piperidinyl}methyl)phenoxy]phenyl}methanesulfonamide hydrochloride TLC:Rf 0.29(ethyl acetate:methanol=10:1);
NMR (CD$_3$OD): δ 0.95 (t, J=7.2 Hz, 3H), 1.23-1.42 (m, 6H), 1.47-1.61 (m, 2H), 1.65-1.77 (m, 2H), 1.88-2.05 (m, 4H), 2.05-2.22 (m, 2H), 2.95 (s, 3H), 3.02-3.20 (m, 4H), 3.34-3.48 (m, 2H), 3.50-3.59 (m, 2H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 25(2)

N-{4-[4-({4-[butyl({[(1S,2S)-2-hydroxycyclohexyl]amino}carbonyl)amino]-1-piperidinyl}methyl)phenoxy]phenyl}methanesulfonamide hydrochloride TLC:Rf 0.29(ethyl acetate:methanol=10:1);
NMR (CD$_3$OD): δ 0.95 (t, J=7.2 Hz, 3H), 1.23-1.42 (m, 6H), 1.47-1.61 (m, 2H), 1.65-1.77 (m, 2H), 1.88-2.05 (m, 4H), 2.05-2.22 (m, 2H), 2.95 (s, 3H), 3.02-3.20 (m, 4H), 3.34-3.48 (m, 2H), 3.50-3.59 (m, 2H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 25(3)

N-{4-[4-({4-[({[(1-hydroxycyclohexyl)methyl]amino}carbonyl)amino]-1-piperidinyl}methyl)phenoxy]phenyl}methanesulfonamide hydrochloride TLC:Rf 0.23(ethyl acetate:methanol=5:1);
NMR (CD$_3$OD): δ 1.26-1.75 (m, 11H), 2.02 (m, 1H), 2.10-2.21 (m, 2H), 2.95 (s, 3H), 3.03-3.16 (m, 4H), 3.45-3.55 (m, 2H), 3.72 (m, 1H), 4.27 (s, 2H), 7.03 (d, J=8.7 Hz, 2H), 7.05 (d, J=8.7 Hz, 2H), 7.29 (d, J=8.7 Hz, 2H), 7.49 (d, J=8.7 Hz, 2H).

Example 25(4)

N-{4-[4-({4-[({[(1R,2R)-2-hydroxycyclohexyl]amino}carbonyl)amino]-1-piperidinyl}methyl)phenoxy]phenyl}methanesulfonamide hydrochloride TLC:Rf 0.64(methylene chloride:methanol=4:1);
NMR (CD$_3$OD): δ 1.12-1.40 (m, 4H), 1.59-1.76 (m, 3H), 1.88-2.06 (m, 3H), 2.11-2.21 (m, 2H), 2.95 (s, 3H), 3.02-3.14 (m, 2H), 3.18-3.38 (m, 2H), 3.46-3.55 (m, 2H), 3.73 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 25(5)

N-{4-[4-({4-[({[(1S,2S)-2-hydroxycyclohexyl]amino}carbonyl)amino]-1-piperidinyl}methyl)phenoxy]phenyl}methanesulfonamide hydrochloride TLC:Rf 0.64(methylene chloride:methanol=4:1);
NMR (CD$_3$OD): δ 1.12-1.40 (m, 4H), 1.59-1.76 (m, 3H), 1.88-2.06 (m, 3H), 2.11-2.21 (m, 2H), 2.95 (s, 3H), 3.02-3.14 (m, 2H), 3.18-3.38 (m, 2H), 3.46-3.55 (m, 2H), 3.73 (m, 1H), 4.27 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 25(6)

N-(4-{4-[(4-{butyl[(4-piperidinylamino)carbonyl]amino}-1-piperidinyl)methyl]phenoxy}phenyl)methanesulfonamide dihydrochloride TLC:Rf 0.24(n-butanol:acetic acid:water=4:2:1);
NMR (CD₃OD): δ 0.95 (t, J=7.2 Hz, 3H), 1.30-1.40 (m, 2H), 1.40-1.50 (m, 2H), 1.70-1.80 (m, 2H), 1.80-2.00 (m, 2H), 2.00-2.20 (m, 4H), 2.95 (s, 3H), 3.00-3.20 (m, 6H), 3.02-3.15 (m, 4H), 3.22-3.32 (m, 2H), 3.48-3.59 (m, 3H), 4.14 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 25(10)

N-{4-[4-({4-[butyl({[(1-hydroxycyclohexyl)methyl]amino}carbonyl)amino]-1-piperidinyl}methyl)phenoxy]phenyl}methane sulfonamide hydrochloride

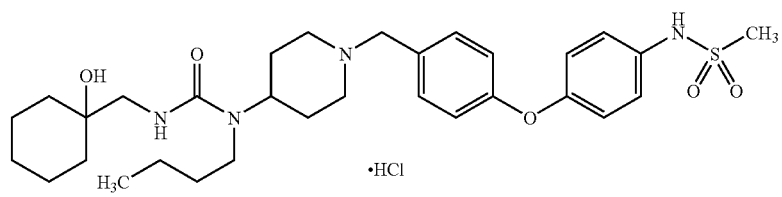

3.30-3.50 (m, 2H), 3.50-3.60 (m, 2H), 3.80 (m, 1H), 4.10 (m, 1H), 4.28 (s, 2H), 7.02-7.08 (m, 4H), 7.29 (d, J=8.7 Hz, 2H), 7.50 (d, J=8.7 Hz, 2H).

Example 25(7)

N-[4-(4-{[4-({[(2-hydroxybutyl)amino]carbonyl}amino)-1-piperidinyl]methyl}phenoxy)phenyl]methanesulfonamide hydrochloride TLC:Rf 0.48(methylene chloride:methanol=4:1);
NMR (CD₃OD): δ 0.94 (t, J=7.2 Hz, 3H), 1.32-1.52 (m, 2H), 1.58-1.75 (m, 1.6H), 1.98-2.08 (m, 0.4H), 2.10-2.20 (m, 2H), 2.95 (s, 3H), 3.00-3.14 (m, 2H), 3.16-3.40 (m, 2.6H), 3.45-3.54 (m, 2.4H), 3.68-3.78 (m, 0.8H), 3.90-3.95 (m, 0.2H), 4.27 (s, 1.6H), 4.33 (s, 0.4H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 25(8)

N-[4-(4-{[4-({[(3-hydroxybutyl)amino]carbonyl}amino)-1-piperidinyl]methyl}phenoxy)phenyl]methanesulfonamide hydrochloride TLC:Rf 0.33(methylene chloride:methanol=4:1);
NMR (CD₃OD): δ 1.16 (d, J=6.3 Hz, 2.4H), 1.17 (d, J=6.3 Hz, 0.6H), 1.48-1.75 (m, 3.6H), 1.98-2.05 (m, 0.4H), 2.10-2.20 (m, 2H), 2.95 (s, 3H), 3.02-3.30 (m, 4H), 3.48-3.55 (m, 2H), 3.65-3.83 (m, 2H), 4.27 (s, 1.6H), 4.32 (s, 0.4H), 7.03 (d, J=8.7 Hz, 2H), 7.05 (d, J=8.7 Hz, 2H), 7.29 (d, J=8.7 Hz, 2H), 7.49 (d, J=8.7 Hz, 2H).

Example 25(9)

N-[4-(4-{[4-(butyl{[(2-hydroxybutyl)amino]carbonyl}amino)-1-piperidinyl]methyl}phenoxy)phenyl]methanesulfonamide hydrochloride TLC:Rf 0.48(methylene chloride:methanol=9:1);
NMR (CD₃OD): δ 0.95 (t, J=7.2 Hz, 6H), 1.28-1.61 (m, 6H), 1.88-1.97 (m, 2H), 2.04-2.22 (m, 2H), 2.95 (s, 3H), TLC:Rf 0.56(ethyl acetate:methanol=10:1);
NMR (CD₃OD): δ 0.96 (t, J=7.5 Hz, 3H), 1.27-1.70 (m, 14H), 1.88-1.97 (m, 2H), 2.04-2.21 (m, 2H), 2.95 (s, 3H), 3.02-3.18 (m, 4H), 3.20 (s, 2H), 3.48-3.60 (m, 2H), 4.15 (m, 1H), 4.28 (s, 2H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 26

N-butyl-N-[1-(4-{4-[(methylsulfonyl)amino]phenoxy}benzyl)-4-piperidinyl]-1-piperidinecarboxamide hydrochloride

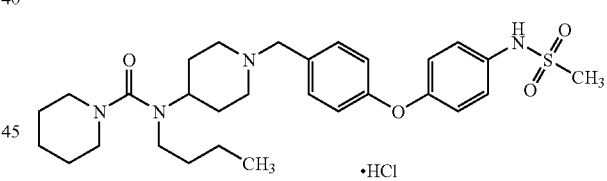

Under an atmosphere of argon, to a solution of the compound prepared in Example 3 (50.0 mg) in N,N-dimethylformamide (1 mL) were triethylamine (30.0 μL) and piperidine-1-carbonylchloride (13.4 μL) and the solution was stirred at 40° C. for 12 hours. The reaction mixture was diluted with ethyl acetate. Water was added to the reaction mixture, which was extracted with ethyl acetate. The organic layer was washed with brine, dried over anhydrous and concentrated. The obtained residue was purified by column chromatography on silica gel (chloroform:methanol=7:1), and converted to hydrochloride salt by a conventional method to give the compound of the present invention (14.9 mg) having the following physical data.

TLC:Rf 0.61(chloroform:methanol=5:1);
NMR (CD₃OD): δ 0.92 (t, J=7.5 Hz, 3H), 1.20-1.70 (m, 10H), 1.90-2.05 (m, 2H), 2.06-2.24 (m, 2H), 2.95 (s, 3H), 3.02-3.18 (m, 4H), 3.18-3.38 (m, 4H), 3.45-3.62 (m, 3H), 4.27 (s, 2H), 7.00-7.12 (m, 4H), 7.24-7.34 (m, 2H), 7.44-7.58 (m, 2H).

Example 26(1)-Example 26(4)

By the same procedure as described in Example 26, using a corresponding acid chloride derivative instead of piperidine-1-carbonylchloride, the compounds of the present invention having the following physical data were obtained.

Example 26(1)

N-butyl-N-[1-(4-{4-[(methylsulfonyl)amino]phenoxy}benzyl)-4-piperidinyl]-4-morpholinecarboxamide hydrochloride TLC:Rf 0.64(chloroform:methanol=5:1);
NMR (CD$_3$OD): δ 0.93 (t, J=7.2 Hz, 3H), 1.20-1.40 (m, 2H), 1.42-1.56 (m, 2H), 1.88-2.02 (m, 2H), 2.06-2.30 (m, 2H), 2.95 (s, 3H), 3.02-3.16 (m, 4H), 3.21-3.34 (m, 3H), 3.44-3.70 (m, 8H), 4.23 (s, 2H), 7.00-7.10 (m, 4H), 7.12-7.38 (m, 2H), 7.49 (brd, J=8.7 Hz, 2H).

Example 26(2)

N-(4-{4-[(4-{[(dibutylamino)carbonyl]amino}-1-piperidinyl)methyl]phenoxy}phenyl)methanesulfonamide hydrochloride TLC:Rf 0.55(chloroform:methanol=5:1);
NMR (CD$_3$OD): δ 0.93 (t, J=7.5 Hz, 6H), 1.31 (m, 4H), 1.49 (m, 4H), 1.70-1.88 (m, 2H), 2.04-2.14 (m, 2H), 2.95 (s, 3H), 3.08 (m, 2H), 3.14-3.35 (m, 4H), 3.50 (m, 2H), 3.79 (m, 1H), 4.27 (s, 2H), 7.00-7.10 (m, 4H), 7.22-7.34 (m, 2H), 7.49 (brd, J=8.7 Hz, 2H).

Example 26(3)

N-butyl-N-[1-(4-{4-[(methylsulfonyl)amino]phenoxy}benzyl)-4-piperidinyl]-1-pyrrolidinecarboxamide hydrochloride TLC:Rf 0.63(chloroform:methanol=5:1);
NMR (CD$_3$OD): δ 0.92 (t, J=7.5 Hz, 3H), 1.22-1.36 (m, 2H), 1.38-1.52 (m, 2H), 1.80-2.02 (m, 6H), 2.04-2.24 (m, 2H), 2.95 (s, 3H), 3.02-3.15 (m, 4H), 3.26-3.38 (m, 4H), 3.52 (m, 2H), 3.72 (m, 1H), 4.26 (s, 2H), 7.00-7.10 (m, 4H), 7.22-7.36 (m, 2H), 7.42-7.56 (m, 2H).

Example 26(4)

N-(4-{4-[(4-{butyl[(dibutylamino)carbonyl]amino}-1-piperidinyl)methyl]phenoxy}phenyl)methanesulfonamide hydrochloride TLC:Rf 0.59(chloroform:methanol=5:1);
NMR (CD$_3$OD): δ 0.80-1.02 (m, 9H), 1.20-1.60 (m, 12H), 1.92-2.20 (m, 4H), 2.95 (s, 3H), 3.00-3.40 (m, 7H), 3.44-3.68 (m, 4H), 4.26 (s 2H), 7.00-7.12 (m, 4H), 7.29 (brd, J=9.0 Hz, 2H), 7.48 (brd, J=8.4 Hz, 2H).

Example 27

N-[4-(4-{[4-({[(benzyloxy)amino]carbonyl}amino)-1-piperidinyl]methyl}phenoxy)phenyl]methanesulfonamide hydrochloride

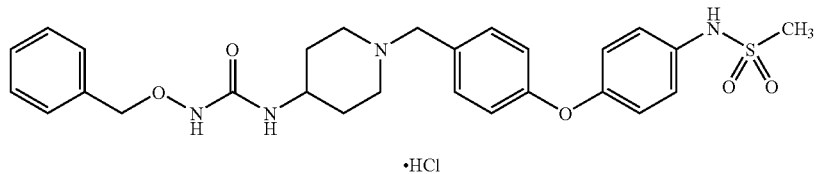

Under cooling with ice and stirring, 1,1'-carbonylbis-1H-imidazole (CDI) (129 mg) in tetrahydrofuran (6.5 mL) was added dropwise to a solution of O-benzylhydroxylamine (100 mg) in tetrahydrofuran (2.5 mL). After stirring for 30 minutes, N-(4-{4-[(4-aminopiperidin-1-yl)methyl]phenoxy}phenyl)methanesulfonamide (200 mg) prepared by a method based on Example 1 was added thereto, and the solution was stirred at 55° C. for 24 hours. Distilled water was added to the reaction mixture, which was extracted with ethyl acetate. The organic layer was dried over anhydrous sodium sulfate and concentrated. The obtained residue was purified by column chromatography on silica gel (ethyl acetate:methanol=10:1), and converted to hydrochloride salt by a conventional method to give the compound of the present invention (144.3 mg) having the following physical data.
TLC:Rf 0.42(ethyl acetate:methanol=5:1);
NMR (CD$_3$OD): δ 1.63-1.79 (m, 2H), 1.96-2.07 (m, 2H), 2.96 (s, 3H), 3.00-3.12 (m, 2H), 3.44-3.54 (m, 2H), 3.74 (m, 1H), 4.26 (s, 2H), 4.76 (s, 2H), 7.04 (d, J=8.7 Hz, 2H), 7.06 (d, J=8.7 Hz, 2H), 7.29 (d, J=8.7 Hz, 2H), 7.33-7.43 (m, 5H), 7.48 (d, J=8.7 Hz, 2H)

Example 28

4-(4-{[4-(butyl{[(2,4-difluorophenyl)amino]carbonyl}amino)piperidin-1-yl]methyl}phenoxy)benzoic acid hydrochloride

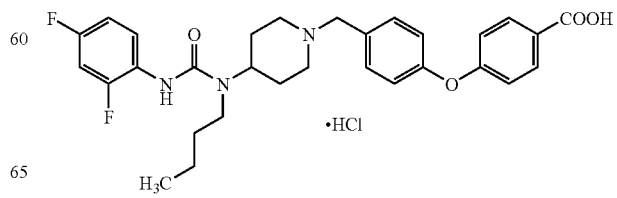

N-t-butoxycarbonylpiperidin-4-one and n-butylamine were subjected to reductive alkylation in acetic acid and dimethylformamide at room temperature using sodium triacetoxyborohydride. The obtained 1-t-butoxycarbonyl-4-aminopiperidine was reacted with 2,4-difluorobenzenisocyanate in dimethylformamide in the presence of triethylamine. The reaction mixture was deprotected by treatment with Hydrochloric acid to give N-butyl-N'-(2,4-difluorophenyl)-N-piperidin-4-ylurea hydrochloride. By the same procedure as described in Example 1 and the conversion to hydrochloride salt by a conventional method, using N-butyl-N'-(2,4-difluorophenyl)-N-piperidin-4-ylurea and 4-(4-formylphenoxy) benzoic acid, the compound of the present invention (48 mg) having the following physical data was obtained.

TLC:Rf 0.78(methylene chloride:methanol=5:1);
NMR (CD$_3$OD): δ 0.98 (t, J=7.2 Hz, 3H), 1.36-1.43 (m, 2H), 1.60-1.70 (m, 2H), 1.99-2.04 (m, 2H), 2.16-2.28 (m, 2H), 3.08-3.17 (m, 2H), 3.24-3.30 (m, 2H), 3.56-3.61 (m, 2H), 4.15 (m, 1H), 4.32 (s, 2H), 6.90-7.05 (m, 2H), 7.07 (d, J=8.7 Hz, 2H), 7.18 (d, J=8.7 Hz, 2H), 7.37 (m, 1H), 7.56 (d, J=8.7 Hz, 2H), 8.04 (d, J=8.7 Hz, 2H).

Example 28(1)-Example 28(18)

By the same procedure as described in Example 28, using N-butyl-N'-(2,4-difluorophenyl)-N-piperidin-4-ylurea or a corresponding piperidine derivative, and using a corresponding aldehyde derivative instead of 4-(4-formylphenoxy)benzoic acid, the following compounds of the present invention data were obtained.

Example 28(1)

4-(4-{[4-(butyl{[(2,4-difluorophenyl)amino]carbonyl}amino)piperidin-1-yl]methyl}phenoxy)benzenesulfonamide hydrochloride TLC:Rf 0.89(methylene chloride:methanol=5:1);
NMR (CD$_3$OD): δ 0.98 (t, J=7.2 Hz, 3H), 1.36-1.45 (m, 2H), 1.59-1.70 (m, 2H), 1.99-2.03 (m, 2H), 2.17-2.30 (m, 2H), 3.08-3.17 (m, 2H), 3.23-3.30 (m, 2H), 3.56-3.60 (m, 2H), 4.15 (m, 1H), 4.32 (s, 2H), 6.90-7.03 (m, 2H), 7.14 (d, J=8.7 Hz, 2H), 7.18 (d, J=8.7 Hz, 2H), 7.37 (m, 1H), 7.57 (d, J=8.7 Hz, 2H), 7.91 (d, J=8.7 Hz, 2H).

Example 28(2)

N-butyl-N'-(2,4-difluorophenyl)-N-[1-({3,5-dimethyl-1-[1-(methylsulfonyl)piperidin-4-yl]-1H-pyrazol-4-yl}methyl)piperidin-4-yl]urea dihydrochloride TLC:Rf 0.12(ethyl acetate:methanol=10:1);
NMR (CD$_3$OD): δ 0.98 (t, J=7.5 Hz, 3H), 1.33-1.45 (m, 2H), 1.59-1.70 (m, 2H), 1.98-2.01 (m, 4H), 2.12-2.30 (m, 4H), 2.33 (s, 3H), 2.43 (s, 3H), 2.89 (s, 3H), 2.93-3.01 (m, 2H), 3.09-3.17 (m, 2H), 3.25-3.30 (m, 2H), 3.58-3.63 (m, 2H), 3.86-3.90 (m, 2H), 4.19 (s, 2H), 4.19 (m, 1H), 4.39 (m, 1H), 6.89-7.03 (m, 2H), 7.37 (m, 1H).

Example 28(3)

N-(3'-{[4-(butyl{[(2,4-difluorophenyl)amino]carbonyl}amino)piperidin-1-yl]methyl}-1,1'-biphenyl-4-yl)methanesulfonamide hydrochloride TLC:Rf 0.78(ethyl acetate:methanol=10:1);
NMR (CD$_3$OD): δ 0.97 (t, J=7.5 Hz, 3H), 1.34-1.44 (m, 2H), 1.58-1.68 (m, 2H), 1.98-2.01 (m, 2H), 2.19-2.32 (m, 2H), 2.99 (s, 3H), 3.12-3.30 (m, 4H), 3.58-3.63 (m, 2H), 4.19 (m, 1H), 4.39 (s, 2H), 6.89-7.02 (m, 2H), 7.36 (d, J=8.4 Hz, 2H), 7.37 (m, 1H), 7.49 (d, J=7.5 Hz, 1H), 7.57 (t, J=7.5 Hz, 1H), 7.68 (d, J=8.4 Hz, 2H), 7.76 (d, J=7.5 Hz, 1H), 7.82 (s, 1H).

Example 28(4)

N-[4-(4-{[4-(butyl{[(2,4-difluorophenyl)amino]carbonyl}amino)piperidin-1-yl]methyl}-3,5-dimethyl-1H-pyrazol-1-yl)phenyl]methanesulfonamide dihydrochloride TLC:Rf 0.29(ethyl acetate:methanol=10:1);
NMR (CD$_3$OD): δ 0.98 (t, J=7.5 Hz, 3H), 1.36-1.44 (m, 2H), 1.60-1.70 (m, 2H), 1.98-2.00 (m, 2H), 2.20-2.35 (m, 2H), 2.35 (s, 3H), 2.35 (s, 3H), 3.03 (s, 3H), 3.03-3.13 (m, 2H), 3.27-3.30 (m, 2H), 3.58-3.62 (m, 2H), 4.17 (m, 1H), 4.17 (s, 2H), 6.90-7.03 (m, 2H), 7.35-7.45 (m, 5H).

Example 28(5)

4-{[4-(butyl{[(2,4-difluorophenyl)amino]carbonyl}amino)piperidin-1-yl]methyl}-N-{4-[(methylsulfonyl)amino]benzyl}benzamide hydrochloride TLC:Rf 0.36(methylene chloride:methanol=10:1);
NMR (CD$_3$OD): δ 0.96 (t, J=7.5 Hz, 3H), 1.28-1.40 (m, 2H), 1.69-1.89 (m, 4H), 2.11-2.18 (m, 2H), 2.92 (s, 3H), 2.96-3.00 (m, 2H), 3.22-3.37 (m, 4H), 3.59 (s, 2H), 4.02 (m, 1H), 4.53 (s, 2H), 6.87-7.01 (m, 2H), 7.21 (d, J=8.7 Hz, 2H), 7.33 (d, J=8.7 Hz, 2H), 7.38 (m, 1H), 7.44 (d, J=8.4 Hz, 2H), 7.82 (d, J=8.4 Hz, 2H).

Example 28(6)

N-(4-{[4-(butyl{[(2,4-difluorophenyl)amino]carbonyl}amino)piperidin-1-yl]methyl}phenyl)-2-{4-[(methylsulfonyl)amino]phenyl}acetamide hydrochloride TLC:Rf 0.26(methylene chloride:methanol=10:1);
NMR (CD$_3$OD): δ 0.97 (t, J=7.5 Hz, 3H), 1.28-1.41 (m, 2H), 1.58-1.69 (m, 2H), 1.96-2.01 (m, 2H), 2.11-2.26 (m, 2H), 2.93 (s, 3H), 3.05-3.26 (m, 2H), 3.23-3.26 (m, 2H), 3.53-3.56 (m, 2H), 3.67 (s, 2H), 4.13 (m, 1H), 4.26 (s, 2H), 6.89-7.02 (m, 2H), 7.21 (d, J=8.7 Hz, 2H), 7.32 (d, J=8.7 Hz, 2H), 7.38 (m, 1H), 7.46 (d, J=8.4 Hz, 2H), 7.70 (d, J=8.4 Hz, 2H).

Example 28(7)

N-{4-[(4-{[4-(butyl{[(2,4-difluorophenyl)amino]carbonyl}amino)piperidin-1-yl]methyl}benzyl)oxy]phenyl}methanesulfonamide hydrochloride TLC:Rf 0.40(methylene chloride:methanol=10:1);
NMR (CD$_3$OD): δ 0.97 (t, J=7.5 Hz, 3H), 1.34-1.42 (m, 2H), 1.55-1.60 (m, 2H), 1.94-2.00 (m, 2H), 2.12-2.20 (m, 2H), 2.99 (s, 3H), 3.03-3.12 (m, 2H), 3.23-3.25 (m, 2H), 3.47-3.51 (m, 2H), 4.13 (m, 1H), 4.25 (s, 2H), 4.85 (s, 2H), 6.68 (d, J=8.7 Hz, 2H), 6.89-7.03 (m, 2H), 7.13 (d, J=8.7 Hz, 2H), 7.36 (m, 1H), 7.42 (s, 4H).

Example 28(8)

4-(4-{[4-(butyl{[(2,4-difluorophenyl)amino]carbonyl}amino)piperidin-1-yl]methyl}-3,5-dimethyl-1H-pyrazol-1-yl)-N-methylbenzenesulfonamide dihydrochloride TLC:Rf 0.38(methylene chloride:methanol=10:1);
NMR (CD$_3$OD): δ 0.98 (t, J=7.5 Hz, 3H), 1.36-1.44 (m, 2H), 1.63-1.68 (m, 2H), 1.97-2.04 (m, 2H), 2.29-2.34 (m, 2H), 2.39 (s, 3H), 2.46 (s, 3H), 2.58 (s, 3H), 3.16-3.36 (m, 4H), 3.66-3.70 (m, 2H), 4.23 (m, 1H), 4.27 (s, 2H), 6.89-7.03 (m, 2H), 7.38 (m, 1H), 7.73 (d, J=8.7 Hz, 2H), 8.00 (d, J=8.7 Hz, 2H).

Example 28(9)

N-[4-(4-{[4-(butyl{[(2,4-difluorophenyl)amino]carbonyl}amino)piperidin-1-yl]methyl}phenoxy)benzyl]methanesulfonamide hydrochloride TLC:Rf 0.30(ethyl acetate);
NMR (CD$_3$OD): δ 0.98 (t, J=7.5 Hz, 3H), 1.33-1.45 (m, 2H), 1.59-1.69 (m, 2H), 1.98-2.02 (m, 2H), 2.15-2.28 (m, 2H), 2.88 (s, 3H), 3.06-3.15 (m, 2H), 3.24-3.30 (m, 2H), 3.54-3.59 (m, 2H), 4.14 (m, 1H), 4.24 (s, 2H), 4.28 (s, 2H), 6.89-7.03 (m, 2H), 7.03 (d, J=8.7 Hz, 2H), 7.06 (d, J=8.7 Hz, 2H), 7.37 (m, 1H), 7.41 (d, J=8.7 Hz, 2H), 7.49 (d, J=8.7 Hz, 2H).

Example 28(10)

N-{4-[(4-{[4-(butyl{[(2,4-difluorophenyl)amino]carbonyl}amino)piperidin-1-yl]methyl}phenoxy)methyl]phenyl}methane sulfonamide hydrochloride TLC:Rf 0.27(ethyl acetate);
NMR (CD$_3$OD): δ 0.97 (t, J=7.5 Hz, 3H), 1.34-1.42 (m, 2H), 1.60-1.66 (m, 2H), 1.96-2.01 (m, 2H), 2.12-2.20 (m, 2H), 2.95 (s, 3H), 3.04-3.11 (m, 2H), 3.23-3.30 (m, 2H), 3.52-3.56 (m, 2H), 4.12 (m, 1H), 4.24 (s, 2H), 5.10 (s, 2H), 6.86-7.03 (m, 2H), 7.10 (d, J=8.7 Hz, 2H), 7.25 (d, J=8.7 Hz, 2H), 7.36 (m, 1H), 7.41 (d, J=8.7 Hz, 2H), 7.42 (d, J=8.7 Hz, 2H).

Example 28(11)

N-[4-(4-{[4-(butyl{[(2,4-difluorophenyl)amino]carbonyl}amino)piperidin-1-yl]methyl}phenoxy)phenyl]acetamide hydrochloride TLC:Rf 0.28(ethyl acetate);
NMR (CD$_3$OD): δ 0.98 (t, J=7.5 Hz, 3H), 1.35-1.45 (m, 2H), 1.58-1.69 (m, 2H), 1.98-2.02 (m, 2H), 2.12 (s, 3H), 2.15-2.27 (m, 2H), 3.06-3.14 (m, 2H), 3.24-3.30 (m, 2H), 3.54-3.58 (m, 2H), 4.14 (m, 1H), 4.28 (s, 2H), 6.89-7.03 (m, 2H), 7.00 (d, J=8.7 Hz, 2H), 7.04 (d, J=8.7 Hz, 2H), 7.36 (m, 1H), 7.47 (d, J=8.7 Hz, 2H), 7.57 (d, J=8.7 Hz, 2H).

Example 28(12)

N-[4-(4-{[4-({butyl[(cyclohexylamino)carbonyl]amino}methyl)piperidin-1-yl]methyl}phenoxy)phenyl]methanesulfonamide hydrochloride TLC:Rf 0.47(chloroform:methanol=5:1);
NMR (CD$_3$OD): δ 0.94 (t, J=7.5 Hz, 3H), 2.00-1.06 (m, 19H), 2.95 (s, 3H), 3.02-2.88 m, 2H), 3.30-3.16 (m, 4H), 3.56-3.44 (m, 3H), 4.25 (s, 2H), 7.10-7.00 (m, 4H), 7.29 (brd, J=9.0 Hz, 2H), 7.48 (brd, J=8.4 Hz, 2H).

Example 28(13)

4-[4-({4-[(N-acetylleucyl)(butyl)amino]piperidin-1-yl}methyl)phenoxy]benzoic acid hydrochloride TLC:Rf 0.24(ethyl acetate:methanol=10:1);
NMR (CD$_3$OD): δ8.04 (d, J=9.0 Hz, 2H), 7.58 (d, J=9.0 Hz, 2H), 7.17 (d, J=9.0 Hz, 2H), 7.07 (d, J=9.0 Hz, 2H), 4.75 (m, 1H), 4.40-4.10 (m, 3H), 3.70-3.05 (m, 6H), 2.40-1.30 (m, 14H), 1.01-0.93 (m, 9H).

Example 28(14)

4-[4-({4-[(N-acetyl-3-cyclohexylalanyl)(butyl)amino]piperidin-1-yl}methyl)phenoxy]benzoic acid hydrochloride TLC:Rf 0.27(ethyl acetate:methanol=10:1);
NMR (CD$_3$OD): δ 8.04 (d, J=9.0 Hz, 2H), 7.58 (d, J=8.7 Hz, 2H), 7.17 (d, J=8.7 Hz, 2H), 7.07 (d, J=9.0 Hz, 2H), 4.75 (m, 1H), 4.40-4.10 (m, 3H), 3.70-3.00 (m, 6H), 2.40-0.80 (m, 27H).

Example 28(15)

N-[4-(4-{[4-(butyl{[(2,4-difluorophenyl)amino]carbonyl}amino)piperidin-1-yl]methyl}benzyl)phenyl]methanesulfonamide hydrochloride TLC:Rf 0.68(methylene chloride:methanol=10:1);
NMR (CD$_3$OD): δ 0.97 (t, J=7.2 Hz, 3H), 1.34-1.41 (m, 2H), 1.58-1.69 (m, 2H), 1.96-2.00 (m, 2H), 2.12-2.23 (m, 2H), 2.91 (s, 3H), 3.05-3.13 (m, 2H), 3.23-3.30 (m, 2H), 3.53-3.56 (m, 2H), 3.99 (s, 2H), 4.10 (m, 1H), 4.27 (s, 2H), 6.89-7.03 (m, 2H), 7.16 (d, J=8.7 Hz, 2H), 7.20 (d, J=8.7 Hz, 2H), 7.35 (m, 1H), 7.35 (d, J=8.0 Hz, 2H), 7.42 (d, J=8.0 Hz, 2H).

Example 28(16)

N-[4-(4-{[4-(butyl{[(2,4-difluorophenyl)amino]carbonyl}amino)piperidin-1-yl]methyl}phenoxy)-3-chlorophenyl]methanesulfonamide hydrochloride TLC:Rf 0.63(methylene chloride:methanol=10:1);
NMR (CD$_3$OD): δ 0.97 (t, J=7.2 Hz, 3H), 1.32-1.45 (m, 2H), 1.59-1.69 (m, 2H), 1.98-2.01 (m, 2H), 2.13-2.26 (m, 2H), 3.01 (s, 3H), 3.06-3.14 (m, 2H), 3.24-3.30 (m, 2H), 3.54-3.58 (m, 2H), 4.13 (m, 1H), 4.28 (s, 2H), 6.90-7.05 (m, 2H), 7.00 (d, J=8.7 Hz, 2H), 7.13 (d, J=8.7 Hz, 1H), 7.24 (dd, J=8.7, 2.7 Hz, 1H), 7.36 (dt, J=8.7, 6.0 Hz, 1H), 7.43 (d, J=2.7 Hz, 1H), 7.48 (d, J=8.7 Hz, 2H).

Example 28(17)

N-butyl-N'-(2,4-difluorophenyl)-N-[1-({3,5-dimethyl-1-[4-(trifluoromethyl)phenyl]-1H-pyrazol-4-yl}methyl)piperidin-4-yl]urea dihydrochloride TLC:Rf 0.74(methylene chloride:methanol=10:1);
NMR (CD$_3$OD): δ 0.99 (t, J=7.5 Hz, 3H), 1.36-1.44 (m, 2H), 1.61-1.71 (m, 2H), 2.00-2.05 (m, 2H), 2.23-2.37 (m, 2H), 2.39 (s, 3H), 2.44 (s, 3H), 3.16-3.24 (m, 2H), 3.27-3.32 (m, 2H), 3.66-3.70 (m, 2H), 4.20 (m, 1H), 4.27 (s, 2H), 6.89-7.03 (m, 2H), 7.38 (dt, J=9.0, 6.0 Hz, 1H), 7.72 (d, J=8.4 Hz, 2H), 7.87 (d, J=8.4 Hz, 2H).

Example 28(18)

N-{4-[(5-{[4-(butyl{[(2,4-difluorophenyl)amino] carbonyl}amino)piperidin-1-yl]methyl}pyridin-2-yl) oxy]phenyl}methanesulfonamide dihydrochloride TLC:Rf 0.31(chloroform:methanol=10:1);
NMR (CD₃OD): δ 0.97 (t, J=7.4 Hz, 3H), 1.30-1.50 (m, 2H), 1.60-1.70 (m, 2H), 1.90-2.10 (m, 2H), 2.20-2.40 (m, 2H), 2.98 (s, 3H), 3.00-3.20 (m, 2H), 3.20-3.40 (m, 2H), 3.50-3.60 (m, 2H), 4.20 (m, 1H), 4.35 (s, 2H), 6.86-7.05 (m, 2H), 7.10-7.17 (m, 3H), 7.32-7.38 (m, 3H), 8.09 (dd, J=8.7, 2.2 Hz, 1H), 8.32 (d, J=2.2 Hz, 1H).

Example 29(1)-Example 29(131)

By the same procedure as described in Example 23 and if necessary, the hydrolysis, deprotection or oxidation by a conventional method, using the compound prepared in Example 3 or a corresponding amine derivative, and using a corresponding carboxylic acid derivative instead of 1-methylcyclohexylcarboxylic acid, the following compounds of the present invention were obtained.

Example 29(1)

N-(4-{4-[(4-{butyl[(pyrimidin-5-ylamino)carbonyl] amino}piperidin-1-yl)methyl]phenoxy}phenyl)methanesulfonamide dihydrochloride

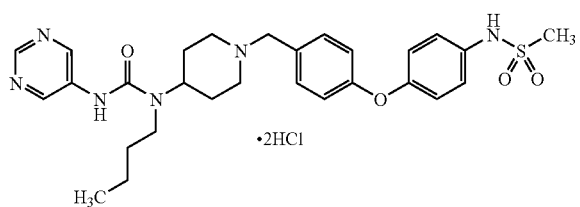

TLC:Rf 0.44(methylene chloride:methanol=9:1);
NMR (CD₃OD): δ 0.98 (t, J=7.2 Hz, 3H), 1.32-1.48 (m, 2H), 1.55-1.70 (m, 2H), 1.97-2.08 (m, 2H), 2.23-2.40 (m, 2H), 2.95 (s, 3H), 3.10-3.23 (m, 2H), 3.29-3.38 (m, 2H), 3.50-3.62 (m, 2H), 4.25 (m, 1H), 4.31 (s, 2H), 7.03 (d, J=8.7 Hz, 2H), 7.06 (d, J=8.7 Hz, 2H), 7.29 (d, J=8.7 Hz, 2H), 7.53 (d, J=8.7 Hz, 2H), 9.03 (s, 1H), 9.27 (s, 2H).

Example 29(2)

N-(4-{4-[(4-{butyl[(pyridazin-4-ylamino)carbonyl] amino}piperidin-1-yl)methyl]phenoxy}phenyl)methanesulfonamide dihydrochloride TLC:Rf 0.45(methylene chloride:methanol=9:1);
NMR (CD₃OD): δ 0.97 (t, J=7.5 Hz, 3H), 1.32-1.47 (m, 2H), 1.55-1.69 (m, 2H), 2.00-2.10 (m, 2H), 2.27-2.45 (m, 2H), 2.95 (s, 3H), 3.12-3.27 (m, 2H), 3.33-3.45 (m, 2H), 3.50-3.62 (m, 2H), 4.24-4.35 (m, 3H), 7.03 (d, J=8.7 Hz, 2H), 7.06 (d, J=8.7 Hz, 2H), 7.29 (d, J=8.7 Hz, 2H), 7.53 (d, J=8.7 Hz, 2H), 8.49 (dd, J=7.2, 2.7 Hz, 1H), 9.13 (d, J=7.2 Hz, 1H), 9.49 (d, J=2.7 Hz, 1H).

Example 29(3)

N-{4-[4-({4-[{[(6-azidopyridin-3-yl)amino]carbonyl}(butyl)amino]piperidin-1-yl}methyl)phenoxy] phenyl}methanesulfonamide hydrochloride TLC:Rf 0.47(methylene chloride:methanol=9:1);
NMR (CD₃OD): δ 0.98 (t, J=7.2 Hz, 3H), 1.30-1.45 (m, 2H), 1.55-1.70 (m, 2H), 1.97-2.08 (m, 2H), 2.24-2.41 (m, 2H), 2.95 (s, 3H), 3.05-3.20 (m, 2H), 3.25-3.38 (m, 2H), 3.55-3.65 (m, 2H), 4.19 (m, 1H), 4.31 (s, 2H), 7.03 (d, J=8.7 Hz, 2H), 7.07 (d, J=8.7 Hz, 2H), 7.29 (d, J=8.7 Hz, 2H), 7.51 (d, J=8.7 Hz, 2H), 7.88 (dd, J=9.6, 1.5 Hz, 1H), 7.99 (dd, J=9.6, 1.5 Hz, 1H), 9.42 (d, J=1.5 Hz, 1H).

Example 29(4)

N-{4-[4-({4-[butyl({[3-(trifluoromethoxy)phenyl] amino}carbonyl)amino]piperidin-1-yl}methyl)phenoxy]phenyl}methanesulfonamide hydrochloride TLC:Rf 0.49(chloroform:methanol=10:1);
NMR (CD₃OD): δ 0.97 (t, J=7.4 Hz, 3H), 1.30-1.50 (m, 2H), 1.50-1.70 (m, 2H), 2.00-2.10 (m, 2H), 2.20-2.30 (m, 2H), 2.95 (s, 3H), 3.10-3.20 (m, 2H), 3.20-3.40 (m, 2H), 3.50-3.60 (m, 2H), 4.17 (m, 1H), 4.29 (s, 2H), 6.93 (m, 1H), 7.02-7.08 (m, 4H), 7.27-7.34 (m, 4H), 7.45 (m, 1H), 7.50 (d, J=8.7 Hz, 2H).

Example 29(5)

N-{4-[4-({4-[{[(4-acetylphenyl)amino]carbonyl}(butyl)amino]piperidin-1-yl}methyl)phenoxy] phenyl}methanesulfonamide hydrochloride TLC:Rf 0.42(chloroform:methanol=10:1);
NMR (CD₃OD): δ 0.96 (t, J=7.2 Hz, 3H), 1.30-1.50 (m, 2H), 1.50-1.70 (m, 2H), 2.00-2.10 (m, 2H), 2.20-2.40 (m, 2H), 2.55 (s, 3H), 2.95 (s, 3H), 3.00-3.20 (m, 2H), 3.20-3.40 (m, 2H), 3.50-3.60 (m, 2H), 4.10 (m, 1H), 4.30 (s, 2H), 7.03 (d, J=8.9 Hz, 2H), 7.07 (d, J=8.9 Hz, 2H), 7.29 (d, J=8.9 Hz, 2H), 7.50 (d, J=8.1 Hz, 2H), 7.53 (d, J=8.1 Hz, 2H), 7.92 (d, J=8.9 Hz, 2H).

Example 29(6)

N-{4-[4-({4-[butyl({[2-(trifluoromethoxy)phenyl] amino}carbonyl)amino]piperidin-1-yl}methyl)phenoxy]phenyl}methanesulfonamide hydrochloride TLC:Rf 0.51(chloroform:methanol=10:1);
NMR (CD₃OD): δ 0.98 (t, J=7.2 Hz, 3H), 1.35-1.50 (m, 2H), 1.60-1.80 (m, 2H), 1.90-2.10 (m, 2H), 2.20-2.40 (m, 2H), 2.95 (s, 3H), 3.00-3.20 (m, 2H), 3.20-3.40 (m, 2H), 3.40-3.60 (m, 2H), 4.16 (m, 1H), 4.29 (s, 2H), 7.02-7.08 (m, 4H), 7.19-7.34 (m, 5H), 7.48-7.51 (m, 2H), 7.60 (m, 1H).

Example 29(7)

N-{4-[4-({4-[[(benzoylamino)carbonyl](butyl) amino]piperidin-1-yl}methyl)phenoxy] phenyl}methanesulfonamide hydrochloride TLC:Rf 0.60(chloroform:methanol=10:1);
NMR (CD₃OD): δ 0.92 (t, J=7.4 Hz, 3H), 1.30-1.40 (m, 2H), 1.60-1.70 (m, 2H), 2.00-2.10 (m, 2H), 2.30-2.40 (m, 2H), 2.95 (s, 3H), 3.05-3.20 (m, 2H), 3.30-3.40 (m, 2H), 3.50-3.60 (m, 2H), 4.10 (m, 1H), 4.27 (s, 2H), 7.02-7.06 (m, 4H), 7.29 (d, J=9.0 Hz, 2H), 7.48-7.53 (m, 4H), 7.61 (m, 1H), 7.87 (d, J=7.2 Hz, 2H).

Example 29(8)

N-[4-(4-{[4-(butyl{[(2,6-difluorophenyl)amino]carbonyl}amino)piperidin-1-yl]methyl}phenoxy)phenyl]methanesulfonamide hydrochloride TLC:Rf 0.56(chloroform:methanol=10:1);
NMR (CD$_3$OD): δ 0.98 (t, J=7.4 Hz, 3H), 1.30-1.50 (m, 2H), 1.50-1.70 (m, 2H), 1.90-2.10 (m, 2H), 2.10-2.30 (m, 2H), 2.95 (s, 3H), 3.00-3.20 (m, 2H), 3.20-3.30 (m, 2H), 3.50-3.60 (m, 2H), 4.15 (m, 1H), 4.28 (s, 2H), 6.97-7.08 (m, 6H), 7.28-7.31 (m, 3H), 7.49-7.52 (m, 2H).

Example 29(9)

N-{4-[4-({4-[butyl({[4-(trifluoromethoxy)phenyl]amino}carbonyl)amino]piperidin-1-yl}methyl)phenoxy]phenyl}methanesulfonamide hydrochloride TLC:Rf 0.47(chloroform:methanol=10:1);
NMR (CD$_3$OD): δ 0.97 (t, J=7.4 Hz, 3H), 1.30-1.50 (m, 2H), 1.50-1.70 (m, 2H), 1.90-2.10 (m, 2H), 2.20-2.40 (m, 2H), 2.95 (s, 3H), 3.05-3.20 (m, 2H), 3.20-3.40 (m, 2H), 3.50-3.60 (m, 2H), 4.20 (m, 1H), 4.29 (s, 2H), 7.01-7.08 (m, 4H), 7.18 (d, J=9.0 Hz, 2H), 7.29 (d, J=9.3 Hz, 2H), 7.43 (d, J=9.3 Hz, 2H), 7.51 (d, J=9.0 Hz, 2H).

Example 29(10)

N-(4-{4-[(4-{butyl[(quinolin-3-ylamino)carbonyl]amino}piperidin-1-yl)methyl]phenoxy}phenyl)methanesulfonamide dihydrochloride TLC:Rf 0.40(chloroform:methanol=10:1);
NMR (CD$_3$OD): δ 0.99 (t, J=7.4 Hz, 3H), 1.40-1.50 (m, 2H), 1.60-1.70 (m, 2H), 2.00-2.10 (m, 2H), 2.30-2.40 (m, 2H), 2.95 (s, 3H), 3.20-3.30 (m, 2H), 3.20-3.40 (m, 2H), 3.55-3.65 (m, 2H), 4.30 (m, 1H), 4.32 (s, 2H), 7.02-7.09 (m, 4H), 7.30 (d, J=8.9 Hz, 2H), 7.54 (d, J=8.9 Hz, 2H), 7.91 (td, J=7.2, 1.2 Hz, 1H), 8.02 (td, J=7.2, 1.2 Hz, 1H), 8.14 (d, J=8.4 Hz, 1H), 8.20 (d, J=8.4 Hz, 1H), 9.05 (d, J=2.4 Hz, 1H), 9.53 (d, J=2.4 Hz, 1H).

Example 29(11)

N-(4-{4-[(4-{butyl[(cyclopent-3-en-1-ylamino)carbonyl]amino}piperidin-1-yl)methyl]phenoxy}phenyl)methanesulfonamide hydrochloride TLC:Rf 0.72(chloroform:methanol=5:1);
NMR (CD$_3$OD): δ 0.93 (t, J=7.2 Hz, 3H), 1.20-1.40 (m, 2H), 1.40-1.60 (m, 2H), 1.80-2.00 (m, 2H), 2.00-2.20 (m, 2H), 2.24 (dd, J=14.6, 5.6 Hz, 2H) 2.69 (dd, J=14.6, 8.0 Hz, 2H) 2.95 (s, 3H), 3.00-3.20 (m, 4H), 3.50-3.60 (m, 2H), 4.15 (m, 1H), 4.28 (s, 2H), 4.39 (m, 1H), 5.69 (s, 2H), 7.02-7.07 (m, 4H), 7.29 (d, J=8.9 Hz, 2H), 7.51 (d, J=8.9 Hz, 2H).

Example 29(12)

N-[4-(4-{[4-(butyl{[(4-chloro-3-hydroxyphenyl)amino]carbonyl}amino)piperidin-1-yl]methyl}phenoxy)phenyl]methanesulfonamide hydrochloride TLC:Rf 0.41(chloroform:methanol=10:1);
NMR (CD$_3$OD): δ 0.96 (t, J=7.4 Hz, 3H), 1.30-1.50 (m, 2H), 1.50-1.70 (m, 2H), 1.90-2.00 (m, 2H), 2.10-2.30 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 6.77 (dd, J=8.9, 2.4 Hz, 1H), 7.02-7.08 (m, 5H), 7.15 (d, J=9.0 Hz, 1H), 7.29-7.31 (m, 2H), 7.47-7.51 (m, 2H).

Example 29(13)

N-[4-(4-{[4-(butyl{[(4-fluoro-3-hydroxyphenyl)amino]carbonyl}amino)piperidin-1-yl]methyl}phenoxy)phenyl]methanesulfonamide hydrochloride TLC:Rf 0.40(chloroform:methanol=10:1);
NMR (CD$_3$OD): δ 0.97 (t, J=7.4 Hz, 3H), 1.30-1.50 (m, 2H), 1.50-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 6.70 (m, 1H), 6.90-7.00 (m, 2H), 7.02-7.08 (m, 4H), 7.29 (d, J=8.9 Hz, 2H), 7.49 (d, J=8.9 Hz, 2H).

Example 29(14)

N-(4-{4-[(4-{butyl[(quinolin-6-ylamino)carbonyl]amino}piperidin-1-yl)methyl]phenoxy}phenyl)methanesulfonamide dihydrochloride TLC:Rf 0.44(chloroform:methanol=10:1);
NMR (CD$_3$OD): δ 0.98 (t, J=7.2 Hz, 3H), 1.30-1.50 (m, 2H), 1.60-1.80 (m, 2H), 2.00-2.10 (m, 2H), 2.20-2.40 (m, 2H), 2.95 (s, 3H), 3.10-3.30 (m, 2H), 3.30-3.50 (m, 2H), 3.50-3.70 (m, 2H), 4.30 (m, 1H), 4.32 (s, 2H), 7.02-7.09 (m, 4H), 7.30 (d, J=8.9 Hz, 2H), 7.53 (d, J=8.9 Hz, 2H), 8.01 (dd, J=8.6, 5.6 Hz, 1H), 8.15 (d, J=9.3 Hz, 1H), 8.31 (dd, J=9.3, 2.4 Hz, 1H), 8.42 (m, 1H), 9.01-9.05 (m, 2H).

Example 29(15)

N-{4-[4-({4-[butyl({[2-(trifluoromethyl)phenyl]amino}carbonyl)amino]piperidin-1-yl}methyl)phenoxy]phenyl}methanesulfonamide TLC:Rf 0.69(chloroform:methanol=10:1);
NMR (CD$_3$OD): δ 0.97 (t, J=7.4 Hz, 3H), 1.30-1.50 (m, 2H), 1.60-1.90 (m, 4H), 2.00-2.20 (m, 2H), 2.93 (s, 3H), 2.95-3.05 (m, 2H), 3.20-3.40 (m, 4H), 3.51 (s, 2H), 4.05 (m, 1H), 6.93-6.98 (m, 4H), 7.24 (d, J=9.0 Hz, 2H), 7.32 (d, J=9.0 Hz, 2H), 7.34 (m, 1H), 7.58-7.60 (m, 2H), 7.66 (d, J=7.8 Hz, 1H).

Example 29(16)

N-[4-(4-{[4-(butyl{[(6-oxo-1,6-dihydropyridin-3-yl)amino]carbonyl}amino)piperidin-1-yl]methyl}phenoxy)phenyl]methanesulfonamide hydrochloride TLC:Rf 0.45(methylene chloride:methanol=4:1);
NMR (CD$_3$OD): δ 0.96 (t, J=7.2 Hz, 3H), 1.30-1.45 (m, 2H), 1.50-1.65 (m, 2H), 1.92-2.05 (m, 2H), 2.18-2.35 (m, 2H), 2.95 (s, 3H), 3.08-3.35 (m, 4H), 3.50-3.60 (m, 2H), 4.21 (m, 1H), 4.30 (s, 2H), 6.68 (d, J=9.6 Hz, 1H), 7.03 (d, J=8.7 Hz, 2H), 7.06 (d, J=8.7 Hz, 2H), 7.29 (d, J=8.7 Hz, 2H), 7.53 (d, J=8.7 Hz, 2H), 7.72 (d, J=3.0 Hz, 1H), 7.79 (dd, J=9.6, 3.0 Hz, 1H).

Example 29(17)

N-[4-(4-{[4-(butyl{[(4-oxocyclohexyl)amino]carbonyl}amino)piperidin-1-yl]methyl}phenoxy)phenyl]methanesulfonamide hydrochloride TLC:Rf 0.47(methylene chloride:methanol=9:1);
NMR (CD₃OD): δ 0.94 (t, J=7.2 Hz, 3H), 1.26-1.58 (m, 7H), 1.70-1.80 (m, 2H), 1.85-2.20 (m, 7H), 2.95 (s, 3H), 3.02-3.17 (m, 4H), 3.48-3.65 (m, 3H), 4.13 (m, 1H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 29(18)

N-{4-[4-({4-[{[(4-fluorophenyl)amino]carbonyl}(3-hydroxybenzyl)amino]piperidin-1-yl}methyl)phenoxy]phenyl}methanesulfonamide hydrochloride TLC:Rf 0.80(chloroform:methanol=5:1);
NMR (CD₃OD): δ 1.88-2.24 (m, 4H), 2.95 (s, 3H), 3.08 (m, 2H), 3.48 (m, 2H), 4.24 (s, 2H), 4.34 (m, 1H), 4.58 (s, 2H), 6.60-6.84 (m, 3H), 6.90-7.10 (m, 6H), 7.16 (m, 1H), 7.22-7.38 (m, 4H), 7.38-7.52 (m, 2H).

Example 29(19)

N-[4-(4-{[4-(butyl{[(2,6-dimethylphenyl)amino]carbonyl}amino)piperidin-1-yl]methyl}phenoxy)phenyl]methanesulfonamide hydrochloride TLC:Rf 0.59(chloroform:methanol=10:1);
NMR (CD₃OD): δ 0.98 (t, J=7.2 Hz, 3H), 1.30-1.50 (m, 2H), 1.60-1.80 (m, 2H), 1.90-2.10 (m, 2H), 2.20 (s, 6H), 2.20-2.30 (m, 2H), 2.95 (s, 3H), 3.00-3.20 (m, 2H), 3.20-3.40 (m, 2H), 3.50-3.60 (m, 2H), 4.20 (m, 1H), 4.28 (s, 2H), 7.02-7.07 (m, 7H), 7.29 (d, J=8.9 Hz, 2H), 7.52 (d, J=8.9 Hz, 2H).

Example 29(20)

N-{4-[4-({4-[{[(4-fluorophenyl)amino]carbonyl}(2-methoxybutyl)amino]piperidin-1-yl}methyl)phenoxy]phenyl}methanesulfonamide hydrochloride TLC:Rf 0.34(methylene chloride:methanol=9:1);
NMR (CD₃OD): δ 1.00 (t, J=7.5 Hz, 3H), 1.57-1.70 (m, 2H), 1.93-2.30 (m, 4H), 2.95 (s, 3H), 3.02-3.20 (m, 3H), 3.35-3.45 (m, 2H), 3.50 (s, 3H), 3.50-3.60 (m, 2H), 4.10 (m, 1H), 4.28 (s, 2H), 6.97-7.10 (m, 6H), 7.21-7.33 (m, 2H), 7.29 (d, J=8.7 Hz, 2H), 7.50 (d, J=8.7 Hz, 2H).

Example 29(21)

N-{4-[4-({4-[4-ethyl-3-(4-fluorophenyl)-2-oxo-2,3-dihydro-1H-imidazol-1-yl]piperidin-1-yl}methyl)phenoxy]phenyl}methanesulfonamide hydrochloride TLC:Rf 0.33(methylene chloride:methanol=9:1);
NMR (CD₃OD): δ 1.02 (t, J=7.5 Hz, 3H), 2.15-2.25 (m, 4H), 2.28 (q, J=7.5 Hz, 2H), 2.96 (s, 3H), 3.13-3.29 (m, 2H), 3.58-3.70 (m, 2H), 4.26 (m, 1H), 4.33 (s, 2H), 6.39 (s, 1H), 7.04 (d, J=8.7 Hz, 2H), 7.09 (d, J=8.7 Hz, 2H), 7.20-7.35 (m, 6H), 7.52 (d, J=8.7 Hz, 2H).

Example 29(22)

N-[4-(4-{[4-({[(4-fluorophenyl)amino]carbonyl}{2-[(methylsulfonyl)amino]butyl}amino)piperidin-1-yl]methyl}phenoxy)phenyl]methanesulfonamide hydrochloride TLC:Rf 0.31(methylene chloride:methanol=9:1);
NMR (CD₃OD): δ 1.06 (t, J=7.5 Hz, 3H), 1.48 (m, 1H), 1.69 (m, 1H), 2.05-2.18 (m, 2H), 2.21-2.43 (m, 2H), 2.95 (s, 3H), 2.97 (s, 3H), 3.03-3.14 (m, 2H), 3.34 (d, J=7.5 Hz, 2H), 3.42-3.61 (m, 3H), 3.95 (m, 1H), 4.28 (s, 2H), 6.96-7.10 (m, 6H), 7.26-7.40 (m, 4H), 7.50 (d, J=8.7 Hz, 2H).

Example 29(23)

N-(4-{4-[(4-{{[(4-fluorophenyl)amino]carbonyl}[(2S)-2-methylbutyl]amino}piperidin-1-yl)methyl]phenoxy}phenyl)methanesulfonamide hydrochloride TLC:Rf 0.39(methylene chloride:methanol=9:1);
NMR (CD₃OD): δ 0.94 (d, J=7.5 Hz, 3H), 0.95 (t, J=7.5 Hz, 3H), 1.16 (m, 1H), 1.50 (m, 1H), 1.74 (m, 1H), 1.95-2.07 (m, 2H), 2.28-2.47 (m, 2H), 2.95 (s, 3H), 3.02-3.24 (m, 4H), 3.50-3.60 (m, 2H), 3.90 (m, 1H), 4.28 (s, 2H), 6.96-7.10 (m, 6H), 7.25-7.32 (m, 2H), 7.29 (d, J=8.7 Hz, 2H), 7.50 (d, J=8.7 Hz, 2H).

Example 29(24)

N-[4-(4-{[4-((2-ethylbutyl){[(4-fluorophenyl)amino]carbonyl}amino)piperidin-1-yl]methyl}phenoxy)phenyl]methanesulfonamide hydrochloride TLC:Rf 0.39(methylene chloride:methanol=9:1);
NMR (CD₃OD): δ 0.93 (t, J=7.5 Hz, 6H), 1.27-1.50 (m, 4H), 1.60 (m, 1H), 1.97-2.08 (m, 2H), 2.30-2.50 (m, 2H), 2.95 (s, 3H), 3.03-3.18 (m, 2H), 3.26 (d, J=7.5 Hz, 2H), 3.50-3.60 (m, 2H), 3.87 (m, 1H), 4.28 (s, 2H), 6.96-7.10 (m, 6H), 7.24-7.33 (m, 4H), 7.49 (d, J=8.7 Hz, 2H).

Example 29(25)

N-{4-[4-({4-[{[(4-fluorophenyl)amino]carbonyl}(thien-2-ylmethyl)amino]piperidin-1-yl}methyl)phenoxy]phenyl}methanesulfonamide hydrochloride TLC:Rf 0.34(methylene chloride:methanol=9:1);
NMR (CD₃OD): δ 1.94-2.05 (m, 2H), 2.12-2.30 (m, 2H), 2.95 (s, 3H), 3.02-3.17 (m, 2H), 3.50-3.58 (m, 2H), 4.26 (s, 2H), 4.27 (m, 1H), 4.79 (s, 2H), 6.94-7.08 (m, 8H), 7.26-7.34 (m, 5H), 7.48 (d, J=8.7 Hz, 2H).

Example 29(26)

N-{3-[({butyl[1-(4-{4-[(methylsulfonyl)amino]phenoxy}benzyl)piperidin-4-yl]amino}carbonyl)amino]phenyl}acetamide hydrochloride TLC:Rf 0.73(ethyl acetate:methanol=5:1);
NMR (CD₃OD): δ 0.97 (t, J=7.2 Hz, 3H), 1.28-1.45 (m, 2H), 1.56-1.67 (m, 2H), 1.98-2.02 (m, 2H), 2.11 (s, 3H), 2.16-2.28 (m, 2H), 2.96 (s, 3H), 3.07-3.15 (m, 2H), 3.26-3.30 (m, 2H), 3.55-3.59 (m, 2H), 4.16 (m, 1H), 4.29 (s, 2H), 7.04 (d, J=8.7 Hz, 2H), 7.07 (d, J=8.7 Hz, 2H), 7.10-7.23 (m, 3H), 7.30 (d, J=8.7 Hz, 2H), 7.50 (d, J=8.7 Hz, 2H), 7.69 (m, 1H).

Example 29(27)

N-{4-[({butyl[1-(4-{4-[(methylsulfonyl)amino]phenoxy}benzyl)piperidin-4-yl]amino}carbonyl)amino]phenyl}acetamide hydrochloride TLC:Rf 0.70(ethyl acetate:methanol=5:1);
NMR (CD$_3$OD): δ 0.97 (t, J=7.5 Hz, 3H), 1.29-1.42 (m, 2H), 1.55-1.67 (m, 2H), 1.98-2.02 (m, 2H), 2.10 (s, 3H), 2.13-2.28 (m, 2H), 2.96 (s, 3H), 3.03-3.15 (m, 2H), 3.25-3.30 (m, 2H), 3.55-3.59 (m, 2H), 4.16 (m, 1H), 4.29 (s, 2H), 7.04 (d, J=8.7 Hz, 2H), 7.07 (d, J=8.7 Hz, 2H), 7.27 (d, J=8.7 Hz, 2H), 7.30 (d, J=8.7 Hz, 2H) 7.46 (d, J=8.7 Hz, 2H), 7.50 (d, J=8.7 Hz, 2H).

Example 29(28)

N-{4-[4-({4-[{[(4-fluorophenyl)amino]carbonyl}(2,2,3,3,4,4,4-heptafluorobutyl)amino]piperidin-1-yl}methyl)phenoxy]phenyl}methanesulfonamide hydrochloride TLC:Rf 0.57(methylene chloride:methanol=9:1);
NMR (CD$_3$OD): δ 2.08-2.38 (m, 4H), 2.95 (s, 3H), 3.08-3.11 (m, 2H), 3.52-3.65 (m, 2H), 4.04 (m, 1H), 4.18-4.35 (m, 4H), 6.99-7.08 (m, 6H), 7.26-7.37 (m, 4H), 7.50 (d, J=8.7 Hz, 2H).

Example 29(29)

N-{4-[4-({4-[{[(4-fluorophenyl)amino]carbonyl}(isopentyl)amino]piperidin-1-yl}methyl)phenoxy]phenyl}methanesulfonamide hydrochloride TLC:Rf 0.52(methylene chloride:methanol=9:1);
NMR (CD$_3$OD): δ 0.96 (d, J=6.6 Hz, 6H), 1.45-1.55 (m, 2H), 1.65 (m, 1H), 1.95-2.05 (m, 2H), 2.12-2.30 (m, 2H), 2.95 (s, 3H), 3.05-3.10 (m, 2H), 3.22-3.33 (m, 2H), 3.51-3.61 (m, 2H), 4.19 (m, 1H), 4.29 (s, 2H), 6.97-7.10 (m, 6H), 7.26-7.33 (m, 4H), 7.50 (d, J=8.7 Hz, 2H).

Example 29(30)

N-[4-(4-{[4-((2,6-difluorobenzyl){[(4-fluorophenyl)amino]carbonyl}amino)piperidin-1-yl]methyl}phenoxy)phenyl]methanesulfonamide hydrochloride TLC:Rf 0.54(methylene chloride:methanol=9:1);
NMR (CD$_3$OD): δ 1.88-1.99 (m, 2H), 2.19-2.34 (m, 2H), 2.95 (s, 3H), 2.99-3.12 (m, 2H), 3.44-3.52 (m, 2H), 3.98 (m, 1H), 4.24 (s, 2H), 4.75 (s, 2H), 6.95-7.08 (m, 8H), 7.25-7.40 (m, 5H), 7.45 (d, J=8.7 Hz, 2H).

Example 29(31)

N-{4-[4-({4-[{[(4-fluorophenyl)amino]carbonyl}(pyridin-2-ylmethyl)amino]piperidin-1-yl}methyl)phenoxy]phenyl}methanesulfonamide dihydro chloride TLC:Rf 0.56(methylene chloride:methanol=9:1);
NMR (CD$_3$OD): δ 2.03-2.36 (m, 4H), 2.95 (s, 3H), 3.13-3.26 (m, 2H), 3.54-3.64 (m, 2H), 4.32 (s, 2H), 4.45 (m, 1H), 4.87 (s, 2H), 7.00 (d, J=9.0 Hz, 2H), 7.02 (d, J=8.7 Hz, 2H), 7.05 (d, J=8.7 Hz, 2H), 7.29 (d, J=8.7 Hz, 2H), 7.39 (dd, J=9.0, 5.0 Hz, 2H), 7.56 (d, J=8.7 Hz, 2H), 7.94 (t, J=6.0 Hz, 1H), 8.03 (d, J=8.0 Hz, 1H), 8.54 (dt, J=1.8, 8.0 Hz, 1H), 8.75 (dd, J=6.0, 1.8 Hz, 1H).

Example 29(32)

N-{4-[4-({4-[{[(4-fluorophenyl)amino]carbonyl}(pyridin-3-ylmethyl)amino]piperidin-1-yl}methyl)phenoxy]phenyl}methanesulfonamide dihydro chloride TLC:Rf 0.47(methylene chloride:methanol=9:1);
NMR (CD$_3$OD): δ 1.98-2.10 (m, 2H), 2.18-2.35 (m, 2H), 2.95 (s, 3H), 3.10-3.23 (m, 2H), 3.50-3.60 (m, 2H), 4.30 (s, 2H), 4.43 (m, 1H), 4.80 (s, 2H), 7.00 (d, J=9.0 Hz, 2H), 7.02 (d, J=8.7 Hz, 2H), 7.05 (d, J=8.7 Hz, 2H), 7.29 (d, J=8.7 Hz, 2H), 7.38 (dd, J=9.0, 5.0 Hz, 2H), 7.55 (d, J=8.7 Hz, 2H), 8.05 (dd, J=8.4, 5.7 Hz, 1H), 8.59 (d, J=8.4 Hz, 1H), 8.75 (d, J=5.7 Hz, 1H), 8.84 (s, 1H).

Example 29(33)

N-{4-[4-({4-[{[(4-fluorophenyl)amino]carbonyl}(pyridin-4-ylmethyl)amino]piperidin-1-yl}methyl)phenoxy]phenyl}methanesulfonamide dihydrochloride TLC:Rf 0.47(methylene chloride:methanol=9:1);
NMR (CD$_3$OD): δ 2.02-2.30 (m, 4H), 2.95 (s, 3H), 3.10-3.23 (m, 2H), 3.50-3.60 (m, 2H), 4.30 (s, 2H), 4.48 (m, 1H), 4.88 (s, 2H), 6.99 (d, J=9.0 Hz, 2H), 7.02 (d, J=8.7 Hz, 2H), 7.05 (d, J=8.7 Hz, 2H), 7.29 (d, J=8.7 Hz, 2H), 7.36 (dd, J=9.0, 5.0 Hz, 2H), 7.54 (d, J=8.7 Hz, 2H), 8.02 (d, J=6.6 Hz, 2H), 8.77 (d, J=6.6 Hz, 2H).

Example 29(34)

N-(4-{4-[(4-{butyl[(methylamino)carbonyl]amino}piperidin-1-yl)methyl]phenoxy}phenyl)methanesulfonamide hydrochloride TLC:Rf 0.50(chloroform:methanol=10:1);
NMR (CD$_3$OD): δ 0.94 (t, J=7.5 Hz, 3H), 1.30-1.40 (m, 2H), 1.40-1.60 (m, 2H), 1.80-2.00 (m, 2H), 2.10-2.20 (m, 2H), 2.72 (s, 3H), 2.95 (s, 3H), 3.00-3.15 (m, 4H), 3.50-3.60 (m, 2H), 4.12 (m, 1H), 4.27 (s, 2H), 7.02-7.08 (m, 4H), 7.29 (d, J=8.9 Hz, 2H), 7.49 (d, J=8.9 Hz, 2H).

Example 29(35)

N-[4-(4-{[4-(butyl{[(5-hydroxypyridin-3-yl)amino]carbonyl}amino)piperidin-1-yl]methyl}phenoxy)phenyl]methanesulfonamide dihydrochloride TLC:Rf 0.50(chloroform:methanol=5:1);
NMR (CD$_3$OD): δ 0.97 (t, J=7.4 Hz, 3H), 1.30-1.50 (m, 2H), 1.50-1.70 (m, 2H), 1.90-2.10 (m, 2H), 2.20-2.30 (m, 2H), 2.95 (s, 3H), 3.10-3.30 (m, 4H), 3.50-3.60 (m, 2H), 4.30 (m, 1H), 4.31 (s, 2H), 7.02-7.08 (m, 4H), 7.29 (d, J=8.9 Hz, 2H), 7.54 (d, J=8.9 Hz, 2H), 7.93 (d, J=2.1 Hz, 1H) 8.12 (d, J=2.1 Hz, 1H), 8.68 (d, J=1.5 Hz, 1H).

Example 29(36)

N-[4-(4-{[4-(butyl{[(1-isopropyl-1H-1,2,3-benzotriazol-5-yl)amino]carbonyl}amino)piperidin-1-yl]methyl}phenoxy)phenyl]methanesulfonamide dihydrochloride TLC:Rf 0.65(chloroform:methanol=5:1);
NMR (CD₃OD): δ 0.98 (t, J=7.4 Hz, 3H), 1.30-1.50 (m, 2H), 1.60-1.80 (m, 2H), 1.74 (d, J=6.6 Hz, 6H), 2.00-2.10 (m, 2H), 2.20-2.40 (m, 2H), 2.96 (s, 3H), 3.10-3.30 (m, 2H), 3.30-3.40 (m, 2H), 3.50-3.60 (m, 2H), 4.30 (m, 1H), 4.32 (s, 2H), 5.34 (m, 1H), 7.02-7.08 (m, 4H), 7.30 (d, J=8.9 Hz, 2H), 7.54 (d, J=8.9 Hz, 2H), 7.77 (dd, J=9.0, 1.5 Hz, 1H) 7.95 (d, J=9.0 Hz, 1H), 8.17 (d, J=1.5 Hz, 1H).

Example 29(37)

N-(4-{4-[(4-{{[(4-fluorophenyl)amino]carbonyl}[(6-methylpyridin-2-yl)methyl]amino}piperidin-1-yl)methyl]phenoxy}phenyl)methanesulfonamide dihydrochloride TLC:Rf 0.50(methylene chloride:methanol=9:1);
NMR (CD₃OD): δ 2.08-2.18 (m, 2H), 2.20-2.38 (m, 2H), 2.80 (s, 3H), 2.95 (s, 3H), 3.14-3.26 (m, 2H), 3.52-3.62 (m, 2H), 4.32 (s, 2H), 4.47 (m, 1H), 4.83 (s, 2H), 7.00 (d, J=9.0 Hz, 2H), 7.02 (d, J=8.7 Hz, 2H), 7.05 (d, J=8.7 Hz, 2H), 7.29 (d, J=8.7 Hz, 2H), 7.37 (dd, J=9.0, 5.0 Hz, 2H), 7.57 (d, J=8.7 Hz, 2H), 7.76 (d, J=8.0 Hz, 1H), 7.78 (d, J=8.0 Hz, 1H), 8.40 (t, J=8.0 Hz, 1H).

Example 29(38)

N-[4-(4-{[4-(butyl{[(3-cyanophenyl)amino]carbonyl}amino)piperidin-1-yl]methyl}phenoxy)phenyl]methanesulfonamide hydrochloride TLC:Rf 0.52(methylene chloride:methanol=10:1);
NMR (CD₃OD): δ 0.97 (t, J=7.2 Hz, 3H), 1.28-1.44 (m, 2H), 1.55-1.66 (m, 2H), 1.98-2.03 (m, 2H), 2.20-2.33 (m, 2H), 2.95 (s, 3H), 3.09-3.17 (m, 2H), 3.30-3.40 (m, 2H), 3.55-3.59 (m, 2H), 4.17 (m, 1H), 4.30 (s, 2H), 7.03 (d, J=8.7 Hz, 2H), 7.07 (d, J=8.7 Hz, 2H), 7.29 (d, J=8.7 Hz, 2H), 7.36 (m, 1H), 7.44 (t, J=8.0 Hz, 1H), 7.51 (d, J=8.7 Hz, 2H), 7.64 (m, 1H), 7.82 (m, 1H).

Example 29(39)

N-{4-[4-({4-[{[(4-fluorophenyl)amino]carbonyl}(tetrahydro-2H-pyran-4-ylmethyl)amino]piperidin-1-yl}methyl)phenoxy]phenyl}methanesulfonamide hydrochloride TLC:Rf 0.57(methylene chloride:methanol=9:1);
NMR (CD₃OD): δ 1.27-1.42 (m, 2H), 1.60-1.70 (m, 2H), 1.87-2.08 (m, 3H), 2.25-2.42 (m, 2H), 2.95 (s, 3H), 3.02-3.15 (m, 2H), 3.19-3.28 (m, 2H), 3.31-3.42 (m, 2H), 3.48-3.60 (m, 2H), 3.88-4.00 (m, 3H), 4.28 (s, 2H), 6.97-7.10 (m, 6H), 7.25-7.33 (m, 4H), 7.50 (d, J=8.7 Hz, 2H).

Example 29(40)

N-{4-[4-({4-[{[(4-fluorophenyl)amino]carbonyl}(2-phenylethyl)amino]piperidin-1-yl}methyl)phenoxy]phenyl}methanesulfonamide hydrochloride TLC:Rf 0.68(methylene chloride:methanol=9:1);
NMR (CD₃OD): δ 1.82-2.92 (m, 2H), 2.10-2.28 (m, 2H), 2.93 (t, J=7.5 Hz, 2H), 2.95 (s, 3H), 3.00-3.12 (m, 2H), 3.49-3.59 (m, 4H), 4.10 (m, 1H), 4.27 (s, 2H), 6.97-7.10 (m, 6H), 7.18-7.37 (m, 9H), 7.50 (d, J=8.7 Hz, 2H).

Example 29(41)

N-{4-[4-({4-[{[(4-fluorophenyl)amino]carbonyl}(2-pyridin-2-ylethyl)amino]piperidin-1-yl}methyl)phenoxy]phenyl}methanesulfonamide dihydrochloride TLC:Rf 0.59(methylene chloride:methanol=9:1);
NMR (CD₃OD): δ 1.98-2.10 (m, 2H), 2.28-2.44 (m, 2H), 2.95 (s, 3H), 3.09-3.22 (m, 2H), 3.34 (t, J=7.2 Hz, 2H), 3.55-3.63 (m, 2H), 3.75 (t, J=7.2 Hz, 2H), 4.25 (m, 1H), 4.33 (s, 2H), 6.97-7.10 (m, 6H), 7.26-7.33 (m, 4H), 7.57 (d, J=8.7 Hz, 2H), 7.92 (ddd, J=8.1, 5.7, 1.8 Hz, 1H), 8.06 (d, J=8.1 Hz, 1H), 8.53 (dt, J=1.8, 8.1 Hz, 1H), 8.74 (d, J=5.7 Hz, 1H).

Example 29(42)

N-[4-(4-{[4-(butyl{[(4-methyl-1,2,3-thiadiazol-5-yl)amino]carbonyl}amino)piperidin-1-yl]methyl}phenoxy)phenyl]methanesulfonamide dihydrochloride TLC:Rf 0.78(chloroform:methanol=5:1);
NMR (CD₃OD): δ 0.99 (t, J=7.2 Hz, 3H), 1.30-1.50 (m, 2H), 1.50-1.70 (m, 2H), 1.90-2.10 (m, 2H), 2.30-2.40 (m, 2H), 2.68 (s, 3H), 2.96 (s, 3H), 3.10-3.20 (m, 2H), 3.40-3.50 (m, 2H), 3.50-3.60 (m, 2H), 4.20 (m, 1H), 4.31 (s, 2H), 7.02-7.08 (m, 4H), 7.29 (d, J=8.9 Hz, 2H), 7.53 (d, J=8.9 Hz, 2H).

Example 29(43)

N-[4-(4-{[4-(butyl{[(2-chloro-4-fluorophenyl)amino]carbonyl}amino)piperidin-1-yl]methyl}phenoxy)phenyl]methanesulfonamide hydrochloride TLC:Rf 0.72(chloroform:methanol=5:1);
NMR (CD₃OD): δ 0.98 (t, J=7.2 Hz, 3H), 1.30-1.50 (m, 2H), 1.60-1.80 (m, 2H), 2.00-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.20 (m, 1H), 4.29 (s, 2H), 7.02-7.08 (m, 5H), 7.27 (m, 1H), 7.29 (d, J=9.0 Hz, 2H), 7.50 (d, J=9.0 Hz, 2H), 7.51 (m, 1H).

Example 29(44)

N-[4-(4-{[4-(butyl{[(4-cyanophenyl)amino]carbonyl}amino)piperidin-1-yl]methyl}phenoxy)phenyl]methanesulfonamide hydrochloride TLC:Rf 0.71(methylene chloride:methanol=10:1);
NMR (CD₃OD): δ 0.96 (t, J=7.2 Hz, 3H), 1.34-1.41 (m, 2H), 1.57-1.62 (m, 2H), 1.98-2.01 (m, 2H), 2.20-2.33 (m, 2H), 2.95 (s, 3H), 3.08-3.16 (m, 2H), 3.30-3.40 (m, 2H), 3.55-3.59 (m, 2H), 4.17 (m, 1H), 4.29 (s, 2H), 7.04 (d, J=8.9 Hz, 2H), 7.07 (d, J=8.9 Hz, 2H), 7.29 (d, J=8.9 Hz, 2H), 7.50 (d, J=8.9 Hz, 2H), 7.58 (d, J=9.0 Hz, 2H), 7.61 (d, J=9.0 Hz, 2H).

Example 29(45)

N-[4-(4-{[4-(butyl{[(2,2-difluoro-1,3-benzodioxol-5-yl)amino]carbonyl}amino)piperidin-1-yl]methyl}phenoxy)phenyl]methanesulfonamide hydrochloride TLC:Rf 0.64(methylene chloride:methanol=10:1);
NMR (CD$_3$OD): δ 0.97 (t, J=7.2 Hz, 3H), 1.34-1.42 (m, 2H), 1.55-1.65 (m, 2H), 1.98-2.03 (m, 2H), 2.15-2.25 (m, 2H), 2.95 (s, 3H), 3.07-3.15 (m, 2H), 3.25-3.30 (m, 2H), 3.55-3.59 (m, 2H), 4.14 (m, 1H), 4.29 (s, 2H), 7.02-7.11 (m, 6H), 7.29 (d, J=8.7 Hz, 2H), 7.33 (m, 1H), 7.49 (d, J=8.7 Hz, 2H).

Example 29(46)

N-[4-(4-{[4-(butyl{[(4-chloro-2-fluorophenyl)amino]carbonyl}amino)piperidin-1-yl]methyl}phenoxy)phenyl]methanesulfonamide hydrochloride TLC:Rf 0.46(chloroform:methanol=10:1);
NMR (CD$_3$OD): δ 0.97 (t, J=7.4 Hz, 3H), 1.30-1.50 (m, 2H), 1.60-1.80 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 7.02-7.08 (m, 4H), 7.15 (m, 1H), 7.22 (dd, J=6.3, 2.1 Hz, 1H), 7.29 (d, J=8.9 Hz, 2H), 7.43 (m, 1H), 7.43 (d, J=8.9 Hz, 2H).

Example 29(47)

N-[4-(4-{[4-(butyl{[(1-methyl-1H-1,2,3-benzotriazol-5-yl)amino]carbonyl}amino)piperidin-1-yl]methyl}phenoxy)phenyl]methanesulfonamide dihydrochloride TLC:Rf 0.40(chloroform:methanol=10:1);
NMR (CD$_3$OD): δ 0.98 (t, J=7.4 Hz, 3H), 1.30-1.50 (m, 2H), 1.60-1.70 (m, 2H), 2.00-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.30 (m, 1H), 4.31 (s, 2H), 4.39 (s, 3H), 7.02-7.08 (m, 4H), 7.29 (d, J=9.0 Hz, 2H), 7.53 (d, J=9.0 Hz, 2H), 7.69 (dd, J=9.0, 1.8 Hz, 1H), 7.80 (d, J=9.0 Hz, 1H), 8.09 (d, J=1.8 Hz, 1H).

Example 29(48)

2-[({butyl[1-(4-{4-[(methylsulfonyl)amino]phenoxy}benzyl)piperidin-4-yl]amino}carbonyl)amino]benzamide TLC:Rf 0.60(methylene chloride:methanol=10:1);
NMR (CD$_3$OD): δ 0.96 (t, J=7.2 Hz, 3H), 1.37-1.44 (m, 2H), 1.59-1.91 (m, 6H), 2.15-2.22 (m, 2H), 2.93 (s, 3H), 3.00-3.04 (m, 2H), 3.22-3.27 (m, 2H), 3.54 (s, 2H), 4.05 (m, 1H), 6.93-7.02 (m, 5H), 7.25 (d, J=8.7 Hz, 2H), 7.32 (d, J=8.7 Hz, 2H), 7.42 (t, J=8.3 Hz, 1H), 7.69 (d, J=8.3 Hz, 1H), 8.27 (d, J=8.3 Hz, 1H).

Example 29(49)

N-[4-(4-{[4-(butyl{[(2,4-dimethylpyridin-3-yl)amino]carbonyl}amino)piperidin-1-yl]methyl}phenoxy)phenyl]methanesulfonamide dihydrochloride TLC:Rf 0.45(methylene chloride:methanol=10:1);
NMR (CD$_3$OD): δ 1.00 (t, J=7.5 Hz, 3H), 1.39-1.46 (m, 2H), 1.63-1.70 (m, 2H), 2.01-2.06 (m, 2H), 2.22-2.35 (m, 2H), 2.52 (s, 3H), 2.64 (s, 3H), 2.95 (s, 3H), 3.12-3.20 (m, 2H), 3.30-3.37 (m, 2H), 3.56-3.60 (m, 2H), 4.24 (m, 1H), 4.30 (s, 2H), 7.03 (d, J=8.9 Hz, 2H), 7.06 (d, J=8.9 Hz, 2H), 7.29 (d, J=8.9 Hz, 2H), 7.52 (d, J=8.9 Hz, 2H), 7.83 (d, J=6.3 Hz, 1H), 8.48 (d, J=6.3 Hz, 1H).

Example 29(50)

N-[4-(4-{[4-(butyl{[(4-fluoro-2-hydroxyphenyl)amino]carbonyl}amino)piperidin-1-yl]methyl}phenoxy)phenyl]methanesulfonamide hydrochloride TLC:Rf 0.50(chloroform:methanol=10:1);
NMR (CD$_3$OD): δ 0.99 (t, J=7.5 Hz, 3H), 1.30-1.50 (m, 2H), 1.60-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 4.20 (m, 1H), 4.29 (s, 2H), 6.53-6.60 (m, 2H), 7.02-7.08 (m, 4H), 7.29 (d, J=8.7 Hz, 2H), 7.46 (m, 1H), 7.49 (d, J=8.7 Hz, 2H).

Example 29(51)

N-{4-[4-({4-[{[(4-fluorophenyl)amino]carbonyl}(2-hydroxy-3-methylbutyl)amino]piperidin-1-yl}methyl)phenoxy]phenyl}methanesulfonamide hydrochloride TLC:Rf 0.45(methylene chloride:methanol=9:1);
NMR (CD$_3$OD): δ 0.99 (d, J=6.9 Hz, 3H), 1.00 (d, J=6.9 Hz, 3H), 1.74 (m, 1H), 1.95-2.25 (m, 4H), 2.95 (s, 3H), 3.07-3.20 (m, 2H), 3.25-3.42 (m, 2H), 3.47-3.62 (m, 3H), 4.16 (m, 1H), 4.29 (s, 2H), 6.99 (d, J=9.0 Hz, 2H), 7.03 (d, J=8.7 Hz, 2H), 7.06 (d, J=8.7 Hz, 2H), 7.24 (dd, J=9.0, 5.0 Hz, 2H), 7.29 (d, J=8.7 Hz, 2H), 7.50 (d, J=8.7 Hz, 2H).

Example 29(52)

N-{4-[4-({4-[{[(4-fluorophenyl)amino]carbonyl}(3-hydroxy-3-methylbutyl)amino]piperidin-1-yl}methyl)phenoxy]phenyl}methanesulfonamide hydrochloride TLC:Rf 0.44(methylene chloride:methanol=9:1);
NMR (CD$_3$OD): δ 1.25 (s, 6H), 1.79 (t, J=7.5 Hz, 2H), 1.92-2.02 (m, 2H), 2.08-2.23 (m, 2H), 2.95 (s, 3H), 3.08-3.18 (m, 2H), 3.40 (t, J=7.5 Hz, 2H), 3.52-3.62 (m, 2H), 4.26-4.36 (m, 3H), 6.98 (d, J=9.0 Hz, 2H), 7.03 (d, J=8.7 Hz, 2H), 7.06 (d, J=8.7 Hz, 2H), 7.29 (d, J=8.7 Hz, 2H), 7.36 (dd, J=9.0, 5.0 Hz, 2H), 7.50 (d, J=8.7 Hz, 2H).

Example 29(53)

N-[4-(4-{[4-(butyl{[(2,4-dimethyl-1-oxidopyridin-3-yl)amino]carbonyl}amino)piperidin-1-yl]methyl}phenoxy)phenyl]methanesulfonamide hydrochloride TLC:Rf 0.43(methylene chloride:methanol=5:1);
NMR (CD$_3$OD): δ 1.00 (t, J=7.2 Hz, 3H), 1.39-1.46 (m, 2H), 1.63-1.75 (m, 2H), 1.97-2.05 (m, 2H), 2.23-2.35 (m, 2H), 2.43 (s, 3H), 2.59 (s, 3H), 2.96 (s, 3H), 3.10-3.20 (m, 2H), 3.30-3.38 (m, 2H), 3.53-3.59 (m, 2H), 4.21 (m, 1H), 4.30

(s, 2H), 7.04 (d, J=8.7 Hz, 2H), 7.07 (d, J=8.7 Hz, 2H), 7.30 (d, J=8.7 Hz, 2H), 7.52 (d, J=8.7 Hz, 2H), 7.66 (d, J=6.9 Hz, 1H), 8.59 (d, J=6.9 Hz, 1H).

Example 29(54)

N-[4-(4-{[4-(butyl{[(1-oxidopyridin-4-yl)amino]carbonyl}amino)piperidin-1-yl]methyl}phenoxy)phenyl]methanesulfonamide hydrochloride TLC:Rf 0.35(methylene chloride:methanol=5:1);
NMR (CD$_3$OD): δ 0.96 (t, J=7.2 Hz, 3H), 1.34-1.44 (m, 2H), 1.55-1.65 (m, 2H), 1.98-2.05 (m, 2H), 2.26-2.38 (m, 2H), 2.95 (s, 3H), 3.13-3.21 (m, 2H), 3.33-3.38 (m, 2H), 3.56-3.60 (m, 2H), 4.24 (m, 1H), 4.31 (s, 2H), 7.04 (d, J=8.7 Hz, 2H), 7.07 (d, J=8.4 Hz, 2H), 7.29 (d, J=8.7 Hz, 2H), 7.52 (d, J=8.4 Hz, 2H), 8.06 (d, J=7.0 Hz, 2H), 8.59 (d, J=7.0 Hz, 2H).

Example 29(55)

N-[4-(4-{[4-(butyl{[(1-methyl-1H-pyrazol-4-yl)amino]carbonyl}amino)piperidin-1-yl]methyl}phenoxy)phenyl]methanesulfonamide dihydrochloride TLC:Rf 0.40(chloroform:methanol=10:1);
NMR (CD$_3$OD): δ 0.97 (t, J=7.2 Hz, 3H), 1.30-1.50 (m, 2H), 1.50-1.70 (m, 2H), 1.90-2.10 (m, 2H), 2.20-2.30 (m, 2H), 2.95 (s, 3H), 3.10-3.30 (m, 4H), 3.50-3.60 (m, 2H), 3.97 (s, 3H), 4.20 (m, 1H), 4.30 (s, 2H), 7.02-7.08 (m, 4H), 7.29 (d, J=8.9 Hz, 2H), 7.52 (d, J=8.9 Hz, 2H), 7.88 (s, 1H), 7.99 (s, 1H);

amorphous;

softening point: about 156-159° C.

Example 29(56)

N-{4-[4-({4-[{[(2,4-difluorophenyl)amino]carbonyl}(2-hydroxybutyl)amino]piperidin-1-yl}methyl)phenoxy]phenyl}methanesulfonamide hydrochloride TLC:Rf 0.51(methylene chloride:methanol=9:1);
NMR (CD$_3$OD): δ 1.00 (t, J=7.5 Hz, 3H), 1.40-1.60 (m, 2H), 1.97-2.31 (m, 4H), 2.95 (s, 3H), 3.02-3.41 (m, 4H), 3.50-3.71 (m, 3H), 4.12 (m, 1H), 4.28 (s, 2H), 6.83-7.02 (m, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H), 7.63 (dt, J=5.7, 9.0 Hz, 1H).

Example 29(57)

N-(4-{4-[(4-{{[(4-fluorophenyl)amino]carbonyl}[(3-methylpyridin-2-yl)methyl]amino}piperidin-1-yl)methyl]phenoxy}phenyl)methanesulfonamide dihydrochloride TLC:Rf 0.56(methylene chloride:methanol=9:1);
NMR (CD$_3$OD): δ 2.01-2.30 (m, 4H), 2.62 (s, 3H), 2.95 (s, 3H), 3.16-3.30 (m, 2H), 3.50-3.61 (m, 2H), 4.31 (s, 2H), 4.51 (m, 1H), 4.88 (s, 2H), 6.98-7.08 (m, 6H), 7.28 (d, J=8.7 Hz, 2H), 7.42-7.50 (m, 2H), 7.56 (d, J=8.7 Hz, 2H), 7.86 (t, J=6.5 Hz, 1H), 8.39 (d, J=6.5 Hz, 1H), 8.54 (d, J=6.5 Hz, 1H).

Example 29(58)

N-[4-(4-{[4-((cyclopentylmethyl){[(4-fluorophenyl)amino]carbonyl}amino)piperidin-1-yl]methyl}phenoxy)phenyl]methanesulfonamide hydrochloride TLC:Rf 0.57(methylene chloride:methanol=9:1);
NMR (CD$_3$OD): δ 1.20-1.35 (m, 2H), 1.52-1.87 (m, 6H), 1.98-2.07 (m, 2H), 2.22 (m, 1H), 2.30-2.48 (m, 2H), 2.95 (s, 3H), 3.03-3.18 (m, 2H), 3.28-3.33 (m, 2H), 3.50-3.60 (m, 2H), 3.88 (m, 1H), 4.28 (s, 2H), 6.98-7.08 (m, 6H), 7.24-7.32 (m, 4H), 7.49 (d, J=8.7 Hz, 2H).

Example 29(59)

N-[4-(4-{[4-(butyl{[(2-fluoro-5-methoxyphenyl)amino]carbonyl}amino)piperidin-1-yl]methyl}phenoxy)phenyl]methanesulfonamide hydrochloride TLC:Rf 0.52(chloroform:methanol=10:1);
NMR (CD$_3$OD): δ 0.98 (t, J=7.4 Hz, 3H), 1.30-1.50 (m, 2H), 1.60-1.70 (m, 2H), 1.90-2.10 (m, 2H), 2.20-2.30 (m, 2H), 2.95 (s, 3H), 3.10-3.20 (m, 2H), 3.20-3.40 (m, 2H), 3.50-3.60 (m, 2H), 3.75 (s, 3H), 4.20 (m, 1H), 4.29 (s, 2H), 6.67 (m, 1H), 7.02-7.12 (m, 6H), 7.29 (d, J=8.9 Hz, 2H), 7.52 (d, J=8.9 Hz, 2H).

Example 29(60)

N-[4-(4-{[4-(butyl{[(2-fluoro-3-methoxyphenyl)amino]carbonyl}amino)piperidin-1-yl]methyl}phenoxy)phenyl]methanesulfonamide hydrochloride TLC:Rf 0.52(chloroform:methanol=10:1);
NMR (CD$_3$OD): δ 0.98 (t, J=7.4 Hz, 3H), 1.30-1.50 (m, 2H), 1.60-1.70 (m, 2H), 1.90-2.10 (m, 2H), 2.20-2.40 (m, 2H), 2.95 (s, 3H), 3.10-3.20 (m, 2H), 3.20-3.40 (m, 2H), 3.50-3.60 (m, 2H), 3.85 (s, 3H), 4.20 (m, 1H), 4.29 (s, 2H), 6.89 (m, 1H), 7.02-7.08 (m, 6H), 7.29 (d, J=9.0 Hz, 2H), 7.50 (d, J=9.0 Hz, 2H).

Example 29(61)

N-[4-(4-{[4-(butyl{[(2-fluoro-4-methylphenyl)amino]carbonyl}amino)piperidin-1-yl]methyl}phenoxy)phenyl]methanesulfonamide hydrochloride TLC:Rf 0.56(chloroform:methanol=10:1);
NMR (CD$_3$OD): δ 0.98 (t, J=7.4 Hz, 3H), 1.30-1.40 (m, 2H), 1.60-1.70 (m, 2H), 1.90-2.10 (m, 2H), 2.20-2.30 (m, 2H), 2.31 (s, 3H), 2.95 (s, 3H), 3.10-3.20 (m, 2H), 3.20-3.40 (m, 2H), 3.50-3.60 (m, 2H), 4.15 (m, 1H), 4.28 (s, 2H), 6.90-7.00 (m, 2H), 7.02-7.08 (m, 4H), 7.26-7.31 (m, 3H), 7.50 (d, J=9.0 Hz, 2H).

Example 29(62)

N-{4-[4-({4-[{[(4-fluorophenyl)amino]carbonyl}(1,3-thiazol-2-ylmethyl)amino]piperidin-1-yl}methyl)phenoxy]phenyl}methanesulfonamide hydrochloride TLC:Rf 0.63(chloroform:methanol=5:1);
NMR (CD$_3$OD): δ 2.00-2.13 (m, 2H), 2.13-2.31 (m, 2H), 2.95 (s, 3H), 3.16 (m, 2H), 3.58 (m, 2H), 4.31 (s, 2H), 4.38 (m, 1H), 4.93 (s, 2H), 6.98-7.18 (m, 6H), 7.24-7.42 (m, 4H), 7.52 (brd, J=8.7 Hz, 2H), 7.75 (d, J=3.6 Hz, 1H), 7.93 (d, J=3.6 Hz, 1H).

Example 29(63)

3-[({butyl[1-(4-{4-[(methylsulfonyl)amino]phenoxy}benzyl)piperidin-4-yl]amino}carbonyl)amino]-N-methylbenzamide hydrochloride TLC:Rf 0.34(chloroform:methanol=10:1);
NMR (CD₃OD): δ 0.97 (t, J=7.4 Hz, 3H), 1.30-1.50 (m, 2H), 1.50-1.70 (m, 2H), 1.90-2.10 (m, 2H), 2.10-2.30 (m, 2H), 2.90 (s, 3H), 2.95 (s, 3H), 3.00-3.20 (m, 2H), 3.20-3.40 (m, 2H), 3.50-3.60 (m, 2H), 4.15 (m, 1H), 4.29 (s, 2H), 7.02-7.08 (m, 4H), 7.29 (d, J=8.7 Hz, 2H), 7.30-7.50 (m, 3H), 7.50 (d, J=8.7 Hz, 2H), 7.79 (s, 1H).

Example 29(64)

N-{4-[4-({4-[butyl({[3-(dimethylamino)phenyl]amino}carbonyl)amino]piperidin-1-yl}methyl)phenoxy]phenyl}methanesulfonamide dihydrochloride TLC:Rf 0.50(chloroform:methanol=10:1);
NMR (CD₃OD): δ 0.97 (t, J=7.4 Hz, 3H), 1.30-1.50 (m, 2H), 1.50-1.70 (m, 2H), 1.90-2.10 (m, 2H), 2.20-2.40 (m, 2H), 2.95 (s, 3H), 3.10-3.40 (m, 4H), 3.28 (s, 6H), 3.50-3.60 (m, 2H), 4.30 (m, 1H), 4.31 (s, 2H), 7.02-7.08 (m, 4H), 7.28-7.31 (m, 3H), 7.48-7.54 (m, 4H), 7.90 (m, 1H).

Example 29(65)

N-[4-(4-{[4-(butyl{[(4-fluoro-2-methylphenyl)amino]carbonyl}amino)piperidin-1-yl]methyl}phenoxy)phenyl]methanesulfonamide hydrochloride TLC:Rf 0.47(chloroform:methanol=10:1);
NMR (CD₃OD): δ 0.98 (t, J=7.4 Hz, 3H), 1.30-1.50 (m, 2H), 1.60-1.80 (m, 2H), 1.90-2.10 (m, 2H), 2.10-2.30 (m, 2H), 2.21 (s, 3H), 2.95 (s, 3H), 3.00-3.20 (m, 2H), 3.20-3.40 (m, 2H), 3.50-3.60 (m, 2H), 4.20 (m, 1H), 4.28 (s, 2H), 6.88 (m, 1H), 6.94-7.14 (m, 6H), 7.29 (d, J=8.7 Hz, 2H), 7.51 (d, J=8.7 Hz, 2H).

Example 29(66)

N-[4-(4-{[4-(butyl{[(2-fluoro-4-methoxyphenyl)amino]carbonyl}amino)piperidin-1-yl]methyl}phenoxy)phenyl]methanesulfonamide hydrochloride TLC:Rf 0.63 (chloroform:methanol=10:1);
NMR (CD₃OD): δ 0.98 (t, J=7.4 Hz, 3H), 1.30-1.50 (m, 2H), 1.60-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 3.77 (s, 3H), 4.15 (m, 1H), 4.28 (s, 2H), 6.70-6.75 (m, 2H), 7.02-7.08 (m, 4H), 7.22 (m, 1H), 7.29 (d, J=8.7 Hz, 2H), 7.49 (d, J=8.7 Hz, 2H).

Example 29(67)

N-[4-(4-{[4-(butyl{[(3-ethylphenyl)amino]carbonyl}amino)piperidin-1-yl]methyl}phenoxy)phenyl]methanesulfonamide hydrochloride TLC:Rf 0.58(chloroform:methanol=10:1);
NMR (CD₃OD): δ 0.97 (t, J=7.4 Hz, 3H), 1.22 (t, J=7.5 Hz, 3H), 1.30-1.50 (m, 2H), 1.50-1.70 (m, 2H), 1.90-2.10 (m, 2H), 2.10-2.30 (m, 2H), 2.60 (q, J=7.1 Hz, 2H), 2.95 (s, 3H), 3.00-3.20 (m, 2H), 3.20-3.40 (m, 2H), 3.50-3.60 (m, 2H), 4.19 (m, 1H), 4.29 (s, 2H), 6.89 (m, 1H), 7.01-7.08 (m, 4H), 7.12-7.20 (m, 3H), 7.29-7.32 (m, 2H), 7.49-7.52 (m, 2H).

Example 29(68)

N-(4-{4-[(4-{{[(4-fluorophenyl)amino]carbonyl}[(1-oxidopyridin-2-yl)methyl]amino}piperidin-1-yl)methyl]phenoxy}phenyl)methanesulfonamide hydrochloride TLC:Rf 0.14(methylene chloride:methanol=9:1);
NMR (CD₃OD): δ 2.02-2.30 (m, 4H), 2.95 (s, 3H), 3.12-3.25 (m, 2H), 3.50-3.60 (m, 2H), 4.30 (s, 2H), 4.43 (m, 1H), 6.95-7.08 (m, 6H), 7.29 (d, J=8.7 Hz, 2H), 7.35 (dd, J=9.0, 5.0 Hz, 2H), 7.52 (d, J=8.7 Hz, 2H), 7.73 (t, J=7.5 Hz, 1H), 7.85 (d, J=7.5 Hz, 1H), 8.01 (t, J=7.5 Hz, 1H), 8.68 (d, J=7.5 Hz, 1H).

Example 29(69)

N-[4-(4-{[4-(butyl{[(2-fluoro-4-hydroxyphenyl)amino]carbonyl}amino)piperidin-1-yl]methyl}phenoxy)phenyl]methanesulfonamide hydrochloride TLC:Rf 0.44(chloroform:methanol=10:1);
NMR (CD₃OD): δ 0.97 (t, J=7.2 Hz, 3H), 1.30-1.50 (m, 2H), 1.60-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 6.52-6.56 (m, 2H), 7.02-7.09 (m, 6H), 7.29 (d, J=8.7 Hz, 2H), 7.49 (d, J=8.7 Hz, 2H).

Example 29(70)

N-[4-(4-{[4-(butyl{[(1-methyl-1H-indol-3-yl)amino]carbonyl}amino)piperidin-1-yl]methyl}phenoxy)phenyl]methanesulfonamide dihydrochloride TLC:Rf 0.42(chloroform:methanol=10:1);
NMR (CD₃OD): δ 0.99 (t, J=7.4 Hz, 3H), 1.40-1.50 (m, 2H), 1.60-1.80 (m, 2H), 1.90-2.10 (m, 2H), 2.10-2.40 (m, 2H), 2.95 (s, 3H), 3.00-3.20 (m, 2H), 3.20-3.40 (m, 2H), 3.50-3.60 (m, 2H), 3.76 (s, 3H), 4.25 (m, 1H), 4.26 (s, 2H), 7.02-7.07 (m, 5H), 7.10-7.20 (m, 2H), 7.29 (d, J=9.0 Hz, 2H), 7.30 (m, 1H), 7.45 (m, 1H), 7.49 (d, J=9.0 Hz, 2H).

Example 29(71)

N-{4-[4-({4-[butyl({[3-(methylsulfonyl)phenyl]amino}carbonyl)amino]piperidin-1-yl}methyl)phenoxy]phenyl}methanesulfonamide hydrochloride TLC:Rf 0.26(chloroform:methanol=10:1);
NMR (CD₃OD): δ 0.97 (t, J=7.4 Hz, 3H), 1.30-1.50 (m, 2H), 1.50-1.70 (m, 2H), 1.90-2.10 (m, 2H), 2.20-2.40 (m, 2H), 2.95 (s, 3H), 3.00-3.20 (m, 2H), 3.10 (s, 3H), 3.20-3.40 (m, 2H), 3.50-3.60 (m, 2H), 4.10 (m, 1H), 4.30 (s, 2H), 7.02-7.08 (m, 4H), 7.29 (d, J=8.3 Hz, 2H), 7.51 (d, J=8.3 Hz, 2H) 7.54-7.59 (m, 2H), 7.69 (m, 1H), 8.07 (m, 1H).

Example 29(72)

N-[4-(4-{[4-(butyl{[(3-chloro-1-methyl-1H-pyrazol-4-yl)amino]carbonyl}amino)piperidin-1-yl]methyl}phenoxy)phenyl]methanesulfonamide dihydrochloride TLC:Rf 0.42(chloroform:methanol=10:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 3.81 (s, 3H), 4.10 (m, 1H), 4.28 (s, 2H), 7.02-7.08 (m, 4H), 7.29 (d, J=8.7 Hz, 2H), 7.45 (s, 1H), 7.49 (d, J=8.7 Hz, 2H).

Example 29(73)

N-[4-(4-{[4-((2,6-dimethylbenzyl) {[(4-fluorophenyl)amino]carbonyl}amino)piperidin-1-yl]methyl}phenoxy)phenyl]methanesulfonamide TLC:Rf 0.50(methylene chloride:methanol=9:1);
NMR (CD$_3$OD): δ 1.40-1.49 (m, 2H), 1.79-1.90 (m, 2H), 2.15-2.32 (m, 2H), 2.39 (s, 6H), 2.80-2.90 (m, 2H), 2.92 (s, 3H), 3.14 (m, 1H), 3.40 (s, 2H), 4.68 (s, 2H), 6.87-7.15 (m, 10H), 7.20-7.32 (m, 5H).

Example 29(74)

N-[4-(4-{[4-((2-cyclopropylethyl){[(4-fluorophenyl)amino]carbonyl}amino)piperidin-1-yl]methyl}phenoxy)phenyl]methanesulfonamide hydrochloride TLC:Rf 0.56(methylene chloride:methanol=9:1);
NMR (CD$_3$OD): δ 0.10-0.16 (m, 2H), 0.44-0.53 (m, 2H), 0.74 (m, 1H), 1.48-1.60 (m, 2H), 1.95-2.07 (m, 2H), 2.12-2.30 (m, 2H), 2.95 (s, 3H), 3.07-3.19 (m, 2H), 3.35-3.43 (m, 2H), 3.51-3.62 (m, 2H), 4.17 (m, 1H), 4.29 (s, 2H), 6.97-7.10 (m, 6H), 7.26-7.37 (m, 4H), 7.50 (d, J=8.7 Hz, 2H).

Example 29(75)

N-{4-[4-({4-[{[(2,4-difluorophenyl)amino]carbonyl}(pyridin-2-ylmethyl)amino]piperidin-1-yl}methyl)phenoxy]phenyl}methanesulfonamide dihydrochloride TLC:Rf 0.71(chloroform:methanol=5:1);
NMR (CD$_3$OD): δ 2.06-2.38 (m, 4H), 2.95 (s, 3H), 3.18 (m, 2H), 3.59 (m, 2H), 4.32 (s, 2H), 4.40 (m, 1H), 4.88 (s, 2H), 6.88-7.08 (m, 6H), 7.21-7.34 (m, 2H), 7.41 (m, 1H), 7.56 (brd, J=8.4 Hz, 2H), 7.91 (m, 1H), 8.00 (m, 1H), 8.52 (m, 1H), 8.76 (brd, J=5.4 Hz, 1H).

Example 29(76)

N-[4-(4-{[4-(but-3-enyl {[(2,4-difluorophenyl)amino]carbonyl}amino)piperidin-1-yl]methyl}phenoxy)phenyl]methanesulfonamide hydrochloride TLC:Rf 0.82(chloroform:methanol=5:1);
NMR (CD$_3$OD): δ 2.01 (m, 2H), 2.25 (m, 2H), 2.42 (m, 2H), 2.95 (s, 3H), 3.10 (m, 2H), 3.37 (m, 2H), 3.56 (m, 2H), 4.12 (m, 1H), 4.28 (m, 2H), 5.09 (brd, J=9.9 Hz, 1H), 5.16 (brd, J=17.1 Hz, 1H), 5.88 (m, 1H), 6.88-7.12 (m, 6H), 7.22-7.42 (m, 3H), 7.42-7.52 (m, 2H).

Example 29(77)

3-[({butyl[1-(4-{4-[(methylsulfonyl)amino]phenoxy}benzyl)piperidin-4-yl]amino}carbonyl)amino]benzamide hydrochloride TLC:Rf 0.45(chloroform:methanol=5:1);
NMR (CD$_3$OD): δ 0.97 (t, J=7.2 Hz, 3H), 1.30-1.50 (m, 2H), 1.50-1.70 (m, 2H), 1.90-2.10 (m, 2H), 2.20-2.30 (m, 2H), 2.95 (s, 3H), 3.00-3.20 (m, 2H), 3.20-3.40 (m, 2H), 3.50-3.60 (m, 2H), 4.20 (m, 1H), 4.30 (s, 2H), 7.02-7.08 (m, 4H), 7.29 (d, J=9.0 Hz, 2H), 7.38 (m, 1H), 7.49-7.52 (m, 4H), 7.84 (m, 1H).

Example 29(78)

N-(4-{4-[(4-{butyl[(1H-pyrazol-4-ylamino)carbonyl]amino}piperidin-1-yl)methyl]phenoxy}phenyl)methanesulfonamide dihydrochloride TLC:Rf 0.47(chloroform:methanol=5:1);
NMR (CD$_3$OD): δ 0.97 (t, J=7.2 Hz, 3H), 1.30-1.50 (m, 2H), 1.50-1.70 (m, 2H), 1.90-2.10 (m, 2H), 2.20-2.30 (m, 2H), 2.95 (s, 3H), 3.10-3.20 (m, 2H), 3.20-3.40 (m, 2H), 3.50-3.60 (m, 2H), 4.20 (m, 1H), 4.30 (s, 2H), 7.02-7.08 (m, 4H), 7.29 (d, J=9.0 Hz, 2H), 7.52 (d, J=9.0 Hz, 2H), 8.10 (s, 2H).

Example 29(79)

N-{4-[4-({4-[butyl({[1-methyl-5-(trifluoromethyl)-1H-pyrazol-4-yl]amino}carbonyl)amino]piperidin-1-yl}methyl)phenoxy]phenyl}methanesulfonamide dihydrochloride TLC:Rf 0.88(chloroform:methanol=5:1);
NMR (CD$_3$OD): δ 0.97 (t, J=7.4 Hz, 3H), 1.30-1.50 (m, 2H), 1.60-1.80 (m, 2H), 1.90-2.10 (m, 2H), 2.10-2.30 (m, 2H), 2.95 (s, 3H), 3.00-3.20 (m, 2H), 3.20-3.30 (m, 2H), 3.50-3.60 (m, 2H), 3.90 (s, 3H), 4.10 (m, 1H), 4.28 (s, 2H), 7.02-7.08 (m, 4H), 7.29 (d, J=9.0 Hz, 2H), 7.49 (d, J=9.0 Hz, 2H), 7.71 (s, 1H).

Example 29(80)

N-{4-[4-({4-[{[(4-fluorophenyl)amino]carbonyl}(1H-tetrazol-5-ylmethyl)amino]piperidin-1-yl}methyl)phenoxy]phenyl}methanesulfonamide hydrochloride TLC:Rf 0.29(n-butanol:acetic acid:water=20:4:1);
NMR (CD$_3$OD): δ 1.98-2.25 (m, 4H), 2.95 (s, 3H), 3.15 (m, 2H), 3.58 (m, 2H), 4.30 (s, 2H), 4.34 (m, 1H), 4.84 (s, 2H), 6.98-7.08 (m, 6H), 7.24-7.41 (m, 4H), 7.51 (brd, J=8.7 Hz, 2H).

Example 29(81)

N-[4-(4-{[4-(but-3-enyl{[(1-methyl-1H-pyrazol-4-yl)amino]carbonyl}amino)piperidin-1-yl]methyl}phenoxy)phenyl]methanesulfonamide dihydrochloride TLC:Rf 0.75(chloroform:methanol=5:1);
NMR (CD$_3$OD): δ 1.98 (m, 2H), 2.21 (m, 2H), 2.35 (m, 2H), 2.95 (s, 3H), 3.12 (m, 2H), 3.24-3.38 (m, 2H), 3.57 (m, 2H), 3.87 (s, 3H), 4.12 (m, 1H), 4.29 (s, 2H), 5.00-5.20 (m, 2H), 5.76-5.94 (m, 1H), 7.00-7.10 (m, 4H), 7.22-7.34 (m, 2H), 7.42-7.60 (m, 3H), 7.73 (m, 1H).

Example 29(82)

N-{4-[4-({4-[{[(6-methylpyridin-3-yl)amino]carbonyl}(pyridin-2-ylmethyl)amino]piperidin-1-yl}methyl)phenoxy]phenyl}methanesulfonamide trihydrochloride TLC:Rf 0.68(chloroform:methanol=5:1);
NMR (CD$_3$OD): δ 2.00 (m, 2H), 2.22 (m, 2H), 2.70 (s, 3H), 2.95 (s, 3H), 3.17 (m, 2H), 3.55 (m, 2H), 4.30 (s, 2H), 4.48 (m, 1H), 4.75 (s, 2H), 6.98-7.10 (m, 4H), 7.29 (brd, J=9.0 Hz, 2H), 7.48-7.56 (m, 3H), 7.62 (m, 1H), 7.80 (d, J=8.7 Hz, 1H), 8.02 (m, 1H), 8.42 (m, 1H), 8.63 (m, 1H), 9.02 (d, J=1.8 Hz, 1H).

Example 29(83)

N-{4-[4-({4-[{[(4-fluorophenyl)amino]carbonyl}(phenyl)amino]piperidin-1-yl}methyl)phenoxy]phenyl}methanesulfonamide hydrochloride TLC:Rf 0.49(methylene chloride:methanol=9:1);
NMR (CD$_3$OD): δ 1.60-1.80 (m, 2H), 2.12-2.21 (m, 2H), 2.95 (s, 3H), 3.10-3.21 (m, 2H), 3.42-3.52 (m, 2H), 4.22 (s, 2H), 4.66 (m, 1H), 6.95 (t, J=9.0 Hz, 2H), 7.01 (d, J=8.7 Hz, 2H), 7.03 (d, J=8.7 Hz, 2H), 7.19-7.35 (m, 6H), 7.42 (d, J=8.7 Hz, 2H), 7.46-7.57 (m, 3H).

Example 29(84)

N-(4-{4-[(4-{butyl[(1H-indol-5-ylamino)carbonyl]amino}piperidin-1-yl)methyl]phenoxy}phenyl)methanesulfonamide hydrochloride TLC:Rf 0.65(chloroform:methanol=5:1);
NMR (CD$_3$OD): δ 0.98 (t, J=7.4 Hz, 3H), 1.30-1.50 (m, 2H), 1.60-1.70 (m, 2H), 1.90-2.00 (m, 2H), 2.10-2.30 (m, 2H), 2.95 (s, 3H), 3.00-3.20 (m, 2H), 3.20-3.40 (m, 2H), 3.50-3.60 (m, 2H), 4.20 (m, 1H), 4.25 (s, 2H), 7.02-7.07 (m, 6H), 7.21 (s, 1H), 7.28-7.32 (m, 3H), 7.44 (m, 1H), 7.50 (d, J=9.0 Hz, 2H).

Example 29(85)

N-{4-[4-({4-[butyl({[1-methyl-3-(trifluoromethyl)-1H-pyrazol-4-yl]amino}carbonyl)amino]piperidin-1-yl}methyl)phenoxy]phenyl}methanesulfonamide dihydrochloride TLC:Rf 0.84(chloroform:methanol=5:1);
NMR (CD$_3$OD): δ 0.96 (t, J=7.2 Hz, 3H), 1.30-1.40 (m, 2H), 1.50-1.70 (m, 2H), 1.90-2.00 (m, 2H), 2.20-2.30 (m, 2H), 2.95 (s, 3H), 3.00-3.20 (m, 2H), 3.20-3.40 (m, 2H), 3.50-3.60 (m, 2H), 3.90 (s, 3H), 4.15 (m, 1H), 4.28 (s, 2H), 7.02-7.07 (m, 4H), 7.29 (d, J=9.0 Hz, 2H) 7.51 (d, J=9.0 Hz, 2H), 7.71 (s, 1H).

Example 29(86)

N-[4-(4-{4-[(4-(butyl{[(2-fluoro-5-hydroxyphenyl)amino]carbonyl}amino)piperidin-1-yl]methyl}phenoxy)phenyl]methanesulfonamide hydrochloride TLC:Rf 0.82(chloroform:methanol=5:1);
NMR (CD$_3$OD): δ 0.97 (t, J=7.4 Hz, 3H), 1.30-1.50 (m, 2H), 1.60-1.70 (m, 2H), 1.90-2.00 (m, 2H), 2.10-2.30 (m, 2H), 2.95 (s, 3H), 3.00-3.20 (m, 2H), 3.20-3.40 (m, 2H), 3.50-3.60 (m, 2H), 4.20 (m, 1H), 4.29 (s, 2H), 6.52 (m, 1H), 6.88 (m, 1H), 6.95 (m, 1H), 7.02-7.08 (m, 4H), 7.29 (d, J=8.9 Hz, 2H), 7.51 (d, J=8.9 Hz, 2H).

Example 29(87)

N-{4-[4-({4-[[(cyclobutylamino)carbonyl](1,3-thiazol-2-ylmethyl)amino]piperidin-1-yl}methyl)phenoxy]phenyl}methanesulfonamide hydrochloride TLC:Rf 0.68(chloroform:methanol=5:1);
NMR (CD$_3$OD): δ 1.60-1.78 (m, 2H), 1.84-2.36 (m, 8H), 2.95 (s, 3H), 3.12 (m, 2H), 3.56 (m, 2H), 4.16-4.30 (m, 2H), 4.29 (s, 2H), 4.81 (m, 2H), 7.00-7.12 (m, 4H), 7.29 (brd, J=8.7 Hz, 2H), 7.52 (brd, J=8.7 Hz, 2H), 7.77 (brd, J=3.6 Hz, 1H), 7.92 (brd, J=3.6 Hz, 1H).

Example 29(88)

N-{4-[4-({4-[{[(6-methylpyridin-3-yl)amino]carbonyl}(1,3-thiazol-2-ylmethyl)amino]piperidin-1-yl}methyl)phenoxy]phenyl}methanesulfonamide dihydrochloride TLC:Rf 0.61(chloroform:methanol=5:1);
NMR (CD$_3$OD): δ 2.00-2.18 (m, 2H), 2.18-2.40 (m, 2H), 2.71 (s, 3H), 2.95 (s, 3H), 3.29 (m, 2H), 3.57 (m, 2H), 4.32 (s, 2H), 4.59 (m, 1H), 5.00 (s, 2H), 7.00-7.12 (m, 4H), 7.29 (brd, J=9.0 Hz, 2H), 7.55 (brd, J=8.4 Hz, 2H), 7.77 (m, 1H), 7.82 (d, J=9.0 Hz, 1H), 7.94 (brd, J=2.1 Hz, 1H), 8.58 (m, 1H), 9.08 (brd, J=2.1 Hz, 1H).

Example 29(89)

N-{4-[4-({4-[{[(2,4-difluorophenyl)amino]carbonyl}(1,3-thiazol-2-ylmethyl)amino]piperidin-1-yl}methyl)phenoxy]phenyl}methanesulfonamide hydrochloride TLC:Rf 0.73(chloroform:methanol=5:1);
NMR (CD$_3$OD): δ 2.00-2.32 (m, 4H), 2.95 (s, 3H), 3.12 (m, 2H), 3.57 (m, 2H), 4.29 (s, 2H), 4.32 (m, 1H), 4.91 (s, 2H), 6.90-7.12 (m, 6H), 7.29 (brd, J=9.0 Hz, 2H), 7.39-7.60 (m, 3H), 7.70 (brd, J=3.3 Hz, 1H), 7.88 (brd, J=3.3 Hz, 1H).

Example 29(90)

N-(4-{4-[(4-{{[(4-fluorophenyl)amino]carbonyl}[(2-methylpyridin-3-yl)methyl]amino}piperidin-1-yl)methyl]phenoxy}phenyl)methanesulfonamide dihydrochloride TLC:Rf 0.67(chloroform:methanol=5:1);
NMR (CD$_3$OD): δ 2.00-2.11 (m, 2H), 2.12-2.38 (m, 2H), 2.82 (s, 3H), 2.95 (s, 3H), 3.13 (m, 2H), 3.54 (m, 2H), 4.29 (s, 2H), 4.49 (m, 1H), 4.69 (s, 2H), 6.96-7.10 (m, 6H), 7.14-7.38 (m, 4H), 7.54 (brd, J=8.4 Hz, 2H), 7.82 (m, 1H), 8.32 (m, 1H), 8.56 (d, J=5.4 Hz, 1H).

Example 29(91)

N-(4-{4-[(4-{{[(2,4-difluorophenyl)amino]carbonyl}[(3-methylpyridin-2-yl)methyl]amino}piperidin-1-yl)methyl]phenoxy}phenyl)methanesulfonamide dihydrochloride TLC:Rf 0.55(methylene chloride:methanol=9:1);
NMR (CD$_3$OD): δ 2.08-2.35 (m, 4H), 2.62 (s, 3H), 2.95 (s, 3H), 3.12-3.25 (m, 2H), 3.52-3.61 (m, 2H), 4.31 (s, 2H), 4.47

(m, 1H), 4.92 (s, 2H), 6.90-7.00 (m, 2H), 7.02 (d, J=8.7 Hz, 2H), 7.04 (d, J=8.7 Hz, 2H), 7.28 (d, J=8.7 Hz, 2H), 7.47 (dt, J=6.0, 9.0 Hz, 1H), 7.56 (d, J=8.7 Hz, 2H), 7.89 (dd, J=7.5, 5.7 Hz, 1H), 8.44 (d, J=7.5 Hz, 1H), 8.57 (d, J=5.7 Hz, 1H).

Example 29(92)

N-(4-{4-[(4-{[(cyclobutylamino)carbonyl][(3-methylpyridin-2-yl)methyl]amino}piperidin-1-yl)methyl]phenoxy}phenyl)methanesulfonamide dihydrochloride TLC:Rf 0.50(methylene chloride:methanol=9:1);
NMR (CD$_3$OD): δ 1.63-1.75 (m, 2H), 1.95-2.30 (m, 8H), 2.59 (s, 3H), 2.95 (s, 3H), 3.10-3.22 (m, 2H), 3.49-3.58 (m, 2H), 4.20-4.37 (m, 4H), 4.74 (s, 2H), 7.02 (d, J=8.7 Hz, 2H), 7.04 (d, J=8.7 Hz, 2H), 7.28 (d, J=8.7 Hz, 2H), 7.54 (d, J=8.7 Hz, 2H), 7.86 (dd, J=7.5, 6.0 Hz, 1H), 8.40 (d, J=7.5 Hz, 1H), 8.51 (d, J=6.0 Hz, 1H).

Example 29(93)

N-(4-{4-[(4-{{[(6-methylpyridin-3-yl)amino]carbonyl}[(3-methylpyridin-2-yl)methyl]amino}piperidin-1-yl)methyl]phenoxy}phenyl)methanesulfonamide trihydrochloride TLC:Rf 0.47(methylene chloride:methanol=9:1);
NMR (CD$_3$OD): δ 2.10-2.39 (m, 4H), 2.64 (s, 3H), 2.71 (s, 3H), 2.95 (s, 3H), 3.22-3.35 (m, 2H), 3.50-3.60 (m, 2H), 4.32 (s, 2H), 4.75 (m, 1H), 4.96 (s, 2H), 7.02 (d, J=8.7 Hz, 2H), 7.04 (d, J=8.7 Hz, 2H), 7.28 (d, J=8.7 Hz, 2H), 7.57 (d, J=8.7 Hz, 2H), 7.83 (d, J=8.7 Hz, 1H), 7.89 (dd, J=7.5, 5.1 Hz, 1H), 8.44 (d, J=7.5 Hz, 1H), 8.57 (d, J=5.1 Hz, 1H), 8.68 (dd, J=8.7, 2.4 Hz, 1H), 9.12 (d, J=2.4 Hz, 1H).

Example 29(94)

N-{4-[4-({4-[{[(4-fluorophenyl)amino]carbonyl}(pyrimidin-2-ylmethyl)amino]piperidin-1-yl}methyl)phenoxy]phenyl}methanesulfonamide dihydro chloride TLC:Rf 0.40(methylene chloride:methanol=9:1);
NMR (DMSO-d$_6$): δ 1.80-1.89 (m, 2H), 2.10-2.30 (m, 2H), 2.96 (s, 3H), 2.97-3.10 (m, 2H), 4.21 (s, 2H), 4.36 (m, 1H), 4.70 (s, 2H), 6.98-7.07 (m, 6H), 7.28 (d, J=8.7 Hz, 2H), 7.35-7.43 (m, 3H), 7.55 (d, J=8.7 Hz, 2H), 8.60 (m, 1H), 8.78 (d, J=5.1 Hz, 2H), 9.35 (m, 1H).

Example 29(95)

N-[4-(4-{[4-(butyl{[(2,4,6-trifluorophenyl)amino]carbonyl}amino)piperidin-1-yl]methyl}phenoxy)phenyl]methanesulfonamide hydrochloride TLC:Rf 0.71(chloroform:methanol=5:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.15 (m, 1H), 4.28 (s, 2H), 6.88-6.94 (m, 2H), 7.02-7.07 (m, 4H), 7.29 (d, J=9.2 Hz, 2H), 7.51 (d, J=9.2 Hz, 2H).

Example 29(96)

N-(4-{4-[(4-{{[(2-hydroxybutyl)amino]carbonyl}[(3-methylpyridin-2-yl)methyl]amino}piperidin-1-yl)methyl]phenoxy}phenyl)methanesulfonamide dihydrochloride TLC:Rf 0.39(methylene chloride:methanol=9:1);
NMR (CD$_3$OD): δ 0.96 (t, J=7.2 Hz, 3H), 1.37-1.58 (m, 2H), 1.97-2.25 (m, 4H), 2.60 (s, 3H), 2.95 (s, 3H), 3.10-3.23 (m, 4H), 3.50-3.67 (m, 3H), 4.27-4.38 (m, 3H), 4.80 (s, 2H), 7.02 (d, J=8.7 Hz, 2H), 7.04 (d, J=8.7 Hz, 2H), 7.29 (d, J=8.7 Hz, 2H), 7.55 (d, J=8.7 Hz, 2H), 7.88 (dd, J=7.8, 6.0 Hz, 1H), 8.42 (d, J=7.8 Hz, 1H), 8.54 (d, J=6.0 Hz, 1H).

Example 29(97)

N-{4-[4-({4-[[(cyclobutylamino)carbonyl](pyridin-2-ylmethyl)amino]piperidin-1-yl}methyl)phenoxy]phenyl}methanesulfonamide dihydrochloride TLC:Rf 0.54(chloroform:methanol=5:1);
NMR (CD$_3$OD): δ 1.60-1.74 (m, 2H), 1.90-2.30 (m, 8H), 2.95 (s, 3H), 3.11 (m, 2H), 3.56 (m, 2H), 4.18-4.32 (m, 2H), 4.30 (s, 2H), 4.72 (s, 2H), 7.00-7.10 (m, 4H), 7.29 (brd, J=9.0 Hz, 2H), 7.53 (brd, J=8.7 Hz, 2H), 7.80-7.92 (m, 2H), 8.44 (m, 1H), 8.71 (brd, J=5.4 Hz, 1H).

Example 29(98)

N-{4-[4-({4-[{[(2-hydroxybutyl)amino]carbonyl}(2-methylbenzyl)amino]piperidin-1-yl}methyl)phenoxy]phenyl}methanesulfonamide hydrochloride TLC:Rf 0.61(chloroform:methanol=5:1);
NMR (CD$_3$OD): δ 0.90 (t, J=7.5 Hz, 3H), 1.20-1.50 (m, 2H), 1.90-2.02 (m, 4H), 2.32 (s, 3H), 2.95 (s, 3H), 3.00-3.34 (m, 4H), 3.42-3.51 (m, 3H), 4.24 (s, 2H), 4.39 (s, 2H), 4.41 (m, 1H), 6.98-7.04 (m, 4H), 7.08-7.20 (m, 4H), 7.28 (brd, 9.0 Hz, 2H), 7.45 (brd, J=8.4 Hz, 2H).

Example 29(99)

5-[({butyl[1-(4-{4-[(methylsulfonyl)amino]phenoxy}benzyl)piperidin-4-yl]amino}carbonyl)amino]-2-fluorobenzamide hydrochloride TLC:Rf 0.67(chloroform:methanol=5:1);
NMR (CD$_3$OD): δ 0.97 (t, J=7.2 Hz, 3H), 1.30-1.50 (m, 2H), 1.50-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 7.02-7.07 (m, 4H), 7.13 (m, 1H), 7.29 (d, J=9.0 Hz, 2H), 7.50 (d, J=9.0 Hz, 2H), 7.52 (m, 1H), 7.78 (m, 1H).

Example 29(100)

3-[({butyl[1-(4-{4-[(methylsulfonyl)amino]phenoxy}benzyl)piperidin-4-yl]amino}carbonyl)amino]-2,6-difluorobenzamide hydrochloride TLC:Rf 0.64(chloroform:methanol=5:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.10-2.20 (m, 2H), 2.95 (s, 3H), 3.00-3.20 (m, 2H), 3.20-3.40 (m, 2H), 3.50-3.60 (m, 2H), 4.15 (m, 1H), 4.28 (s, 2H), 7.02-7.07 (m, 5H), 7.29 (d, J=8.7 Hz, 2H), 7.44 (m, 1H), 7.49 (d, J=8.7 Hz, 2H).

Example 29(101)

5-[({butyl[1-(4-{4-[(methylsulfonyl)amino] phenoxy}benzyl)piperidin-4-yl]amino}carbonyl) amino]-2,4-difluorobenzamide hydrochloride TLC:Rf 0.65(chloroform:methanol=5:1);
NMR (CD$_3$OD): δ 0.98 (t, J=7.2 Hz, 3H), 1.30-1.50 (m, 2H), 1.60-1.80 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.10 (m, 1H), 4.28 (s, 2H), 7.02-7.07 (m, 4H), 7.17 (t, J=10.5 Hz, 1H), 7.29 (d, J=9.0 Hz, 2H), 7.49 (d, J=9.0 Hz, 2H), 7.85 (m, 1H).

Example 29(102)

N-[4-(4-{[4-(butyl{[(3-cyano-4-fluorophenyl)amino] carbonyl}amino)piperidin-1-yl]methyl}phenoxy) phenyl]methanesulfonamide hydrochloride TLC:Rf 0.66(chloroform:methanol=5:1);
NMR (CD$_3$OD): δ 0.97 (t, J=7.4 Hz, 3H), 1.30-1.50 (m, 2H), 1.50-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 7.02-7.07 (m, 4H), 7.23-7.31 (m, 3H), 7.50 (d, J=8.7 Hz, 2H), 7.66 (m, 1H), 7.91 (m, 1H).

Example 29(103)

N-[4-(4-{[4-(butyl{[(5-cyano-2,4-difluorophenyl) amino]carbonyl}amino)piperidin-1-yl] methyl}phenoxy)phenyl]methanesulfonamide hydrochloride TLC:Rf 0.64(chloroform:methanol=5:1);
NMR (CD$_3$OD): δ 0.98 (t, J=7.4 Hz, 3H), 1.30-1.50 (m, 2H), 1.50-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.10 (m, 1H), 4.29 (s, 2H), 7.02-7.08 (m, 4H), 7.29 (d, J=8.9 Hz, 2H), 7.35 (m, 1H) 7.49 (d, J=8.9 Hz, 2H), 7.87 (m, 1H).

Example 29(104)

N-[4-(4-{[4-((2-fluorophenyl){[(4-fluorophenyl) amino]carbonyl}amino)piperidin-1-yl] methyl}phenoxy)phenyl]methanesulfonamide hydrochloride TLC:Rf 0.51(methylene chloride:methanol=9:1);
NMR (CD$_3$OD): δ 1.55-1.80 (m, 2H), 2.16-2.23 (m, 2H), 2.95 (s, 3H), 3.10-3.22 (m, 2H), 3.47-3.56 (m, 2H), 4.23 (s, 2H), 4.64 (m, 1H), 6.93-7.06 (m, 6H), 7.20-7.45 (m, 9H), 7.51 (m, 1H).

Example 29(105)

N-[4-(4-{[4-((3-fluorophenyl){[(4-fluorophenyl) amino]carbonyl}amino)piperidin-1-yl] methyl}phenoxy)phenyl]methanesulfonamide hydrochloride TLC:Rf 0.52(methylene chloride:methanol=9:1);
NMR (CD$_3$OD): δ 1.63-1.82 (m, 2H), 2.12 2.23 (m, 2H), 2.95 (s, 3H), 3.10-3.21 (m, 2H), 3.44-3.55 (m, 2H), 4.23 (s, 2H), 4.64 (m, 1H), 6.93-7.07 (m, 6H), 7.15 (d, J=6.9 Hz, 2H), 7.20-7.32 (m, 5H), 7.42 (d, J=8.7 Hz, 2H), 7.54 (q, J=6.9 Hz, 1H).

Example 29(106)

N-[4-(4-{[4-((4-fluorophenyl){[(4-fluorophenyl) amino]carbonyl}amino)piperidin-1-yl] methyl}phenoxy)phenyl]methanesulfonamide hydrochloride TLC:Rf 0.54(methylene chloride:methanol=9:1);
NMR (CD$_3$OD): δ 1.59-1.79 (m, 2H), 2.10-2.20 (m, 2H), 2.95 (s, 3H), 3.09-3.21 (m, 2H), 3.45-3.54 (m, 2H), 4.22 (s, 2H), 4.64 (m, 1H), 6.91-7.05 (m, 6H), 7.20-7.38 (m, 8H), 7.43 (d, J=8.7 Hz, 2H).

Example 29(107)

N-[4-(4-{[4-(butyl{[(4-cyano-2-fluorophenyl)amino] carbonyl}amino)piperidin-1-yl]methyl}phenoxy) phenyl]methanesulfonamide hydrochloride TLC:Rf 0.81(chloroform:methanol=5:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.20 (m, 1H), 4.29 (s, 2H), 7.02-7.07 (m, 4H), 7.29 (d, J=8.7 Hz, 2H), 7.50 (m, 1H), 7.50 (d, J=8.7 Hz, 2H), 7.56 (dd, J=10.5, 1.8 Hz, 1H), 7.83 (m, 1H).

Example 29(108)

N-{4-[4-({4-[{[(4-fluorophenyl)amino]carbonyl} (pyridin-3-yl)amino]piperidin-1-yl}methyl)phenoxy] phenyl}methanesulfonamide dihydrochloride TLC:Rf 0.46(methylene chloride:methanol=9:1);
NMR (CD$_3$OD): δ 1.95-2.10 (m, 2H), 2.18-2.24 (m, 2H), 2.95 (s, 3H), 3.11-3.23 (m, 2H), 3.49-3.58 (m, 2H), 4.26 (s, 2H), 4.64 (m, 1H), 6.97-7.07 (m, 6H), 7.26-7.35 (m, 4H), 7.50 (d, J=8.7 Hz, 2H), 8.15 (dd, J=8.7, 5.7 Hz, 1H), 8.58 (dq, J=8.7, 2.4 Hz, 1H), 8.89 (d, J=5.7 Hz, 1H), 9.04 (d, J=2.4 Hz, 1H).

Example 29(109)

N-{4-[4-({4-[{[(4-fluorophenyl)amino]carbonyl}(2-methylphenyl)amino]piperidin-1-yl}methyl)phenoxy]phenyl}methanesulfonamide hydrochloride TLC:Rf 0.57(methylene chloride:methanol=9:1);
NMR (CD$_3$OD): δ 1.62 (m, 1H), 1.97-2.10 (m, 2H), 2.28-2.40 (m, 4H), 2.95 (s, 3H), 3.07-3.20 (m, 2H), 3.40-3.57 (m, 2H), 4.22 (s, 2H), 4.55 (m, 1H), 6.95 (t, J=9.0 Hz, 2H), 7.01 (d, J=8.7 Hz, 2H), 7.03 (d, J=8.7 Hz, 2H), 7.08-7.47 (m, 10H).

Example 29(110)

N-{4-[4-({4-[{[(4-fluorophenyl)amino]carbonyl}(3-methylphenyl)amino]piperidin-1-yl}methyl)phenoxy]phenyl}methanesulfonamide hydrochloride TLC:Rf 0.57(methylene chloride:methanol=9:1);
NMR (CD$_3$OD): δ 1.62-1.80 (m, 2H), 2.11-2.20 (m, 2H), 2.40 (s, 3H), 2.95 (s, 3H), 3.09-3.21 (m, 2H), 3.45-3.54 (m, 2H), 4.23 (s, 2H), 4.63 (m, 1H), 6.95 (t, J=9.0 Hz, 2H), 7.01 (d, J=8.7 Hz, 2H), 7.03 (d, J=8.7 Hz, 2H), 7.12 (d, J=7.5 Hz, 1H), 7.15 (s, 1H), 7.21 (dd, J=9.0, 5.0 Hz, 2H), 7.25-7.35 (m, 3H), 7.40 (d, J=7.5 Hz, 1H), 7.42 (d, J=8.7 Hz, 2H).

Example 29(111)

N-{4-[4-({4-[{[(4-fluorophenyl)amino]carbonyl}(4-methylphenyl)amino]piperidin-1-yl}methyl)phenoxy]phenyl}methanesulfonamide hydrochloride TLC:Rf 0.58(methylene chloride:methanol=9:1);
NMR (CD$_3$OD): δ 1.59-1.78 (m, 2H), 2.10-2.20 (m, 2H), 2.40 (s, 3H), 2.95 (s, 3H), 3.08-3.20 (m, 2H), 3.44-3.50 (m, 2H), 4.21 (s, 2H), 4.67 (m, 1H), 6.95 (t, J=9.0 Hz, 2H), 6.98-7.08 (m, 4H), 7.18-7.23 (m, 4H), 7.29 (d, J=8.7 Hz, 2H), 7.36 (d, J=7.8 Hz, 2H), 7.42 (d, J=8.7 Hz, 2H).

Example 29(112)

N-[4-(4-{[4-(butyl{[(2-hydroxyphenyl)amino]carbonyl}amino)piperidin-1-yl]methyl}phenoxy)phenyl]methanesulfonamide hydrochloride TLC:Rf 0.63(ethyl acetate);
NMR (CD$_3$OD): δ 1.00 (t, J=7.2 Hz, 3H), 1.37-1.49 (m, 2H), 1.63-1.71 (m, 2H), 1.98-2.03 (m, 2H), 2.14-2.27 (m, 2H), 2.96 (s, 3H), 3.09-3.17 (m, 2H), 3.25-3.30 (m, 2H), 3.55-3.59 (m, 2H), 4.24 (m, 1H), 4.30 (s, 2H), 6.76-6.94 (m, 3H), 7.04 (d, J=8.7 Hz, 2H), 7.07 (d, J=8.7 Hz, 2H), 7.30 (d, J=8.7 Hz, 2H), 7.50 (d, J=8.7 Hz, 2H), 7.59 (dd, J=7.8, 1.5 Hz, 1H).

Example 29(113)

N-{2-[({butyl[1-(4-{4-[(methylsulfonyl)amino]phenoxy}benzyl)piperidin-4-yl]amino}carbonyl)amino]phenyl}methanesulfonamide hydrochloride TLC:Rf 0.50(chloroform:methanol=10:1);
NMR (CD$_3$OD): δ 0.98 (t, J=7.2 Hz, 3H), 1.30-1.50 (m, 2H), 1.60-1.80 (m, 2H), 2.00-2.10 (m, 2H), 2.10-2.20 (m, 2H), 2.95 (s, 3H), 2.97 (s, 3H), 3.00-3.20 (m, 2H), 3.20-3.40 (m, 2H), 3.60-3.80 (m, 2H), 4.20 (m, 1H), 4.29 (s, 2H), 7.02-7.08 (m, 4H), 7.15 (m, 1H), 7.26-7.31 (m, 4H), 7.50 (d, J=9.0 Hz, 2H), 7.75 (d, J=8.1 Hz, 1H).

Example 29(114)

N-{4-[4-({4-[{[(4-fluorophenyl)amino]carbonyl}(4-methylbenzyl)amino]piperidin-1-yl}methyl)phenoxy]phenyl}methanesulfonamide hydrochloride TLC:Rf 0.71(chloroform:methanol=5:1);
NMR (CD$_3$OD): δ 7.47 (brd, J=8.7 Hz, 2H), 7.36-7.14 (m, 8H), 7.10-6.92 (m, 6H), 4.60 (brs, 2H), 4.37 (m, 1H), 4.25 (s, 2H), 3.50 (m, 2H), 3.09 (m, 2H), 2.95 (s, 3H), 2.30 (s, 3H), 2.26-1.84 (m, 4H).

Example 29(115)

N-[4-(4-{[4-(butyl{[(3,4-dihydroxyphenyl)amino]carbonyl}amino)piperidin-1-yl]methyl}phenoxy)phenyl]methanesulfonamide hydrochloride TLC:Rf 0.40(chloroform:methanol=10:1);
NMR (CD$_3$OD): δ 0.96 (t, J=7.4 Hz, 3H), 1.30-1.50 (m, 2H), 1.50-1.70 (m, 2H), 1.90-2.10 (m, 2H), 2.10-2.30 (m, 2H), 2.95 (s, 3H), 3.00-3.20 (m, 2H), 3.20-3.40 (m, 2H), 3.50-3.60 (m, 2H), 4.15 (m, 1H), 4.28 (s, 2H), 6.58 (dd, J=8.4, 2.4 Hz, 1H), 6.68 (d, J=8.4 Hz, 1H), 6.79 (d, J=2.4 Hz, 1H), 7.02-7.08 (m, 4H), 7.29 (d, J=8.9 Hz, 2H), 7.50 (d, J=8.9 Hz, 2H).

Example 29(116)

N-[4-(4-{[4-((cyanomethyl){[(4-fluorophenyl)amino]carbonyl}amino)piperidin-1-yl]methyl}phenoxy)phenyl]methanesulfonamide hydrochloride TLC:Rf 0.55(chloroform:methanol=5:1);
NMR (CD$_3$OD): δ 2.00-2.28 (m, 4H), 2.95 (s, 3H), 3.00-3.10 (m, 2H), 3.50-3.65 (m, 2H), 4.04-4.30 (m, 5H), 7.00-7.20 (m, 4H), 7.25-7.52 (m, 8H).

Example 29(117)

N-{4-[4-({4-[butyl({[3-(2H-tetrazol-5-yl)phenyl]amino}carbonyl)amino]piperidin-1-yl}methyl)phenoxy]phenyl}methanesulfonamide hydrochloride TLC:Rf 0.09(chloroform:methanol=5:1);
NMR (CD$_3$OD): δ 0.97 (t, J=7.2 Hz, 3H), 1.40 (m, 3H), 1.62 (m, 3H), 1.88 (m, 2H), 2.60 (m, 4H), 2.94 (s, 3H), 3.24 (m, 2H), 3.92 (s, 2H), 4.18 (m, 1H), 7.00 (m, 4H), 7.20-7.50 (m, 5H), 7.71 (brd, J=7.8 Hz, 1H), 7.86 (m, H).

Example 29(118)

N-[4-(4-{[4-(but-3-en-1-yl{[(6-methylpyridin-3-yl)amino]carbonyl}amino)piperidin-1-yl]methyl}phenoxy)phenyl]methanesulfonamide dihydrochloride TLC:Rf 0.51(methylene chloride:methanol=9:1);
NMR (CD$_3$OD): δ 1.98-2.09 (m, 2H), 2.22-2.45 (m, 4H), 2.70 (s, 3H), 2.95 (s, 3H), 3.12-3.25 (m, 2H), 3.42 (t, J=7.8 Hz, 2H), 3.54-3.66 (m, 2H), 4.26 (m, 1H), 4.31 (s, 2H), 5.08 (d, J=10.2 Hz, 1H), 5.15 (d, J=17.1 Hz, 1H), 5.85 (m, 1H), 7.03 (d, J=8.7 Hz, 2H), 7.07 (d, J=8.7 Hz, 2H), 7.29 (d, J=8.7 Hz, 2H), 7.52 (d, J=8.7 Hz, 2H), 7.80 (d, J=9.0 Hz, 1H), 8.47 (dd, J=9.0, 2.4 Hz, 1H), 9.02 (d, J=2.4 Hz, 1H).

Example 29(119)

N-(4-{4-[(4-{but-3-en-1-yl[(cyclobutylamino)carbonyl]amino}piperidin-1-yl)methyl]phenoxy}phenyl)methanesulfonamide hydrochloride TLC:Rf 0.61(methylene chloride:methanol=9:1);
NMR (CD$_3$OD): δ 1.62-1.74 (m, 2H), 1.88-2.35 (m, 10H), 2.95 (s, 3H), 3.02-3.15 (m, 2H), 3.20 (t, J=7.8 Hz, 2H), 3.50-3.59 (m, 2H), 4.06 (m, 1H), 4.20 (m, 1H), 4.28 (s, 2H), 5.05 (d, J=10.2 Hz, 1H), 5.11 (dd, J=17.1, 2.1 Hz, 1H), 5.81 (m, 1H), 7.03 (d, J=8.7 Hz, 2H), 7.06 (d, J=8.7 Hz, 2H), 7.29 (d, J=8.7 Hz, 2H), 7.49 (d, J=8.7 Hz, 2H).

Example 29(120)

N-{4-[4-({4-[[(cyclobutylamino)carbonyl](3-methylbut-2-en-1-yl)amino]piperidin-1-yl}methyl)phenoxy]phenyl}methanesulfonamide hydrochloride TLC:Rf 0.60(methylene chloride:methanol=9:1);
NMR (CD$_3$OD): δ 1.60-2.18 (m, 14H), 2.20-2.30 (m, 2H), 2.95 (s, 3H), 3.02-3.15 (m, 2H), 3.49-3.59 (m, 2H), 3.77-3.82

(m, 2H), 4.15-4.25 (m, 2H), 4.27 (s, 2H), 5.06 (m, 1H), 7.03 (d, J=8.7 Hz, 2H), 7.05 (d, J=8.7 Hz, 2H), 7.29 (d, J=8.7 Hz, 2H), 7.49 (d, J=8.7 Hz, 2H).

Example 29(121)

N-{4-[4-({4-[{[(cis-4-hydroxycyclohexyl)amino]carbonyl}(3-methylbut-2-en-1-yl)amino]piperidin-1-yl}methyl)phenoxy]phenyl}methanesulfonamide hydrochloride TLC:Rf 0.45(methylene chloride:methanol=9:1);
NMR (CD$_3$OD): δ 1.54-1.70 (m, 8H), 1.74 (s, 6H), 1.80-2.10 (m, 4H), 2.95 (s, 3H), 3.05-3.15 (m, 2H), 3.49-3.66 (m, 3H), 3.74-3.84 (m, 3H), 4.27 (s, 2H), 4.31 (m, 1H), 5.08 (m, 1H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 29(122)

N-{4-[4-({4-[{[(cis-4-hydroxycyclohexyl)amino]carbonyl}(2-methylbenzyl)amino]piperidin-1-yl}methyl)phenoxy]phenyl}methanesulfonamide hydrochloride TLC:Rf 0.51(methylene chloride:methanol=9:1);
NMR (CD$_3$OD): δ 1.50-1.60 (m, 8H), 1.90-2.03 (m, 4H), 2.33 (s, 3H), 2.95 (s, 3H), 3.02-3.14 (m, 2H), 3.45-3.53 (m, 2H), 3.63 (m, 1H), 3.79 (m, 1H), 4.24 (s, 2H), 4.40 (s, 2H), 4.45 (m, 1H), 7.01 (d, J=8.7 Hz, 2H), 7.04 (d, J=8.7 Hz, 2H), 7.07-7.21 (m, 4H), 7.28 (d, J=8.7 Hz, 2H), 7.46 (d, J=8.7 Hz, 2H).

Example 29(123)

N-[4-(4-{[4-((2-methylbenzyl){[(1-methyl-1H-pyrazol-4-yl)amino]carbonyl}amino)piperidin-1-yl]methyl}phenoxy)phenyl]methanesulfonamide dihydrochloride TLC:Rf 0.53(methylene chloride:methanol=9:1);
NMR (CD$_3$OD): δ 1.91-2.19 (m, 4H), 2.35 (s, 3H), 2.95 (s, 3H), 3.06-3.17 (m, 2H), 3.44-3.52 (m, 2H), 3.94 (s, 3H), 4.29 (s, 2H), 4.49 (m, 1H), 4.52 (s, 2H), 7.02 (d, J=8.7 Hz, 2H), 7.03 (d, J=8.7 Hz, 2H), 7.06-7.20 (m, 4H), 7.28 (d, J=8.7 Hz, 2H), 7.48 (d, J=8.7 Hz, 2H), 7.77 (s, 1H), 7.94 (s, 1H).

Example 29(124)

N-(4-{4-[(4-{{[(1-methyl-1H-pyrazol-4-yl)amino]carbonyl}[(3-methylpyridin-2-yl)methyl]amino}piperidin-1-yl)methyl]phenoxy}phenyl)methanesulfonamide trihydrochloride TLC:Rf 0.49(methylene chloride:methanol=9:1);
NMR (CD$_3$OD): δ 2.00-2.10 (m, 2H), 2.18-2.35 (m, 2H), 2.63 (s, 3H), 2.95 (s, 3H), 3.18-3.34 (m, 2H), 3.50-3.60 (m, 2H), 3.96 (s, 3H), 4.32 (s, 2H), 4.54 (m, 1H), 4.91 (s, 2H), 7.02 (d, J=8.7 Hz, 2H), 7.04 (d, J=8.7 Hz, 2H), 7.28 (d, J=8.7 Hz, 2H), 7.57 (d, J=8.7 Hz, 2H), 7.89 (dd, J=7.8, 6.0 Hz, 1H), 7.94 (s, 1H), 8.06 (s, 1H), 8.45 (d, J=7.8 Hz, 1H), 8.54 (d, J=6.0 Hz, 1H).

Example 29(125)

N-[4-(4-{[4-((3-methylbut-2-en-1-yl){[(1-methyl-1H-pyrazol-4-yl)amino]carbonyl}amino)piperidin-1-yl]methyl}phenoxy)phenyl]methanesulfonamide dihydrochloride TLC:Rf 0.52(methylene chloride:methanol=9:1);
NMR (CD$_3$OD): δ 1.72 (s, 3H), 1.73 (s, 3H), 1.90-2.22 (m, 4H), 2.95 (s, 3H), 3.08-3.20 (m, 2H), 3.50-3.60 (m, 2H), 3.90-3.97 (m, 2H), 3.97 (s, 3H), 4.23-4.32 (m, 3H), 5.12 (m, 1H), 7.03 (d, J=8.7 Hz, 2H), 7.06 (d, J=8.7 Hz, 2H), 7.29 (d, J=8.7 Hz, 2H), 7.51 (d, J=8.7 Hz, 2H), 7.85 (s, 1H), 7.98 (s, 1H).

Example 29(126)

N-{3-[({butyl[1-(4-{4-[(methylsulfonyl)amino]phenoxy}benzyl)piperidin-4-yl]amino}carbonyl)amino]-2,4-difluorophenyl}acetamide hydrochloride TLC:Rf 0.44(chloroform:methanol=5:1);
NMR (CD$_3$OD): δ 0.98 (t, J=7.4 Hz, 3H), 1.30-1.50 (m, 2H), 1.60-1.70 (m, 2H), 1.90-2.10 (m, 2H), 2.14 (s, 3H), 2.20-2.30 (m, 2H), 2.95 (s, 3H), 3.00-3.20 (m, 2H), 3.20-3.40 (m, 2H), 3.50-3.60 (m, 2H), 4.15 (m, 1H), 4.28 (s, 2H), 6.97-7.08 (m, 5H), 7.29 (d, J=9.0 Hz, 2H), 7.49 (d, J=9.0 Hz, 2H), 7.65 (m, 1H).

Example 29(127)

N-{5-[({butyl[1-(4-{4-[(methylsulfonyl)amino]phenoxy}benzyl)piperidin-4-yl]amino}carbonyl)amino]-2,4-difluorophenyl}acetamide hydrochloride TLC:Rf 0.56(chloroform:methanol=5:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.14 (s, 3H), 2.20-2.30 (m, 2H), 2.95 (s, 3H), 3.00-3.20 (m, 2H), 3.20-3.40 (m, 2H), 3.50-3.60 (m, 2H), 4.15 (m, 1H), 4.28 (s, 2H), 7.02-7.10 (m, 5H), 7.29 (d, J=8.9 Hz, 2H), 7.49 (d, J=8.9 Hz, 2H), 7.95 (t, J=7.5 Hz, 1H).

Example 29(128)

N-{3-[({butyl[1-(4-{4-[(methylsulfonyl)amino]phenoxy}benzyl)piperidin-4-yl]amino}carbonyl)amino]-4-fluorophenyl}acetamide hydrochloride TLC:Rf 0.48(chloroform:methanol=5:1);
NMR (CD$_3$OD): δ 0.98 (t, J=7.5 Hz, 3H), 1.30-1.50 (m, 2H), 1.60-1.70 (m, 2H), 1.90-2.10 (m, 2H), 2.10 (s, 3H), 2.20-2.30 (m, 2H), 2.95 (s, 3H), 3.00-3.20 (m, 2H), 3.20-3.40 (m, 2H), 3.50-3.60 (m, 2H), 4.15 (m, 1H), 4.29 (s, 2H), 7.02-7.09 (m, 5H), 7.25 (m, 1H), 7.29 (d, J=8.7 Hz, 2H), 7.49 (d, J=8.7 Hz, 2H), 7.77 (dd, J=6.9, 2.4 Hz, 1H).

Example 29(129)

N-{4-[4-({4-[{[(4-fluorophenyl)amino]carbonyl}(tetrahydro-2H-pyran-4-yl)amino]piperidin-1-yl}methyl)phenoxy]phenyl}methanesulfonamide hydrochloride TLC:Rf 0.50(methylene chloride:methanol=9:1);
NMR (CD$_3$OD): δ 1.65-1.78 (m, 2H), 1.80-1.90 (m, 2H), 1.95-2.08 (m, 2H), 2.78-2.92 (m, 2H), 2.95 (s, 3H), 3.03-3.18

(m, 2H), 3.47-3.60 (m, 5H), 3.88-4.05 (m, 3H), 4.27 (s, 2H), 6.97-7.09 (m, 6H), 7.23-7.31 (m, 4H), 7.48 (d, J=8.7 Hz, 2H).

Example 29(130)

N-[4-(4-{[4-(butyl{[(1,3-dimethyl-1H-pyrazol-4-yl)amino]carbonyl}amino)piperidin-1-yl]methyl}phenoxy)phenyl]methanesulfonamide dihydrochloride TLC:Rf 0.66(chloroform:methanol=4:1);
NMR (CD$_3$OD): δ 0.97 (t, J=7.5 Hz, 3H), 1.30-1.50 (m, 2H), 1.60-1.80 (m, 2H), 1.90-2.10 (m, 2H), 2.20-2.40 (m, 2H), 2.28 (s, 3H), 2.95 (s, 3H), 3.00-3.20 (m, 2H), 3.20-3.40 (m, 2H), 3.50-3.60 (m, 2H), 3.99 (s, 3H), 4.20 (m, 1H), 4.29 (s, 2H), 7.02-7.08 (m, 4H), 7.29 (d, J=9.0 Hz, 2H), 7.52 (d, J=9.0 Hz, 2H), 7.95 (m, 1H).

Example 29(131)

N-[4-(4-{[4-({[(4-fluorophenyl)amino]carbonyl}{[3-(trifluoromethyl)pyridin-2-yl]methyl}amino)piperidin-1-yl]methyl}phenoxy)phenyl]methanesulfonamide dihydrochloride TLC:Rf 0.56(methylene chloride:methanol=9:1);
NMR (CD$_3$OD): δ 1.95-2.12 (m, 4H), 2.95 (s, 3H), 3.08-3.21 (m, 2H), 3.47-3.58 (m, 2H), 4.27 (s, 2H), 4.38 (m, 1H), 4.90 (s, 2H), 6.95-7.06 (m, 6H), 7.25-7.35 (m, 4H), 7.48 (d, J=8.7 Hz, 2H), 7.62 (dd, J=8.0, 5.0 Hz, 1H), 8.28 (d, J=8.0 Hz, 1H), 8.81 (d, J=5.0 Hz, 1H).

Example 30(1)-Example 30(12)

By the same procedure as described in Example 25, using a corresponding amine derivative instead of (3-{[t-butyl(dimethyl)silyloxy}butyl)amine, the following compounds of the present invention were obtained.

Example 30(1)

N-[4-(4-{[4-(butyl{[(3S)-piperidin-3-ylamino]carbonyl}amino)piperidin-1-yl]methyl}phenoxy)phenyl]methanesulfonamide dihydrochloride

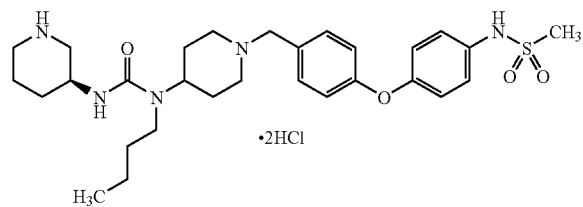

TLC:Rf 0.15 (n-butanol: acetic acid:water=4:2:1);
NMR (DMSO-d$_6$): δ 0.91 (t, J=7.1 Hz, 3H), 1.20-1.40 (m, 2H), 1.40-1.60 (m, 2H), 1.60-2.00 (m, 6H), 2.20-2.40 (m, 2H), 2.80-3.60 (m, 10H), 2.96 (s, 3H), 3.99 (m, 1H), 4.15 (m, 1H), 4.18 (s, 2H), 6.23 (m, 1H), 7.03 (d, J=7.2 Hz, 4H), 7.28 (d, J=8.7 Hz, 2H), 7.61 (d, J=8.7 Hz, 2H), 8.83 (m, 1H), 9.35 (m, 1H), 9.47 (m, 1H).

Example 30(2)

N-[4-(4-{[4-(butyl{[(3R)-piperidin-3-ylamino]carbonyl}amino)piperidin-1-yl]methyl}phenoxy)phenyl]methanesulfonamide dihydrochloride TLC:Rf 0.15(n-butanol:acetic acid:water=4:2:1);
NMR (DMSO-d$_6$): δ 0.91 (t, J=7.4 Hz, 3H), 1.20-1.40 (m, 2H), 1.40-1.60 (m, 2H), 1.60-2.00 (m, 6H), 2.20-2.40 (m, 2H), 2.80-3.60 (m, 10H), 2.96 (s, 3H), 3.98 (m, 1H), 4.15 (m, 1H), 4.20 (s, 2H), 6.22 (m, 1H), 7.03 (d, J=8.7 Hz, 4H), 7.28 (d, J=7.7 Hz, 2H), 7.61 (d, J=7.7 Hz, 2H), 8.83 (m, 1H), 9.36 (m, 1H), 9.47 (m, 1H).

Example 30(3)

N-[4-(4-{[4-(butyl{[(3-methylisothiazol-5-yl)amino]carbonyl}amino)piperidin-1-yl]methyl}phenoxy)phenyl]methanesulfonamide hydrochloride TLC:Rf 0.35 (chloroform:methanol=10:1);
NMR (CD$_3$OD): δ 0.98 (t, J=7.2 Hz, 3H), 1.30-1.50 (m, 2H), 1.50-1.70 (m, 2H), 2.00-2.10 (m, 2H), 2.30-2.40 (m, 2H), 2.56 (s, 3H), 2.95 (s, 3H), 3.10-3.20 (m, 2H), 3.30-3.40 (m, 2H), 3.50-3.60 (m, 2H), 4.20 (m, 1H), 4.31 (s, 2H), 7.02-7.08 (m, 5H), 7.29 (d, J=8.9 Hz, 2H), 7.53 (d, J=8.9 Hz, 2H).

Example 30(4)

N-[4-(4-{[4-(butyl{[(3-methyl-1,2-benzisothiazol-5-yl)amino]carbonyl}amino)piperidin-1-yl]methyl}phenoxy)phenyl]methanesulfonamide hydrochloride TLC:Rf 0.46(chloroform:methanol=10:1);
NMR (CD$_3$OD): δ 0.98 (t, J=7.2 Hz, 3H), 1.30-1.50 (m, 2H), 1.60-1.80 (m, 2H), 2.00-2.10 (m, 2H), 2.20-2.40 (m, 2H), 2.70 (s, 3H), 2.95 (s, 3H), 3.10-3.20 (m, 2H), 3.30-3.40 (m, 2H), 3.50-3.60 (m, 2H), 4.20 (m, 1H), 4.30 (s, 2H), 7.02-7.08 (m, 4H), 7.29 (d, J=8.9 Hz, 2H), 7.52 (d, J=8.9 Hz, 2H), 7.60 (dd, J=9.0, 1.7 Hz, 1H), 7.90 (d, J=9.0 Hz, 1H), 8.08 (d, J=1.7 Hz, 1H).

Example 30(5)

N-[4-(4-{[4-(butyl{[(1-methyl-1H-pyrazol-5-yl)amino]carbonyl}amino)piperidin-1-yl]methyl}phenoxy)phenyl]methanesulfonamide dihydrochloride TLC:Rf 0.30(chloroform:methanol=10:1);
NMR (CD$_3$OD): δ 0.98 (t, J=7.4 Hz, 3H), 1.30-1.50 (m, 2H), 1.60-1.70 (m, 2H), 2.00-2.10 (m, 2H), 2.20-2.40 (m, 2H), 2.95 (s, 3H), 3.10-3.20 (m, 2H), 3.30-3.40 (m, 2H), 3.50-3.60 (m, 2H), 3.78 (s, 3H), 4.20 (m, 1H), 4.29 (s, 2H), 6.34 (d, J=2.4 Hz, 1H), 7.02-7.08 (m, 4H), 7.29 (d, J=8.9 Hz, 2H), 7.51 (d, J=8.9 Hz, 2H), 7.79 (d, J=2.4 Hz, 1H).

Example 30(6)

N-[4-(4-{[4-(butyl{[(3-hydroxycyclohexyl)amino]carbonyl}amino)piperidin-1-yl]methyl}phenoxy)phenyl]methanesulfonamide hydrochloride TLC:Rf 0.24(methylene chloride:methanol=9:1);
NMR (CD$_3$OD): δ 0.95 (t, J=7.2 Hz, 3H), 1.23-2.20 (m, 16H), 2.95 (s, 3H), 3.02-3.16 (m, 4H), 3.50-3.59 (m, 2H), 3.66 (m, 1H), 3.95-4.22 (m, 2H), 4.28 (s, 2H), 7.03 (d, J=8.7 Hz, 2H), 7.06 (d, J=8.7 Hz, 2H), 7.29 (d, J=8.7 Hz, 2H), 7.50 (d, J=8.7 Hz, 2H).

Example 30(7)

N-[4-(4-{[4-(butyl{[(1,3,5-trimethyl-1H-pyrazol-4-yl)amino]carbonyl}amino)piperidin-1-yl]methyl}phenoxy)phenyl]methanesulfonamide dihydrochloride TLC:Rf 0.60(chloroform:methanol=5:1);
NMR (CD$_3$OD): δ 0.98 (t, J=7.2 Hz, 3H), 1.30-1.50 (m, 2H), 1.60-1.70 (m, 2H), 1.90-2.10 (m, 2H), 2.20-2.40 (m, 2H), 2.27 (s, 6H), 2.95 (s, 3H), 3.10-3.20 (m, 2H), 3.20-3.40 (m, 2H), 3.50-3.60 (m, 2H), 3.93 (s, 3H), 4.24 (m, 1H), 4.30 (s, 2H), 7.02-7.07 (m, 4H), 7.29 (d, J=8.7 Hz, 2H), 7.54 (d, J=8.7 Hz, 2H).

Example 30(8)

5-[({butyl[1-(4-{4-[(methylsulfonyl)amino]phenoxy}benzyl)piperidin-4-yl]amino}carbonyl)amino]-2,4-difluorobenzoic acid hydrochloride TLC:Rf 0.17(chloroform:methanol=5:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.20-2.30 (m, 2H), 2.95 (s, 3H), 3.00-3.20 (m, 2H), 3.20-3.40 (m, 2H), 3.50-3.60 (m, 2H), 4.10 (m, 1H), 4.25 (s, 2H), 7.01-7.06 (m, 5H), 7.29 (d, J=8.7 Hz, 2H), 7.50 (d, J=8.7 Hz, 2H), 7.89 (m, 1H).

Example 30(9)

5-[({butyl[1-(4-{4-[(methylsulfonyl)amino]phenoxy}benzyl)piperidin-4-yl]amino}carbonyl)amino]-2-fluorobenzoic acid hydrochloride TLC:Rf 0.21(ethyl acetate:methanol=7:1);
NMR (CD$_3$OD): δ 0.97 (t, J=7.4 Hz, 3H), 1.30-1.50 (m, 2H), 1.50-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.20 (m, 1H), 4.30 (s, 2H), 7.02-7.08 (m, 4H), 7.12 (d, J=9.0 Hz, 1H), 7.29 (d, J=8.7 Hz, 2H), 7.53 (d, J=8.7 Hz, 2H), 7.58 (m, 1H), 7.92 (m, 1H).

Example 30(10)

3-[({butyl[1-(4-{4-[(methylsulfonyl)amino]phenoxy}benzyl)piperidin-4-yl]amino}carbonyl)amino]-2,6-difluorobenzoic acid hydrochloride TLC:Rf 0.21(ethyl acetate:methanol=7:1);
NMR (CD$_3$OD): δ 0.97 (t, J=7.4 Hz, 3H), 1.30-1.50 (m, 2H), 1.60-1.70 (m, 2H), 1.90-2.10 (m, 2H), 2.20-2.40 (m, 2H), 2.95 (s, 3H), 3.00-3.20 (m, 2H), 3.20-3.40 (m, 2H), 3.50-3.60 (m, 2H), 4.20 (m, 1H), 4.28 (s, 2H), 6.90 (m, 1H), 7.02-7.07 (m, 4H), 7.29 (d, J=8.9 Hz, 2H), 7.40 (m, 1H), 7.50 (d, J=8.9 Hz, 2H).

Example 30(11)

2,4-difluoro-5-[({[[(3-methylpyridin-2-yl)methyl][1-(4-{4-[(methylsulfonyl)amino]phenoxy}benzyl)piperidin-4-yl]amino}carbonyl)amino]benzamide dihydrochloride TLC:Rf 0.70(chloroform:methanol=4:1);
NMR (CD$_3$OD): δ 2.10-2.20 (m, 2H), 2.20-2.40 (m, 2H), 2.62 (s, 3H), 2.95 (s, 3H), 3.00-3.20 (m, 2H), 3.50-3.60 (m, 2H), 4.31 (s, 2H), 4.50 (m, 1H), 7.00-7.06 (m, 4H), 7.17 (t, J=10.2 Hz, 1H), 7.28 (d, J=9.0 Hz, 2H), 7.56 (d, J=9.0 Hz, 2H), 7.90-7.98 (m, 2H), 8.44 (d, J=7.2 Hz, 1H), 8.57 (d, J=8.7 Hz, 1H).

Example 30(12)

5-[({but-3-en-1-yl[1-(4-{4-[(methylsulfonyl)amino]phenoxy}benzyl)piperidin-4-yl]amino}carbonyl)amino]-2,4-difluorobenzamide hydrochloride TLC:Rf 0.63(chloroform:methanol=4:1);
NMR (CD$_3$OD): δ 2.10-2.20 (m, 2H), 2.20-2.30 (m, 2H), 2.40-2.50 (m, 2H), 2.95 (s, 3H), 3.00-3.20 (m, 2H), 3.30-3.40 (m, 2H), 3.50-3.60 (m, 2H), 4.10 (m, 1H), 4.29 (s, 2H), 5.08-5.19 (m, 2H), 5.85 (m, 1H), 7.02-7.08 (m, 4H), 7.14 (t, J=10.4 Hz, 1H), 7.29 (d, J=8.9 Hz, 2H), 7.49 (d, J=8.9 Hz, 2H), 7.86 (m, 1H).

Example 31(1) and Example 31(2)

By the same procedure as described in Example 27, using O-benzylhydroxyamine or a corresponding amine derivative, and using the compound prepared in Example 3 instead of N-(4-{4-[(4-aminopiperidin-1-yl)methyl]phenoxy}phenyl)methanesulfonamide, the following compounds of the present invention were obtained.

Example 31(1)

N-{4-[4-({4-[{[(benzyloxy)amino]carbonyl}(butyl)amino]piperidin-1-yl}methyl)phenoxy]phenyl}methanesulfonamide hydrochloride

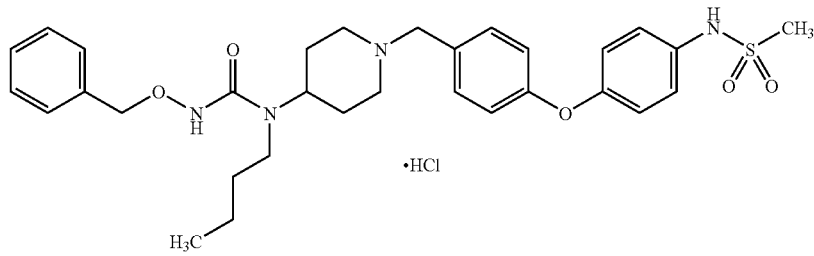

TLC:Rf 0.53(methylene chloride:methanol=9:1);
NMR (CD$_3$OD): δ 0.90 (t, J=7.2 Hz, 3H), 1.21-1.32 (m, 2H), 1.40-1.52 (m, 2H), 1.87-1.97 (m, 2H), 2.11-2.30 (m, 2H), 2.95 (s, 3H), 2.98-3.13 (m, 4H), 3.47-3.58 (m, 2H), 3.97 (m, 1H), 4.27 (s, 2H), 4.79 (s, 2H), 7.03 (d, J=8.7 Hz, 2H), 7.06 (d, J=8.7 Hz, 2H), 7.27-7.44 (m, 7H), 7.49 (d, J=8.7 Hz, 2H).

Example 31(2)

N-[4-(4-{[4-(butyl{[(2-methyl-1,3-benzothiazol-6-yl)amino]carbonyl}amino)piperidin-1-yl]methyl}phenoxy)phenyl]methanesulfonamide dihydrochloride TLC:Rf 0.74(chloroform:methanol=5:1);
NMR (CD$_3$OD): δ 0.96 (t, J=7.1 Hz, 3H), 1.30-1.50 (m, 2H), 1.50-1.70 (m, 2H), 1.90-2.10 (m, 2H), 2.20-2.40 (m, 2H), 2.95 (s, 3H), 2.99 (s, 3H), 3.10-3.30 (m, 2H), 3.30-3.40 (m, 2H), 3.50-3.60 (m, 2H), 4.30 (m, 1H), 4.31 (s, 2H), 7.01-7.05 (m, 4H), 7.29 (d, J=8.9 Hz, 2H), 7.56 (d, J=8.9 Hz, 2H), 7.67 (d, J=8.3 Hz, 1H), 7.97 (d, J=8.3 Hz, 1H), 8.23 (s, 1H).

Example 32

N-[4-(4-{[4-([(3,5-dimethylisoxazol-4-yl)methyl]{[(4-fluorophenyl)amino]carbonyl}amino)piperidin-1-yl]methyl}phenoxy)phenyl]methanesulfonamide hydrochloride

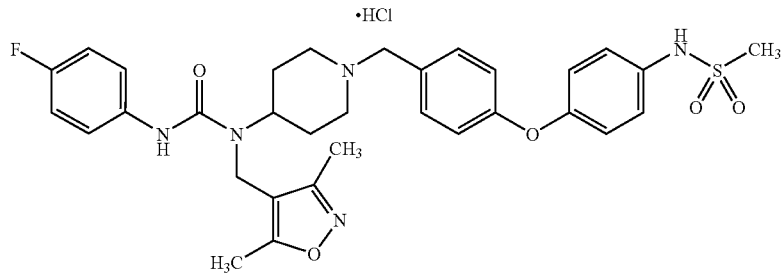

By the same procedure as described in Example 1, using N-(4-{4-[(4-aminopiperidin-1-yl)methyl]phenoxy}phenyl)methanesulfonamide used in Example 27 and 3,5-dimethylisoxazole-4-carbaldehyde instead of 4-hydroxypiperidine and 4-(4-methylsulfonylaminophenoxy)benzaldehyde respectively, a compound was obtained. By the same procedure as described in Example 23, using the obtained compound and 4-fluorobenzoic acid instead of the compound prepared in Example 3 and 1-methylcyclohexane respectively, the title compound (100.2 mg) having the following physical data was obtained.

TLC:Rf 0.56(methylene chloride:methanol=9:1);
NMR (CD$_3$OD): δ 1.91-2.00 (m, 2H), 2.12-2.32 (m, 2H), 2.25 (s, 3H), 2.39 (s, 3H), 2.95 (s, 3H), 3.02-3.16 (m, 2H), 3.48-3.57 (m, 2H), 4.05 (m, 1H), 4.26 (s, 2H), 4.42 (s, 2H), 6.97-7.08 (m, 6H), 7.25-7.37 (m, 4H), 7.49 (d, J=8.7 Hz, 2H).

Example 32(1)-Example 32(4)

By the same procedure as described in Example 32, using a corresponding aldehyde derivative instead of 3,5-dimethylisoxazole-4-carbaldehyde, the following compounds of the present invention were obtained.

Example 32(1)

N-[4-(4-{[4-([(5-chloro-1,3-dimethyl-1H-pyrazol-4-yl)methyl]{[(4-fluorophenyl)amino]carbonyl}amino)piperidin-1-yl]methyl}phenoxy)phenyl]methanesulfonamide dihydrochloride TLC:Rf 0.55(methylene chloride:methanol=9:1);
NMR (CD$_3$OD): δ 1.92-2.01 (m, 2H), 2.15-2.31 (m, 2H), 2.23 (s, 3H), 2.95 (s, 3H), 3.00-3.15 (m, 2H), 3.43-3.55 (m, 2H), 3.76 (s, 3H), 4.01 (m, 1H), 4.25 (s, 2H), 4.48 (s, 2H), 6.97-7.08 (m, 6H), 7.25-7.37 (m, 4H), 7.49 (d, J=8.7 Hz, 2H).

Example 32(2)

N-{4-[4-({4-[{[(4-fluorophenyl)amino]carbonyl}(1,3-thiazol-4-ylmethyl)amino]piperidin-1-yl}methyl)phenoxy]phenyl}methanesulfonamide hydrochloride TLC:Rf 0.42(chloroform:methanol=5:1);
NMR (CD$_3$OD): δ 1.92-2.04 (m, 2H), 2.16-2.33 (m, 2H), 2.95 (s, 3H), 3.11 (m, 2H), 3.54 (m, 2H), 4.29 (s, 2H), 4.31 (m, 1H), 4.69 (s, 2H), 6.98-7.08 (m, 6H), 7.22-7.40 (m, 4H), 7.44-7.58 (m, 2H), 7.64 (m, 1H), 9.22 (m, 1H).

Example 32(3)

N-(4-{4-[(4-{{[(4-fluorophenyl)amino]carbonyl}[(6-oxo-1,6-dihydropyridin-2-yl)methyl]amino}piperidin-1-yl)methyl]phenoxy}phenyl)methanesulfonamide hydrochloride TLC:Rf 0.17(methylene chloride:methanol=9:1);
NMR (CD$_3$OD): δ 2.00-2.30 (m, 4H), 2.95 (s, 3H), 3.10-3.22 (m, 2H), 3.50-3.62 (m, 2H), 4.30 (s, 2H), 4.38 (m, 1H), 4.57 (s, 2H), 6.78 (d, J=9.0 Hz, 1H), 6.82 (d, J=7.5 Hz, 1H), 7.01 (t, J=9.0 Hz, 2H), 7.02 (d, J=8.7 Hz, 2H), 7.05 (d, J=8.7 Hz, 2H), 7.29 (d, J=8.7 Hz, 2H), 7.37 (dd, J=9.0, 5.0 Hz, 2H), 7.53 (d, J=8.7 Hz, 2H), 7.90 (dd, J=9.0, 7.5 Hz, 1H).

Example 32(4)

N-{4-[4-({4-[{[(4-fluorophenyl)amino]carbonyl}(1H-imidazol-4-ylmethyl)amino]piperidin-1-yl}methyl)phenoxy]phenyl}methanesulfonamide dihydrochloride TLC:Rf 0.13(methylene chloride:methanol=9:1);
NMR (CD$_3$OD): δ 1.97-2.08 (m, 2H), 2.20-2.40 (m, 2H), 2.95 (s, 3H), 3.08-3.21 (m, 2H), 3.52-2.60 (m, 2H), 4.25-4.40

(m, 3H), 4.62 (s, 2H), 6.98-7.08 (m, 6H), 7.29 (d, J=8.7 Hz, 2H), 7.40 (dd, J=9.0, 5.0 Hz, 2H), 7.51 (s, 1H), 7.56 (d, J=8.7 Hz, 2H), 8.80 (s, 1H).

Example 33

4-[4-({4-[(allyloxy)imino]piperidin-1-yl}methyl) phenoxy]-N-methylbenzamide hydrochloride

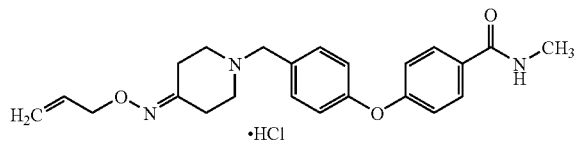

By the same procedure as described in Example 16, using N-methyl-4-{4-[(4-oxopiperidin-1-yl)methyl] phenoxy}benzamide and O-allylhydroxylamine instead of the compound prepared in Example 15 and n-butylamine respectively, the compound of the present invention having the following physical data was obtained.
TLC:Rf 0.60(chloroform:methanol=10:1);
NMR (CD$_3$OD): δ 7.84 (d, J=9.0 Hz, 2H), 7.57 (d, J=8.4 Hz, 2H), 7.15 (d, J=8.4 Hz, 2H), 7.08 (d, J=9.0 Hz, 2H), 5.97 (m, 1H), 5.30-5.15 (m, 2H), 4.54 (dt, J=5.7, 1.5 Hz, 2H), 4.38 (s, 2H), 3.68-3.59 (m, 2H), 3.44 (m, 1H), 3.23-3.07 (m, 2H), 2.91 (s, 3H), 2.68-2.63 (m, 2H), 2.40 (m, 1H).

Reference Example 11

2-[4-(4-nitrophenoxy)phenyl]ethanol

To a solution of 4-(2-hydroxyethyl)phenol (2.94 g) and 1-fluoro-4-nitrobenzene (3.0 g) in dimethylformamide (21 mL) was added potassium carbonate (4.41 g) and the solution was stirred at 120° C. for 4 hours. After cooling to room temperature, water was added to the reaction solution, which was extracted with ethyl acetate. The organic layer was washed with brine, dried over anhydrous sodium sulfate and concentrated. The obtained residue was purified by column chromatography on silica gel (hexane:ethyl acetate=1:1) to give the title compound having the following physical data.
TLC:Rf 0.80(chloroform:methanol=5:1).

Reference Example 12

2-[4-(4-aminophenoxy)phenyl]ethanol

Under an atmosphere of hydrogen, to a solution of the compound prepared in Reference Example 11 (803 mg) in ethanol (15 mL) was added palladium-carbon (wet, 10%, 100 mg) at room temperature for 1.5 hours. The reaction solution was filtrated through CELITE (brand name) and concentrated. The obtained residue was washed with t-butoxymethyl to give the title compound (641.5 mg) having the following physical data.
TLC:Rf 0.55(chloroform:methanol=5:1);
NMR (CDCl$_3$): δ 1.37 (t, J=6.6 Hz, 1H), 2.83 (t, J=6.6 Hz, 2H), 3.57 (m, 2H), 3.84 (q, J=6.6 Hz, 2H), 6.62-6.70 (m, 2H), 6.80-6.92 (m, 4H), 7.12-7.20 (m, 2H).

Reference Example 13

2-(4-{4-[bis(methylsulfonyl)amino]phenoxy}phenyl) ethyl methanesulfonate

To a solution of the compound prepared in Reference Example 12 (196.5 mg) in methylene chloride (8.6 mL) were added triethylamine (0.239 mL) and mesyl chloride (0.133 mL) at 0° C. for 30 minutes. The reaction solution was stirred at room temperature for 12 hours. An aqueous solution of sodium hydrogen carbonate was added to the reaction solution, which was extracted with methylene chloride. The organic layer was washed with brine, dried over anhydrous sodium sulfate and concentrated to give the title compound (292.4 mg) having the following physical data.
TLC:Rf 0.89(chloroform:methanol=5:1);
NMR (CD$_3$OD): δ 2.97 (s, 3H), 3.05 (t, J=6.6 Hz, 2H), 3.41 (s, 6H), 4.43 (t, J=6.6 Hz, 2H), 6.98-7.08 (m, 4H), 7.30-7.42 (m, 4H).

Example 34

N-(4-{4-[2-(4-{butyl[(cyclohexyl amino)carbonyl] amino}piperidin-1-yl)ethyl]phenoxy}phenyl)-N-(methylsulfonyl)methanesulfonamide To a solution of the compound prepared in Reference Example 13 (68.6 mg) and N-butyl-N'-cyclohexyl-N-piperidin-4-ylurea (100 mg) in dimethylformamide (2 mL) were added triethylamine (60.2 µL) and sodium iodide (64.6 mg) at room temperature for 12 hours. Water was added to the reaction solution, which was extracted with ethyl acetate. The organic layer was washed with brine, dried over anhydrous sodium sulfate and concentrated. The obtained residue was purified by column chromatography on silica gel (hexane: ethyl acetate=2:1) to give the compound of the present invention (32.2 mg) having the following physical data.
TLC:Rf 0.74(chloroform:methanol=5:1).

Example 35

N-(4-{4-[2-(4-{butyl[(cyclohexylamino)carbonyl] amino}piperidin-1-yl)ethyl]phenoxy}phenyl)methanesulfonamide hydrochloride

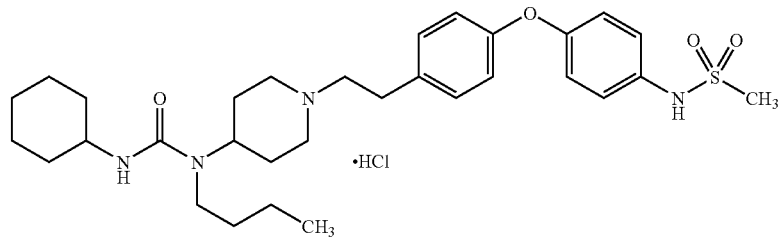

To a solution of the compound prepared in Example 34 (32.2 mg) in ethanol (5 mL) and water (1 mL) was added potassium carbonate (13.7 mg) and the solution was stirred at 60° C. for 3 hours. The reaction solution was concentrated. The obtained residue was purified by column chromatography on silica gel (ethyl acetate), and converted to hydrochloride salt by a conventional method to give the compound of the present invention (30.3 mg) having the following physical data.

TLC:Rf 0.69(chloroform:methanol=5:1);

NMR (CD₃OD): δ 0.97 (t, J=7.2 Hz, 3H), 2.00-1.10 (m, 16H), 2.25-2.08 (m, 2H), 2.93 (s, 3H), 3.16-3.00 (m, 6H), 3.38-3.24 (m, 2H), 3.38-3.24 (m, 2H), 3.55 (m, 1H), 3.71 (m, 2H), 4.13 (m, 1H), 7.00-6.90 (m, 4H), 7.32-7.20 (m, 4H).

Reference Example 14 t-butyl[1-(4-hydroxyphenyl)ethyl]carbamate

To a solution of 4-(1-aminoethyl)phenol (1.0 g) in ethanol (24 mL) were added di-t-butyl dicarbonate (4.77 g) and sodium hydroxide (146 mg) at 0° C. and the solution was stirred at room temperature for 4.5 hours. The reaction solution was concentrated and water was added thereto. The solution was extracted with ethyl acetate. The organic layer was washed with brine, dried over anhydrous magnesium sulfate and concentrated. The obtained residue was purified by column chromatography on silica gel (hexane:ethyl acetate=7:1) to give the title compound (2.18 g) having the following physical data.

TLC:Rf 0.88 (chloroform:methanol=5:1);

NMR (CDCl₃): δ 1.36-1.50 (m, 13H), 4.79 (m, 1H), 7.10-7.18 (m, 2H), 7.26-7.32 (m, 2H).

Reference Example 15

{1-[4-(4-nitrophenoxy)phenyl]ethyl}amine hydrochloride

To a solution of the compound prepared in Reference Example 14 (2.18 g) and 1-fluoro-4-nitrobenzene (1.028 g) in dimethylformamide (30 mL) was added potassium carbonate (1.21 g) and the solution was stirred at 150° C. for 3 hours. After cooling to room temperature, water was added to the reaction solution, which was extracted with ethyl acetate. The organic layer was washed with brine, dried over anhydrous magnesium sulfate and concentrated. The obtained residue was purified by column chromatography on silica gel (hexane:ethyl acetate=6:1). To a solution of the compound (2.05 g) in ethyl acetate (30 mL) was added 4N hydrochloric acid/ethyl acetate solution (7.15 mL). the solution was stirred at 40° C. for 4 hours and moreover at room temperature for 3 days. The precipitate was corrected to give the title compound (1.37 g) having the following physical data.

NMR (DMSO-d₆): δ 1.52 (d, J=6.6 Hz, 3H), 4.45 (m, 1H), 7.12 (brd, J=9.3 Hz, 2H), 7.26 (brd, J=8.7 Hz, 2H), 7.62 (brd, J=8.7 Hz, 2H), 8.28 (brd, J=9.3 Hz, 2H), 8.44 (m, 2H).

Example 36

1-{1-[4-(4-nitrophenoxy)phenyl]ethyl}piperidin-4-one hydrochloride

To a solution of the compound prepared in Reference Example 15 (550 mg) in ethanol (9.33 mL) and water (4.67 mL) were added N-benzyl-N-methyl-4-piperidone iodide (927 mg) and potassium carbonate (670 mg) and the solution was refluxed for 5 hours. After cooling to room temperature, water was added to the reaction solution, which was extracted with ethyl acetate. The organic layer was washed with brine, dried over anhydrous magnesium sulfate and concentrated. The obtained residue was purified by column chromatography on silica gel (hexane:ethyl acetate=3:1), and converted to hydrochloride salt by a conventional method to give the compound of the present invention (515 mg) having the following physical data.

TLC:Rf 0.79(chloroform:methanol=9:1);

NMR (DMSO-d₆): δ 1.75 (d, J=6.9 Hz, 3H), 3H), 2.38-3.20 (m, 6H), 3.52 (m, 1H), 3.82 (m, 1H), 4.78 (m, 1H), 7.19 (d, J=9.0 Hz, 2H), 7.29 (d, J=9.0 Hz, 2H), 7.73 (d, J=9.0 Hz, 2H), 8.27 (d, J=9.0 Hz, 2H).

Example 37

N-(4-{4-[1-(4-{butyl[(cyclohexylamino)carbonyl]amino}piperidin-1-yl)ethyl]phenoxy}phenyl)methanesulfonamide hydrochloride

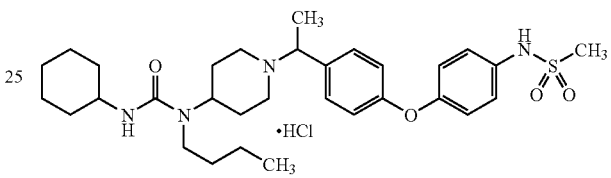

By the same procedure as described in Example 3, using the compound prepared in Example 36 instead of the compound prepared in Example 2, a compound was obtained. By the same procedure as described in Example 23→Reference Example 12→Reference Example 13, using the obtained compound and cyclohexylcarboxylic acid, the compound of the present invention (107 mg) having the following physical data was obtained.

TLC:Rf 0.39(chloroform:methanol=9:1);

NMR (CD₃OD): δ 0.94 (t, J=7.2 Hz, 3H), 1.14-2.28 (m, 18H), 1.76 (d, J=6.9 Hz, 3H), 2.80-3.05 (m, 2H), 2.95 (s, 3H), 3.12 (m, 2H), 3.41 (m, 1H), 3.52 (m, 1H), 3.74 (m, 1H), 4.02 (m, 1H), 4.46 (m, 1H), 7.00-7.19 (m, 4H), 7.29 (brd, J=9.3 Hz, 2H), 7.50 (brd, J=8.7 Hz, 2H).

Example 38 ethyl N-[1-(4-{4-[(methylsulfonyl)amino]phenoxy}benzyl)piperidin-4-yl]glycinate hydrochloride To a solution of the compound prepared in Example 2 (510 mg) and ethyl glycinate (190 mg) in dimethylformamide (10 mL) and acetic acid (1 mL) was added sodium triacetoxyborohydride (345 mg) and was stirred at room temperature for 12 hours. The reaction solution was concentrated. The obtained residue was purified by column chromatography on silica gel (ethyl acetate), and converted to hydrochloride salt by a conventional method to give the compound of the present invention (583 mg) having the following physical data.

TLC:Rf 0.53 (chloroform:methanol=5:1).

Example 39

N-butyl-N-[1-(4-{4-[(methylsulfonyl)amino]phenoxy}benzyl)piperidin-4-yl]glycine

To a solution of the hydrochloride salt of the compound prepared in Example 38 (303 mg) in dimethylformamide (6 mL) and acetic acid (0.6 mL) were added butanal (56.2 μL) and sodium triacetoxyborohydride (144 mg) sequentially. The solution was stirred at room temperature for 12 hours. The reaction solution was concentrated. Water was added thereto and the solution was extracted with ethyl acetate. The organic layer was washed with brine, dried over anhydrous sodium sulfate and concentrated. The obtained residue was purified by column chromatography on silica gel (ethyl acetate). To a solution of the obtained compound (179.2 mg) in ethanol (15 mL) was added 2N aqueous solution of sodium hydroxide (0.91 mL) and the solution was stirred at 40° C. for 12 hours. The reaction solution was concentrated and purified by column chromatography on silica gel (ethylacetate:methanol=2:1) to give the compound of the present invention having the following physical data.

TLC:Rf 0.19(chloroform:methanol=5:1).

Example 40

N2-butyl-N-1-cyclohexyl-N2-[1-(4-{4-[(methylsulfonyl)amino]phenoxy}benzyl)piperidin-4-yl]glycinamide dihydrochloride

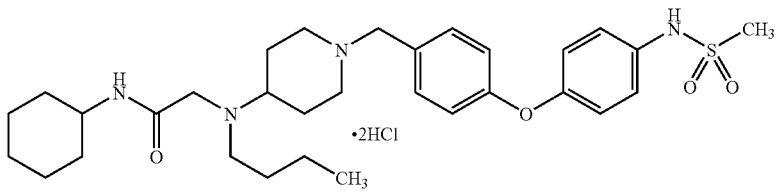

To a solution of the compound prepared in Example 39 in dimethylformamide (5 mL) were added cyclohexylamine (41.7 μL), 1-ethyl-3-(3-dimethylaminopropyl)-carbodiimide hydrochloride (87.2 mg) and 1-hydroxy-7-azabenzotriazole (61.9 mg) and the solution was stirred at room temperature for 12 hours. The reaction solution was concentrated and purified by column chromatography on silica gel (ethyl acetate), and converted to hydrochloride salt by a conventional method to give the compound of the present invention (41.4 mg) having the following physical data.

TLC:Rf 0.71(chloroform:methanol=5:1);
NMR (CD₃OD): δ 0.98 (t, J=7.2 Hz, 3H), 1.16-1.48 (m, 7H), 1.58-1.94 (m, 7H), 2.08-2.38 (m, 4H), 2.95 (s, 3H), 3.08-3.35 (m, 4H), 3.56-4.15 (m, 6H), 4.31 (s, 2H), 7.00-7.08 (m, 4H), 7.24-7.34 (m, 2H), 7.55 (brd, J=8.7 Hz, 2H).

Reference Example 16

1-(2-chloropyrimidin-4-yl)azepane

To a solution of 2,4-dichloropyrimidine (25 g) in triethylamine (47 mL) and tetrahydrofuran (300 mL) was added azepane (17 g) at 0° C. After returning to room temperature, the solution was stirred for 1 hour. Water was added to thereto and the solution was extracted with ethyl acetate. The organic layer was washed with brine, dried over anhydrous sodium sulfate and concentrated. The obtained residue was purified by column chromatography on silica gel (ethyl acetate:hexane=1:5→1:2) to give the title compound (7.25 g) having the following physical data.

TLC:Rf 0.43(hexane:ethyl acetate=3:1);
NMR (CDCl₃): δ 1.57 (m, 4H), 1.79 (m, 4H), 3.45 (m, 2H), 3.79 (m, 2H), 6.29 (d, J=6.3 Hz, 1H), 7.98 (d, J=6.3 Hz, 1H).

Reference Example 17

4-azepan-1-yl-N-piperidin-4-ylpyrimidin-2-amine trihydrochloride

A mixture of the compound prepared in Reference Example 16 (500 mg) and 1-t-butoxycarbonyl-4-aminopiperidine was stirred at 125° C. for 6 hours. After cooling, a saturated aqueous solution of sodium hydrogen carbonate was added to the reaction mixture, which was extracted with ethyl acetate. The organic layer was washed with brine, dried over anhydrous sodium sulfate and concentrated. The obtained residue was purified by column chromatography on silica gel (hexane:ethyl acetate=3:10:1). To a solution of the obtained residue in ethyl acetate (1 mL) was added 4N hydrochloric acid/ethyl acetate solution (4 mL) and the solution was stirred for 1.5 hours at room temperature. The reaction solution was concentrated to give the title compound (290 mg) having the following physical data.

TLC:Rf 0.23 (dichloromethane:methanol:acetic acid=5:1:0.1);
NMR (CD₃OD): δ 1.59-1.61 (m, 4H), 1.83-1.92 (m, 6H), 2.22-2.27 (m, 2H), 3.14-3.22 (m, 2H), 3.44-3.49 (m, 2H), 3.69 (t, J=6.1 Hz, 2H), 3.91 (t, J=6.1 Hz, 2H), 4.17 (m, 1H), 6.41 (d, J=7.5 Hz, 1H), 7.68 (d, J=7.5 Hz, 1H).

Example 41

N-{4-[4-({4-[(4-azepan-1-ylpyrimidin-2-yl)amino]piperidin-1-yl}methyl)phenoxy]phenyl}methanesulfonamide trihydrochloride

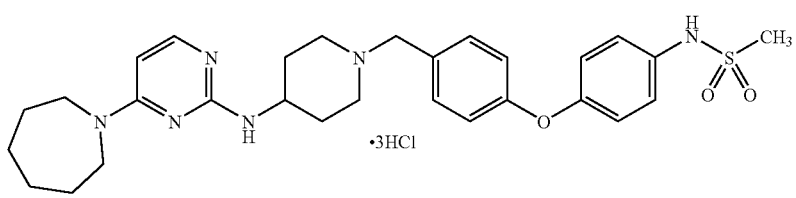

By the same procedure as described in Example 1, using the compound prepared in Reference Example 17 instead of 4-hydroxypiperidine, the compound of the present invention (159 mg) having the following physical data was obtained.

TLC:Rf 0.38(methylene chloride:methanol=10:1);

NMR (CD$_3$OD): δ 1.61-1.62 (m, 4H), 1.83-1.98 (m, 6H), 2.20-2.33 (m, 2H), 2.95 (s, 3H), 3.16-3.24 (m, 2H), 3.55-3.61 (m, 2H), 3.69 (t, J=6.0 Hz, 2H), 3.91 (t, J=6.0 Hz, 2H), 4.15 (m, 1H), 4.31 (s, 2H), 6.40 (d, J=7.5 Hz, 1H), 7.03 (d, J=8.7 Hz, 2H), 7.06 (d, J=8.7 Hz, 2H), 7.29 (d, J=8.7 Hz, 2H), 7.54 (d, J=8.7 Hz, 2H), 7.66 (d, J=7.5 Hz, 1H).

Example 41(1)

N-{4-[4-({3-[(4-azepan-1-ylpyrimidin-2-yl)amino] piperidin-1-yl}methyl)phenoxy] phenyl}methanesulfonamide trihydro chloride By the same procedure as described in Reference Example 17→Example 37, using 1-t-butoxycarbonyl-3-aminopiperidine instead of 1-t-butoxycarbonyl-4-aminopiperidine, the compound of the present invention (51 mg) having the following physical data was obtained.

TLC:Rf 0.53 (methylene chloride:methanol=10:1);

NMR (CD$_3$OD): δ 1.55-1.80 (m, 9H), 2.00-2.17 (m, 3H), 2.79 (m, 1H), 2.95 (s, 3H), 3.04 (m, 1H), 3.53-3.86 (m, 7H), 4.25 (d, J=13.5 Hz, 1H), 4.33 (m, 1H), 4.44 (d, J=13.5 Hz, 1H), 6.40 (d, J=7.5 Hz, 1H), 7.02 (d, J=8.7 Hz, 2H), 7.04 (d, J=8.7 Hz, 2H), 7.29 (d, J=8.7 Hz, 2H), 7.55 (d, J=8.7 Hz, 2H), 7.66 (d, J=7.5 Hz, 1H).

BIOLOGICAL EXAMPLE

The fact that the compound of the present invention has CCR5 antagonism was demonstrated, for example, by the following experiment. The total operation was based on the basic genetic engineering to prepare gene-highly expressing cells, and the ordinary methods were utilized. Also, in the assaying method of the present invention, in order to evaluate the compound of the present invention, assaying accuracy and/or assaying sensitivity was improved as described below. The detailed experimental methods are shown below.

Biological Example 1

Inhibition test on the binding of RANTES to CCR5:
(1) Isolation of Human CCR5 Gene Human placental cDNA was prepared using Marathon cDNA amplification kit (Clontech). PCR primers hCCR5Xbal-F1:

(SEQ ID NO:1)
5'-AGCTAGTCTAGATCCGTTCCCCTACAAGAAACTCTCC-3' and hCCR5Xbal-R1:

(SEQ ID NO:2)
5'-AGCTAGTCTAGAGTGCACAACTCTGACTGGGTCACCA-3' were designed based on the sequence of GenBank U54994.

Using the human placental cDNA as the template and using Ex Taq (Takara), PCR reaction (2 minutes at 95° C.→(30 seconds at 95° C., 45 seconds at 60° C., 1 minute at 72° C.)×35 times) was carried out. The thus amplified PCR product was subjected to a 1% agarose gel electrophoresis, purified using QIAquick Gel Extraction Kit (QUIAGEN) and then digested with a restriction enzyme XbaI. The digested fragments were ligated to an expression vector pEF-BOS-bsr using DNA Ligation Kit Ver. 2 (Takara) and transformed into *Escherichia coli* DH5a. By preparing the resulting plasmid pEF-BOS-bsr/hCCR5, its DNA sequence was verified.

(2) Culturing of CHO Cell

CHO-dhfr(−) was cultured using Ham's F-12 (containing fetal bovine serum (10%), penicillin (50 U/mL) and streptomycin (50 mg/mL)). Also, the transduced cell was cultured by adding blasticidin (5 mg/mL) to the above medium.

(3) Transduction into CHO Cell

The plasmid pEF-BOS-bsr/hCCR5 was transduced into the CHO-dhfr(−) cell using DMRIE-C reagent (Gibco BRL). After 48 hours, the medium was replaced with a medium containing 5 mg/ml of blasticidin to carry out the selection, thereby establishing a stably over-expressing cell.

(4) Inhibition Test on the Binding of RANTES to CCR5 (Activity of RANTES to Induce Transient Increase of Ca Ion).

The thus established human CCR5 stably over-expressing CHO cell (CCR5/CHO cell) was suspended in Ham's F-12 medium containing FBS (10%) and seeded at a density of 3.0×10$^6$ cells/well into a 96 well plate. One day after culturing at 37° C., the culture supernatant was discarded, and Ham's F-12 medium (containing Fura-2AM (5 μM), Probenecid (2.5 mM) and HEPES (20 mM; pH 7.4)) was dispensed in 80 Owen portions to carry out 1 hour of incubation at 37° C. under shaded condition. After washing twice with 1× Hanks/ HEPES (20 mM; pH 7.4) solution, the same solution was dispensed in 100 μl/well portions. Each of the test compounds was added to the thus Fura-2AM-incorporated CCR5/CHO cell, and 3 minutes thereafter, a recombinant human RANTES (PeproTach) diluted with 1× Hanks/HEPES (20 mM; pH 7.4) solution was added thereto to a final concentration of 10 nM. Transient increase in the intracellular Ca$^{2+}$ concentration induced by the human RANTES was measured using a Ca$^{2+}$ detector for 96 well use (Hamamatsu Photonics), and inhibition ratio (%) of the test compound was calculated by the following calculation formula.

Inhibition ratio=(*Ec*−*Ea*)/*Ec*×100

Ec: measured value of Ca$^{2+}$ transient increase by RANTES
Ea: measured value of Ca$^{2+}$ transient increase by RANTES when a test compound was added.

As a result, the compounds of the present invention showed an inhibition ratio of 50% or more at 10 μM. For example, the compound of Example 5(2) showed an IC$_{50}$ value of 0.077 μM.

Biological Example 2

Migration test of human CCR5 expressing cell (hCCR5-Ba/F3 cell):
(1) Establishment of Human CCR5 Expressing Cell
(1-A) Isolation of Human CCR5 Gene The isolation was carried out according to the method of the isolation of human CCR5 gene as described in the above Example 1.

(1-B) Culturing of Ba/F3 Cell

Ba/F3 cells were statically cultured by using RMMI-1640 medium (Gibco BRL) containing antibiotics (Antibiotic-Antimycotic) (final concentration: penicillin G sodium (100 U/mL), streptomycin sulfate (100 μg/mL), amphotericin B (0.25 μg/mL)) (Gibco BRL), fetal bovine serum (FBS) (10%), 2-mercaptoethanol (55 μM) and mouse interleukin-3 (IL-3) (5 ng/mL) (Pepro Tech, Inc) in a carbon dioxide incubator (temperature: 37° C., CO$_2$ concentration: 5%, humidity:

95%). Exogenous gene stable hyperexpression cells were cultured in the above medium to which blasticidin (Kaken Pharmaceutical) was added to give a final concentration of 10 µg/ml.

(1-C) Transformation to Ba/F3 Cell

A plasmid for human CCR5 expression (pEF-BOS-bsr/hCCR5) was digested with AatII for linearization. The linearized plasmid was purified by QIA quick PCR Purification Kit (QIAGEN), and introduced into Ba/F3 cells by electroporation (Gene Pulser (BIO RAD), 960 µF/250V). The cells were seeded into a 96-well culture plate at a density of 1,000, 100, 10 cells/100 µl/well, and cultured for 48 hours. Then, blasticidin was added thereto to give a final concentration of 10 µg/ml, followed by cloning of a blasticidin-resistant cell line to thereby establish a stable hyperexpression clone expressing the introduced exogenous gene (hCCR5-Ba/F3 cell).

(1-D) Analysis of CCR5 Expression

The human CCR5 expression level in the clone obtained by the method described in the above (1-C) was detected with FAC Sort (trade name, Becton, Dickinson) by detecting the cells with a fluorescence isothiocyanate (FITC)-labeled anti-human CCR5 antibody (BD Pharmingen) and analyzed. In this connection, FITC-labeled mouse IgG2aκ (BD Pharmingen) was used as an isotype control antibody.

(2) Cell Migration Test

Influence of a test compound on the migration ability of the human CCR5 expressing Ba/F3 cell against RANTES, MIP-1α or MIP-1β was examined. First, 0.3 ml of 0 or 3 nM chemokine (RANTES, MIP-1α or MIP-1β-containing medium was respectively added to the low room of Chemo Tx96 well plate (Neuro Probe). Next, a filter (pore size: 5 µm) was set and a mixture solution ($1 \times 10^5$ cells/well) of the test compound and the CCR5-Ba/F3 cell prepared in advance was added at 65 µl. The test compound to be added was prepared by diluting it with 0.1% DMSO-containing medium to give a final concentration on the filter of 0, 0.01, 0.03, 0.1 or 0.3 µM. These cells were cultured in a $CO_2$ incubator (37° C., 5% $CO_2$, relative humidity: 95%) for 3 hours, and then the medium and unmigrated cells on the filter were eliminated. Furthermore, the filter was removed, the microplate was centrifuged (1,500 rpm, 10 min, RT) and the supernatant was removed by decantation. The cells on the microplate were suspended in 100 µl of a phosphate buffer (PBS), and 1/10 portion thereof was further diluted with 90 µl of PBS, moved on a white plate for fluorescence assay, and used as an assay sample for migrated cell numbers (final: 100 µl/well).

Next, Cell Titer-Glo Reagent (trade name, Promega) which was previously prepared at room temperature was added to the above assay sample for migrated cell numbers (100 µl/well), followed by gently mixing (300 rpm, 2 min with KA-SCHUTTLER MTS4) for lysating the cells, the mixture was incubated at room temperature for 10 minutes, and the fluorescence was measured with wallac ARVO SX 1420 MULTILABEL COUNTER (trade name, Perkin Elmer) (detection by count/second).

The migrated cell numbers (naturally falling cell numbers) at a chemokine concentration of 0 nmol/l was used as the background, and the inhibition ratio of the test compound against the 0.1% DMSO control group was calculated.

The inhibition migration ratio (%) of the test compound was calculated by the following equation:

$$\text{Inhibition ratio} = \frac{(Ec - Ea)}{Ec} \times 100$$

Ec: (fluorescence measured value at the addition of 0.1% DMSO)–(fluorescence measured value of the naturally falling cells)

Ea: (fluorescence measured value at the addition of the test compound)–(fluorescence measured value of the naturally falling cells)

Results:

The compound produced in Example 23(126) showed cell migration inhibition ratios of 42% and 77% at concentrations of 10 and 30 µM, respectively, against RANTES.

Formulation Example 1

The following components were admixed in a conventional manner, punched out to give 100 tablets each containing 50 mg of active ingredient.

| | |
|---|---|
| N-butyl-N-[1-(4-{4-[(methylsulfonyl)amino]phenoxy}benzyl)piperidin-4-yl]cyclohexanecarboxamide hydrochloride | 5.0 g |
| calcium carboxymethyl cellulose (disintegrant) | 0.2 g |
| magnesium stearate (lubricant) | 0.1 g |
| microcrystalline cellulose | 4.7 g |

Formulation Example 2

The following components were admixed in a conventional technique. The solution was sterilized in a conventional technique, filled in ampoules 5 ml each and freeze-dried over in a conventional technique to give 100 ampoules each containing 20 mg of active ingredient.

| | |
|---|---|
| N-butyl-N-[1-(4-{4-[(methylsulfonyl)amino]phenoxy}benzyl)piperidin-4-yl]cyclohexanecarboxamide hydrochloride | 2.0 g |
| mannitol | 20 g |
| distilled water | 500 ml |

Formulation Example 3

The following components were admixed in a conventional manner, punched out to give 10,000 tablets each containing 10 mg of active ingredient.

| | |
|---|---|
| N-butyl-N-[1-(4-{4-[(methylsulfonyl)amino]phenoxy}benzyl)piperidin-4-yl]cyclohexanecarboxamide hydrochloride | 100 g |
| calcium carboxymethyl cellulose (disintegrant) | 20.0 g |
| magnesium stearate (lubricant) | 10.0 g |
| microcrystalline cellulose | 870 g |

Formulation Example 4

Each of the following components was mixed by a standard method and filtered through a dustproofing filter, and then 5 ml aliquots were charged into ampoules, which were autoclaved to thereby obtain 10,000 ampoules each containing 20 mg of the active ingredient.

| | |
|---|---|
| N-butyl-N-[1-(4-{4-[(methylsulfonyl)amino]phenoxy}benzyl)piperidin-4-yl]cyclohexanecarboxamide hydrochloride | 200 g |
| mannitol | 2 kg |
| distilled water | 50 L |

INDUSTRIAL APPLICABILITY

The compounds of the present invention represented by formula (I) regulate the effect of CCR5 receptor, so they are useful in preventing and/or treating various inflammatory diseases (asthma, nephritis, nephropathy, hepatitis, arthritis, rheumatoid arthritis, rhinitis, conjunctivitis, ulcerative colitis, etc.), immunological diseases (autoimmune diseases, rejection in organ transplantation, immunosuppression, psoriasis, multiple sclerosis, etc.), infection with human immunodeficiency virus (acquired immunodeficiency syndrome, etc.), allergic diseases (atopic dermatitis, urticaria, allergic bronchopulmonary aspergillosis, allergic eosinophilic gastroenteritis, etc.), ischemic reperfusion injury, acute respiratory distress syndrome, shock accompanying bacterial infection, diabetes, cancer metastasis and so on. Therefore, CCR5 antagonist is useful as medicament.

X represents —O—;
Y represents —CH$_2$—;
ring A represents benzene which may have a substituent(s) of C1-4 alkyl and/or a halogen atom(s);
ring B represents pyridine, which may have a substituent(s) of C1-4 alkyl and/or a halogen atom(s)
ring D represents a piperidine;
R$^2$ represents

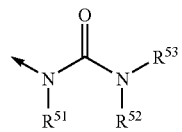

wherein the arrow represents a binding position to ring D;

R$^{51}$ represents (1) C1-6 alkyl which may have a substituent(s) selected from the group consisting of (a) hydroxy, (b) methoxy, (c) cyano, (d) carboxy, (e) a halogen atom(s), (f) methylsulfonylamino, and (g) thienyl, pyrazolyl, tetrahydropyranyl, thiazolyl, isoxazolyl, imidazolyl, tetrazolyl, pyridyl or pyrimidinyl, each of which may have methyl and/or trifluromethyl,

---

---

The invention claimed is:

1. A compound represented by formula (I):

R$^1$—(A)—X—(B)—Y—N(D)—R$^2$    (I)

wherein R$^1$ represents —SO$_2$NR$^{102}$R$^{103}$, —NR$^{101}$SO$_2$R$^{104}$ or —COOR$^{105}$.

R$^{101}$ represents a hydrogen atom;
R$^{102}$ and R$^{103}$ each independently represents a hydrogen atom or C1-4 alkyl;
R$^{104}$ represents C1-4 alkyl;
R$^{105}$ represents a hydrogen atom or C1-4 alkyl;

(2) C2-10 alkenyl,
(3) C2-10 alkynyl,
(4) phenyl which may have C1-4 alkyl and/or a halogen atom(s),
(5) C7-16 aralkyl which may have a substituent(s) of methyl, a halogen atom(s), hydroxy and/or methoxy, or
(6) (C3-8 cycloalkyl)-(C1-4 alkyl)-which may have a substituent(s) of methyl, a halogen atom(s), hydroxy and/or methoxy;

R$^{52}$ represents
(1) C1-6 alkyl which may have a substituent(s) selected from the group consisting of (a) hydroxy, (b) methoxy, (c) carboxy, (d) C3-8 cycloalkyl, (e) phenyl, and (f) oxo,
(2) C3-8 cycloalkyl or phenyl, each of which may have a substituent(s) selected from the group consisting of C1-4 alkyl, hydroxy, cyano, oxo, carbamoyl, N-methylaminocarbonyl, carboxy, a halogen atom(s), methoxy, trifluoromethoxy, methylthio, methylsulfonyl, acetylamino, dimethylamino, acetyl, tetrazolyl, trifluoromethyl, and methylsulfonylamino,
(3) C3-10 cycloalkenyl, or
(4) thienyl, pyrazolyl, tetrahydropyranyl, isoxazolyl, isothiazolyl, thiadiazolyl, piperidinyl, pyridyl, pyrimidinyl, pyridazinyl, quinolyl, indolyl, benzothiazolyl, benzoisothiazolyl, benzotriazolyl, dioxaindanyl or benzodioxanyl, each of which may have a substituent(s) of C1-4 alkyl, hydroxy, oxo, a halogen atom(s), azide and/or trifluoromethyl; and
$R^{53}$ represents a hydrogen atom,
or a salt thereof.

2. A pharmaceutical composition, which comprises the compound represented by formula (I) according to claim 1 or a salt thereof, and a pharmaceutically acceptable carrier.

3. The compound according to claim 1, which is represented by formula (Id):

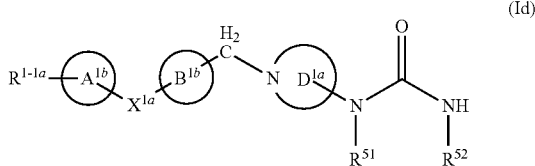

(Id)

wherein ring $A^{1b}$ represents benzene which may have a substituent(s) of C1-4 alkyl and/or a halogen atom(s)
ring $B^{1b}$ represents pyridine which may have a substituent(s) of C1-4 alkyl and/or a halogen atom(s);
$R^{1-1a}$ is —SO$_2$NR$^{102}$R$^{103}$ or —NR$^{101}$SO$_2$R$^{104}$;
$X^{1a}$ is —O—;
ring $D^{1a}$ is piperidine; and
other symbols have the same meaning as described in claim 1.

4. The compound according to claim 3, wherein ring $A^{1b}$ is benzene which may have a substituent(s) of methyl and/or a halogen atoms(s).

5. The compound according to claim 3, wherein ring $B^{1b}$ is pyridine which has a substituent(s) of methyl and/or a halogen atom(s).

6. The compound according to claim 3, wherein $R^{51}$ is
(1) C1-6 alkyl which may have a substituent(s) selected from the group consisting of (a) hydroxy, (b) methoxy, (c) cyano, (d) carboxy, and (e) thienyl, tetrahydropyranyl, imidazolyl, or pyridyl, each of which may have methyl and/or trifluromethyl, (2) C2-10 alkenyl, (3) C2-10 alkynyl, or (4) phenyl which may have methyl and/or a halogen atom(s).

7. The compound according to claim 3, wherein $R^{52}$ is (1) C1-6 alkyl which may have a substituent(s) selected from the group consisting of (a) hydroxy, (b) methoxy, (c) carboxy, (d) cyclohexyl, (e) phenyl, and (f) oxo, (2) C3-8 cycloalkyl or phenyl, each of which may have a substituent(s) selected from the group consisting of C1-4 alkyl, hydroxy, cyano, oxo, carbamoyl, N-methylaminocarbonyl, carboxy, a halogen atom(s), methoxy, trifluoromethoxy, methylthio, methylsulfonyl, acetylamino, acetyl, trifluoromethyl, and methylsulfonylamino, (3) cyclopentenyl, or (4) thienyl, pyrazolyl, tetrahydropyranyl, piperidinyl, pyridyl, quinolyl, or indolyl, each of which may have a substituent(s) of C1-4 alkyl, hydroxy, oxo, a halogen atom(s), and/or trifluoromethyl.

8. The compound according to claim 6, wherein $R^{51}$ is C1-6 alkyl.

9. The compound according to claim 7, wherein $R^{52}$ is phenyl which may have a substituent(s) of methyl, ethyl, hydroxy, cyano, carbamoyl, N-methylaminocarbonyl, carboxy, a halogen atom(s), methoxy, trifluoromethoxy, methylthio, methylsulfonyl, acetylamino, acetyl, trifluoromethyl, and/or methylsulfonylamino.

10. A compound represented by formula (I):

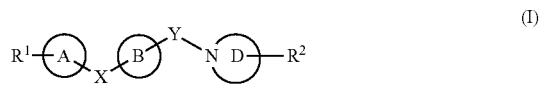

(I)

wherein $R^1$ represents —SO$_2$NR$^{102}$R$^{103}$ or —NR$^{101}$SO$_2$R$^{104}$;
$R^{101}$ represents a hydrogen atom;
$R^{102}$ and $R^{103}$ each independently represents a hydrogen atom or C1-4 alkyl;
$R^{104}$ represents C1-4 alkyl;
X represents —O—;
Y represents —CH$_2$—;
ring A represents benzene which may have a substituent(s) of methyl and/or a halogen atom(s);
ring B represents pyridine which may have a substituent(s) of methyl and/or a halogen atom(s)
ring D represents a piperidine;
$R^2$ represents

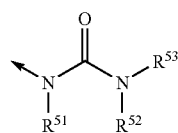

wherein the arrow represents a binding position to ring D;
$R^{51}$ represents C1-6 alkyl;
$R^{52}$ represents phenyl which may have a substituent(s) of methyl, ethyl, hydroxy, cyano, carbamoyl, N-methylaminocarbonyl, carboxy, a halogen atom(s), methoxy, trifluoromethoxy, methylthio, methylsulfonyl, acetylamino, acetyl, trifluoromethyl, and/or methylsulfonylamino;
$R^{53}$ represents a hydrogen atom,
or a salt thereof.

11. A pharmaceutical composition, which comprises the compound represented by formula (I) according to claim 10 or a salt thereof, and a pharmaceutically acceptable carrier.

* * * * *